United States Patent
Alexander et al.

(10) Patent No.: US 11,560,371 B2
(45) Date of Patent: Jan. 24, 2023

(54) CEREBLON BINDING COMPOUNDS, COMPOSITIONS THEREOF, AND METHODS OF TREATMENT THEREWITH

(71) Applicant: Celgene Corporation, Summit, NJ (US)

(72) Inventors: Matthew D. Alexander, San Diego, CA (US); Matthew D. Correa, San Diego, CA (US); Deepak Dalvie, Carlsbad, CA (US); Virginia Heather Sharron Grant, San Diego, CA (US); Joshua Hansen, La Jolla, CA (US); Roy L. Harris, III, San Diego, CA (US); Evan J. Horn, San Diego, CA (US); Dehua Huang, San Diego, CA (US); Christopher Mayne, Boulder, CO (US); Stephen Norris, San Diego, CA (US); Veronique Plantevin-Krenitsky, San Francisco, CA (US); John J. Sapienza, Chula Vista, CA (US); Lida Tehrani, San Diego, CA (US); Brandon W. Whitefield, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 17/356,283

(22) Filed: Jun. 23, 2021

(65) Prior Publication Data

US 2022/0002273 A1 Jan. 6, 2022

Related U.S. Application Data

(60) Provisional application No. 63/043,650, filed on Jun. 24, 2020.

(51) Int. Cl.
| | | |
|---|---|---|
| C07D 403/14 | (2006.01) | |
| A61P 35/00 | (2006.01) | |
| C07D 401/14 | (2006.01) | |

(52) U.S. Cl.
CPC ............ *C07D 403/14* (2013.01); *A61P 35/00* (2018.01); *C07D 401/14* (2013.01)

(58) Field of Classification Search
CPC ...... C07D 403/14; C07D 401/14; A61P 35/00
See application file for complete search history.

(56) References Cited

U.S. PATENT DOCUMENTS

| | | | |
|---|---|---|---|
| 10,849,982 B2 * | 12/2020 | Phillips | ............... C07D 221/22 |
| 11,149,007 B2 | 10/2021 | Ammirante et al. | |
| 11,325,889 B2 | 5/2022 | Ammirante et al. | |
| 2016/0214972 A1 | 7/2016 | Jin et al. | |
| 2019/0076542 A1 | 3/2019 | Phillips et al. | |
| 2021/0403453 A1 | 12/2021 | Alexander et al. | |
| 2021/0403454 A1 | 12/2021 | Alexander et al. | |

OTHER PUBLICATIONS

Brinkmann et al., 1999, "Mechanisms of androgen receptor activation and function," The Journal of Steroid Biochemistry and Molecular Biology, 69:307-313.
Chen et al., 2009, "Anti-androgens and androgen-depleting therapies in prostate cancer: new agents for an established target," The Lancet Oncology, 10:981-991.
Gustafson et al., 2015, "Small Molecule Mediated Degradation of the Androgen Receptor Through Hydrophobic Tagging," Angewandte Chemie International Edition in English, 54(33):9659-9662, especially: p. 8, Figure 1A, RU59063.
International Search Report and Written Opinion dated Oct. 14, 2021 for PCT/US2021/038629 (7 pages).
Mills, I G, 2014, "Maintaining and reprogramming genomic androgen receptor activity in prostate cancer," Nature Reviews Cancer. 14:187-198.
Murtha et al., 1993, "Androgen induction of a human prostate specific kallikrein hKLK2: characterization of an androgen response element in the 5' promoter region of the gene," Biochemistry, 32:6459-6464.
Taplin, M, 2007, "Drag insight: role of the androgen receptor in the development and progression of prostate cancer," Nature Clinical Practice Oncology, 236-244.
Tran et al., 2009. "Development of a second-generation antiandrogen for treatment of advanced prostate cancer," Science, 324: 787-790.
Wirth et al., 2007, "Antiandrogens in the treatment of prostate cancer," European Urology, 5 1(2):306-3 13.

* cited by examiner

*Primary Examiner* — Kamal A Saeed
(74) *Attorney, Agent, or Firm* — Jones Day

(57) ABSTRACT

Provided herein are piperidine dione compounds having the following structure:

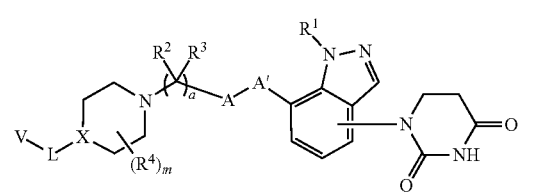

I wherein $R^1$, $R^2$, $R^3$, $R^4$, L, V, X, A, A', a and m are as defined herein, compositions comprising an effective amount of a piperidine dione compound, and methods for treating or preventing an androgen receptor mediated disease.

18 Claims, No Drawings

CEREBLON BINDING COMPOUNDS, COMPOSITIONS THEREOF, AND METHODS OF TREATMENT THEREWITH

RELATED APPLICATIONS

This application claims the benefit of U.S. Provisional Application No. 63/043,650, filed Jun. 24, 2020, the disclosure of which is incorporated herein by reference in its entirety.

FIELD

Provided herein are compounds, compositions comprising an effective amount of such compounds, and methods for treating or preventing androgen receptor mediated diseases, comprising administering an effective amount of such compounds to a subject in need thereof. Also provided herein are the compounds and compositions for use in these methods.

BACKGROUND

Androgen receptor signaling is known to play a crucial role in the pathogenesis of prostate cancer and is involved in the development of other androgen receptor positive cancers (Chen Y et al., *Lancet Oncol*, 2009, 10:981-91; Mills I G, *Nat Rev Cancer*, 2014, 14:187-98; Taplin M E, *Nat Clin Pract Oncol*, 2007, 4:236-44; Wirth M P et al., *Eur Urol*, 2007, 51(2):306-13). The inhibition of androgen receptor signaling with anti-androgens that antagonize the androgen receptor has been used or proposed for the treatment of prostate cancer.

The androgen receptor normally resides in the cytoplasm bound to chaperones such as HSP90 (Brinkmann A O et al., *J Steroid Biochem Mot Blol*, 1999, 69:307-13). Upon binding of dihydrotestosterone (DHT) the androgen receptor changes its conformation and translocates to the nucleus, where it binds androgen responsive elements (AREs) driving the transcription of canonical targets such as KLK3 (also known as prostate specific antigen PSA), TMPRSS2 and KLK2 (Tran C et al., *Science*, 2009, 324:787-90; Murtha P et al., *Biochemistry* (Mosc.), 1993, 32:6459-64).

Prostate cancer (PCa) is one of the most frequently diagnosed non-cutaneous cancers among men in the US and is the second most common cause of cancer deaths with more than 200,000 new cases and over 30,000 deaths each year in the United States.

Androgen-deprivation therapy (ADT) is the standard of treatment for advanced PCa. Patients with advanced PCa undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

There remains a significant need for safe and effective methods of treating, preventing and managing AR mediated diseases, particularly for AR mediated diseases that are refractory to standard treatments, such as surgery, radiation therapy, chemotherapy and hormonal therapy, while reducing or avoiding the toxicities and/or side effects associated with conventional therapies.

Citation or identification of any reference in this section of this application is not to be construed as an admission that the reference is prior art to the present application.

SUMMARY

Provided herein are compounds having the following formula I:

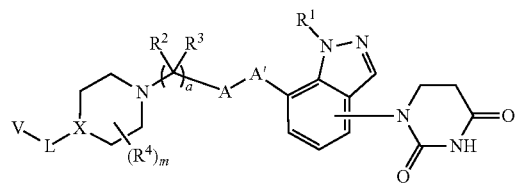

or a pharmaceutically acceptable salt, tautomer, isotopolog, or stereoisomer thereof, wherein $R^1$, $R^2$, $R^3$, $R^4$, L, V, X, a and m are as defined herein.

A compound of formula I or a pharmaceutically acceptable salt, tautomer, isotopolog, or stereoisomer thereof is useful for treating or preventing androgen receptor mediated diseases in a subject.

In one aspect, provided herein are compounds as described in the instant disclosure, such as, for example, in Table 1.

In one aspect, provided herein are pharmaceutical compositions comprising an effective amount of a compound as described herein, and a pharmaceutically acceptable carrier, excipient or vehicle. In one aspect, provided herein are pharmaceutical compositions comprising an effective amount of a compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing androgen receptor mediated diseases in a subject, comprising administering to a subject in need thereof an effective amount of a compound as described herein; and a pharmaceutically acceptable carrier, excipient or vehicle. In one aspect, provided herein are methods for treating or preventing androgen receptor mediated diseases in a subject, comprising administering to a subject in need thereof an effective amount of a compound as described herein; and a pharmaceutically acceptable carrier, excipient or vehicle. In another aspect, provided herein are compounds for use in methods of treatment of androgen receptor mediated diseases. In another aspect, provided herein are compounds for use in methods of treatment of androgen receptor mediated diseases.

In another aspect provided herein are methods for preparing compounds as described herein. In another aspect provided herein are methods for preparing compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, the alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)2. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocyclylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —NH$_2$, —NH(R$^\#$), or —N(R$^\#$)$_2$, wherein each W is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or —N(alkyl)$_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

A "carboxy" group is a radical of the formula: —C(O)OH.

As used herein and unless otherwise specified, an "acyl" group is a radical of the formula: —C(O)(R#) or —C(O)H, wherein R# is defined above. A "formyl" group is a radical of the formula: —C(O)H.

As used herein and unless otherwise specified, an "amido" group is a radical of the formula: —C(O)—NH$_2$, —C(O)—NH(R#), —C(O)—N(R#)$_2$, —NH—C(O)H, —NH—C(O)—(R#), —N(R#)—C(O)H, or —N(R#)—C(O)—(R#), wherein each W is independently defined above.

In one embodiment, an "amido" group is an "aminocarbonyl" group, which is a radical of the formula: —C(O)—NH$_2$, —C(O)—NH(R#), —C(O)—N(R#)$_2$, wherein each R# is independently defined above.

In one embodiment, an "amido" group is an "acylamino" group, which is a radical of the formula: —NH—C(O)H, —NH—C(O)—(R#), —N(R#)—C(O)H, or —N(R#)—C(O)—(R#), wherein each R# is independently defined above.

A "sulfonylamino" group is a radical of the formula: —NHSO$_2$(R#) or —N(alkyl)SO$_2$(R#), wherein each alkyl and R# are defined above.

A "urea" group is a radical of the formula: —N(alkyl)C(O)N(R#)$_2$, —N(alkyl)C(O)NH(R#), —N(alkyl)C(O)NH$_2$, —NHC(O)N(R#)$_2$, —NHC(O)NH(R#), or —NH(CO)NH$_2$, wherein each alkyl and R# are independently as defined above.

When the groups described herein, with the exception of alkyl group, are said to be "substituted," they may be substituted with any appropriate substituent or substituents.

Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula I include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride formic, and mesylate salts. Others are well known in the art, see for example, *Remington's Pharmaceutical Sciences,* 18th eds., Mack Publishing, Easton Pa. (1990) or *Remington: The Science and Practice of Pharmacy,* 19$^{th}$ eds., Mack Publishing, Easton Pa. (1995).

As used herein and unless otherwise indicated, the term "stereoisomer" or "stereoisomerically pure" means one stereoisomer of a compound provided herein that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments disclosed herein, including mixtures thereof.

The use of stereoisomerically pure forms of such compounds, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It should also be noted the compounds can include E and Z isomers, or a mixture thereof, and cis and trans isomers or a mixture thereof. In certain embodiments, the compounds are isolated as either the E or Z isomer. In other embodiments, the compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

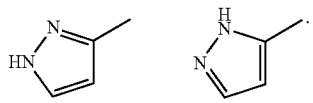

As readily understood by one skilled in the art, a wide variety of functional groups and other structures may exhibit tautomerism and all tautomers of compounds of formula I are within the scope of the present invention.

It should also be noted the compounds provided herein can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, and/or nitrogen-15 enriched compounds. As used herein, "deuterated", means a compound wherein at least one hydrogen (H) has been replaced by deuterium (indicated by D or $^2$H), that is, the compound is enriched in deuterium in at least one position.

It is understood that, independently of stereoisomerical or isotopic composition, each compound referred to herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is an androgen receptor mediated disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is an androgen receptor mediated disease, as described herein, or symptoms thereof.

The term "effective amount" in connection with a compound means an amount capable of treating or preventing a disorder, disease or condition, or symptoms thereof, disclosed herein.

The terms "subject" and "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an androgen receptor mediated disease, or a symptom thereof.

The term "androgen receptor" or "AR" or "NR3C4" as used herein refers to a nuclear hormone receptor activated by binding of the androgenic hormones, including testosterone or dihydrotestosterone. The term "androgen receptor" may refer to the nucleotide sequence or protein sequence of human androgen receptor (e.g., Entrez 367, Uniprot P10275, RefSeq NM_000044, or RefSeq NP_000035).

The term "AR-full length" (AR-FL) as used herein refers to AR protein that contains all four functional domains, including the N-terminal transactivation domain (NTD, exon 1), the DNA-binding domain (DBD, exons 2-3), the hinge domain (exon 4), and the C-terminal ligand binding domain (LBD, exons 4-8).

The term "castration resistant prostate cancer" (CRPC) refers to advanced prostate cancer that is worsening or progressing while the patient remains on androgen deprivation therapy or other therapies to reduce testosterone, or prostate cancer which is considered hormone refractory, hormone naive, androgen independent or chemical or surgical castration resistant. Castration resistant prostate cancer (CRPC) is an advanced prostate cancer that developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq®, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

COMPOUNDS

In certain embodiments, provided herein are compounds of formula I

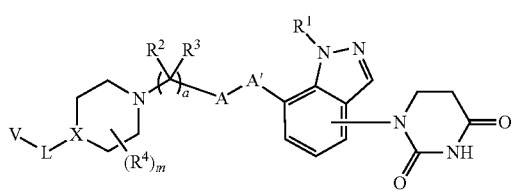

I or pharmaceutically acceptable salts, tautomers, isotopologs, or stereoisomers thereof, wherein $R^1$ is $C_{1-3}$ alkyl;

A is $CH_2$ or C=O;

A' is NH or O;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

L is substituted or unsubstituted —O($C_{1-6}$ alkyl)-, —($C_{1-6}$ alkyl)O—, —O($C_{1-6}$ alkyl)O— or —($C_{1-9}$ alkyl)-;

X is N or $CR^X$;

$R^X$ is hydrogen, halogen, —O($C_{1-6}$ alkyl) or —($C_{1-9}$ alkyl);

V is

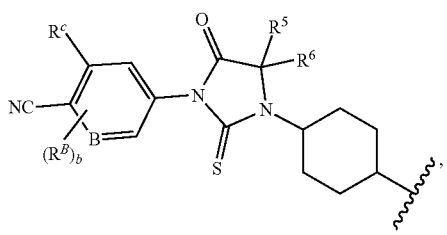

wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

In certain embodiments, provided herein are compounds of formula I

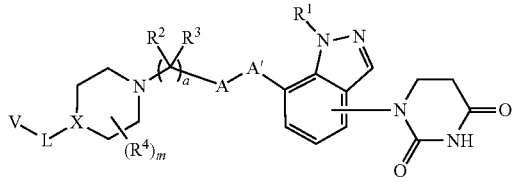

I or pharmaceutically acceptable salts, tautomers, isotopologs, or stereoisomers thereof, wherein $R^1$ is $C_{1-3}$ alkyl;

A is $CH_2$ or C=O;

A' is NH or O;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

L is substituted or unsubstituted —O($C_{1-6}$ alkyl)-, —($C_{1-6}$ alkyl)O— or —($C_{1-9}$ alkyl)-;

X is N or $CR^X$;

$R^X$ is hydrogen, halogen, —O($C_{1-6}$ alkyl) or —($C_{1-9}$ alkyl);

V is

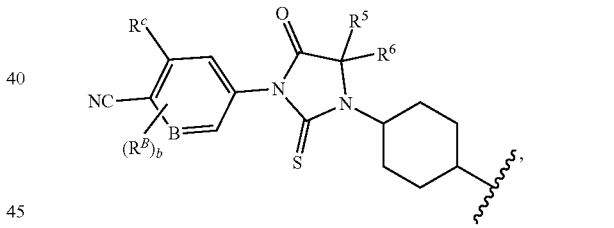

wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

In some embodiments of compounds of formula I, $R^1$ is methyl. In some embodiments of compounds of formula I, a is 1, and $R^2$ and $R^3$ are both H. In some embodiments of compounds of formula I, a is 2, and $R^2$ and $R^3$ are both H. In some embodiments of compounds of formula I, each $R^4$ is substituted or unsubstituted methyl. In some embodiments of compounds of formula I, each $R^4$ is independently selected from methyl and $CF_3$.

In some embodiments of compounds of formula I, A is C=O. In some embodiments of compounds of formula I, A is $CH_2$.

In some embodiments of compounds of formula I, A' is NH. In some embodiments of compounds of formula I, A' or O.

In some embodiments of compounds of formula I, m is 0, 1, 2, 3 or 4. In some embodiments of compounds of formula I, m is 1 or 2.

In some embodiments of compounds of formula I, X is N. In some embodiments of compounds of formula I, X is $CR^X$; and $R^X$ is hydrogen, halogen, —O($C_{1-6}$ alkyl) or —($C_{1-9}$ alkyl). In some embodiments of compounds of formula I, X is CH.

In some embodiments of compounds of formula I, L is substituted or unsubstituted —O($CH_2$)$_p$—, —($C_{1-6}$ alkyl)O—, —O($C_{1-6}$ alkyl)O— or —($CH_2$)$_p$—, and p is 1-4.

In some embodiments of compounds of formula I, L is substituted or unsubstituted —O($CH_2$)$_p$—, and p is 2 or 3.

In some embodiments of compounds of formula I, L is substituted or unsubstituted —O($CH_2$)$_p$O—, and p is 2 or 3.

In some embodiments of compounds of formula I, L is substituted or unsubstituted —($CH_2$)$_p$—, and p is 3 or 4.

In some embodiments of compounds of formula I, L is —O($CH_2$)($CH_2$)—, —O($CH_2$)($CH_2$)($CH_2$)—, —O($CH_2$)($CH_2$)—, —($CH_2$)($CH_2$)—, —($CH_2$)($CH_2$)($CH_2$)—, or —($CH_2$)($CH_2$)($CH_2$)($CH_2$)—.

In some embodiments of compounds of formula I, L is —O($CH_2$)($CH_2$)—, —O($CH_2$)($CH_2$)($CH_2$)—, —($CH_2$)($CH_2$)—, —($CH_2$)($CH_2$)($CH_2$)—, or —($CH_2$)($CH_2$)($CH_2$)—. In some embodiments of compounds of formula I, L is —O($CH_2$)($CH_2$)—, —O($CH_2$)($CH_2$)O— or —($CH_2$)($CH_2$)($CH_2$)—. In some embodiments of compounds of formula I, L is —O($CH_2$)($CH_2$)— or —($CH_2$)($CH_2$)($CH_2$)—.

In some embodiments of compounds of formula I, B is CH. In some embodiments of compounds of formula I, B is N.

In some embodiments of compounds of formula I, b is 0. In some embodiments of compounds of formula I, $R^C$ is $CF_3$, Cl or $SF_5$. In some embodiments of compounds of formula I, $R^C$ is $CF_3$. In some embodiments of compounds of formula I, $R^5$ and $R^6$ are methyl.

In some embodiments of compounds of formula I, the compound is

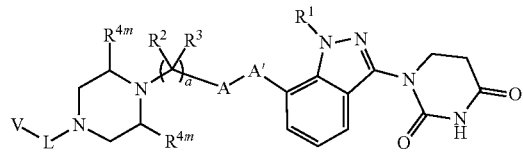

II or a pharmaceutically acceptable salt, tautopolog, or stereoisomer thereof,
where the variables are as described elsewhere herein.

In some embodiments of compounds of formula I, the compound is

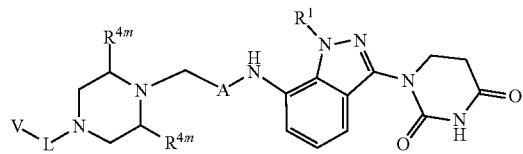

III or a pharmaceutically acceptable salt, tautomer, isotopolog, or stereoisomer thereof, wherein $R^1$ is methyl;

A is $CH_2$ or C=O;

each $R^{4m}$ is independently hydrogen or substituted or unsubstituted methyl, wherein the substituents, when present are selected from 1 to 5 halo;

L is substituted or unsubstituted —O($C_{1-3}$ alkyl)-, —O($C_{1-3}$ alkyl)O— or —($C_{1-4}$ alkyl)-;

V is

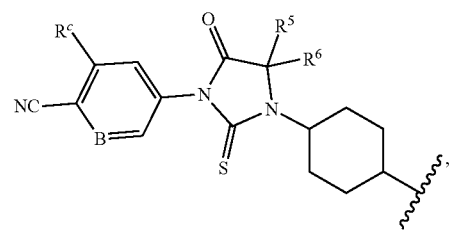

B is N or CH;

$R^C$ is halogen, $CF_3$ or $SF_5$; and $R^5$ and $R^6$ are $C_{1-3}$ alkyl.

In some embodiments of compounds of formula I, the compound is

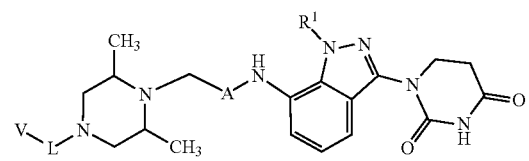

IV or a pharmaceutically acceptable salt, tautomer, isotopolog, or stereoisomer thereof, wherein $R^1$ is methyl;

A is $CH_2$ or C=O;

L is substituted or unsubstituted —O($C_{1-3}$ alkyl)-, —O($C_{1-3}$ alkyl)O— or —($C_{1-4}$ alkyl)-;

V is

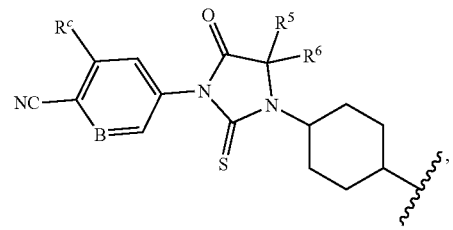

B is N or CH;

$R^C$ is halogen, $CF_3$ or $SF_5$; and $R^5$ and $R^6$ are $C_{1-3}$ alkyl.

In some embodiments of compounds of formula I, the compound is

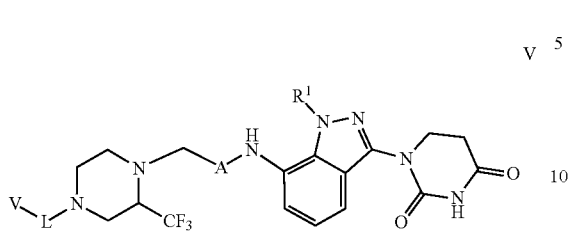

V or a pharmaceutically acceptable salt, tautomer, isotopolog, or stereoisomer thereof, wherein $R^1$ is methyl;

A is $CH_2$ or C=O;

L is substituted or unsubstituted —O($C_{1-3}$ alkyl)-, —O($C_{1-3}$ alkyl)O— or —($C_{1-4}$ alkyl)-;

V is

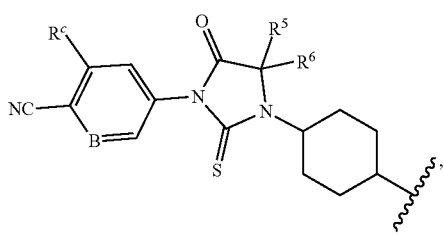

B is N or CH;

$R^C$ is halogen, $CF_3$ or $SF_5$; and $R^5$ and $R^6$ are $C_{1-3}$ alkyl.

In some embodiments of compounds of formula I, the compound is

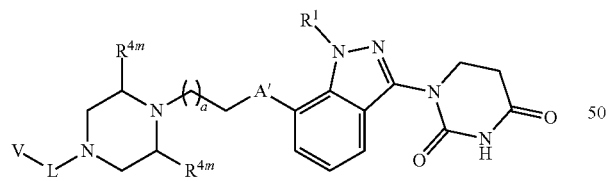

VI or a pharmaceutically acceptable salt, tautomer, isotopolog, or stereoisomer thereof, wherein $R^1$ is methyl;

A' is NH or O;

a is 1 or 2;

each $R^{4m}$ is independently hydrogen or substituted or unsubstituted methyl, wherein the substituents, when present are selected from 1 to 5 halo;

L is substituted or unsubstituted —O($C_{1-3}$ alkyl)-, —O($C_{1-3}$ alkyl)O— or —($C_{1-4}$ alkyl)-;

V is

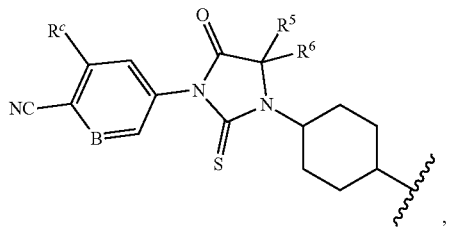

B is N or CH;

$R^C$ is halogen, $CF_3$ or $SF_5$; and $R^5$ and $R^6$ are $C_{1-3}$ alkyl.

In some embodiments of compounds of formula I, the compound is

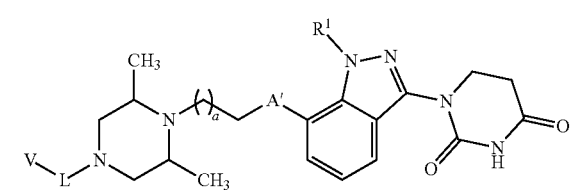

VII or a pharmaceutically acceptable salt, tautomer, isotopolog, or stereoisomer thereof, wherein $R^1$ is methyl;

A' is NH or O;

a is 1 or 2;

L is substituted or unsubstituted —O($C_{1-3}$ alkyl)-, —O($C_{1-3}$ alkyl)O— or —($C_{1-4}$ alkyl)-;

V is

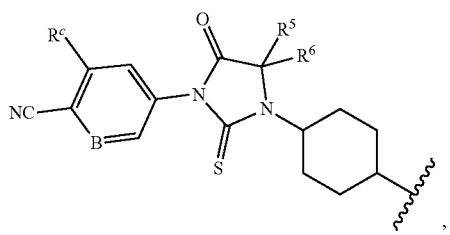

B is N or CH;

$R^C$ is halogen, $CF_3$ or $SF_5$; and $R^5$ and $R^6$ are $C_{1-3}$ alkyl.

In some embodiments of compounds of formula I, the compound is

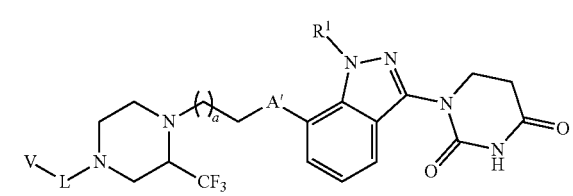

VIII or a pharmaceutically acceptable salt, tautomer, isotopolog, or stereoisomer thereof, wherein $R^1$ is methyl;
A is $CH_2$ or C=O;
a is 1 or 2;
L is substituted or unsubstituted —O($C_{1-3}$ alkyl)-, —O($C_{1-3}$ alkyl)O— or —($C_{1-4}$ alkyl)-;
V is

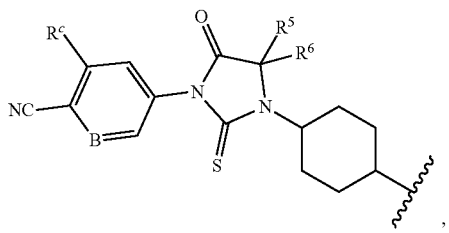

B is N or CH;
$R^C$ is halogen, $CF_3$ or $SF_5$; and
$R^5$ and $R^6$ are $C_{1-3}$ alkyl.

In certain embodiments of compounds of formula I, II, III, IV and V, A is C=O.

In certain embodiments of compounds of formula I, II, III, IV and V, A is $CH_2$.

In certain embodiments of compounds of formula VI, VII and VIII, A' is O. In certain embodiments of formula VI, VII and VIII, A' is NH.

In some embodiments of compounds of formula I, II, III, IV, V, VI, VII and VIII, $R^1$ is methyl; X is N or $CR^X$, $R^X$ is hydrogen, halogen, —O($C_{1-6}$ alkyl) or —($C_{1-9}$ alkyl); L is substituted or unsubstituted —O($CH_2$)$_p$—, —O($CH_2$)$_p$O— or —($CH_2$)$_p$—, p is 1-4; B is CH or N; b is 0; $R^C$ is $CF_3$, Cl or $SF_5$; $R^{C'}$ is $CF_3$; and $R^5$ and $R^6$ are methyl.

In some embodiments of compounds of formula I, II, III, IV, V, VI, VII and VIII, $R^1$ is methyl; X is N or $CR^X$, $R^X$ is hydrogen, halogen, —O($C_{1-6}$ alkyl) or —($C_{1-9}$ alkyl); L is substituted or unsubstituted —O($CH_2$)$_p$— or —($CH_2$)$_p$—, p is 1-4; B is CH or N; b is 0; $R^C$ is $CF_3$, Cl or $SF_5$; $R^{C'}$ is $CF_3$; and $R^5$ and $R^6$ are methyl.

In some embodiments of compounds of formula I, II, III, IV, V, VI, VII and VIII, L is —O($CH_2$)($CH_2$)—, —O($CH_2$)($CH_2$)($CH_2$)—, —O($CH_2$)($CH_2$)O—, —($CH_2$)($CH_2$)—, —($CH_2$)($CH_2$)($CH_2$)—, or —($CH_2$)($CH_2$)($CH_2$)($CH_2$)—.

In some embodiments of compounds of formula I, II, III, IV, V, VI, VII and VIII, L is —O($CH_2$)($CH_2$)—, —O($CH_2$)($CH_2$)($CH_2$)—, —($CH_2$)($CH_2$)—, —($CH_2$)($CH_2$)($CH_2$)—, or —($CH_2$)($CH_2$)($CH_2$)($CH_2$)—.

Further embodiments provided herein include any combination of one or more of the particular embodiments set forth above.

In some embodiments of compounds of formula I, the compound is a compound from Table 1.

The compounds set forth in Table 1 were tested in the AR mediated assays described herein and were found to have activity therein. In one embodiment, the compounds described herein, at a concentration of 1 µM, leads to degradation of AR protein, by at least about 50% or more.

METHODS FOR MAKING PIPERIDINE DIONE COMPOUNDS

The compounds described herein can be made using conventional organic syntheses and commercially available starting materials, or the methods provided herein. By way of example and not limitation, compounds of formula I, wherein $R^1$, $R^2$, $R^3$, $R^4$, $R^5$, $R^6$, $R^B$, $R^C$, L, V, X, m, a and b are as defined herein, can be prepared as outlined in the schemes shown below, as well as in the examples set forth herein. It should be noted that one skilled in the art would know how to modify the procedures set forth in the illustrative schemes and examples to arrive at the desired products.

Scheme 1

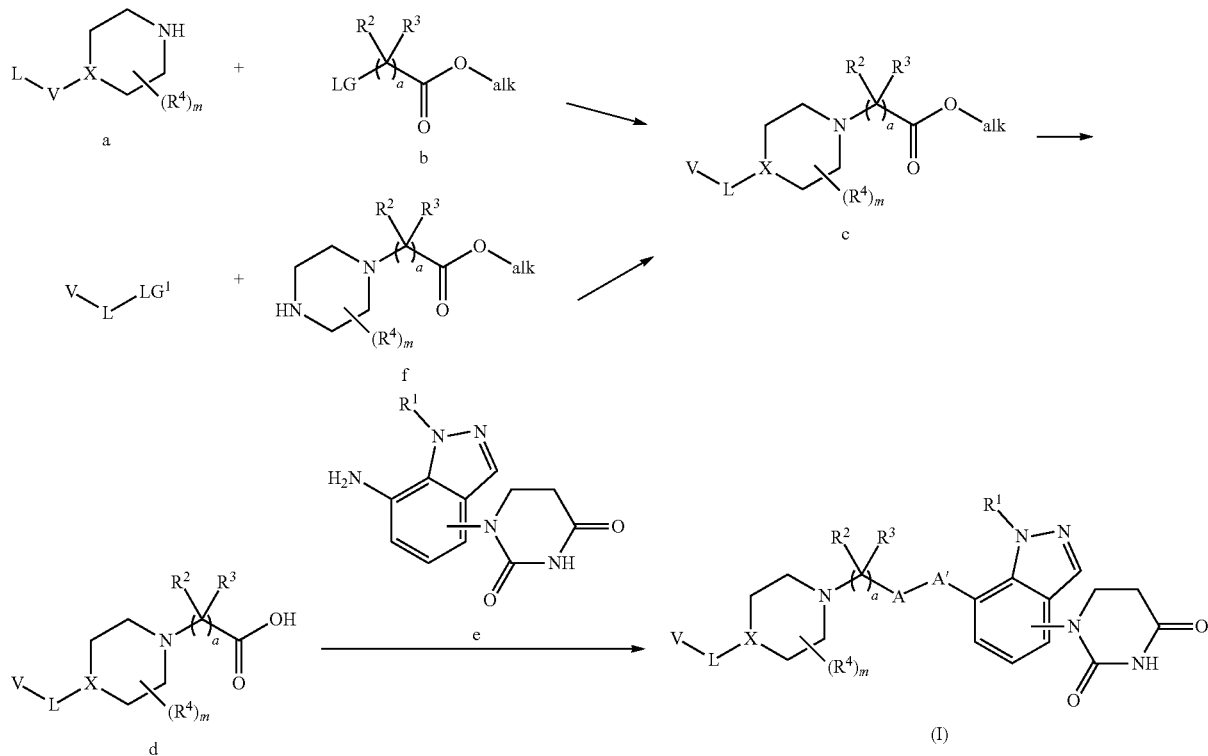

As shown in Scheme 1, compounds of formula (I), wherein X is N or $CR^X$, L is —O($C_{1-3}$ alkyl)-, —($C_{1-3}$ alkyl)O—, or —($C_{1-4}$ alkyl)-, A is CO, and A' is NH can be prepared starting by reacting the piperidine derivative a with ester intermediate b (where LG is a leaving group such as Cl, Br, I triflate or alkyl sulfonate, and alk is an alkyl group such as Me, Et, Bn, or tert-Bu) in the presence of a base, in a solvent (for example, N,N-diisopropylethylamine in DMF, or $K_2CO_3$ in acetonitrile) at elevated temperature (for example, between about 40° C. and about 100° C.) to provide intermediate c. In some cases, an iodide salt is used to facilitate this transformation (such as sodium iodide or potassium iodide). Removal of the ester protecting group from intermediate c (for example when alk=Me, Et or other alkyl, by treatment with a hydroxide base in a solvent, for example LiOH in THF and water, or when alk=tert-butyl, by treatment with an acid in a solvent such as trifluoroacetic acid in dichloromethane or hydrochloric acid in 1,4-dioxane), provides intermediate d. Coupling of intermediate d with a piperidine dione intermediate e in the presence of a coupling agent (for example HATU, HBTU, or EDC or TCFH, optionally in combination with HOBt), and a base (for example N,N-diisopropylethylamine, triethylamine, or N-methylimidazole), in a solvent, for example, DCM, DMF, NMP or mixtures thereof) at a temperature between 0° C. to about 70° C. provides compounds of formula (I), wherein X is N or $CR^X$, L is —O($C_{1-3}$ alkyl)-, —($C_{1-3}$ alkyl)O—, or —($C_{1-4}$ alkyl)-, A is CO, and A' is NH. Alternatively, intermediate c wherein X is N and L is —O($C_{1-3}$ alkyl)- or —($C_{1-4}$ alkyl)-, can be prepared starting by reacting the derivative V-L-LG (LG is an appropriate leaving group such as Cl, Br, I, triflate or alkyl sulfonate) with an appropriately derivatized piperidyl ester derivative f (for example, wherein alk is an alkyl group such as Me, Et, Bn, or tert-Bu) in the presence of a base, in a solvent (for example, N,N-diisopropylethylamine in DMF, or $K_2CO_3$ in acetonitrile), at elevated temperature (for example, between about 40° C. and about 80° C.) to provide intermediate c. Which can be further reacted to provide compounds of formula (I) wherein X is N and L is —O($C_{1-3}$ alkyl)- or —($C_{1-4}$ alkyl)-, A is CO, and A' is NH.

Compounds of formula (I) wherein X is N and L is —O($C_{1-3}$ alkyl)- or —($C_{1-4}$ alkyl)-, can also be prepared according to an alternative sequence shown in Scheme 2 by reacting the derivative V-L-LG (LG is an appropriate leaving group such as Cl, Br, I, triflate or alkyl sulfonate) with an appropriately derivatized intermediate g in the presence of a base, in a solvent (for example, N,N-diisopropylethylamine in DMF, or $K_2CO_3$ in acetonitrile) at elevated temperature (for example, between about 40° C. and about 100° C.). In some cases, an iodide salt is used to facilitate this transformation (such as sodium iodide or potassium iodide). Alternatively, compounds of formula (I) wherein X is N or $CR^X$ and L is —O($C_{1-3}$ alkyl)-, —($C_{1-3}$ alkyl)O—, or —($C_{1-4}$ alkyl)-, A is CO, and A' is NH can be prepared starting by reacting compound e with an appropriately functionalized carbonyl intermediate h (where LG is a leaving group such as Cl, Br, I triflate or alkyl sulfonate) in the presence of a base, in a solvent (for example, N,N-diisopropylethylamine in DCM, or triethylamine in pyridine) at a temperature between 0° C. to about 60° C. to provide intermediate i. Reacting i (where LG is a leaving group such as Cl, Br, I triflate or alkyl sulfonate) with amine intermediate a in the presence of a base, in a solvent (for example, N,N-diisopropylethylamine in DMF, or $K_2CO_3$ in acetonitrile), at elevated temperature (for example, between about 40° C. and about 80° C.) provides compound of formula (I) wherein X is N or $CR^X$ and L is —O($C_{1-3}$ alkyl)-, —($C_{1-3}$ alkyl)O—, or —($C_{1-4}$ alkyl)-, A is CO, and A' is NH.

Scheme 3

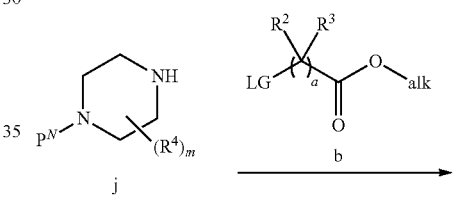

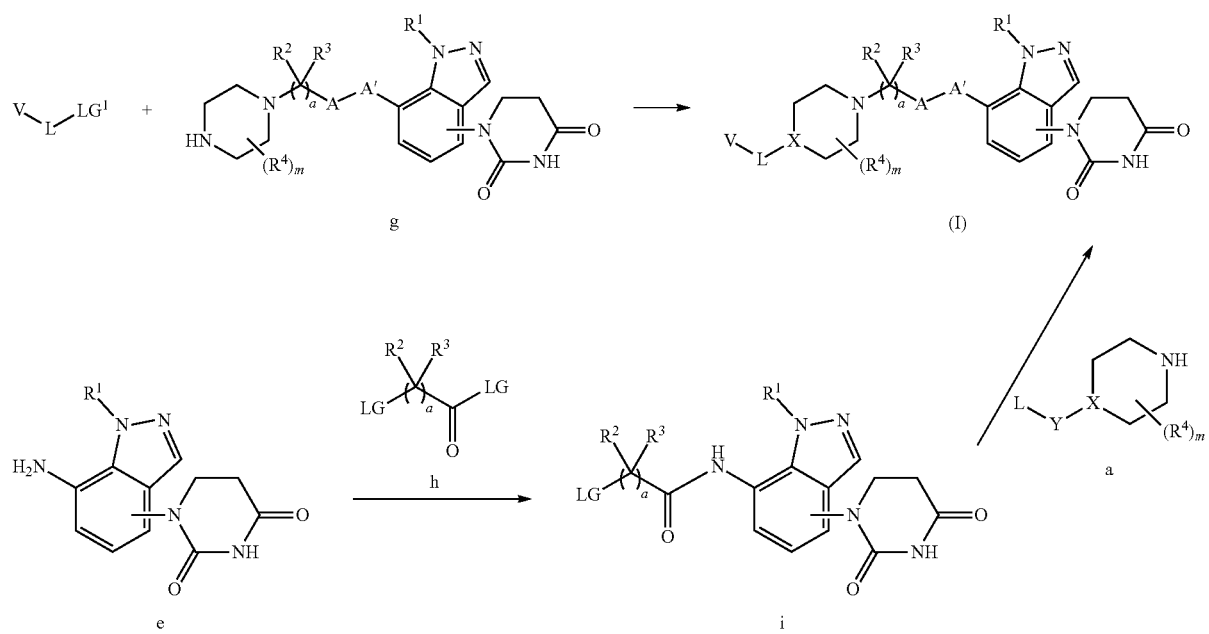

Scheme 2

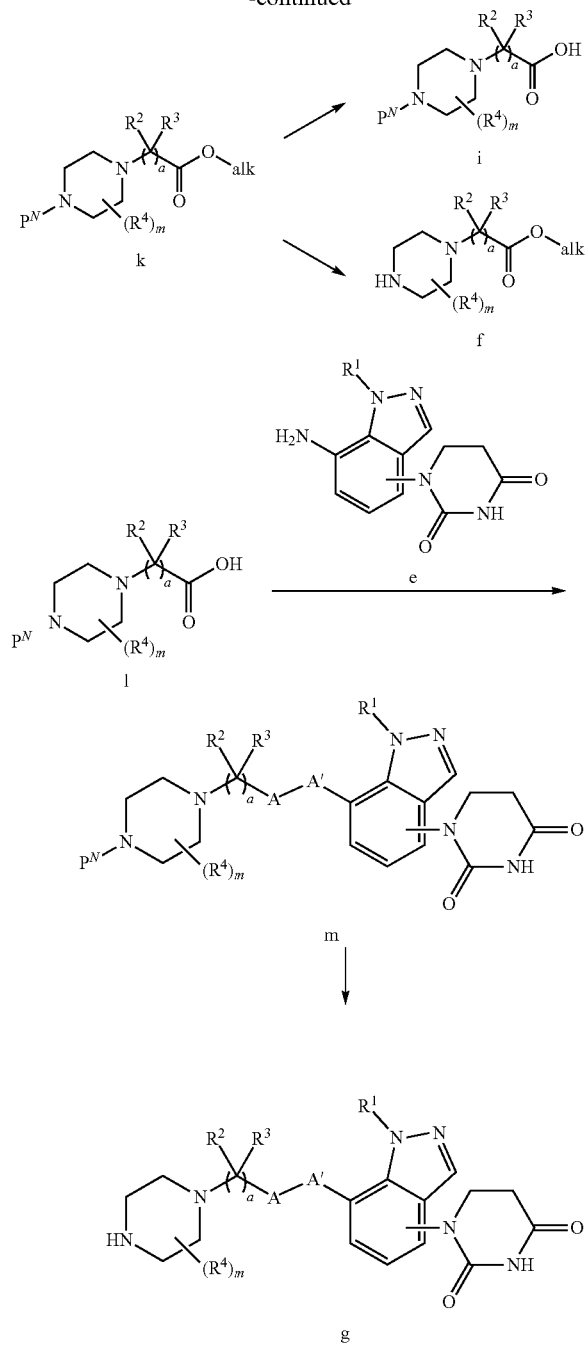

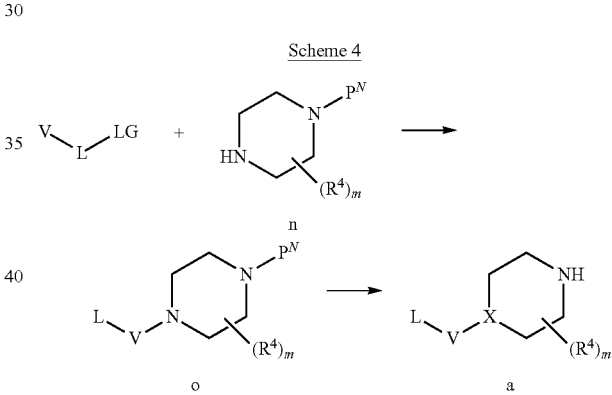

potassium iodide). Removal of the ester protecting group from intermediate k (for example when alk=Me, Et or other alkyl, by treatment with a hydroxide base in a solvent, for example LiOH in THF and water, or when alk=tert-butyl, by treatment with an acid in a solvent such as trifluoroacetic acid in dichloromethane or hydrochloric acid in 1,4-dioxane), provides intermediate l. Coupling of intermediate l with a piperidine dione intermediate e in the presence of a coupling agent (for example HATU, HBTU, or EDC or TCFH, optionally in combination with HOBt), and a base (for example N,N-diisopropylethylamine, triethylamine, or N-methylimidazole), in a solvent, for example, DCM, DMF, NMP or mixtures thereof) at a temperature between 0° C. to about 70° C. provides amine intermediate g, which can be further reacted to provide compounds of formula (I) wherein L is —O($C_{1-3}$ alkyl)-, —($C_{1-3}$ alkyl)O—, or —($C_{1-4}$ alkyl)-, A is CO, and A' is NH. Intermediates such as amine f can be prepared by removal of the N-protecting group $P^N$ from intermediate k, (for example, when $P^N$ is Boc, by treatment with an acid in a solvent, for example, HCl in dioxane or EtOAc, at room temperature, or with TFA in DCM, at room temperature or when $P^N$ is Bn or Cbz by hydrogenation with a metal catalyst, in a solvent such as palladium on carbon in methanol).

Scheme 4

Intermediates such as amine g, wherein L is —O($C_{1-3}$ alkyl)-, —($C_{1-3}$ alkyl)O—, or —($C_{1-4}$ alkyl)-, A is CO, and A' is NH, can be prepared according to Scheme 3. Starting by reacting an appropriately functionalized piperazine j with ester intermediate b (where LG is a leaving group such as Cl, Br, I triflate or alkyl sulfonate, and alk is an alkyl group such as Me, Et, Bn, or tert-Bu) in the presence of a base, in a solvent (for example, N,N-diisopropylethylamine in DMF, or $K_2CO_3$ in acetonitrile) at elevated temperature (for example, between about 40° C. and about 100° C.) to provide intermediate k. In some cases, an iodide salt is used to facilitate this transformation (such as sodium iodide or potassium iodide).

Intermediates such as a wherein X is N and L is —O($C_{1-3}$ alkyl)- or —($C_{1-4}$ alkyl)- can be prepared according to Scheme 4. Treating V-L-LG (where L is —O($C_{1-3}$ alkyl)- or —($C_{1-4}$ alkyl)- and LG is a leaving group such as Cl, Br, I triflate or alkyl sulfonate) with amine n in the presence of a base, in a solvent (for example, N,N-diisopropylethylamine in DMF, or $K_2CO_3$ in acetonitrile) at elevated temperature (for example, between about 40° C. and about 100° C.) to provide intermediate o. In some cases, an iodide salt is used to facilitate this transformation (such as sodium iodide or potassium iodide). Removal of the N-protecting group $P^N$ from intermediate o, (for example, when $P^N$ is Boc, by treatment with an acid in a solvent, for example, HCl in dioxane or EtOAc, at room temperature, or with TFA in DCM, at room temperature or when $P^N$ is Bn or Cbz by hydrogenation with a metal catalyst, in a solvent such as palladium on carbon in methanol) provides intermediate a wherein X is N and L is —O($C_{1-3}$ alkyl)- or —($C_{1-4}$ alkyl)-.

Scheme 5

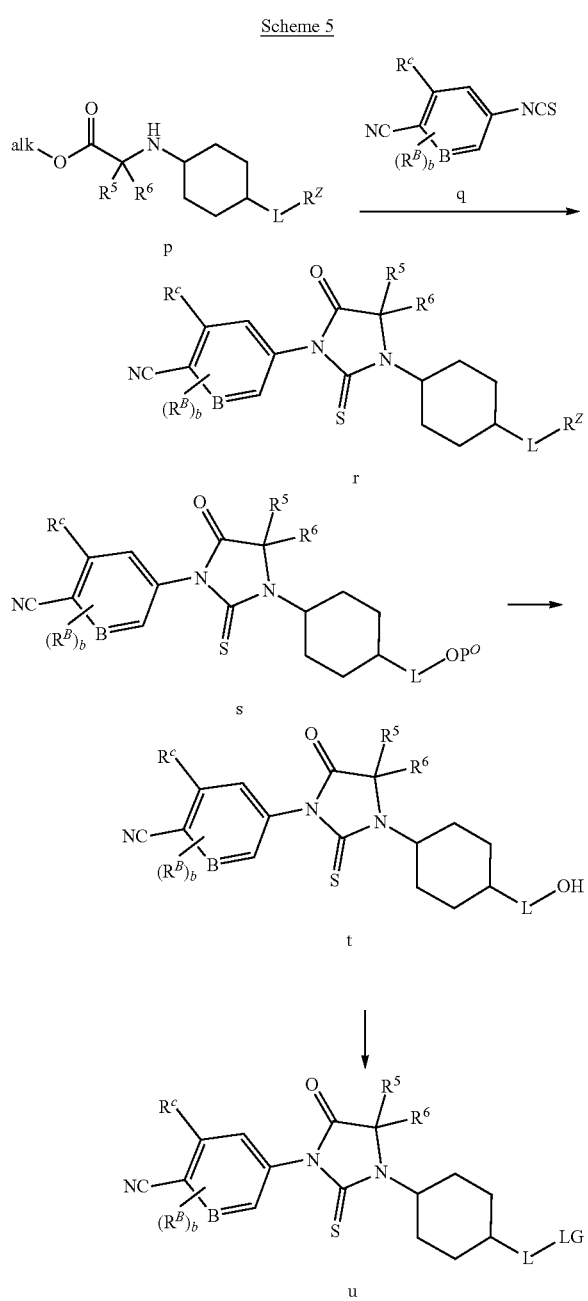

Scheme 6

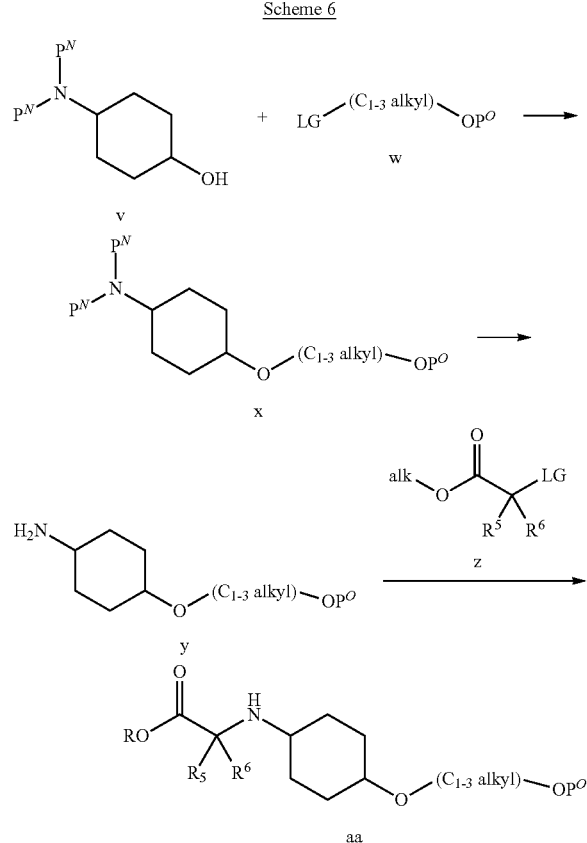

Intermediates such as V-L-$R^Z$ (for example, intermediate r) where $R^Z$ is an alcohol, protected alcohol, leaving group or heterocycle (such as a substituted piperidine or piperazine) can be prepared according to Scheme 5. Treatment of ester intermediate p (where alk is an alkyl group such as Me, Et, Bn, or tert-Bu) with an appropriately derivatized 4-isothiocyanatobenzonitrile or 5-isothiocyanatopicolinonitrile q, in the presence of a base, such as triethylamine, in a solvent, such as EtOAc, at elevated temperature, for example, between about 70° C. and about 90° C. provides intermediate r. Intermediates such as u wherein LG is a leaving group (such as Cl, Br, I triflate or alkyl sulfonate), and L is —O($C_{1-3}$ alkyl)- or —($C_{1-4}$ alkyl)- can be prepared from intermediate s (where P° is an alcohol protecting group such as THP, TBS, acetate or benzyl). Removal of the protecting group P° (for example, when P° is THP by treatment with catalytic acid in a solvent, for example HCl in dioxane) in s provides alcohol intermediate t. Activation of the alcohol functional group in t to a leaving group (for example when LG is Br by treatment of t with thionyl bromide in dichloromethane) provides intermediate u wherein LG is a leaving group (such as Cl, Br, I triflate or alkyl sulfonate), and L is —O($C_{1-3}$ alkyl)- or —($C_{1-4}$ alkyl)-, which can be further reacted to provide compounds of formula (I).

Intermediates p, wherein L is —O($C_{1-3}$ alkyl)- and $R^Z$ is a protected alcohol $OP^O$ (for example a THP ether or TBS ether), for example aa, can be prepared according to Scheme 6. Starting from alcohol intermediate v (where $P^N$ is an amine protecting group such as Bn or Boc), reacting with electrophile w (where LG is a leaving group such as Cl, Br, I triflate or alkyl sulfonate, and P° is an oxygen protecting group such as THP or TBS) in the presence of a base, optionally with a catalyst, in a solvent (for example KOH and tetrabutylammonium bromide in xylene) at elevated temperature, for example between 70° C. and 130° C. provides intermediate x. Removal of the protecting group $P^N$ in x (for example, when $P^N$ is Bn by hydrogenation with palladium on carbon in methanol, or when $P^N$ is Boc by treatment with HCL in dioxane) provides amine intermediate y. Reacting amine y with ester z (where alk is an alkyl group such as Me, Et, Bn, or tert-Bu, and LG is a leaving group such as Cl, Br, I triflate or alkyl sulfonate) in the presence of a base, possibly with an iodide salt, in a solvent (for example, potassium carbonate and potassium iodide in acetonitrile), at an elevated temperature (for example between about 70° C. and 130° C.) provides intermediate aa, which can be further reacted to provide compounds of formula (I) where in L=—O($C_{1-3}$ alkyl)-.

Scheme 7

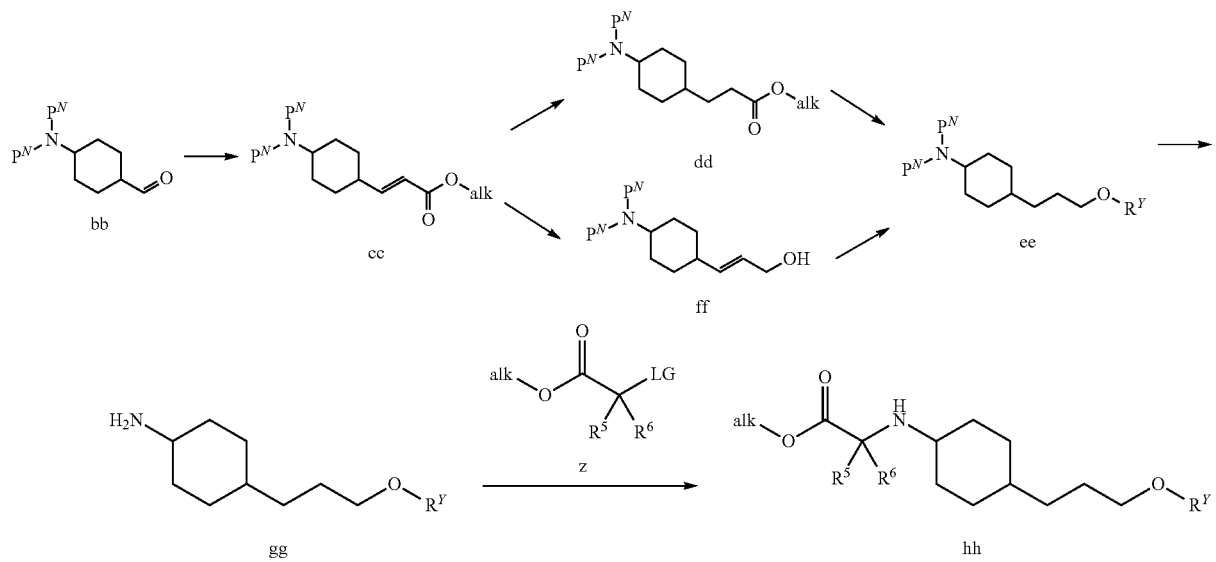

Intermediates p, wherein L is —(C$_{1-3}$ alkyl)- and R$^Z$ is an alcohol or a protected alcohol (for example a THP ether or TBS ether), for example hh, can be prepared according to Scheme 6. Starting from aldehyde intermediate bb (where P$^N$ is an amine protecting group such as Bn or Boc), reacting with an olefination reagent, in the presence of a base, in a solvent (for example, ethyl 2-(diethoxyphosphoryl)acetate and sodium hydride in THF) at a temperature between 0° C. and 60° C. provides olefin intermediate cc. Reduction of cc by hydrogenation, in the presence of a catalyst, in a solvent (for example, palladium on carbon in methanol under a hydrogen atmosphere), at elevated pressure (for example between 10 and 100 psi) provides intermediate dd. Reduction of the ester functional group can be accomplished by treatment with a reducing agent, in a solvent (for example, diisobutylaluminum hydride in DCM) at a temperature between −78° C. and 25° C. provides intermediate ee, wherein R$^Y$ is H. Alternatively, intermediate ee can be prepared by treatment of intermediate cc with a reducing agent, in a solvent (for example, diisobutylaluminum hydride in DCM) at a temperature between −78° C. and 25° C. to provide intermediate ff. Hydrogenation of ff, in the presence of a catalyst, in a solvent (for example, palladium on carbon, in methanol, under a hydrogen atmosphere), at elevated pressure (for example between 10 and 100 psi) provides intermediate ee. Removal of the protecting group P$^N$ in ee (for example, when P$^N$ is Bn, by hydrogenation with palladium on carbon in methanol, or when P$^N$ is Boc by treatment with HCL in dioxane) provides amine intermediate gg. Reacting amine gg with ester z (where alk is an alkyl group such as Me, Et, Bn, or tert-Bu, and LG is a leaving group such as Cl, Br, I triflate or alkyl sulfonate) in the presence of a base, optionally with an iodide salt, in a solvent (for example, potassium carbonate and potassium iodide in acetonitrile), at an elevated temperature (for example between about 70° C. and 130° C.) provides intermediate hh, where R$^Y$ is H or an alcohol protecting group (for example THP, TBS or Tr) which can be further reacted to provide compounds of formula (I) where in L —(C$_{1-3}$ alkyl)-.

Scheme 8

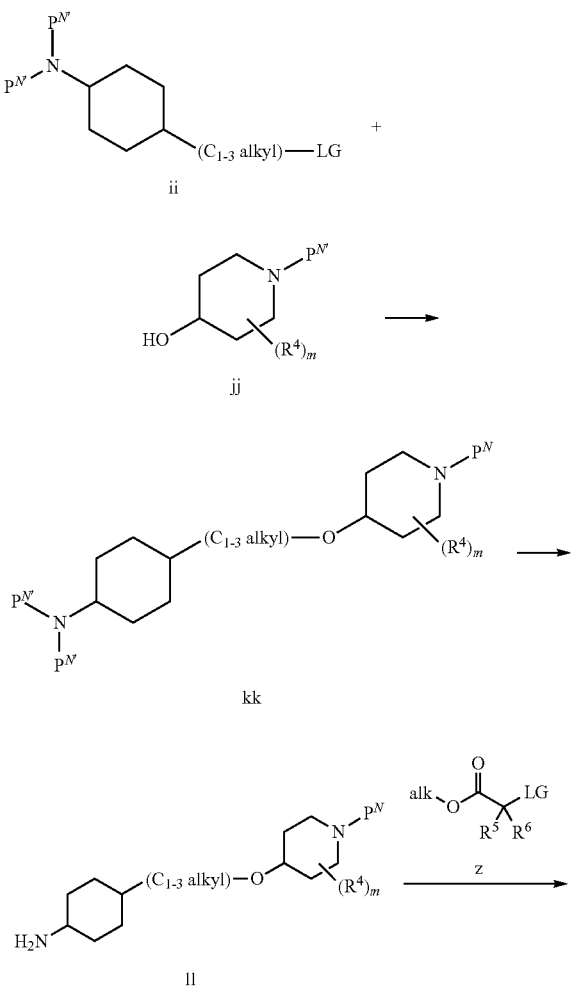

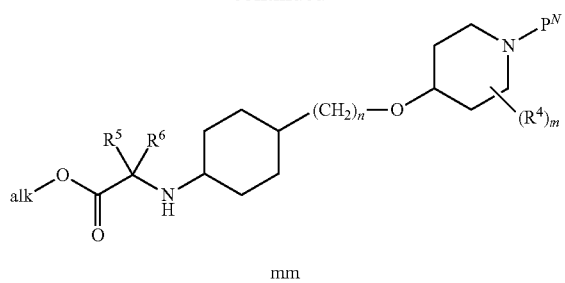

mm

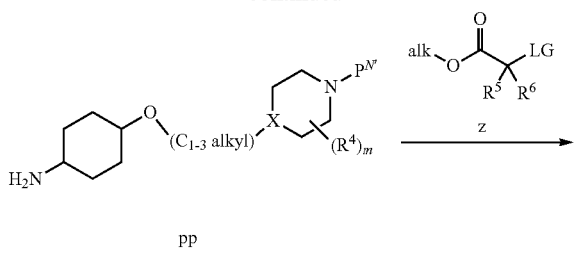

pp

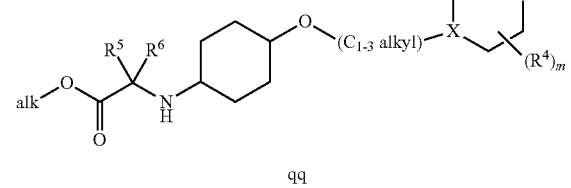

qq

Intermediates p wherein L is —(C$_{1-3}$ alkyl)O— and R$^Z$ is a heterocycle or cycloalkyl group, for example mm, can be prepared according to Scheme 8. Starting from intermediate ii (where P$^{N'}$ is an amine protecting group for example Bn or Boc), and LG is a leaving group, for example Cl, Br, I triflate or alkyl sulfonate), reacting with alcohol jj (where P$^N$ is an amine protecting group for example Bn or Boc), in the presence of a base, optionally with a catalyst, in a solvent (for example KOH and tetrabutylammonium bromide in xylene) at elevated temperature (for example between 70° C. and 130° C.), provides ether intermediate kk. Removal of the protecting group P$^{N'}$ in kk (for example, when P$^{N'}$ is Bn, by hydrogenation with palladium on carbon in methanol, or when P$^{N'}$ is Boc by treatment with HCl in dioxane) provides amine intermediate ll.

Reacting amine ll with ester z (where alk is an alkyl group such as Me, Et, Bn, or tert-Bu, and LG is a leaving group such as Cl, Br, I triflate or alkyl sulfonate) in the presence of a base, optionally with an iodide salt, in a solvent (for example, potassium carbonate and potassium iodide in acetonitrile), at an elevated temperature (for example between about 70° C. and 130° C.) provides intermediate mm, which can be further reacted to provide compounds of formula (I) wherein L is —(C$_{1-3}$ alkyl)O—.

For certain intermediates p wherein L is —O(C$_{1-3}$ alkyl)- and R$^Z$ is a protected heterocycle or cycloalkyl group, for example qq, a modified sequence can be used, shown in Scheme 9. Starting from alcohol v (wherein P$^N$ is an amine protecting group such as Bn or Boc), reacting with electrophile intermediate nn (where LG is a leaving group, for example Cl, Br, I, triflate or alkyl sulfonate, and P$^{N'}$ is an amine protecting group such as Bn or Boc) in the presence of a base, optionally with a catalyst, in a solvent (for example KOH and tetrabutylammonium bromide in xylene) at elevated temperature (for example between 70° C. and 130° C.), provides ether intermediate oo. Removal of the protecting group P$^N$ in oo (for example, when P$^{N'}$ is Bn, by hydrogenation with palladium on carbon in methanol, or when P$^N$ is Boc by treatment with HCl in dioxane) provides amine intermediate pp. Reacting amine pp with ester z (where alk is an alkyl group such as Me, Et, Bn, or tert-Bu, and LG is a leaving group such as Cl, Br, I triflate or alkyl sulfonate) in the presence of a base, optionally with an iodide salt, in a solvent (for example, potassium carbonate and potassium iodide in acetonitrile), at an elevated temperature (for example between about 70° C. and 130° C.) provides intermediate qq, which can be further reacted to provide compounds of formula (I) wherein L is —O(C$_{1-3}$ alkyl)-.

Scheme 9

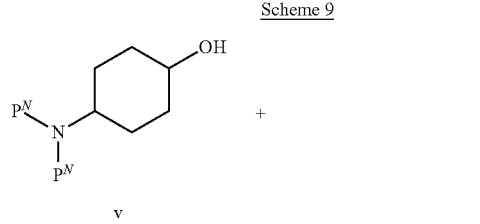

v

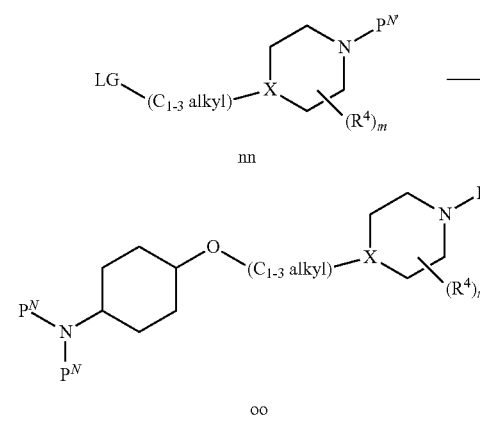

oo

Scheme 10

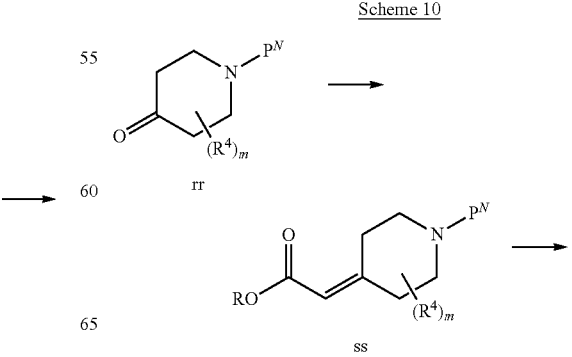

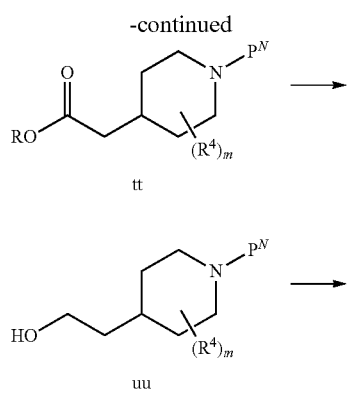

of a catalyst, in a solvent (for example, palladium on carbon in methanol under a hydrogen atmosphere), at elevated pressure (for example between 10 and 100 psi) provides intermediate tt. Reduction of the ester functional group in tt is accomplished by treatment with a reducing agent, in a solvent (for example, diisobutylaluminum hydride in DCM) at a temperature between −78° C. and 25° C. provides intermediate uu. Activation of the alcohol uu to a leaving group LG (for example, if LG is Br, by treatment with thionyl bromide in dichloromethane and DMF, or if LG is triflate, by treatment with triflic anhydride in dichloromethane) provides intermediate vv, which can be further reacted to provide compounds of formula (I) wherein L is —O($C_{1-3}$ alkyl)- and X is $CR^X$.

Scheme 11

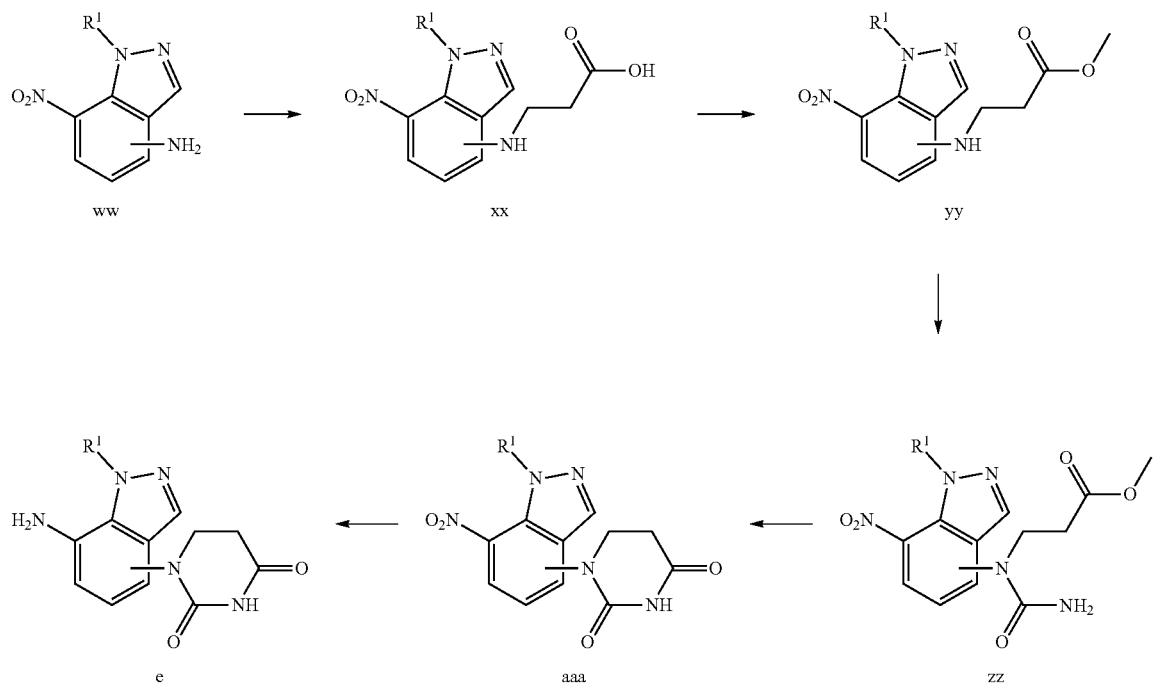

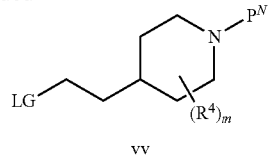

Certain examples of intermediates nn wherein X is $CR^Z$, for example vv, were prepared according to Scheme 10. Olefination of ketone intermediate rr, wherein $P^N$ is an amine protecting group (for example Bn, Boc, or Cbz) with an olefination reagent and a base, in a solvent (for example, ethyl 2-(diethoxyphosphoryl)acetate and sodium hydride in THF) at a temperature between 0° C. and 60° C. provides olefin intermediate ss. Hydrogenation of ss, in the presence Piperidine dihydrouracils e, can be prepared from indazole derivatives ww by treatment with acrylic acid, in the presence of a lewis acid catalyst, in a solvent (for example, aluminum oxide in dioxane) at an elevated temperature (for example, between 60° C. and 150° C.) to provide intermediate xx. Methylation of the carboxylic acid in xx (for example, by treatment with diazomethane in toluene and methanol, or treatment with catalytic sulfuric acid in methanol) provides methyl ester yy, which when reacted with an isocyanate salt (for example, potassium isocyanate or sodium isocyanate) in a solvent (for example, acetic acid) give urea intermediate zz. Cyclization of aaa (by treatment with strong acid such as concentrated aqueous hydrochloric acid) followed reduction of the nitro group (for example, by treatment with a reducing agent, for example $H_2$, in the presence of a catalyst, such as Pd/C, in a solvent, such as EtOH or MeOH; or Fe and $NH_4Cl$, in a solvent such as EtOH and $H_2O$), provides intermediate e, which can be further reacted to provide compounds of formula (I) wherein A is CO, and A' is NH.

Scheme 12

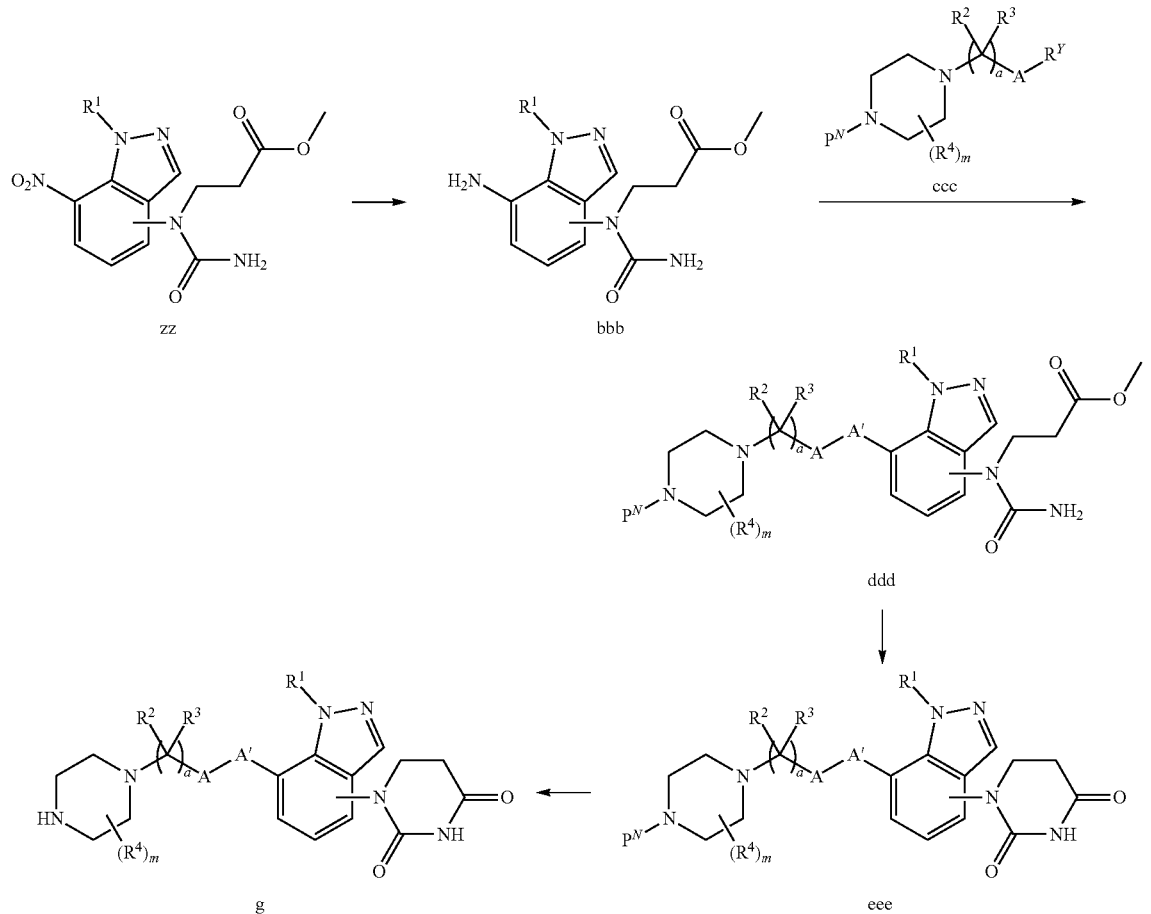

Amine intermediates g, wherein A is CH₂ and A' is NH can be prepared according to Scheme 12. Reduction of the nitro group in intermediate zz by treatment with a reducing agent (for example, H₂, in the presence of a catalyst, such as Pd/C, in a solvent, such as EtOH or MeOH; or Fe and NH₄C₁, in a solvent such as EtOH and H₂O) provides intermediate bbb. Coupling bbb with an appropriately derived piperazine intermediate ccc, wherein P$^N$ is an amine protecting group (for example, Bn or Cbz), A is CH₂ and R$^Y$ is a leaving group (for example, Cl, Br, I, OTf or OMs), in the presence of a base, possibly with an iodide salt, in a solvent (for example, N,N-diisopropylethylamine and sodium iodide in acetonitrile) at an elevated temperature (for example, between 50° C. to about 120° C.) provides intermediate ddd. Cyclization of intermediate ddd to intermediate eee can be accomplished by treatment with a strong acid (for example, concentrated aqueous hydrochloric acid), and subsequent removal of the P$^N$ protecting group (for example, when P$^N$ is Cbz, by hydrogenation in the presence of a catalyst, in a solvent, for example palladium on carbon in ethyl acetate) provides intermediate g, which can be further reacted to provide compounds of formula (I), wherein wherein A is CH₂ and A' is NH.

Scheme 13

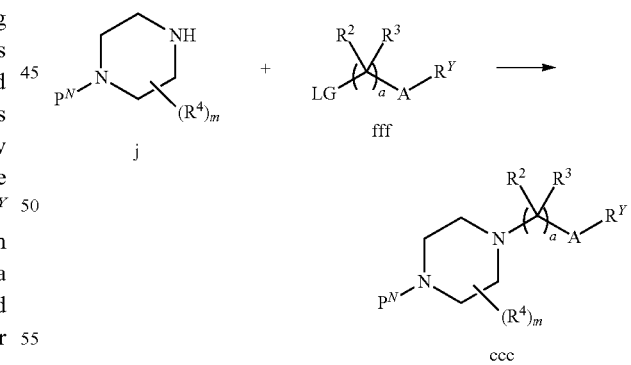

Intermediate ccc, wherein P$^N$ is an amine protecting group (for example, Bn or Cbz), A is CH₂ and R$^Y$ is a leaving group (for example, Cl, Br, I, OTf or OMs), an alcohol, or a protected alcohol (for example, OTBS, OPiv or OTHP), can be prepared according to Scheme 13. Reacting piperazine intermediate j, wherein P$^N$ is an amine protecting group (for example, Bn or Cbz) with intermediate fff, wherein LG is a leaving group (for example, Cl, Br, I, OTf or OMs) A is CH₂, and R$^Y$ is a leaving group (for example, Cl, Br, I, OTf or OMs), an alcohol, or a protected alcohol (for example, OTBS, OPiv or OTHP) in the presence of a base, optionally with an iodide salt, in a solvent (for example, N,N-diisopropylethylamine and sodium iodide in DMF) at an elevated temperature (for example, between 40° C. and about 100° C.) provides intermediate ccc wherein $P^N$ is an amine protecting group (for example, Bn or Cbz), A is $CH_2$ and $R^Y$ is a leaving group (for example, Cl, Br, I, OTf or OMs), an alcohol, or a protected alcohol (for example, OTBS, OPiv or OTHP). Intermediates ccc, wherein $R^Y$ is an alcohol or protected alcohol, can be converted to intermediates ccc, wherein $R^Y$ is a leaving group (for example, Cl, Br, I, OTf or OMs), by treatment under alcohol activation conditions (for example, formation of ccc wherein $R^Y$ is Br can be accomplished by treatment under bromination conditions, for example, thionly bromide in dichloromethane and DMF; or when $R^Y$ is OTf, by treatment under triflation conditions, for example, by treating with triflic anhydride in dichloromethane).

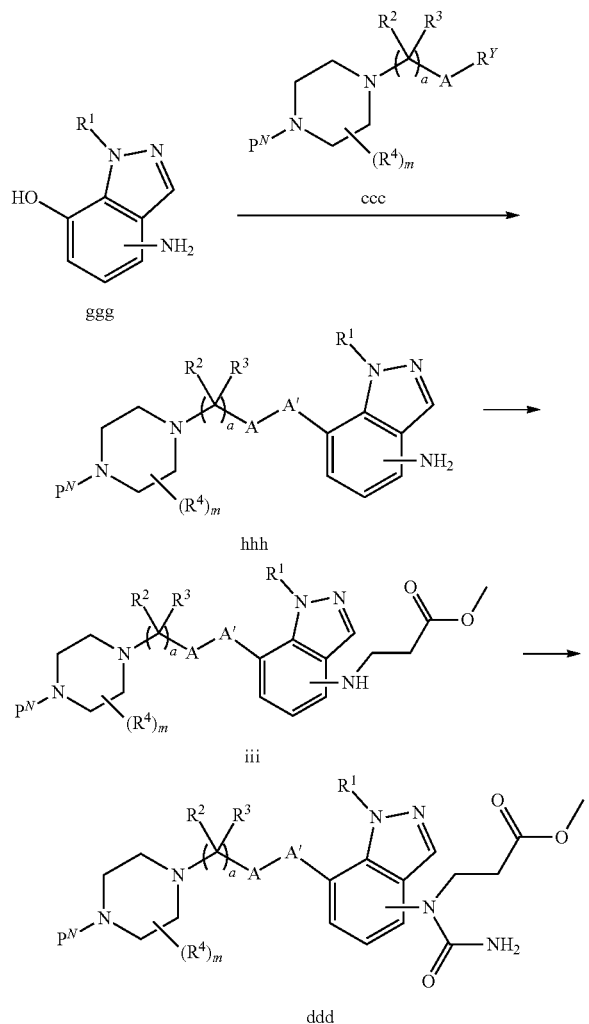

Scheme 14

Intermediates such as ddd, wherein $P^N$ is an amine protecting group (for example, Boc, Cbz, or Bn), A is $CH_2$, and A' is O, can be prepared according to Scheme 14. Coupling of indazole ggg with electrophile ccc, wherein $P^N$ is an amine protecting group (for example, Boc, Cbz, or Bn), A is $CH_2$, and $R^Y$ is a leaving group (for example Cl, Br, I, OTf or OMs), in the presence of a base, optionally with an iodide salt, in a solvent (for example, potassium carbonate in MeCN; or, N,N-diisopropylethylamine and sodium iodide in DMF) to give intermediate hhh. Coupling hhh with methyl acrylate, in the presence of a catalyst, in a solvent (for example, aluminum oxide in methyl acrylate) provides intermediate iii, which can be reacted with an isocyanate salt (for example, sodium isocyanate of potassium isocyanate) in a solvent (for example, potassium iscyanate in acetic acid) to give intermediate ddd, wherein A' is O.

METHODS OF USE

In one embodiment, the compounds described herein have utility as pharmaceuticals to treat, prevent or improve conditions in animals or humans. The compounds described herein have utility as pharmaceuticals to treat, prevent or improve conditions in animals or humans. Accordingly, provided herein are many uses of compounds, including the treatment or prevention of those diseases set forth below. In one embodiment, the methods provided herein comprise the administration of an effective amount of a compound to a subject in need thereof.

The methods provided herein comprise the administration of an effective amount of one or more compound(s) to a subject in need thereof.

Provided herein are methods for treating or preventing an androgen receptor (AR) mediated disease in a subject, the method comprising administering to a subject in need thereof an effective amount of a compound as described herein.

Provided herein are methods for treating or preventing an AR mediated disease in a subject, the method comprising administering to a subject in need thereof an effective amount of a compound as described herein.

In another aspect, provided herein are compounds for use in the treatment or prevention of an AR mediated disease in a subject, comprising administering to a subject in need thereof an effective amount of a compound as described herein. In some embodiments, provided herein are compounds for use in the treatment of an AR mediated disease in a subject, comprising administering to a subject in need thereof an effective amount of a compound as described herein. In some embodiments, provided herein are compounds for use in the prevention of an AR mediated disease in a subject, comprising administering to a subject in need thereof an effective amount of a compound as described herein.

In some embodiments, the compound used in the methods herein is a compound as described herein. In some embodiments, the compound is a compound of formula I. In some embodiments, the compound is a compound of formula II. In some embodiments, the compound is a compound of formula III. In some embodiments, the compound is a compound of formula IV. In some embodiments, the compound is a compound of formula V. In some embodiments, the compound is a compound of formula VI. In some embodiments, the compound is a compound of formula VII. In some embodiments, the compound is a compound of formula VIII. In some embodiments, the compound is a compound from Table 1.

In some embodiments, the AR mediated disease is AR wild-type mediated disease. In other embodiments, the AR mediated disease is the result of AR amplification.

In certain embodiments, the AR mediated disease is prostate cancer. In some such embodiments, the prostate cancer is castration resistant prostate cancer (CRPC). In some such embodiments, the prostate cancer is metastatic castration resistant prostate cancer (mCRPC). In still another embodiment, the prostate cancer is non-metastatic CRPC (nmCRPC). In some embodiments, the prostate cancer is hormone refractory. In some embodiments, the prostate cancer is resistant to treatment with an AR antagonist. For example, the prostate cancer is resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

Provided herein are methods of reducing AR levels, the method comprising administering to a subject an effective amount of a compound. Also provided herein are compounds for use in methods of reducing AR levels in a cell in vivo, ex vivo or in vitro, comprising contacting the cell with an effective amount of a compound. In one embodiment, the cell is in a patient. In one embodiment, the cell is not in a patient. In one embodiment, provided herein are methods of reducing levels of wild-type AR within a tumor, the method comprising administering a therapeutically effective amount of a compound, to reduce the level of wild-type AR within the tumor. In one embodiment, provided herein are methods of reducing levels of AR-full length (AR-FL) within a tumor, the method comprising administering a therapeutically effective amount of a compound, to reduce the level of AR-full length (AR-FL) within the tumor. In some embodiments, the AR levels are reduced compared to the AR levels prior to compound administration. In some embodiments, the AR levels are reduced by 20%, 30%, 40%, 50%, 60%, 70%, 80%, 90%, 95%, or 99% compared to the AR levels prior to compound administration.

Also provided herein are methods for regulating protein activity of AR in a patient in need thereof, comprising administering to said patient an amount of a compound. In some such embodiments, provided herein are methods for decreasing protein activity of AR in a patient in need thereof, comprising administering to said patient an amount of a compound. In some embodiments, the protein activity of AR is reduced compared to the protein activity of AR prior to compound administration. In some embodiments, the protein activity of AR is reduced by 20%, 30%, 40%, 50%, 60%, 70%, 80%, 90%, 95%, or 99% compared to the protein activity of AR prior to compound administration.

In some embodiments of the methods described herein, the methods additionally comprise administering one or more second agents selected from an AR antagonist (such as cyproterone acetate, spironolactone, bicalutamide, and enzalutamide), a 5α-reductase inhibitor (such as finasteride and dutasteride), a CYP17A1 inhibitor (such as abiraterone acetate), a gonadotropin-releasing hormone (GnRH) analog (such as leuprorelin and cetrorelix), and an anti-gonadotropin (such as megestrol acetate and medroxyprogesterone acetate).

In some embodiments, the compounds provided herein may be used in any of the above-mentioned methods.

In some embodiments, the compound provided herein may be used in any of the above-mentioned methods.

PHARMACEUTICAL COMPOSITIONS AND ROUTES OF ADMINISTRATION

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound to be administered to a subject is rather widely variable and can be subject to the judgment of a health-care practitioner. In general, the compounds can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound administered will depend on such factors as the solubility of the active component, the formulation used and the route of administration.

In another embodiment, provided herein are methods for the treatment or prevention of a disease or disorder comprising the administration of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day of a compound to a subject in need thereof.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound.

In a particular embodiment, provided herein are unit dosage formulations comprising about 0.1 mg or 100 mg of a compound.

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a compound.

An compound can be administered once, twice, three, four or more times daily. In a particular embodiment, doses of 100 mg or less are administered as a once daily dose and doses of more than 100 mg are administered twice daily in an amount equal to one half of the total daily dose.

An compound can be administered orally for reasons of convenience. In one embodiment, when administered orally, a compound is administered with a meal and water. In another embodiment, the compound is dispersed in water or juice (e.g., apple juice or orange juice) or any other liquid and administered orally as a solution or a suspension.

The compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound without an additional carrier, excipient or vehicle.

In another embodiment, provided herein are compositions comprising an effective amount of a compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound can be delayed or prolonged by proper formulation. For example, a slowly soluble pellet of the compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles that allow it to disperse slowly in the serum.

ENUMERATED EMBODIMENTS

The invention may be defined by reference to the following enumerated, illustrative embodiments.

1. A compound of formula I

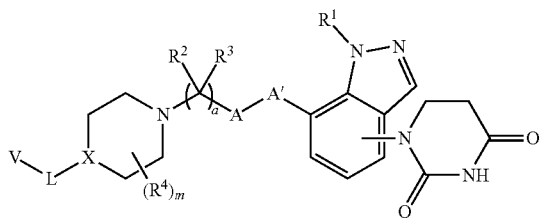

or a pharmaceutically acceptable salt, tautomer, isotopolog, or stereoisomer thereof, wherein $R^1$ is $C_{1-3}$ alkyl;

A is $CH_2$ or C=O;

A' is NH or O;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

L is substituted or unsubstituted —O($C_{1-6}$ alkyl)-, —($C_{1-6}$ alkyl)O—, —O($C_{1-6}$ alkyl)O— or —($C_{1-9}$ alkyl)-;

X is N or $CR^X$;

$R^X$ is hydrogen, halogen, —O($C_{1-6}$ alkyl) or —($C_{1-9}$ alkyl);

V is

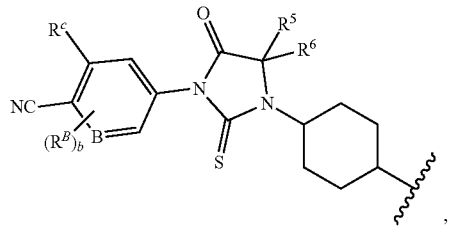

, wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

2. The compound of embodiment 1, wherein $R^1$ is methyl.

3. The compound of embodiment 1 or 2, wherein a is 1, and $R^2$ and $R^3$ are both H.

4. The compound of any one of embodiments 1 to 3, wherein A is C=O.

5. The compound of any one of embodiments 1 to 3, wherein A is $CH_2$.

6. The compound of any one of embodiments 1 to 5, wherein A' is NH.

7. The compound of any one of embodiments 1 to 5, wherein A' or O.

8. The compound of any one of embodiments 1 to 7, wherein each $R^4$ is substituted or unsubstituted methyl.

9. The compound of any one of embodiments 1 to 8, wherein each $R^4$ is independently selected from methyl and $CF_3$.

10. The compound of any one of embodiments 1 to 9, wherein m is 0, 1, 2, 3 or 4.

11. The compound of any one of embodiments 1 to 10, wherein m is 1 or 2.

12. The compound of any one of embodiments 1 to 11, wherein X is N.

13. The compound of any one of embodiments 1 to 11, wherein X is $CR^X$; and $R^X$ is hydrogen, halogen, —O($C_{1-6}$ alkyl) or —($C_{1-9}$ alkyl).

14. The compound of any one of embodiments 1-13, wherein L is substituted or unsubstituted —O($CH_2$)$_p$—, O($CH_2$)$_p$O— or —($CH_2$)$_p$—, and p is 1-4.

15. The compound of any one of embodiments 1 to 13, wherein L is substituted or unsubstituted —O($CH_2$)$_p$—, and p is 2 or 3.

16. The compound of any one of embodiments 1 to 13, wherein L is substituted or unsubstituted —O($CH_2$)$_p$O—, and p is 2 or 3.

17. The compound of any one of embodiments 1 to 13, wherein L is substituted or unsubstituted —($CH_2$)$_p$—, and p is 3 or 4.

18. The compound of any one of embodiments 1 to 13, wherein L is —O($CH_2$)($CH_2$)—, —O($CH_2$)($CH_2$)O— or —($CH_2$)($CH_2$)($CH_2$)—.

19. The compound of any one of embodiments 1 to 18, wherein B is CH.

20. The compound of any one of embodiments 1 to 19, wherein B is N.

21. The compound of any one of embodiments 1 to 20, wherein b is 0.

22. The compound of any one of embodiments 1 to 21, wherein $R^C$ is $CF_3$, Cl or $SF_5$.

23. The compound of any one of embodiments 1 to 22, wherein $R^C$ is $CF_3$.

24. The compound of any one of embodiments 1 to 23, wherein $R^5$ and $R^6$ are methyl.

25. The compound of embodiment 1, having formula II

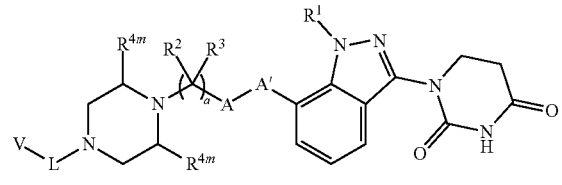

or a pharmaceutically acceptable salt, tautomer, isotopolog, or stereoisomer thereof.

26. The compound of embodiment 1, having formula III

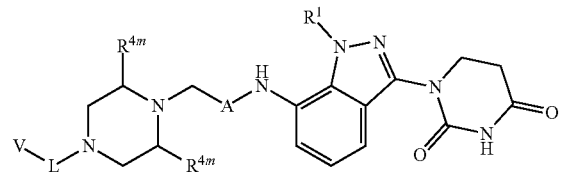

or a pharmaceutically acceptable salt, tautomer, isotopolog, or stereoisomer thereof, wherein $R^1$ is methyl;

A is $CH_2$ or C=O;

each $R^{4m}$ is independently hydrogen or substituted or unsubstituted methyl, wherein the substituents, when present are selected from 1 to 5 halo;

L is substituted or unsubstituted —O($C_{1-3}$ alkyl)-, —O($C_{1-3}$ alkyl)O— or —($C_{1-4}$ alkyl)-;

V is

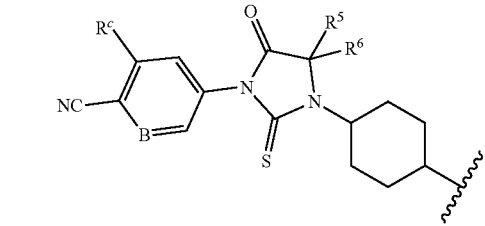

,

B is N or CH;
$R^C$ is halogen, $CF_3$ or $SF_5$; and
$R^5$ and $R^6$ are $C_{1-3}$ alkyl.

27. The compound of embodiment 1, having formula IV

IV

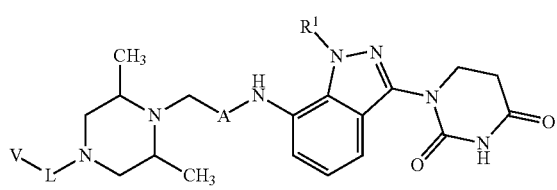

or a pharmaceutically acceptable salt, tautomer, isotopolog, or stereoisomer thereof,
wherein
L is substituted or unsubstituted —O($C_{1-3}$ alkyl)-, —O($C_{1-3}$ alkyl)O— or —($C_{1-4}$ alkyl)-;
$R^1$ is methyl;
A is $CH_2$ or C=O;
V is

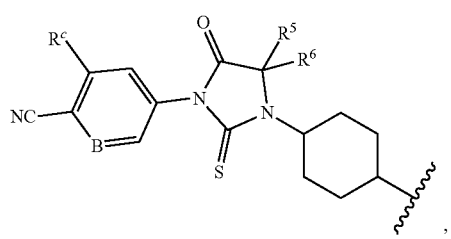

B is N or CH;
$R^C$ is halogen, $CF_3$ or $SF_5$; and
$R^5$ and $R^6$ are $C_{1-3}$ alkyl.

28. The compound of embodiment 1, having formula V

V

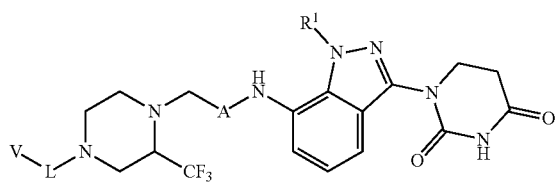

or a pharmaceutically acceptable salt, tautomer, isotopolog, or stereoisomer thereof,
wherein
$R^1$ is methyl;
A is $CH_2$ or C=O;
L is substituted or unsubstituted —O($C_{1-3}$ alkyl)-, —O($C_{1-3}$ alkyl)O— or —($C_{1-4}$ alkyl)-;

V is

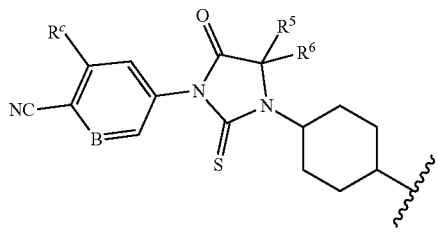

B is N or CH;
$R^C$ is halogen, $CF_3$ or $SF_5$; and
$R^5$ and $R^6$ are $C_{1-3}$ alkyl.

29. The compound of embodiment 1, having formula VI

VI

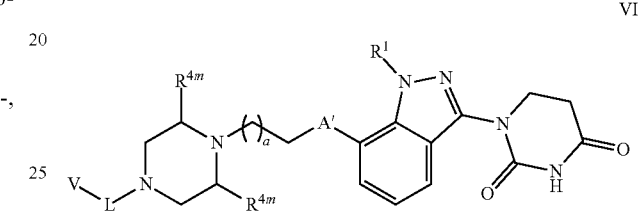

or a pharmaceutically acceptable salt, tautomer, isotopolog, or stereoisomer thereof,
wherein
$R^1$ is methyl;
A' is NH or O;
a is 1 or 2;
each $R^{4m}$ is independently hydrogen or substituted or unsubstituted methyl, wherein the substituents, when present are selected from 1 to 5 halo;
L is substituted or unsubstituted —O($C_{1-3}$ alkyl)-, —O($C_{1-3}$ alkyl)- or —($C_{1-4}$ alkyl)-;
V is

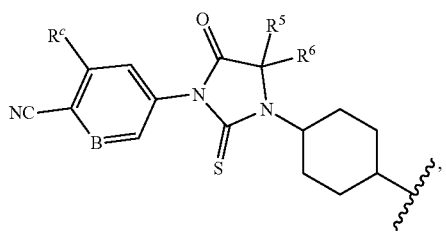

B is N or CH;
$R^C$ is halogen, $CF_3$ or $SF_5$; and
$R^5$ and $R^6$ are $C_{1-3}$ alkyl.

30. The compound of embodiment 1, having formula VII

VII

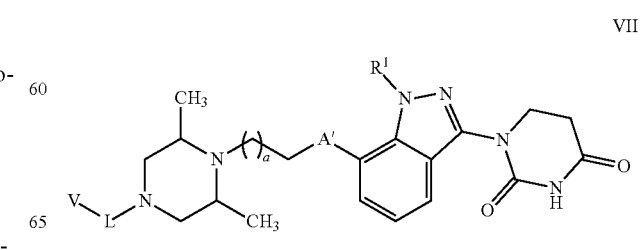

or a pharmaceutically acceptable salt, tautomer, isotopolog, or stereoisomer thereof, wherein $R^1$ is methyl;
A' is NH or O;
a is 1 or 2;
L is substituted or unsubstituted —O($C_{1-3}$ alkyl)-, —O($C_{1-3}$ alkyl)O— or —($C_{1-4}$ alkyl)-;
V is

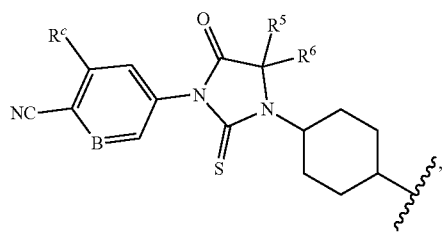

B is N or CH;
$R^C$ is halogen, $CF_3$ or $SF_5$; and
$R^5$ and $R^6$ are $C_{1-3}$ alkyl.

31. The compound of embodiment 1, having formula VIII

VIII

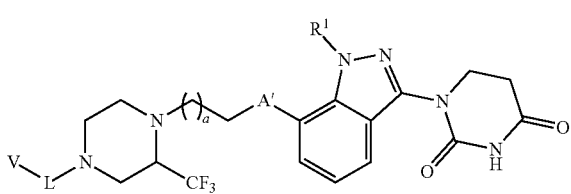

or a pharmaceutically acceptable salt, tautomer, isotopolog, or stereoisomer thereof, wherein A' is NH or O;
a is 1 or 2;
L is substituted or unsubstituted —O($C_{1-3}$ alkyl)-, —O($C_{1-3}$ alkyl)O— or —($C_{1-4}$ alkyl)-;
$R^1$ is methyl;
V is

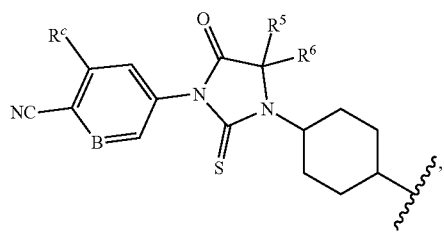

B is N or CH;
$R^C$ is halogen, $CF_3$ or $SF_5$; and
$R^5$ and $R^6$ are $C_{1-3}$ alkyl.

32. The compound of embodiment 1, wherein the compound is selected from Table 1 or a pharmaceutically acceptable salt, tautomer, isotopolog, or stereoisomer thereof.

33. A pharmaceutical composition comprising an effective amount of a compound of any one of embodiments 1 to 32, or a pharmaceutically acceptable salt, tautomer, isotopologue, or stereoisomer thereof, and a pharmaceutically acceptable carrier, excipient or vehicle.

34. A method for the treatment of an androgen receptor mediated disease, the method comprising administering to a subject in need thereof an effective amount of a compound of any one of embodiments 1 to 32.

35. A method for the treatment of an androgen receptor mediated disease, the method comprising administering to a subject in need thereof an effective amount of the pharmaceutical composition of embodiment 33.

36. The method of embodiment 34 or 35, wherein the androgen mediated disease is prostate cancer.

37. The method of embodiment 36, wherein the prostate cancer is castration resistant prostate cancer (CRPC).

EXAMPLES

The following Examples are presented by way of illustration, not limitation.

Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

| Abbreviations used: | |
|---|---|
| DCM | Dichloromethane |
| DIEA | N,N-Diisopropylethylamine |
| DMA | N,N-Dimethylacetamide |
| DMF | N,N-Dimethylformamide |
| DMSO | Dimethylsulfoxide |
| EDCI | 1-Ethyl-3-(3-dimethylaminopropyl)carbodiimide |
| ESI | Electrospray ionization |
| HATU | 1-[Bis(dimethylamino)methylene]-1H-1,2,3-triazolo[4,5-b]pyridinium 3-oxide hexafluorophosphate |
| HPLC | High performance liquid chromatography |
| IBX | 1-Hydroxy-1λ$^5$,2-benziodoxole-1,3-dione |
| LCMS | Liquid chromatography mass spectrometry |
| MeOH | Methanol |
| MS | Mass spectrometry |
| MTBE | Methyl tert-butyl ether |
| NMP | N-Methylpyrrolidone |
| NMR | Nuclear magnetic resonance |
| OMs | Mesylate |
| OTs | Tosylate |
| PPh3 | Triphenylphosphine |
| TFA | Trifluoroacetic acid |
| Tf$_2$O | Triflic anhydride |
| THF | Tetrahydrofuran |
| THP | Tetrahydropyrane |
| TLC | Thin layer chromatography |
| TMSCl | Trimethylsilyl chloride |
| TMSCN | Trimethylsilyl cyanide |
| TMSOTf | Trimethylsilyl trifluoromethanesulfonate |
| TsOH | p-Toluenesulfonic acid |

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

| Abbreviations used: | |
|---|---|
| DCM | Dichloromethane |
| DIEA | N,N-Diisopropylethylamine |
| DMA | N,N-Dimethylacetamide |
| DMF | N,N-Dimethylformamide |
| DMSO | Dimethylsulfoxide |
| EDCI | 1-Ethyl-3-(3-dimethylaminopropyl)carbodiimide |
| ESI | Electrospray ionization |
| HATU | 1-[Bis(dimethylamino)methylene]-1H-1,2,3-triazolo[4,5-b]pyridinium 3-oxide hexafluorophosphate |
| HPLC | High performance liquid chromatography |
| IBX | 1-Hydroxy-1$\lambda^5$,2-benziodoxole-1,3-dione |
| LCMS | Liquid chromatography mass spectrometry |
| MeOH | Methanol |
| MS | Mass spectrometry |
| MTBE | Methyl tert-butyl ether |
| NMP | N-Methylpyrrolidone |
| NMR | Nuclear magnetic resonance |
| OMs | Mesylate |
| OTs | Tosylate |
| PPh3 | Triphenylphosphine |
| TFA | Trifluoracetic acid |
| Tf$_2$O | Triflic anhydride |
| THF | Tetrahydrofuran |
| THP | Tetrahydropyrane |
| TLC | Thin layer chromatography |
| TMSCl | Trimethylsilyl chloride |
| TMSCN | Trimethylsilyl cyanide |
| TMSOTf | Trimethylsilyl trifluoromethanesulfonate |
| TsOH | p-Toluenesulfonic acid |

Example 1: 2-((2S,6R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride

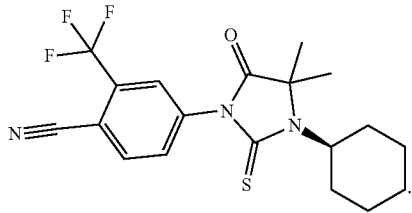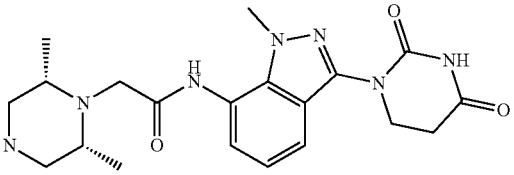

trans-4-(Dibenzylamino)cyclohexan-1-ol. To a mixture of trans-4-aminocyclohexane-1-ol (40 g, 347 mmol, 1.0 equiv.) and cesium carbonate (339 g, 1.04 mol, 3 equiv.) in acetonitrile (900 mL) was added drop wise benzyl bromide (119 g, 698 mmol, 2.01 equiv.). The reaction solution was stirred at room temperature. After 48 h the reaction mixture was filtered and concentrated. The resulting residue was diluted with DCM (300 mL), washed with water (100 mL×3), dried over anhydrous sodium sulfate and concentrated. To provide trans-4-(dibenzylamino)cyclohexan-1-ol (77 g, 261 mmol, 75% yield) as a light red solid. The crude product was carried forward without further purification. MS (ESI) m/z 116.3 [M+1]$^+$; $^1$H NMR 400 MHz DMSO-d$_6$ δ 7.27-7.34 (m, 8H), 7.19-7.21 (m, 2H), 4.42 (d, J=4.8 Hz, 1H), 3.55 (s, 4H), 2.33-2.36 (m, 1H), 1.74-1.84 (m, 4H), 1.40 (dd, J=12.4 Hz, 2.0 Hz, 2H), 0.98 (d, J=13.2 Hz, 2H).

trans-N,N-Dibenzyl-4-(2-((tetrahydro-2H-pyran-2-yl)oxy)ethoxy)cyclohexan-1-amine. To a mixture of trans-4-(dibenzylamino)cyclohexan-1-ol (60 g, 203 mmol, 1.0 equiv.) and tetrabutylammonium hydrogensulfate (13.8 g, 40.6 mmol, 0.2 equiv.) in THF (400 mL) and water (200 mL) was added 2-(2-bromoethoxy)tetrahydro-2H-pyran (84.9 g, 406 mmol, 61.5 mL, 2.0 equiv.) and sodium hydroxide (200 g, 5.00 mol, 24.6 equiv.) at 0° C. The reaction solution was heated to 65° C. After 12 h the reaction solution was poured into ice-water (1.0 L) and the aqueous phase was extracted with ethyl acetate (2×300 mL). The combined organic layers were washed with brine (300 mL), dried with anhydrous sodium sulfate, filtered and concentrated. The resulting crude material was purified by column chromatography (SiO$_2$, 2-50% ethyl acetate in petroleum ether) to give trans-N,N-dibenzyl-4-(2-((tetrahydro-2H-pyran-2-yl)oxy)ethoxy)cyclohexan-1-amine (60 g, 142 mmol, 70% yield) as a colorless oil. $^1$H NMR 400 MHz CDCl$_3$ δ 7.37-7.39 (m, 4H), 7.28-7.32 (m, 4H), 7.22 (m, 2H), 4.63-4.67 (m, 1H), 3.57-3.89 (m, 9H), 3.23-3.25 (m, 1H), 2.55 (m, 1H), 2.08-2.11 (m, 2H), 1.92-1.95 (m, 5H), 1.58-1.64 (m, 6H), 1.54-1.56 (m, 2H), 1.20-1.39 (m, 2H).

trans-4-(2-((Tetrahydro-2H-pyran-2-yl)oxy)ethoxy)cyclohexan-1-amine. To a mixture of trans-N,N-dibenzyl-4-(2-((tetrahydro-2H-pyran-2-yl)oxy)ethoxy)cyclohexan-1-amine (65 g, 153 mmol, 1.0 equiv.) in methanol (500 mL) was added 10% palladium on carbon (6.5 g) under N$_2$. The suspension was degassed under vacuum and purged with hydrogen gas three times. The reaction solution was stirred under an atmosphere of hydrogen gas (15 psi) at room temperature. After 1 h the reaction solution was filtered and the filtrate was concentrated to give trans-4-(2-((tetrahydro-2H-pyran-2-yl)oxy)ethoxy)cyclohexan-1-amine (46 g) as an off-white oil. The crude material was carried forward without further purification. $^1$H NMR 400 MHz CDCl$_3$ δ 7.34-7.36 (m, 1H), 4.63-4.65 (m, 1H), 3.82-3.91 (m, 3H), 3.52-3.66 (m, 5H), 3.28 (m, 1H), 2.70-2.71 (m, 1H), 2.01-2.04 (m, 2H), 1.85-1.89 (m, 3H), 1.58-1.59 (m, 1H), 1.45-1.56 (m, 8H), 1.29-1.32 (m, 2H), 1.11-1.14 (m, 2H).

Methyl 2-methyl-2-((trans-4-(2-((tetrahydro-2H-pyran-2-yl)oxy)ethoxy)cyclohexyl)amino)propanoate. To a mixture of trans-4-(2-((tetrahydro-2H-pyran-2-yl)oxy)ethoxy)cyclohexan-1-amine (25 g, 103 mmol, 1.0 equiv.) in acetonitrile (175 mL) was added methyl 2-bromo-2-methylpropanoate (37.2 g, 205 mmol, 26.6 mL, 2.0 equiv.), potassium carbonate (28.4 g, 205 mmol, 2.0 equiv.) and potassium iodide (1.71 g, 10.3 mmol, 0.1 equiv.). The reaction solution was heated to 110° C. After 16 h the reaction solution was diluted with water (100 mL) and extracted with ethyl acetate (2×75 mL). The combined organic layers were washed with brine (50 mL), dried over anhydrous sodium sulfate concentrated. The resulting crude material was purified by column chromatography (SiO$_2$, 0-50% ethyl acetate in petroleum ether) to afford methyl 2-methyl-2-((trans-4-(2-((tetrahydro-2H-pyran-2-yl)oxy)ethoxy)cyclohexyl)amino)propanoate (18.6 g, 54 mmol, 53% yield) as a yellow oil. MS (ESI) m/z 344.4 [M+1]$^+$; $^1$H NMR (400 MHz CDCl$_3$) δ 4.63 (t, J=3.2 Hz, 1H), 3.82-3.87 (m, 2H), 3.70 (s, 3H), 3.61-3.63 (m, 4H), 3.51-3.60 (m, 2H), 3.22-3.24 (m, 1H), 2.36 (m, 1H), 1.99 (m, 2H), 1.83-1.86 (m, 3H), 1.62 (m, 1H), 1.53-1.60 (m, 6H), 1.30 (m, 6H), 1.12-1.14 (m, 2H).

4-(4,4-Dimethyl-5-oxo-3-(trans-4-(2-((tetrahydro-2H-pyran-2-yl)oxy)ethoxy)cyclohexyl)-2-thioxoimidazolidin-1-yl)-2-(trifluoromethyl)benzonitrile. To a solution of methyl 2-methyl-2-((trans-4-(2-((tetrahydro-2H-pyran-2-yl)oxy)ethoxy)cyclohexyl)amino)propanoate (18.6 g, 54.2 mmol, 1.0 equiv.) in ethyl acetate (130 mL) was added 4-isothiocyanato-2-(trifluoromethyl)benzonitrile (24.7 g, 108 mmol, 2.0 equiv.) and N,N-diisopropylethylamine (14.0 g, 108 mmol, 2.0 equiv.). The reaction solution was heated to 90° C. with stirring. After 12 h the reaction solution was concentrated and the resulting crude material was purified by silica gel column chromatography (0-50% ethyl acetate in petroleum ether) to give 4-(4,4-dimethyl-5-oxo-3-(trans-4-(2-((tetrahydro-2H-pyran-2-yl)oxy)ethoxy)cyclohexyl)-2-thioxoimidazolidin-1-yl)-2-(trifluoromethyl)benzonitrile (25 g, 46.3 mmol, 86% yield) as a yellow oil.

4-(3-(trans-4-(2-Hydroxyethoxy)cyclohexyl)-4,4-dimethyl-5-oxo-2-thioxoimidazolidin-1-yl)-2-(trifluoromethyl)benzonitrile. To a solution of 4-(4,4-dimethyl-5-oxo-3-(trans-4-(2-((tetrahydro-2H-pyran-2-yl)oxy)ethoxy)cyclohexyl)-2-thioxoimidazolidin-1-yl)-2-(trifluoromethyl)benzonitrile (42.5 g, 78.8 mmol, 1.0 equiv.) in dichloromethane (300 mL) was added 4 M hydrochloric acid in 1,4-dioxane (400 mL) drop-wise. The reaction solution was stirred at room temperature. After 1 h the reaction solution was concentrated and purified by silica gel column chromatography (1-20% THF in dichloromethane) to give 4-(3-(trans-4-(2-hydroxyethoxy)cyclohexyl)-4,4-dimethyl-5-oxo-2-thioxoimidazolidin-1-yl)-2-(trifluoromethyl)benzonitrile (21 g, 46.1 mmol, 59% yield) as a yellow glassy oil. MS (ESI) m/z 456.4 [M+1]$^+$; $^1$H NMR (400 MHz CDCl$_3$) δ 7.95 (d, J=8.0 Hz, 1H), 7.85 (m, 1H), 7.72 (dd, J=10.0 Hz, 1.6 Hz, 1H), 3.73-3.77 (m, 4H), 3.60-3.62 (m, 2H), 3.37-3.39 (m, 1H), 2.88-2.91 (m, 2H), 2.21-2.24 (m, 2H), 1.97 (m, 1H), 1.83-1.88 (m, 3H), 1.61 (s, 6H), 1.33-1.41 (m, 2H).

4-(3-(trans-4-(2-Bromoethoxy)cyclohexyl)-4,4-dimethyl-5-oxo-2-thioxoimidazolidin-1-yl)-2-(trifluoromethyl)benzonitrile. To a mixture of 4-(3-(trans-4-(2-hydroxyethoxy)cyclohexyl)-4,4-dimethyl-5-oxo-2-thioxoimidazolidin-1-yl)-2-(trifluoromethyl)benzonitrile (3.500 g, 7.72 mmol, 1.0 equiv.) in dichloromethane (80 mL) was added N,N-dimethylformamide (8 mL) and thionyl bromide (3.201 g, 15.43 mmol, 2.0 equiv.) at 0° C. After 12 h the reaction solution was poured into aqueous saturated sodium bicarbonate solution (100 mL) and extracted with dichloromethane (3×50 mL). The combined organic layers were dried over sodium sulfate, filtered and concentrated under reduced pressure. The crude material was purified by column chromatography (9-20% ethyl acetate in petroleum ether) to give 4-(3-(trans-4-(2-bromoethoxy)cyclohexyl)-4,4-dimethyl-5-oxo-2-thioxoimidazolidin-1-yl)-2-(trifluoromethyl)benzonitrile (4.200 g, 8.13 mmol, crude) as a yellow solid. MS (ESI) m/z 518.1 [M+1]$^+$.

1-Methyl-7-nitro-1H-indazol-3-amine. To a mixture of 2-fluoro-3-nitrobenzonitrile (19.50 g, 117.4 mmol, 1 equiv.) in N,N-dimethylacetamide (30 mL, 3.9 M) was added methylhydrazine (40.56 g, 352.2 mmol, 46.36 mL, 3 equiv.) and N,N-diisopropylethylamine (16.69 g, 129.13 mmol, 22.49 mL, 1.1 equiv.). The mixture was stirred at 20° C. for 30 min. The reaction mixture was diluted with water 1000 mL and extracted with ethyl acetate (100 mL×3). The combined organic layers were washed with brine (300 mL), dried over anhydrous sodium sulfate and concentrated to give 1-methyl-7-nitro-1H-indazol-3-amine (30.50 g, crude) as a white solid. $^1$H NMR (400 MHz, DMSO-d$_6$) δ 8.18-8.16 (m, 1H), 8.07 (dd, J=0.8, 7.6 Hz, 1H), 7.08 (t, J=8.0 Hz, 1H), 5.93 (s, 2H), 3.82 (s, 3H).

3-((1-Methyl-7-nitro-1H-indazol-3-yl)amino)propanoic acid. To a mixture of 1-methyl-7-nitro-1H-indazol-3-amine (30.20 g, 157.2 mmol, 1 equiv.) in 1,4-dioxane (300 mL, 0.52 M) was added aluminium oxide (48.07 g, 471.5 mmol, 3 eq) and acrylic acid (33.97 g, 471.5 mmol, 32.36 mL, 3 equiv.). The mixture was stirred at 110° C. for 12 h. The crude material was purified by silica gel column chromatography (20-100% ethyl acetate in petroleum ether) to give 3-((1-methyl-7-nitro-1H-indazol-3-yl)amino)propanoic acid (17.10 g, 26.7 mmol, 17% yield) as a red solid. MS (ESI) m/z 265.1 [M+1]$^+$ Methyl 3-((1-methyl-7-nitro-1H-indazol-3-yl)amino)propanoate. To a mixture of 3-((1-methyl-7-nitro-1H-indazol-3-yl)amino)propanoic acid (17.10 g, 26.7 mmol, 1 equiv.) in methanol (5 mL, 2.7 M) and toluene (5 mL, 2.7 M) was added trimethylsilyldiazomethane (2 M, 42.37 mL, 3.17 equiv.). The reaction solution was stirred at 25° C. for 8 hrs. The reaction solution was concentrated, diluted with water (200 mL) and extracted with ethyl acetate (3×50 mL). The combined organic layers were washed with brine (80 mL), dried over anhydrous sodium sulfate and concentrated. The crude material was purified by reverse phase HPLC (35-65% acetonitrile+0.225% formic acid in water). The product fractions were adjusted pH=7 with saturated sodium bicarbonate, then extracted with ethyl acetate (3×80 mL). The combined organic layers were washed with brine (100 mL), dried over anhydrous sodium sulfate and concentrated to give methyl 3-((1-methyl-7-nitro-1H-indazol-3-yl)amino) propanoate (7.10 g, 25.5 mmol, 95% yield) as a red solid. MS (ESI) m/z 279.2 [M+1]$^+$; $^1$H NMR (400 MHz, DMSO-d$_6$) δ 8.16 (dd, J=0.8, 7.6 Hz, 1H), 8.10 (dd, J=1.2, 8.0 Hz, 1H), 7.10 (t, J=8.0 Hz, 1H), 6.69 (t, J=6.0 Hz, 1H), 3.85 (s, 3H), 3.62 (s, 3H), 3.56-3.50 (m, 2H), 2.72 (t, J=6.8 Hz, 2H).

Methyl 3-(1-(1-methyl-7-nitro-1H-indazol-3-yl)ureido) propanoate. To a mixture of methyl 3-((1-methyl-7-nitro-1H-indazol-3-yl)amino)propanoate (7.10 g, 25.5 mmol) in acetic acid (70 mL, 0.36 M) was added potassium cyanate (12.42 g, 153.1 mmol, 6 equiv.). The reaction solution was stirred at 25° C. for 8 hrs. The reaction solution was concentrated, diluted with water (200 mL) and extracted with ethyl acetate (3×50 mL). The combined organic layers were washed with brine 80 mL, dried over anhydrous sodium sulfate and concentrated to give the residue. The crude material was purified by silica gel column chromatography (20-100% ethyl acetate in petroleum ether) to give methyl 3-(1-(1-methyl-7-nitro-1H-indazol-3-yl)ureido)propanoate (3.00 g, 9.34 mmol, 37% yield) as a yellow solid. MS (ESI) m/z 321.9 [M+1]$^+$; $^1$H NMR (400 MHz, DMSO-d$_6$) δ 8.20 (dd, J=0.8, 7.6 Hz, 1H), 7.99 (dd, J=0.8, 8.0 Hz, 1H), 7.34 (t, J=8.0 Hz, 1H), 6.16 (s, 2H), 4.06 (s, 3H), 3.93 (t, J=6.8 Hz, 2H), 3.46 (s, 3H), 2.60 (t, J=7.2 Hz, 2H).

1-(1-Methyl-7-nitro-1H-indazol-3-yl)dihydropyrimidine-2,4(1H,3H)-dione. To methyl 3-(1-(1-methyl-7-nitro-1H-indazol-3-yl)ureido)propanoate (3.09 g, 0.38 mmol) was added 4 M hydrochloric acid in 1,4-dioxane (25 mL, 0.02 M). The mixture was stirred at 25° C. for 8 hrs. The reaction solution was filtered and the filter cake was treated with saturated sodium bicarbonate solution to pH 7. The precipitate was filtered to give 1-(1-methyl-7-nitro-1H-indazol-3-yl)dihydropyrimidine-2,4(1H,3H)-dione as a yellow solid. MS (ESI) m/z 290.0 [M+1]$^+$.

1-(7-Amino-1-methyl-1H-indazol-3-yl)dihydropyrimidine-2,4(1H,3H)-dione. To a solution of 1-(1-methyl-7-nitro-1H-indazol-3-yl)dihydropyrimidine-2,4(1H,3H)-dione (2.70 g, 9.33 mmol) in methanol (30 mL, 0.15 M) and tetrahydrofuran (30 mL, 0.15 M) was added 10% palladium on activated carbon (12.5 g, 1.18 mmol, 1.3 equiv.) under hydrogen gas at 15 psi. The mixture was stirred at 25° C. for 8 hrs. The reaction solution was filtered to give 1-(7-amino-1-methyl-1H-indazol-3-yl)dihydropyrimidine-2,4(1H,3H)-dione (2.04 g, 7.19 mmol, 77% yield) as a yellow solid. MS (ESI) m/z 260.3[M+1]$^+$; $^1$H NMR (400 MHz, DMSO-d$_6$) δ 10.50 (s, 1H), 6.90-6.75 (m, 2H), 6.59 (d, J=6.4 Hz, 1H), 5.24 (s, 2H), 4.22 (s, 3H), 3.84 (t, J=6.8 Hz, 2H), 2.75 (t, J=6.4 Hz, 2H).

tert-Butyl (3R,5S)-4-(2-methoxy-2-oxoethyl)-3,5-dimethylpiperazine-1-carboxylate. A solution of tert-butyl (3S,5R)-3,5-dimethylpiperazine-1-carboxylate (5. g, 23.33 mmol, 1 equiv.), methyl bromoacetate (3.57 g, 23.33 mmol, 1 equiv.) and triethylamine (10.2 mL, 70 mmol, 3 equiv.) in THF (100 mL, 0.23 M) was stirred at 50° C. After 18 h the reaction solution was diluted with saturated aqueous sodium bicarbonate (50 mL) and extracted with ethyl acetate (3×100 mL). the combined organic layers were washed with brine (50 mL), dried over anhydrous sodium sulfate and concentrated. The resulting crude material was purified by silica gel column chromatography (10-100% ethyl acetate in hexanes) to give tert-butyl (3R,5S)-4-(2-methoxy-2-oxoethyl)-3,5-dimethylpiperazine-1-carboxylate (6.2 g, 21.6 mmol, 92% yield) as a yellow oil. MS (ESI) m/z 287.2 [M+1]$^+$.

2-((2R,6S)-4-(tert-Butoxycarbonyl)-2,6-dimethylpiperazin-1-yl)acetic acid. To a solution of tert-butyl (3R,5S)-4-(2-methoxy-2-oxoethyl)-3,5-dimethylpiperazine-1-carboxylate (2.27 g, 7.93 mmol, 1 equiv.) in THF (20 mL) was added lithium hydroxide (208.8 mg, 8.7 mmol, 1.1 equiv.) in water (5 mL), and the reaction solution was stirred at room temperature. After 18 h the reaction solution was concentrated under vacuum, and azeotroped three times with chloroform to remove residual water to provide crude 2-((2R,6S)-4-(tert-butoxycarbonyl)-2,6-dimethylpiperazin-1-yl)acetic acid (2.19 g, 7.8 mmol, 99% yield) as an off-white glassy-solid. The material was carried forward without further purification. MS (ESI) m/z 273.2 [M+1]$^+$.

tert-Butyl (3S,5R)-4-(2-((3-(2,4-dioxotetrahydropyrimidin-1(2H)-yl)-1-methyl-1H-indazol-7-yl)amino)-2-oxoethyl)-3,5-dimethylpiperazine-1-carboxylate. To a 20 ml vial containing 2-((2R,6S)-4-(tert-butoxycarbonyl)-2,6-dimethylpiperazin-1-yl)acetic acid (0.20 g, 0.7 mmol, 1 equiv.) and N-(chloro(dimethylamino)methylene)-N-methylmethanaminium hexafluorophosphate (0.45 g, 1.6 mmol, 2.2 equiv.) was added acetonitrile (2 mL) followed by 1-methylimidazole (0.18 mL, 2.2 mmol, 3 equiv.). The reaction solution was stirred at room temperature for 10 min. A solution of 1-(7-amino-1-methyl-1H-indazol-3-yl)dihydropyrimidine-2,4(1H,3H)-dione (0.19 g, 0.73 mmol, 1.0 equiv.) in acetonitrile (1 mL) was then added and the reaction solution stirred at room temperature. After 16 h the reaction solution was diluted with ethyl acetate (100 mL) and water (100 mL). The organic layer was removed and washed with 100 ml brine, dried over magnesium sulfate and concentrated to a yellow oil. The crude material was purified by column chromatography (50 g column, 1-10% methanol in dichloromethane) to give tert-butyl (3S,5R)-4-(2-((3-(2,4-dioxotetrahydropyrimidin-1(2H)-yl)-1-methyl-1H-indazol-7-yl)amino)-2-oxoethyl)-3,5-dimethylpiperazine-1-carboxylate (0.15 g, 0.29 mmol, 40% yield). MS (ESI) m/z 514.0 [M+1]+.

2-((2S,6R)-2,6-Dimethylpiperazin-1-yl)-N-(3-(2,4-dioxotetrahydropyrimidin-1(2H)-yl)-1-methyl-1H-indazol-7-yl)acetamide hydrochloride. To a 20 ml vial containing tert-butyl (3S,5R)-4-(2-((3-(2,4-dioxotetrahydropyrimidin-1(2H)-yl)-1-methyl-1H-indazol-7-yl)amino)-2-oxoethyl)-3,5-dimethylpiperazine-1-carboxylate (0.15 g, 0.29 mmol, 1 equiv.) was added 2 ml dichloromethane followed by 4 M hydrochloric acid in dioxane (1.35 mL, 5.41 mmol, 20 equiv.) and the reaction solution was stirred at room temperature. After 2 h the reaction solution was concentrated and dried under vacuum to provide 2-((2S,6R)-2,6-dimethylpiperazin-1-yl)-N-(3-(2,4-dioxotetrahydropyrimidin-1(2H)-yl)-1-methyl-1H-indazol-7-yl)acetamide hydrochloride (0.1 g, 0.24 mmol, 82.8% yield) as a yellow solid which was carried forward without further purification. MS (ESI) m/z 414.0 [M+1]+.

2-((2S,6R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride. 4-(3-(trans-4-(2-Bromoethoxy)cyclohexyl)-4,4-dimethyl-5-oxo-2-thioxoimidazolidin-1-yl)-2-(trifluoromethyl)benzonitrile (100 mg, 0.19 mmol), 2-((2S,6R)-2,6-dimethylpiperazin-1-yl)-N-(3-(2,4-dioxotetrahydropyrimidin-1(2H)-yl)-1-methyl-1H-indazol-7-yl)acetamide hydrochloride (130 mg, 0.29 mmol, 1.5 equiv.), sodium iodide (43 mg, 0.29 mmol, 1.5 equiv.) and N,N-diisopropylethylamine (0.13 mL, 0.77 mmol, 4 equiv.) were combined in acetonitrile (1 mL, 0.13 M) and N,N-dimethylformamide (0.5 mL, 0.13 M) and heated at 50° C. overnight. The reaction was filtered and purified by standard methods to give 2-((2S,6R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride (8 mg, 0.009 mmol, 5% yield). MS (ESI) m/z 851.0 [M+1]$^+$; $^1$H NMR (400 MHz, DMSO-d$_6$) δ ppm 10.58 (s, 1H), 8.35 (d, J=8.31 Hz, 1H), 8.20 (d, J=1.83 Hz, 1H), 7.98 (dd, J=8.25, 1.77 Hz, 1H), 7.56 (d, J=8.07 Hz, 1H), 7.31 (s, 1H), 7.16-7.24 (m, 2H), 7.09-7.15 (m, 1H), 7.05 (s, 1H), 4.09 (s, 3H), 3.78-3.95 (m, 7H), 3.30-3.44 (m, 3H), 3.24 (br s, 2H), 2.81-3.05 (m, 4H), 2.78 (t, J=6.66 Hz, 2H), 2.09-2.16 (m, 2H), 1.74 (br d, J=11.13 Hz, 2H), 1.56 (s, 6H), 1.33-1.45 (m, 2H), 1.22 (br d, J=1.83 Hz, 6H).

Example 2: 2-((2R,6S)-4-(3-(trans-4-(3-(4-Cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

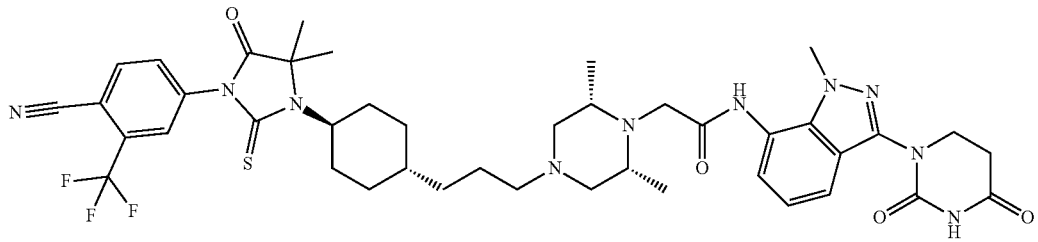 [SMILES: C[C@@H]1CN(CCC[C@H]2CC[C@H](N3C(=S)N(c4ccc(C#N)c(C(F)(F)F)c4)C(=O)C3(C)C)CC2)C[C@H](C)N1CC(=O)Nc1cccc2c(N3CCC(=O)NC3=O)nn(C)c12]

tert-butyl (trans-4-formylcyclohexyl)carbamate. To a mixture of tert-butyl (trans-4-(hydroxymethyl)cyclohexyl) carbamate (240 g, 1.05 mol, 1 equiv.) in acetonitrile (1.60 L) was added IBX (352 g, 1.26 mol, 1.2 equiv.) at 15° C. The reaction was stirred at 65° C. for 1 h. The two batches were combined for work up and purification. The reaction mixture was filtered and the filter was concentrated in vacuum to give tert-butyl (trans-4-formylcyclohexyl)carbamate (470 g, crude) as a white solid. The crude was used for next step directly without further purification. 1H NMR (400 MHz CDCl3) δ 9.62 (s, 1H), 4.43 (s, 1H), 4.41 (s, 1H), 2.10-2.14 (m, 3H), 2.01-2.05 (m, 2H), 1.45 (s, 9H), 1.38-1.41 (m, 2H), 1.14-1.18 (m, 2H).

Ethyl (E)-3-(trans-4-((tert-butoxycarbonyl)amino)cyclohexyl)acrylate. To a mixture of sodium hydride (49.6 g, 1.24 mol, 60% purity, 1.2 equiv.) in THF (900 mL) at 0° C. was added ethyl 2-(diethoxyphosphoryl)acetate (255 g, 1.14 mol, 1.1 equiv.) drop-wise. The reaction was stirred at 0° C. for 1 h. A solution of tert-butyl (trans-4-formylcyclohexyl) carbamate (235 g, 1.03 mol, 1 equiv.) in THF (500 mL) was added drop-wise at 0° C. The reaction was stirred at 25° C. for 2 h. The reaction solution was poured into ice water (3.0 L) and stirred for 20 min. The aqueous phase was extracted with ethyl acetate (800 mL, 500 mL). The combined organic phase was washed with brine (500 mL), dried over anhydrous sodium sulfate and concentrated to give ethyl (E)-3-(trans-4-((tert-butoxycarbonyl)amino)cyclohexyl)acrylate (560 g, crude) as a light yellow solid. The material was carried forward without further purification without further purification. $^1$H NMR (400 MHz CDCl$_3$) δ 6.88 (dd, J=15.6 Hz, 6.8 Hz 1H), 5.75-5.79 (m, 1H), 4.40 (s, 1H), 4.12-4.23 (m, 3H), 3.39 (s, 1H), 2.04-2.08 (m, 3H), 1.81-1.85 (m, 2H), 1.44 (s, 9H), 1.33-1.35 (m, 1H), 1.26-1.30 (m, 6H), 1.10-1.16 (m, 3H).

tert-Butyl ((trans-4-((E)-3-hydroxyprop-1-en-1-yl)cyclohexyl)carbamate. Reaction set up as two reactions in parallel. To a solution of compound ethyl (E)-3-(trans-4-((tert-butoxycarbonyl)amino)cyclohexyl)acrylate (280 g, 942 mmol, 1 equiv.) in dichloromethane (1.12 L) under argon atmosphere at −78° C. was added diisobutylaluminum hydride (1 M, 1.88 L, 2 equiv.). The reaction was stirred at −78° C. for 1 h. The reaction was quenched by MeOH (280 mL) at −60° C. Two reaction mixtures were combined and poured into sat. citric acid (1.0 kg citric acid in 4.0 L H$_2$O) below 10° C. The mixture was extracted with ethyl acetate (2.0 L, 1.5 L). The combined organic layers were washed with aqeuous sodium bicarbonate (2.0 L), brine (2.0 L), dried over anhydrous sodium sulfate and concentrated. The crude material was purified by column chromatography (SiO$_2$, petroleum ether/ethyl acetate=50/1 to 0/1) to provide tert-butyl ((trans-4-((E)-3-hydroxyprop-1-en-1-yl)cyclohexyl)carbamate (420 g, 1.645 mol, 87% yield) as a light yellow solid. $^1$H NMR (400 MHz CDCl$_3$) δ 5.58-5.60 (m, 2H), 4.39 (s, 1H), 4.06-4.07 (m, 2H), 3.35 (s, 1H), 1.80-2.00 (m, 3H), 1.74-1.78 (m, 2H), 1.42 (s, 9H), 1.08-1.20 (m, 4H).

tert-Butyl ((trans-4-(3-hydroxypropyl)cyclohexyl)carbamate. Four batches of this reaction were run in parallel. A mixture of tert-butyl ((trans-4-((E)-3-hydroxyprop-1-en-1-yl)cyclohexyl)carbamate (105 g, 411 mmol, 1 equiv.) and palladium on carbon (10.5 g, 10% purity) in MeOH (600 mL) was degassed and purged with H$_2$ for 3 times, and then the mixture was stirred at 25° C. for 12 h under H$_2$ (15 psi). The four batches were combined for work up and purification. The reaction solutions were filtered and concentrated under reduced pressure. The crude material was purified by column chromatography (SiO$_2$, Petroleum ether/Ethyl acetate=20/1 to 0/1). tert-butyl (trans-4-(3-hydroxypropyl) cyclohexyl)carbamate (82 g, 19% yield) and tert-butyl (trans-4-(3-oxopropyl)cyclohexyl)carbamate (200 g, 48% yield) as white solids. $^1$H NMR (400 MHz CDCl$_3$) δ 4.38 (s, 1H), 3.63 (t, J=6.4 Hz, 2H), 3.37 (s, 1H), 1.98-2.01 (m, 2H), 1.60-1.79 (m, 2H), 1.55-1.59 (m, 2H), 1.44 (s, 9H), 1.22-1.28 (m, 3H), 0.95-1.05 (m, 4H).

3-(trans-4-Aminocyclohexyl)propan-1-ol hydrochloride. Two reactions were carried out in parallel. To a solution of tert-butyl (trans-4-(3-hydroxypropyl)cyclohexyl)carbamate (115 g, 447 mmol, 1 equiv.) in methanol (200 mL) was added 4 M hydrochloric acid in methanol (500 mL). The reaction was stirred at 15° C. for 6 h. The two batches were combined for work up and purification. The reaction solution was filtered and concentrated to give 3-(trans-4-aminocyclohexyl)propan-1-ol hydrochloride (160 g, 92% yield) as a light yellow solid. The material was carried forward without further purification. 1H NMR (400 MHz DMSO-d$_6$) δ 8.09 (s, 4H), 4.62 (s, 2H), 3.35 (t, J=6.8 Hz, 2H), 2.87 (d, J=4.4 Hz, 1H), 1.93 (d, J=10.8 Hz, 2H), 1.73 (d, J=12.8 Hz, 2H), 1.38-1.42 (m, 2H), 1.29-1.31 (m, 3H), 1.13-1.17 (m, 3H), 0.89-0.92 (m, 2H).

Methyl 2-((trans-4-(3-hydroxypropyl)cyclohexyl) amino)-2-methylpropanoate. To a mixture of 3-(trans-4-aminocyclohexyl)propan-1-ol hydrochloride (120 g, 619 mmol, 1 equiv.) in acetonitrile (750 mL) was added potassium carbonate (428 g, 3.10 mol, 5 equiv.) and methyl 2-bromo-2-methylpropanoate (449 g, 2.48 mol, 4 equiv.). The mixture was stirred at 110° C. for 12 h. The reaction solution was filtered and concentrated. The crude material was purified by silica gel column chromatography (5-100% ethyl acetate in petroleum ether) to give methyl 2-((trans-4-(3-hydroxypropyl)cyclohexyl)amino)-2-methylpropanoate (54 g, 210 mmol, 34% yield) as a yellow oil. MS (ESI) m/z 258.2 [M+1]$^+$.

4-(3-(trans-4-(3-Hydroxypropyl)cyclohexyl)-4,4-dimethyl-5-oxo-2-thioxoimidazolidin-1-yl)-2-(trifluoromethyl) benzonitrile. To a solution of methyl 2-((trans-4-(3-hydroxypropyl)cyclohexyl)amino)-2-methylpropanoate (54 g, 210 mmol, 1 equiv.) and 4-isothiocyanato-2-(trifluoromethyl) benzonitrile (62.2 g, 273 mmol, 1.3 equiv.) in ethylacetate (350 mL) was added N,N-diisopropylethylamine (54.2 g, 420 mmol, 2 equiv.). The mixture was stirred at 80° C. for 12 h. The reaction mixture was concentrated under reduced pressure and purified by column chromatography (SiO$_2$, Petroleum ether/Ethyl acetate=15/1 to 0/1) to give 4-(3-(trans-4-(3-hydroxypropyl)cyclohexyl)-4,4-dimethyl-5-oxo-2-thioxoimidazolidin-1-yl)-2-(trifluoromethyl)benzonitrile (63 g, 139 mmol, 66% yield) as a yellow solid. 1H NMR (400 MHz CDCl$_3$) δ7.94-7.96 (m, 1H), 7.85 (m, 1H), 7.72-7.75 (m, 1H), 3.64-3.67 (m, 2H), 2.69 (s, 2H), 1.95 (d, J=12.8 Hz, 2H), 1.84 (d, J=11.2 Hz, 2H), 1.61 (s, 7H), 1.29-1.37 (m, 5H), 1.05-1.08 (m, 2H).

4-(3-(trans-4-(3-Bromopropyl)cyclohexyl)-4,4-dimethyl-5-oxo-2-thioxoimidazolidin-1-yl)-2-(trifluoromethyl)benzonitrile. To a solution of 4-(3-(trans-4-(3-hydroxypropyl) cyclohexyl)-4,4-dimethyl-5-oxo-2-thioxoimidazolidin-1-yl)-2-(trifluoromethyl)benzonitrile (0.820 g, 1.81 mmol, 1 equiv.) in N,N-dimethylformamide (0.800 mL) and dichloromethane (8 mL) was added thionyl bromide (0.752 g, 3.620 mmol, 2 equiv.) slowly at 0° C. After 2 h stirring at 0° C., the reaction solution was concentrated and purified by silica gel column chromatography (15-25% ethyl acetate in petroleum ether) to give 4-(3-(trans-4-(3-bromopropyl)cyclohexyl)-4,4-dimethyl-5-oxo-2-thioxoimidazolidin-1-yl)-2-(trifluoromethyl)benzonitrile (0.650 g, 1.259 mmol, 70% yield) as a brown solid. MS (ESI) m/z 516.1 [M+1]$^+$.

Methyl 2-((2R,6S)-2,6-dimethylpiperazin-1-yl)acetate. To a solution of tert-butyl (3R,5S)-4-(2-methoxy-2-oxoethyl)-3,5-dimethylpiperazine-1-carboxylate (1 g, 3.49 mmol, 1 equiv.) in dichloromethane (3 mL) was added 4 M HCl in 1,4-dioxane (8.7 mL, 34.9 mmol, 10 equiv.) and the reaction solution was stirred at room temperature. After 2 h the reaction solution was concentrated neutralized with aqueous sodium bicarbonate, and extracted with ethyl acetate (5×50 mL). The combined organic layers were dried over anhydrous magnesium sulfate and concentrated to provide methyl 2-((2R,6S)-2,6-dimethylpiperazin-1-yl)acetate (510 mg, 2.72 mmol, 78% yield) as a yellow oil. MS (ESI) m/z 187.5 [M+1]+.

Methyl 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetate. To a solution of 4-(3-(trans-4-(3-bromopropyl)cyclohexyl)-4,4-dimethyl-5-oxo-2-thioxoimidazolidin-1-yl)-2-(trifluoromethyl)benzonitrile (500 mg, 0.968 mmol, 1 equiv.) and methyl 2-((2R,6S)-2,6-dimethylpiperazin-1-yl)acetate (270 mg, 1.45 mmol, 1.5 equiv.) in N,N-dimethylformamide (4.8 mL, 0.2 M) was added N,N-diisoproplyethylamine (0.46 mL, 4.84 mmol, 5 equiv.) and the reaction solution was stirred at 50° C. After 18 h the reaction solution was diluted with ethyl acetate (100 mL) and washed with saturated aqueous sodium bicarbonate (2×100 mL) and brine (100 mL). The organic layer was dried over anhydrous magnesium sulfate and concentrated. The crude material was purified by silica gel column chromatography (1-10% methanol in dichloromethane) to give methyl 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetate (487 mg, 0.784 mmol, 81% yield) as a pale yellow oil. MS (ESI) m/z 622.3 [M+1]+.

2-((2R,6S)-4-(3-(trans-4-(3-(4-Cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetic acid. To a solution of methyl 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetate (500 mg, 0.82 mmol, 1 equiv.), in 5:1 THF/water (4 mL, 0.2 M) was added lithium hydroxide (59 mg, 2.46 mmol, 3 equiv.). The reaction solution was stirred at room temperature. After 12 h the reaction solution was diluted with water (10 mL), adjusted to pH 5 by addition of 2 M HCl and extracted with ethyl acetate (4×50 mL). The combined organic layers were dried over anhydrous sodium sulfate and concentrated to give 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetic acid (364 mg, 0.599 mmol, 73% yield) as an off-white solid. MS (ESI) m/z 608.4 [M+1]+; 1H NMR (400 MHz CDCl3) δ 8.33 (d, J=8.0 Hz, 1H), 8.19 (s, 1H), 7.97 (d, J=8.4 Hz, 1H), 3.83 (s, 1H), 3.37 (s, 2H), 3.14 (s, 2H), 2.89 (s, 2H), 2.73 (s, 2H), 2.40 (s, 2H), 2.00 (s, 2H), 1.81 (d, J=12.0 Hz, 2H), 1.72 (d, J=10.4 Hz, 2H), 1.44-1.54 (m, 8H), 1.15-1.19 (m, 3H), 1.05-1.08 (m, 2H), 1.01 (d, J=6.4 Hz, 6H).

2-((2R,6S)-4-(3-(trans-4-(3-(4-Cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a 2 dram vial containing 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetic acid (0.1 g, 0.16 mmol) and 1-(7-amino-1-methyl-1H-indazol-3-yl)dihydropyrimidine-2,4(1H,3H)-dione (0.06 g, 0.25 mmol, 1.5 equiv.) was added acetonitrile (1.65 mL, 0.2 M). the reaction solution was stirred until all solids were dissolved. 1-Methylimidazole (0.07 mL, 0.84 mmol, 5 equiv.) was added followed N-(chloro(dimethylamino)methylene)-N-methylmethanaminium hexafluorophosphate (0.1 g, 0.36 mmol, 2.2 equiv.) and the reaction solution was stirred at room temperature. After 1 h the reaction solution was diluted with dimethylsulfoxide to a total volume of 3 ml, filtered, and purified by standard methods to give 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (0.03 g, 0.03 mmol, 18% yield). MS (ESI) m/z 849.4 [M+1]+; 1H NMR (DMSO-d6, 400 MHz) δ 10.5-10.7 (m, 1H), 9.7-10.1 (m, 1H), 8.1-8.3 (m, 1H), 7.8-8.0 (m, 1H), 7.4-7.7 (m, 1H), 7.2-7.3 (m, 1H), 6.7-7.1 (m, 1H), 4.0-4.2 (m, 3H), 3.8-4.0 (m, 3H), 3.5-3.6 (m, 2H), 3.1-3.3 (m, 3H), 2.9-3.1 (m, 2H), 2.6-2.9 (m, 6H), 1.6-2.0 (m, 7H), 1.4-1.6 (m, 6H), 1.0-1.4 (m, 12H).

Example 3: 2-((2R,6S)-4-(2-((trans-4-(3-(3-Chloro-4-cyanophenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride

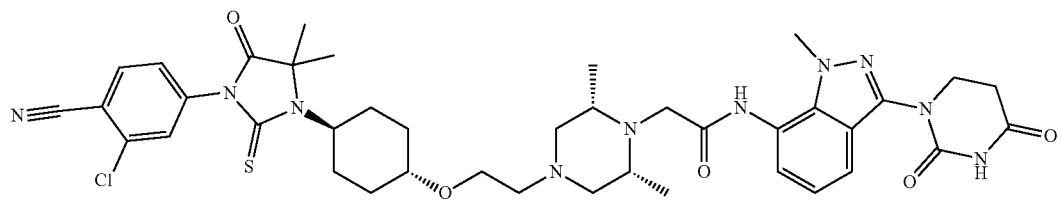 [SMILES: C[C@@H]1CN(CCO[C@H]2CC[C@H](N3C(=S)N(c4ccc(C#N)c(Cl)c4)C(=O)C3(C)C)CC2)C[C@H](C)N1CC(=O)Nc1cccc2c(N3CCC(=O)NC3=O)nn(C)c12]

2-Chloro-4-(4,4-dimethyl-5-oxo-3-(trans-4-(2-((tetrahydro-2H-pyran-2-yl)oxy)ethoxy)cyclohexyl)-2-thioxoimidazolidin-1-yl)benzonitrile. To a solution of methyl 2-methyl-2-((trans-4-(2-((tetrahydro-2H-pyran-2-yl)oxy)ethoxy)cyclohexyl)amino)propanoate (2. g, 5.82 mmol, 1 equiv.) in ethyl acetate (1.3234 mL) was added 2-chloro-4-isothiocyanato-benzonitrile (2.27 g, 11.65 mmol, 2 equiv.) and N,N-diisopropylethylamine (2.03 mL, 11.65 mmol, 2 equiv.). the reaction solution was heated to 90° C. with stirring. After 18 h the reaction solution was concentrated and purified by silica gel column chromatography (0-50% ethyl acetate in hexanes) to give 2-chloro-4-(4,4-dimethyl-5-oxo-3-(trans-4-(2-((tetrahydro-2H-pyran-2-yl)oxy)

ethoxy)cyclohexyl)-2-thioxoimidazolidin-1-yl)benzonitrile. (2 g, 3.9521 mmol, 68% yield) as a white solid. MS (ESI) m/z 506.2 [M+1]⁺.

2-Chloro-4-(3-(trans-4-(2-hydroxyethoxy)cyclohexyl)-4, 4-dimethyl-5-oxo-2-thioxoimidazolidin-1-yl)benzonitrile. To a solution of 2-chloro-4-(4,4-dimethyl-5-oxo-3-(trans-4-(2-((tetrahydro-2H-pyran-2-yl)oxy)ethoxy)cyclohexyl)-2-thioxoimidazolidin-1-yl)benzonitrile (4.0 g, 7.9 mmol, 1 equiv.) was in chloroform (5.7 mL) was added 4 M HCl in dioxane (39.52 mL, 158.08 mmol, 20 equiv.) and the reaction solution was stirred at room temperature. After 12 h the reaction solution was concentrated and purified by silica gel column chromatography (0-40% ethyl acetate in hexanes) to give 2-chloro-4-(3-(trans-4-(2-hydroxyethoxy)cyclohexyl)-4,4-dimethyl-5-oxo-2-thioxoimidazolidin-1-yl)benzonitrile (1.5 g, 2.883 mmol, 36% yield) as an off white solid. MS (ESI) m/z 422.2 [M+1]⁺.

4-(3-(trans-4-(2-Bromoethoxy)cyclohexyl)-4,4-dimethyl-5-oxo-2-thioxoimidazolidin-1-yl)-2-chlorobenzonitrile. To a solution of 2-chloro-4-(3-(trans-4-(2-hydroxyethoxy)cyclohexyl)-4,4-dimethyl-5-oxo-2-thioxoimidazolidin-1-yl)benzonitrile (1.51 g, 3.06 mmol) in dichloromethane (38 mL) and N,N-dimethylformamide (3.8 mL) was added thionyl bromide (0.59 mL, 7.64 mmol, 2.5 equiv.) and the reaction solution was stirred at room temperature. After 1 h the reaction solution was diluted with ethyl acetate (100 mL) and washed with saturated aqueous sodium bicarbonate (100 mL), brine (100 mL), dried over anhydrous magnesium sulfate and concentrated. The crude material was purified by silica gel column chromatography (0-80% ethyl acetate in hexanes) to give 4-(3-(trans-4-(2-bromoethoxy)cyclohexyl)-4,4-dimethyl-5-oxo-2-thioxoimidazolidin-1-yl)-2-chlorobenzonitrile (1.171 g, 2.42 mmol, 79% yield) as a light yellow solid. MS (ESI) m/z 484.0 [M+1]+.

Methyl 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)acetate. To a solution of 4-(3-(trans-4-(2-bromoethoxy)cyclohexyl)-4,4-dimethyl-5-oxo-2-thioxoimidazolidin-1-yl)-2-chlorobenzonitrile (400 mg, 0.825 mmol, 1 equiv.) and methyl 2-((2R,6S)-2,6-dimethylpiperazin-1-yl)acetate hydrochloride (239 mg, 1.073 mmol, 1.3 equiv.) in N,N-dimethylformamide was added N,N-diisopropylethylamine (1.03 mL, 5.94 mmol, 7 equiv.) and the reaction solution was stirred at 60° C. After 18 h the reaction solution was concentrated and purified by silica gel column chromatography (1-10% methanol in dichloromethane) to give methyl 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)acetate (311 mg, 0.528 mmol, 64% yield) as a yellow solid. MS (ESI) m/z 590.0 [M+1]⁺.

2-((2R,6S)-4-(2-((trans-4-(3-(3-Chloro-4-cyanophenyl)-5,5-dimethyl-4-oxo-2-thioxoimidazolidin-1-yl)cyclohexyl)oxy)ethyl)-2,6-dimethylpiperazin-1-yl)acetic acid. To a solution of methyl 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)acetate (311 mg, 0.528 mmol, 1 equiv.) in a 4:1 solution of 1,4-dioxane in water (1 mL) was added lithium hydroxide (38 mg, 1.58 mmol, 3 equiv.) and the reaction solution was stirred at room temperature. After 7 h the reaction solution was diluted with water (10 mL) and adjusted to pH ~7 by addition of 2 M HCl. The solution was extracted with ethyl acetate (4×50 mL), the combined organic layers were dried over anhydrous magnesium sulfate and concentrated to give 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)acetic acid (219 mg, 0.380 mmol, 72% yield) as a pale yellow solid. The material was carried forward without further purification. MS (ESI) m/z 576.0 [M+1]+.

2-((2R,6S)-4-(2-((trans-4-(3-(3-Chloro-4-cyanophenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a solution of 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)acetic acid (100 mg, 0.160 mmol, 1 equiv.) and 1-(7-amino-1-methyl-indazol-3-yl)hexahydropyrimidine-2,4-dione (102 mg, 0.390 mmol, 2.4 equiv.) was added N,N-dimethylformamide (0.82 mL, 0.2 M) and 1-methylimidazole (0.07 mL, 0.830 mmol, 5 equiv.). The reaction solution was stirred at room temperature until all solids had dissolved. After 5 min, N-(chloro(dimethylamino)methylene)-N-methylmethanaminium hexafluorophosphate (101 mg, 0.360 mmol, 2.2 equiv.) was added, and the reaction was stirred at room temperature. After 2 h the reaction solution was diluted with water (50 mL) and extracted with ethyl acetate (3×50 mL). the combined organic layers were washed with brine (30 mL), dried over anhydrous sodium sulfate and concentrated. The resulting crude material was purified by standard methods to give 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride (8.7 mg, 0.0102 mmol, 6% yield) as a white solid. MS (ESI) m/z 817.0 [M+1]⁺; ¹H NMR (DMSO-d₆, 400 MHz) δ 10.57 (s, 1H), 10.16 (br s, 1H), 9.95 (br s, 1H), 8.13 (d, 1H, J=8.3 Hz), 7.92 (d, 1H, J=1.8 Hz), 7.60 (dd, 1H, J=1.9, 8.4 Hz), 7.55 (d, 1H, J=8.2 Hz), 7.19 (d, 1H, J=7.3 Hz), 7.10 (t, 1H, J=7.5 Hz), 4.07 (s, 3H), 3.90 (t, 2H, J=6.7 Hz), 3.81 (t, 2H, J=4.7 Hz), 3.5-3.6 (m, 3H), 3.2-3.3 (m, 5H), 2.8-2.9 (m, 4H), 2.77 (br t, 2H, J=6.7 Hz), 2.5-2.6 (m, 2H), 2.10 (br d, 2H, J=10.8 Hz), 1.72 (br d, 2H, J=11.0 Hz), 1.53 (s, 6H), 1.36 (q, 2H, J=10.6 Hz), 1.19 (d, 6H, J=5.5 Hz).

Example 4: 2-((2R,6S)-4-(2-((trans-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2, 6-dimethylpiperazin-1-yl)-N-(3-(2,4-dioxotetrahydropyrimidin-1(2H)-yl)-1-methyl-1H-indazol-7-yl)acetamide hydrochloride

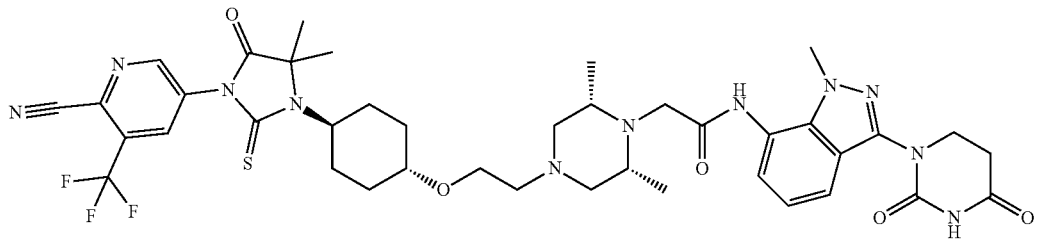 [SMILES: C[C@@H]1CN(CCO[C@H]2CC[C@H](N3C(=S)N(c4cnc(C#N)c(C(F)(F)F)c4)C(=O)C3(C)C)CC2)C[C@H](C)N1CC(=O)Nc1cccc2c(N3CCC(=O)NC3=O)nn(C)c12]

5-(4,4-Dimethyl-5-oxo-3-(trans-4-(2-((tetrahydro-2H-pyran-2-yl)oxy)ethoxy)cyclohexyl)-2-thioxoimidazolidin-1-yl)-3-(trifluoromethyl)picolinonitrile. Methyl 2-methyl-2-((trans-4-(2-((tetrahydro-2H-pyran-2-yl)oxy)ethoxy)cyclohexyl)amino)propanoate (6.70 g, 19.51 mmol, 1 equiv.), 5-isothiocyanato-3-(trifluoromethyl)picolinonitrile (8.94 g, 39.0 mmol, 2 equiv.), and N,N-diisopropylethylamine (6.8 mL, 39.0 mmol, 2 equiv.) were combined in ethyl acetate (56 mL, 0.35 M) and heated to 90° C. in a sealed tube for 16 h. The reaction was diluted with ethyl acetate (100 mL) and washed with water (100 mL), and brine (100 mL), dried over anhydrous magnesium sulfate and concentrated. The crude material was purified by silica gel column chromatography (10%-100% ethyl acetate in hexanes) to afford 5-(4,4-dimethyl-5-oxo-3-(trans-4-(2-((tetrahydro-2H-pyran-2-yl)oxy)ethoxy)cyclohexyl)-2-thioxoimidazolidin-1-yl)-3-(trifluoromethyl)picolinonitrile (3.5 g, 6.4743 mmol, 33% yield) as a brown solid. MS (ESI) m/z 541.3 [M+1]$^+$.

5-(3-(trans-4-(2-Hydroxyethoxy)cyclohexyl)-4,4-dimethyl-5-oxo-2-thioxoimidazolidin-1-yl)-3-(trifluoromethyl)picolinonitrile. To a solution of 5-(4,4-dimethyl-5-oxo-3-(trans-4-(2-((tetrahydro-2H-pyran-2-yl)oxy)ethoxy)cyclohexyl)-2-thioxoimidazolidin-1-yl)-3-(trifluoromethyl)picolinonitrile (3.50 g, 6.47 mmol, 1 equiv.) in dichloromethane (30 mL) was added 4 M hydrochloric acid (16.2 mL, 64.7 mmol, 10 equiv.) and the reaction solution was stirred at room temperature. After 3 h the reaction solution was concentrated to provide 5-(3-(trans-4-(2-hydroxyethoxy)cyclohexyl)-4,4-dimethyl-5-oxo-2-thioxoimidazolidin-1-yl)-3-(trifluoromethyl)picolinonitrile (3.20 g, 6.4 mmol, 99% yield) as a reddish oil. The crude material was carried forward without further purification. MS (ESI) m/z 457.0 [M+1]$^+$.

5-(3-(trans-4-(2-Bromoethoxy)cyclohexyl)-4,4-dimethyl-5-oxo-2-thioxoimidazolidin-1-yl)-3-(trifluoromethyl)picolinonitrile. A solution of 5-(3-(trans-4-(2-hydroxyethoxy)cyclohexyl)-4,4-dimethyl-5-oxo-2-thioxoimidazolidin-1-yl)-3-(trifluoromethyl)picolinonitrile (3.20 g, 6.49 mmol) in dichloromethane (30 mL) and N,N-dimethylformamide (5 mL) was added thionyl bromide (1.26 mL, 16.2 mmol, 2.5 equiv.) and the reaction solution was stirred at room temperature. After 2 h the reaction solution was concentrated and the crude material was purified by silica gel column chromatography (5%-80% ethyl acetate in hexanes) to give 5-(3-(trans-4-(2-bromoethoxy)cyclohexyl)-4,4-dimethyl-5-oxo-2-thioxoimidazolidin-1-yl)-3-(trifluoromethyl)picolinonitrile (2.00 g, 3.85 mmol, 59% yield) as a reddish brown oil. MS (ESI) m/z 519.8 [M+1]$^+$.

2-((2R,6S)-4-(2-((trans-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a 1-dram vial containing 5-(3-(trans-4-(2-bromoethoxy)cyclohexyl)-4,4-dimethyl-5-oxo-2-thioxoimidazolidin-1-yl)-3-(trifluoromethyl)picolinonitrile (0.093 g, 0.18 mmol, 1 equiv.), 2-((2S,6R)-2,6-dimethylpiperazin-1-yl)-N-(3-(2,4-dioxotetrahydropyrimidin-1(2H)-yl)-1-methyl-1H-indazol-7-yl)acetamide hydrochloride (0.097 g, 0.23 mmol, 1.3 equiv.) and sodium iodide (2.7 mg, 0.02 mmol, 0.1 equiv.) was added acetonitrile (2 mL) followed by N,N-diisopropylethylamine (0.19 mL, 1.08 mmol, 6 equiv.). The reaction vial was heated with stirring to 60°. After 16 h the reaction solution was diluted to a total volume of 3 ml with dimethylsulfoxide and purified by standard methods to give 2-((2R,6S)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride (0.04 g, 0.05 mmol, 28% yield). MS (ESI) m/z 853.0 [M+1]$^+$; $^1$H NMR (DMSO-d$_6$, 500 MHz) δ 10.5-10.6 (m, 1H), 9.1-9.2 (m, 1H), 8.7-8.8 (m, 1H), 7.5-7.6 (m, 1H), 7.2-7.3 (m, 1H), 7.1-7.2 (m, 1H), 4.1-4.2 (m, 3H), 4.0-4.1 (m, 1H), 3.8-3.9 (m, 4H), 3.7-3.8 (m, 4H), 3.2-3.3 (m, 3H), 2.7-2.9 (m, 4H), 2.1-2.2 (m, 2H), 1.6-1.8 (m, 4H), 1.5-1.6 (m, 6H), 1.2-1.4 (m, 10H).

Example 5: 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)propanamide

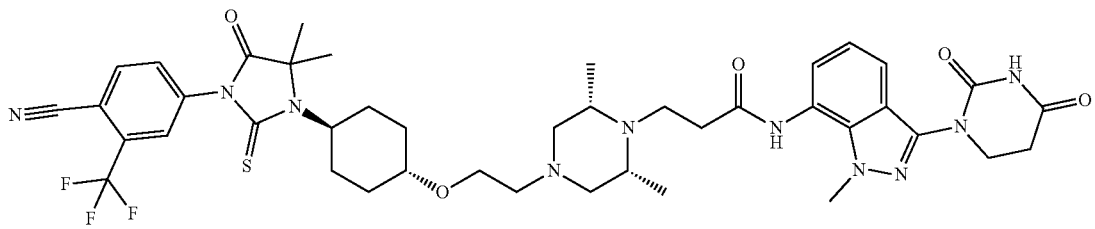 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CCC(=O)Nc1cccc2c(N3CCC(=O)NC3=O)nn(C)c12]

tert-Butyl (3R,5S)-4-(3-ethoxy-3-oxopropyl)-3,5-dimethylpiperazine-1-carboxylate. tert-Butyl (3S,5R)-3,5-dimethylpiperazine-1-carboxylate (5. g, 23.33 mmol, 1 equiv.) was combined with lithium perchlorate (10.02 g, 93.33 mmol, 4 equiv.) and ethyl acrylate (26.7 mL, 233.32 mmol, 10 equiv.) and the reaction solution was heated to 30° C. for 18 h. The solution was concentrated and purified by silica gel column chromatography (1-5% MeOH in dichloromethane) to provide tert-butyl (3R,5S)-4-(3-ethoxy-3-oxopropyl)-3,5-dimethylpiperazine-1-carboxylate (3.43 g, 11.43 mmol, 49% yield). MS (ESI) m/z 301.2 [M+1]$^+$.

Ethyl 3-((2R,6S)-2,6-dimethylpiperazin-1-yl)propanoate. To a 30 ml vial containing tert-butyl (3R,5S)-4-(3-methoxy-3-oxopropyl)-3,5-dimethylpiperazine-1-carboxylate (680. mg, 2.16 mmol) was added dichloromethane (1 mL) followed by 4 M hydrochloric acid in 1,4-dioxane (13.52 mL, 54.07 mmol, 25 equiv.). The reaction solution was stirred at room temperature. After 15 min the reaction solution was concentrated to give a yellow solid. The material was taken up in ethyl acetate and washed with sodium bicarbonate. The organic layer was separated and the aqueous layers were extracted with 3×25 ml ethyl acetate. The organic layers were combined, dried over anhydrous magnesium sulfate and concentrated to provide ethyl 3-((2R,6S)-2,6-dimethylpiperazin-1-yl)propanoate (380 mg, 1.78 mmol, 82% yield) as a yellow oil. MS (ESI) m/z 215.2 [M+1]$^+$.

Ethyl 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoate. To a 20 ml vial containing 4-(3-(trans-4-(2-bromoethoxy)cyclohexyl)-4,4-dimethyl-5-oxo-2-thioxoimidazolidin-1-yl)-2-(trifluoromethyl)benzonitrile (290 mg, 0.56 mmol) and ethyl 3-((2R,6S)-2,6-dimethylpiperazin-1-yl)propanoate (120 mg, 0.56 mmol, 1 equiv.) was added N,N-dimethylformamide (1.1666 mL, 0.48 M) and N,N-diisopropylethylamine (0.59 mL, 3.36 mmol, 6 equiv.). The reaction solution was heated to 50° C. with stirring. After 14 the reaction solution was diluted with 100 ml ethyl acetate and washed with saturated aqueous sodium bicarbonate (100 mL) followed by brine (100 mL). The organic layer was dried over magnesium sulfate and concentrated to give a yellow oil. The crude material was purified by column chromatography (1-8% MeOH in DCM with 0.2% triethylamine) to provide methyl 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoate as a clear, colorless oil. MS (ESI) m/z=652.4 [M+1]$^+$. $^1$H NMR (400 MHz, CDCl$_3$) δ 7.94 (d, J=8.2 Hz, 1H), 7.83 (s, 1H), 7.71 (dd, J=2.1, 8.3 Hz, 1H), 4.12 (q, J=7.1 Hz, 2H), 3.60 (t, J=6.2 Hz, 2H), 3.38-3.25 (m, 1H), 3.20-3.11 (m, 2H), 2.95-2.81 (m, 2H), 2.78 (br d, J=10.6 Hz, 2H), 2.71-2.59 (m, 2H), 2.52 (t, J=6.2 Hz, 2H), 2.44-2.35 (m, 2H), 2.23-2.17 (m, 2H), 1.92 (t, J=10.7 Hz, 2H), 1.86-1.76 (m, 2H), 1.60-1.59 (m, 6H), 1.41-1.29 (m, 2H), 1.26 (t, J=7.1 Hz, 3H), 1.11-1.06 (m, 6H)

3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoic acid. To a 2-dram vial containing methyl 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoate (289. mg, 0.4400 mmol) was added 1,4-Dioxane (1.478 mL) followed by a solution of lithium hydroxide (15.93 mg, 0.6700 mmol) in 0.2 ml water. The reaction solution was stirred at room temperature for 2 hours. The solution was concentrated to provide 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl) propanoic acid (263 mg, 0.4217 mmol, 95% yield) as a glassy oil that was carried forward without further purification. MS (ESI) m/z 624.3 [M+1]$^+$.

3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)propanamide. 33-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoic acid (50.0 mg, 0.08 mmol, 1.0 equiv.), 1-(7-amino-1-methyl-1H-indazol-3-yl) dihydropyrimidine-2,4(1H,3H)-dione (27.0 mg, 0.10 mmol, 1.3 equiv.), N,N-diisopropylethylamine (0.04 mL, 0.24 mmol, 3.0 equiv.) and HATU (67.1 mg, 0.18 mmol, 2.2 equiv.) were combined in N,N-dimethylformamide (0.5 mL) and stirred at room temperature. After 18 h the reaction solution was diluted with brine (50 mL) and extracted with ethyl acetate (3×50 mL). The combined organic layers were dried over anhydrous magnesium sulfate and concentrated. The crude material was purified by standard methods to give 3-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)propanamide (5.1 mg, 0.01 mmol, 7% yield). MS (ESI) m/z 865.0 [M+1]$^+$; $^1$H NMR (400 MHz, DMSO-d$_6$) δ ppm 10.58 (s, 1H), 10.07 (br s, 1H), 8.35 (d, J=8.31 Hz, 1H), 8.20 (s, 1H), 7.97 (d, J=7.80 Hz, 1H), 7.55 (d, J=7.95 Hz, 1H), 7.07-7.19 (m, 2H), 4.06 (s, 5H), 3.73-3.94 (m, 7H), 3.35 (br s, 5H), 2.72-2.93 (m, 5H), 2.67 (br d, J=1.71 Hz, 2H), 2.10 (br d, J=10.15 Hz, 2H), 1.74 (br d, J=12.10 Hz, 2H), 1.56 (s, 6H), 1.37 (br d, J=11.37 Hz, 3H), 1.23 (br s, 6H).

Example 6: 2-((2R,6S)-4-(2-((trans-4-(3-(5-Chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride

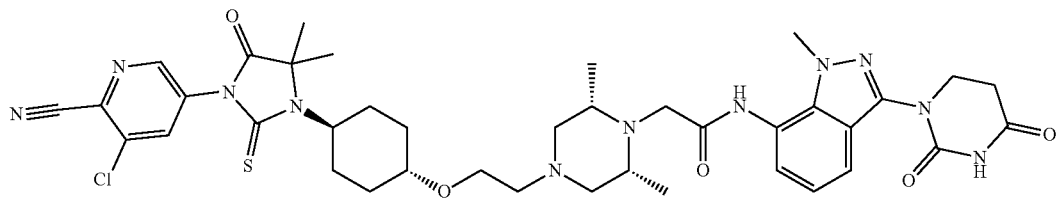 [SMILES: C[C@@H]1CN(CCO[C@H]2CC[C@H](N3C(=S)N(c4cnc(C#N)c(Cl)c4)C(=O)C3(C)C)CC2)C[C@H](C)N1CC(=O)Nc1cccc2c(N3CCC(=O)NC3=O)nn(C)c12]

3-Chloro-5-isothiocyanato-pyridine-2-carbonitrile. To a solution of 5-amino-3-chloro-pyridine-2-carbonitrile (10.00 g, 65.12 mmol, 1 equiv.) in toluene (20 mL) was added thiophosgene (5.96 mL, 78.14 mmol, 1.2 equiv.). The mixture was stirred at 110° C. After 16 h the reaction solution was concentrated and purified by silica gel chromatography (20-50% ethyl acetate in petroleum ether) to give 3-chloro-5-isothiocyanato-pyridine-2-carbonitrile (8.000 g, 40.89 mmol, 63% yield) as a red solid.

3-Chloro-5-(4,4-dimethyl-5-oxo-3-(trans-4-(2-((tetrahydro-2H-pyran-2-yl)oxy)ethoxy)cyclohexyl)-2-thioxoimidazolidin-1-yl)picolinonitrile. A mixture of methyl 3-chloro-5-isothiocyanato-pyridine-2-carbonitrile (4.000 g, 20.45 mmol, 1 equiv.) and methyl 2-methyl-2-((trans-4-(2-((tetrahydro-2H-pyran-2-yl)oxy)ethoxy)cyclohexyl)amino)propanoate (7.720 g, 22.49 mmol, 1.1 equiv.) in ethyl acetate (100 mL, 0.2 M) was added triethylamine (5.7 mL, 40.89 mmol, 2 equiv.), and the reaction solution was stirred at 90° C. After 6 hours the reaction solution was concentrated and purified by silica gel chromatography (10-50% ethyl acetate in petroleum ether) to give 3-chloro-5-(4,4-dimethyl-5-oxo-3-(trans-4-(2-((tetrahydro-2H-pyran-2-yl)oxy)ethoxy)cyclohexyl)-2-thioxoimidazolidin-1-yl)picolinonitrile (4.000 g, 7.89 mmol, 39% yield) as a yellow solid. MS (ESI) m/z=507.2 [M+1]$^+$; $^1$H NMR (400 MHz, DMSO-d$_6$) δ 8.92-8.72 (m, 1H), 8.62-8.31 (m, 1H), 4.68-4.50 (m, 1H), 3.91-3.63 (m, 4H), 3.62-3.52 (m, 3H), 3.50-3.39 (m, 3H), 2.91-2.73 (m, 3H), 2.10-2.03 (m, 2H), 1.75-1.68 (m, 3H), 1.55 (s, 6H), 1.50-1.43 (m, 4H).

3-Chloro-5-(3-(trans-4-(2-hydroxyethoxy)cyclohexyl)-4,4-dimethyl-5-oxo-2-thioxoimidazolidin-1-yl)picolinonitrile. To a solution of 3-chloro-5-(4,4-dimethyl-5-oxo-3-(trans-4-(2-((tetrahydro-2H-pyran-2-yl)oxy)ethoxy)cyclohexyl)-2-thioxoimidazolidin-1-yl)picolinonitrile (4.000 g, 7.89 mmol, 1 equiv.) in methanol (30 mL, 0.27 M) was added 2 M hydrochloride acid (3 mL, 15.78 mmol, 2 equiv.). The reaction solution was stirred at 25° C. After 2 h the pH of the mixture was adjusted to 8 by addition of saturated sodium carbonate. The aqueous phase was extracted with ethyl acetate (250 mL). The combined organic layers were washed with brine (80 mL), dried over anhydrous sodium sulfate, filtered and concentrated under reduced pressure. The crude material was purified by silica gel chromatography (33-100% ethyl acetate in petroleum ether) to give 3-chloro-5-(3-(trans-4-(2-hydroxyethoxy)cyclohexyl)-4,4-dimethyl-5-oxo-2-thioxoimidazolidin-1-yl)picolinonitrile (2.400 g, 0.01 mmol, 69% yield) as a yellow solid. MS (ESI) m/z 423.3 [M+1]$^+$; $^1$H NMR (400 MHz, CDCl$_3$) δ 7.59 (s, 1H), 7.43-7.33 (m, 2H), 7.15 (br d, J=7.0 Hz, 1H), 6.57 (br s, 1H), 4.40 (t, J=6.7 Hz, 2H), 2.98 (s, 3H), 2.70-2.55 (m, 2H), 1.53 (s, 5H), 1.54-1.51 (m, 1H), 1.54-1.51 (m, 1H), 1.54-1.51 (m, 1H), 1.54-1.51 (m, 1H).

5-(3-(trans-4-(2-Bromoethoxy)cyclohexyl)-4,4-dimethyl-5-oxo-2-thioxoimidazolidin-1-yl)-3-chloropicolinonitrile. To a solution of 3-chloro-5-(3-(trans-4-(2-hydroxyethoxy)cyclohexyl)-4,4-dimethyl-5-oxo-2-thioxoimidazolidin-1-yl)picolinonitrile (2.150 g, 5.08 mmol, 1 equiv.) in dichloromethane (5 mL, 1 M) and N,N-dimethylformamide (0.50 mL) was added thionyl bromide (0.65 mL, 10.17 mmol, 2 equiv.) at 0° C. The mixture was stirred at 25° C. for 16 h. The pH of the mixture was adjusted to 8 by saturated sodium carbonate. The organic layer was separated, and the aqueous layer was extracted with ethyl acetate (150 mL×2). The combined organic layers were washed with brine (50 mL), dried over anhydrous sodium sulfate, filtered and concentrated under reduced pressure. The crude material was purified by silica gel chromatography (50-100% ethyl acetate in petroleum ether) to give 5-(3-(trans-4-(2-bromoethoxy)cyclohexyl)-4,4-dimethyl-5-oxo-2-thioxoimidazolidin-1-yl)-3-chloropicolinonitrile (2.3 g, 4.73 mmol, 93% yield) as a red solid. MS (ESI) m/z 485.1 [M+1]$^+$; $^1$H NMR (400 MHz, DMSO-d$_6$) δ 8.90-8.72 (m, 1H), 8.60-8.44 (m, 1H), 3.93-3.81 (m, 1H), 3.79-3.72 (m, 2H), 3.61-3.53 (m, 2H), 3.34 (br s, 1H), 2.90-2.74 (m, 2H), 2.12-2.02 (m, 2H), 1.76-1.67 (m, 2H), 1.59-1.52 (m, 6H), 1.44-1.28 (m, 2H).

2-((2R,6S)-4-(2-((trans-4-(3-(5-Chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a mixture of 2-((2S,6R)-2,6-dimethylpiperazin-1-yl)-N-(3-(2,4-dioxotetrahydropyrimidin-1(2H)-yl)-1-methyl-1H-indazol-7-yl)acetamide hydrochloride (0.122 g, 0.250 mmol, 1.1 equiv.) and 5-(3-(trans-4-(2-bromoethoxy)cyclohexyl)-4,4-dimethyl-5-oxo-2-thioxoimidazolidin-1-yl)-3-chloropicolinonitrile (0.100 g, 0.206 mmol, 1 equiv.) in N,N-dimethylformamide (1.5 mL, 0.14 M)) was added N,N-diisopropylethylamine (0.14 mL, 0.820 mmol, 4 equiv.) and sodium iodide (0.030 g, 0.210 mmol, 1 equiv.). The mixture was stirred at 50° C. After 12 h the reaction solution was poured into water (20 mL) and stirred for 1 min. The aqueous phase was extracted with ethyl acetate (2×20 mL). The combined organic layers were washed with brine (20 mL), dried over anhydrous sodium sulfate, filtered and concentrated. The crude material was purified by standard methods to give 2-((2R,6S)-4-(2-((trans-4-(3-(5-chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride (53.720 mg, 0.066 mmol, 32% yield) as a white solid. MS (ESI) m/z 818.3 [M+1]$^+$; $^1$H NMR (400 MHz, DMSO-d$_6$) δ 10.58 (s, 1H), 10.18-9.73 (m, 1H), 8.82 (d, J=2.0 Hz, 1H), 8.52 (d, J=2.0 Hz, 1H), 7.56 (d, J=8.0 Hz, 1H), 7.25-7.17 (m, 1H), 7.15-7.07 (m, 1H), 4.08 (s, 3H), 3.90 (t, J=6.8 Hz, 2H), 3.83 (br d, J=3.2 Hz, 3H), 3.43-3.33 (m, 4H), 3.31-3.20 (m, 3H), 2.90-2.84 (m, 2H), 2.78 (t, J=6.8 Hz, 2H), 2.53 (br s, 2H), 2.16-2.07 (m, 2H), 1.77-1.68 (m, 2H), 1.56 (s, 6H), 1.43-1.33 (m, 2H), 1.23 (br s, 6H).

Example 7: 2-((2R,6S)-4-(3-((trans-4-(3-(6-Cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

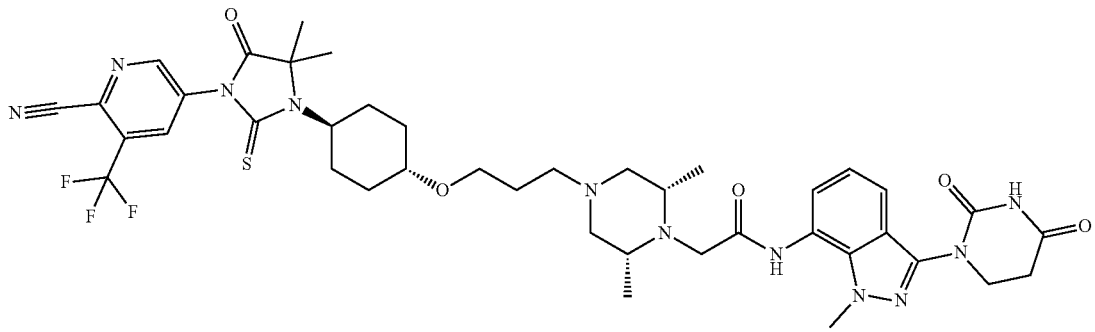 [SMILES: C[C@@H]1CN(CCCO[C@H]2CC[C@H](N3C(=S)N(c4cnc(C#N)c(C(F)(F)F)c4)C(=O)C3(C)C)CC2)C[C@H](C)N1CC(=O)Nc1cccc2c(N3CCC(=O)NC3=O)nn(C)c12]

trans-N,N-Dibenzyl-4-(3-((tetrahydro-2H-pyran-2-yl)oxy)propoxy)cyclohexan-1-amine. To a solution of trans-4-(dibenzylamino)cyclohexanol (60.00 g, 203.1 mmol, 1 equiv.) in xylenes (450 mL, 0.45 M) was added 2-(2-bromoethoxy)tetrahydro-2H-pyran (113.28 g, 507.75 mmol, 2.5 equiv.), tetra-N-butylammonium bromide (13.09 g, 40.62 mmol, 0.2 equiv.) and potassium hydroxide (52.42 g, 934.26 mmol, 4.6 equiv.) and the reaction solution was stirred at room temperature. After 24 h the reaction solution was diluted with ethyl acetate (500 mL) and washed with water (200 mL), brine (200 mL), dried over anhydrous sodium sulfate and concentrated. The crude material was purified by silica gel column chromatography (100% petroleum ether) to give trans-N,N-dibenzyl-4-(3-((tetrahydro-2H-pyran-2-yl)oxy)propoxy)cyclohexan-1-amine (40.0 g, 91.4 mmol, 45% yield) as a light yellow oil. MS (ESI) m/z 438.4 [M+1]$^+$; $^1$H NMR (400 MHz, CDCl$_3$) δ 7.38-7.32 (m, 4H), 7.31-7.28 (m, 4H), 7.24-7.22 (m, 2H), 4.61-4.57 (m, 1H), 3.88-3.84 (m, 2H), 3.63 (s, 4H), 3.55-3.52 (m, 4H), 3.51-3.16 (m, 1H), 2.54-2.09 (m, 1H), 2.08-2.07 (m, 2H), 1.92-1.90 (m, 2H), 1.61-1.60 (m, 2H), 1.59-1.57 (m, 6H), 1.55-1.53 (m, 2H), 1.38-1.16 (m, 2H)

trans-4-(3-((Tetrahydro-2H-pyran-2-yl)oxy)propoxy)cyclohexan-1-amine. To a solution of trans-N,N-dibenzyl-4-(3-((tetrahydro-2H-pyran-2-yl)oxy)propoxy)cyclohexan-1-amine (20.0 g, 45.7 mmol, 1 equiv.) in methanol (100 mL) was added 10% palladium on carbon (10.0 g, 9.39 mmol). The reaction flask was evacuated and purged with hydrogen gas three times and then stirred under hydrogen atmosphere (15 psi) at room temperature. After 12 h the reaction solution was filtered and the filtrate concentrated to provide trans-4-(3-((tetrahydro-2H-pyran-2-yl)oxy)propoxy)cyclohexan-1-amine (11.00 g, 42.74 mmol, 94% yield) as a light yellow oil. The material was carried forward without further purification. $^1$H NMR (400 MHz, DMSO-d$_6$) δ 4.52 (m, 1H), 3.79-3.61 (m, 2H), 3.50-3.30 (m, 4H), 3.18-3.05 (m, 1H), 1.94-1.83 (m, 2H), 1.77-1.65 (m, 6H), 1.64-1.55 (m, 1H), 1.53-1.38 (m, 4H), 1.20-0.91 (m, 4H).

Methyl 2-methyl-2-((trans-4-(3-((tetrahydro-2H-pyran-2-yl)oxy)propoxy)cyclohexyl)amino)propanoate. To a solution of trans-4-(3-((tetrahydro-2H-pyran-2-yl)oxy)propoxy)cyclohexan-1-amine (7.00 g, 27.2 mmol, 1 equiv.) and methyl 2-bromo-2-methyl-propanoate (12.5 mL, 108.79 mmol, 4 equiv.) in acetonitrile (10 mL) was added potassium iodide (0.451 g, 2.72 mmol, 0.1 equiv.) and potassium carbonate (7.518 g, 54.4 mmol, 2 equiv.). The reaction vessel was sealed and heated to 110° C. with stirring. After 12 h the reaction solution was filtered and concentrated. The crude material was purified by silica gel column chromatography (10-80% ethyl acetate in petroleum ether) to give methyl 2-methyl-2-((trans-4-(3-((tetrahydro-2H-pyran-2-yl)oxy)propoxy)cyclohexyl)amino)propanoate (8.00 g, 22.4 mmol, 82% yield) as a light yellow oil. MS (ESI) m/z 358.4 [M+1]$^+$.

5-(4,4-Dimethyl-5-oxo-3-(trans-4-(3-((tetrahydro-2H-pyran-2-yl)oxy)propoxy)cyclohexyl)-2-thioxoimidazolidin-1-yl)-3-(trifluoromethyl)picolinonitrile. To a solution of methyl 2-methyl-2-((trans-4-(3-((tetrahydro-2H-pyran-2-yl)oxy)propoxy)cyclohexyl)amino)propanoate (5.00 g, 14.0 mmol, 1 equiv.) and 5-isothiocyanato-3-(trifluoromethyl)pyridine-2-carbonitrile (6.41 g, 28.0 mmol, 2 equiv.) in ethyl acetate (50 mL, 0.28 M) was added N,N-diisopropylethylamine (4.62 mL, 28.0 mmol, 2 equiv.) and the reaction solution was stirred at 90° C. After 12 h the reaction solution was concentrated and purified by silica gel column chromatography (10-50% ethyl acetate in petroleum ether) to give 5-(4,4-dimethyl-5-oxo-3-(trans-4-(3-((tetrahydro-2H-pyran-2-yl)oxy)propoxy)cyclohexyl)-2-thioxoimidazolidin-1-yl)-3-(trifluoromethyl)picolinonitrile (7.00 g, 12.6 mmol, 90% yield) as a brown oil. $^1$H NMR (400 MHz, CDCl$_3$) δ 8.95 (s, 1H), 8.23 (s, 1H), 4.55-4.51 (m, 1H), 3.81-3.78 (m, 2H), 3.70-3.68 (m, 1H), 3.57-3.54 (m, 2H), 3.48-3.45 (m, 2H), 3.29-2.87 (m, 1H), 2.85 (d, J=10.8 Hz, 2H), 1.85-1.80 (m, 8H), 1.60 (s, 6H), 1.56-1.52 (m, 4H), 1.32-1.29 (m, 2H).

5-(3-(trans-4-(3-Hydroxypropoxy)cyclohexyl)-4,4-dimethyl-5-oxo-2-thioxoimidazolidin-1-yl)-3-(trifluoromethyl)picolinonitrile. To a solution of 5-(4,4-dimethyl-5-oxo-3-(trans-4-(3-((tetrahydro-2H-pyran-2-yl)oxy)propoxy)cyclohexyl)-2-thioxoimidazolidin-1-yl)-3-(trifluoromethyl)picolinonitrile (7.00 g, 12.6 mmol, 1 equiv.) in methanol (50 mL) was added 1 M hydrogen chloride (5.0 mL, 5 mmol) and the reaction solution was stirred at room temperature. After 2 h the reaction solution was diluted with saturated aqueous sodium bicarbonate (20 mL) and extracted with ethyl acetate (2×50 mL). The combined organic layers were washed with brine (50 mL), dried over anhydrous sodium sulfate and concentrated to give 5-(3-(trans-4-(3-hydroxypropoxy)cyclohexyl)-4,4-dimethyl-5-oxo-2-thioxoimidazolidin-1-yl)-3-(trifluoromethyl)picolinonitrile (5.00 g, 10.6 mmol, 84% yield) as a brown oil. MS (ESI) m/z 471.2 [M+1]$^+$.

5-(3-(trans-4-(3-Bromopropoxy)cyclohexyl)-4,4-dimethyl-5-oxo-2-thioxoimidazolidin-1-yl)-3-(trifluoromethyl)picolinonitrile. To a solution of 5-(3-(trans-4-(3-hydroxypropoxy)cyclohexyl)-4,4-dimethyl-5-oxo-2-thioxoimidazolidin-1-yl)-3-(trifluoromethyl)picolinonitrile (5.00 g, 10.6 mmol, 1 equiv.) in dichloromethane (50 mL) and N,N-dimethylformamide (5 mL) was added thionyl bromide (1.7 mL, 21.3 mmol, 2 equiv.) at 0° C. After stirring for 12 h the reaction solution was diluted with saturated aqueous sodium bicarbonate (20 mL) and extracted with dichloromethane (2×50 mL). the combined organic layers were washed with brine (30 mL), dried over anhydrous sodium sulfate and concentrated. The resulting crude material was purified by silica gel column chromatography (10-20% ethyl acetate in petroleum ether) to give 5-(3-(trans-4-(3-bromopropoxy)cyclohexyl)-4,4-dimethyl-5-oxo-2-thioxoimidazolidin-1-yl)-3-(trifluoromethyl)picolinonitrile as a light yellow solid. (ESI) m/z 535.1 [M+1]$^+$; $^1$H NMR (400 MHz, CDCl$_3$) δ 8.98 (d, J=2.0 Hz, 1H), 8.24 (d, J=2.0 Hz, 1H), 3.76-3.65 (m, 1H), 3.62 (t, J=5.6 Hz, 2H), 3.53 (t, J=6.4 Hz, 2H), 3.40-3.29 (m, 1H), 2.89 (s, 2H), 2.30-2.18 (m, 2H), 2.16-2.05 (m, 2H), 1.83 (d, J=12.4 Hz, 2H), 1.63 (s, 6H), 1.45-1.24 (m, 2H).

2-((2R,6S)-4-(3-((trans-4-(3-(6-Cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To the solution of 5-(3-(trans-4-(3-bromopropoxy)cyclohexyl)-4,4-dimethyl-5-oxo-2-thioxoimidazolidin-1-yl)-3-(trifluoromethyl)picolinonitrile (0.150 g, 0.28 mmol, 1 equiv.) and 2-((2R,6S)-2,6-dimethylpiperazin-1-yl)-N-(3-(2,4-dioxotetrahydropyrimidin-1(2H)-yl)-1-methyl-1H-indazol-7-yl)acetamide hydrobromide (0.208 g, 0.42 mmol, 1.5 equiv.) in N,N-dimethylformamide (1 mL, 0.28 M) was added N,N-diisopropylethylamine (0.49 mL, 2.81 mmol, 10 equiv.), the mixture was stirred at 50° C. After 12 h the reaction solution was filtered and purified by standard methods to give 2-((2R,6S)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (120 mg, 0.13 mmol, 48% yield) as a yellow solid. MS (ESI) m/z 866.3 [M+1]$^+$; $^1$H NMR (400 MHz, DMSO-d$_6$) δ 10.57 (s, 1H), 10.42-10.19 (m, 1H), 9.14 (s, 1H), 8.74 (s, 1H), 7.56 (d, J=8.4 Hz, 1H), 7.22 (d, J=7.2 Hz, 1H), 7.11 (t, J=7.6 Hz, 1H), 4.09 (s, 3H), 3.90 (t, J=6.4 Hz, 3H), 3.86-3.85 (m, 1H), 3.29-3.20 (m, 2H), 3.08 (d, J=1.2 Hz, 3H), 3.07-2.93 (m, 1H), 2.91-2.70 (m, 6H), 2.07 (d, J=10.4 Hz, 2H), 1.97 (d, J=2.8 Hz, 2H), 1.72 (d, J=10.4 Hz, 2H), 1.57 (s, 6H), 1.34-1.25 (m, 10H).

Example 8: 2-((2R,6S)-4-(3-((trans-4-(3-(4-Cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

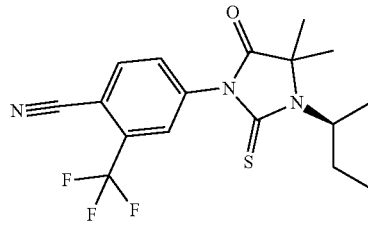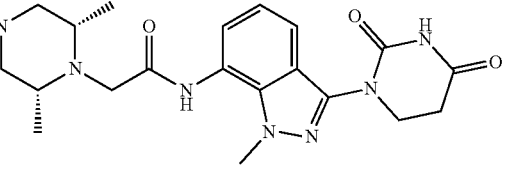

4-(4,4-Dimethyl-5-oxo-3-(trans-4-(3-((tetrahydro-2H-pyran-2-yl)oxy)propoxy)cyclohexyl)-2-thioxoimidazolidin-1-yl)-2-(trifluoromethyl)benzonitrile. To a solution of methyl 2-methyl-2-((trans-4-(3-((tetrahydro-2H-pyran-2-yl)oxy)propoxy)cyclohexyl)amino)propanoate (5.0 g, 14.0 mmol, 1 equiv.) and 4-isothiocyanato-2-(trifluoromethyl)benzonitrile (6.4 g, 28.0 mmol, 2 equiv.) in ethyl acetate (50 mL) was added N,N-diisopropylethylamine (4.6 mL, 28.0 mmol, 2 equiv.) and the reaction solution was stirred at 90° C. After 12 h the reaction solution was concentrated and purified by silica gel column chromatography (10-50% ethyl acetate in petroleum ether) to give 4-(4,4-dimethyl-5-oxo-3-(trans-4-(3-((tetrahydro-2H-pyran-2-yl)oxy)propoxy)cyclohexyl)-2-thioxoimidazolidin-1-yl)-2-(trifluoromethyl)benzonitrile (6.5 g, 11.7 mmol, 84% yield) as a brown oil. MS (ESI) m/z 554.4 [M+1]$^+$; $^1$H NMR (400 MHz, CDCl$_3$) δ 7.95 (d, J=8.4 Hz, 1H), 7.84 (d, J=2.0 Hz, 1H), 7.74-7.71 (m, 1H), 4.60-4.58 (m, 1H), 3.84-3.82 (m, 2H), 3.71-3.61 (m, 1H), 3.60-3.52 (m, 2H), 3.50-3.49 (m, 2H), 3.47-3.32 (m, 1H), 2.22-2.20 (m, 2H), 2.19 (d, J=12.0 Hz, 2H), 1.88-1.87 (m, 6H), 1.85-1.84 (m, 2H), 1.60 (s, 6H), 1.56-1.55 (m, 2H), 1.54-1.35 (m, 2H).

4-(3-(trans-4-(3-Hydroxypropoxy)cyclohexyl)-4,4-dimethyl-5-oxo-2-thioxoimidazolidin-1-yl)-2-(trifluoromethyl)benzonitrile. To a solution of 4-(4,4-dimethyl-5-oxo-3-(trans-4-(3-((tetrahydro-2H-pyran-2-yl)oxy)propoxy)cyclohexyl)-2-thioxoimidazolidin-1-yl)-2-(trifluoromethyl)benzonitrile (6.5 g, 11.7 mmol) in methanol (50 mL) was added 1 M aqueous hydrochloric acid (5.0 mL, 5 mmol) and the reaction solution was stirred at room temperature. After 2 h the reaction solution was diluted with saturated aqueous sodium bicarbonate (30 mL) and extracted with ethyl acetate (2×50 mL). The combined organic layers were washed with brine, dried over anhydrous sodium sulfate and concentrated to give 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.0 g, 10.7 mmol, 91% yield) as a brown oil. MS (ESI) m/z 470.2 [M+1]$^+$.

4-(3-(trans-4-(3-Bromopropoxy)cyclohexyl)-4,4-dimethyl-5-oxo-2-thioxoimidazolidin-1-yl)-2-(trifluoromethyl)benzonitrile. To a solution of give 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.0 g, 10.7 mmol, 1 equiv.) in dichloromethane (50 mL) and N,N-dimethylformamide (5 mL) was added thionyl bromide (1.7 mL, 21.3 mmol, 4 equiv.) at 0° C. and the reaction solution was gradually warmed to room temperature. After 12 h the reaction solution was diluted with saturated aqueous sodium bicarbonate (50 mL) and extracted with ethyl acetate (2×50 mL). The combined organic layers were washed with brine, dried over anhydrous sodium sulfate and concentrated. The resulting crude material was purified by silica gel column chromatography to give 4-(3-(trans-4-(3-bromopropoxy)cyclohexyl)-4,4-dimethyl-5-oxo-2-thioxoimidazolidin-1-yl)-2-(trifluoromethyl)benzonitrile (5.0 g, 9.4 mmol, 88% yield) as a light yellow oil. MS (ESI) m/z 534.1 [M+1]$^+$; $^1$H NMR (400 MHz, CDCl$_3$) δ7.95 (d, J=8.4 Hz, 1H), 7.84 (d, J=2.0 Hz, 1H), 7.74-7.71 (m, 1H), 3.71-3.61 (m, 1H), 3.60-3.53 (m, 2H), 3.52 (t, J=6.4 Hz, 2H), 3.35-3.32 (m, 1H), 2.21 (d, J=12.0 Hz, 2H), 2.19-2.05 (m, 2H), 1.83 (d, J=12.0 Hz, 2H), 1.65 (s, 2H), 1.60 (s, 6H), 1.35-1.32 (m, 2H).

2-((2R,6S)-4-(3-((trans-4-(3-(4-Cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To the solution of 4-(3-(trans-4-(3-bromopropoxy)cyclohexyl)-4,4-dimethyl-5-oxo-2-thioxoimidazolidin-1-yl)-2-(trifluoromethyl)benzonitrile (0.150 g, 0.28 mmol, 1 equiv.) and 2-((2R,6S)-2,6-dimethylpiperazin-1-yl)-N-(3-(2,4-dioxotetrahydropyrimidin-1(2H)-yl)-1-methyl-1H-indazol-7-yl)acetamide hydrobromide (0.208 g, 0.420 mmol, 1.5 equiv.) in N,N-dimethylformamide (1 mL, 0.28 M) was added N,N-diisopropylethylamine (0.49 mL, 2.82 mmol, 10 equiv.). The reaction solution was heated to 50° C. with stirring. After 13 h the reaction solution was filtered and purified by standard methods to provide 2-((2R,6S)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (106.24 mg, 0.12 mmol, 43% yield,) as a yellow solid. MS (ESI) m/z: 865.2 [M+1]$^+$; $^1$H NMR (400 MHz, DMSO-d$_6$) δ 10.58 (s, 1H), 10.31-10.07 (m, 1H), 8.34 (d, J=8.0 Hz, 1H), 8.19 (d, J=1.6 Hz, 1H), 7.98-7.96 (m, 1H), 7.56 (d, J=8.0 Hz, 1H), 7.21 (d, J=7.2 Hz, 1H), 7.13-7.09 (m, 1H), 4.09 (s, 3H), 3.90 (t, J=6.8 Hz, 2H), 3.88-3.79 (m, 2H), 3.52-3.49 (m, 4H), 3.32-3.22 (m, 2H), 3.08 (d, J=1.2 Hz, 2H), 3.02-2.90 (m, 1H), 2.88-2.76 (m, 5H), 2.07-2.02 (m, 2H), 2.01-1.96 (m, 2H), 1.73-1.70 (m, 2H), 1.55 (s, 6H), 1.33-1.27 (m, 8H).

Example 9: 2-((2R,6S)-4-(3-((trans-4-(3-(3-Chloro-4-cyanophenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

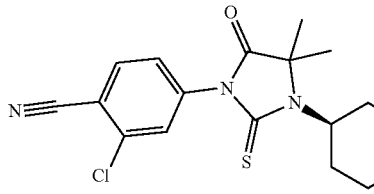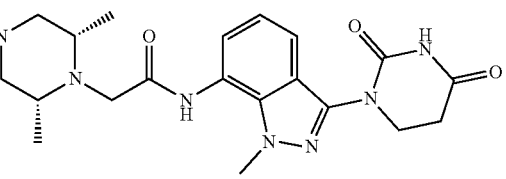

2-Chloro-4-(4,4-dimethyl-5-oxo-3-(trans-4-(3-((tetrahydro-2H-pyran-2-yl)oxy)propoxy)cyclohexyl)-2-thioxoimidazolidin-1-yl)benzonitrile. To a solution of methyl 2-methyl-2-((trans-4-(3-((tetrahydro-2H-pyran-2-yl)oxy)propoxy)cyclohexyl)amino)propanoate (10.0 g, 28.0 mmol, 1 equiv.) in ethyl acetate (100 mL, 0.28 M) was added 2-chloro-4-isothiocyanatobenzonitrile (10.9 g, 56.0 mmol, 2 equiv.) and triethylamine (7.8 mL, 56.0 mmol, 2 equiv.) and the reaction solution was stirred at 80° C. After 8 h the reaction solution was diluted with water (100 mL) and extracted with ethyl acetate (3×40 mL). The combined organic layers were washed brine (40 mL), dried over anhydrous sodium sulfate and concentrated. The crude material was purified by silica gel column chromatography (9-20% ethyl acetate in petroleum ether) to give 2-chloro-4-(4,4-dimethyl-5-oxo-3-(trans-4-(3-((tetrahydro-2H-pyran-2-yl)oxy)propoxy)cyclohexyl)-2-thioxoimidazolidin-1-yl)benzonitrile (8.50 g, 16.3 mmol, 58% yield) as a red oil. MS (ESI) m/z 542.2 [M+23]⁺.

4-(3-(trans-4-(3-Hydroxypropoxy)cyclohexyl)-4,4-dimethyl-5-oxo-2-thioxoimidazolidin-1-yl)-2-(trifluoromethyl)benzonitrile. To a solution of 2-chloro-4-(4,4-dimethyl-5-oxo-3-(trans-4-(3-((tetrahydro-2H-pyran-2-yl)oxy)propoxy)cyclohexyl)-2-thioxoimidazolidin-1-yl)benzonitrile (6.80 g, 13.1 mmol) in methanol (50 mL) was added 1 M hydrochloric acid (5 mL, 13.07 mmol) and the reaction solution was stirred at 25° C. After 2 h the reaction solution was diluted with saturated aqueous sodium bicarbonate (100 mL) and extracted with ethyl acetate (3×50 mL). the combined organic layers were washed with brine, dried over anhydrous sodium sulfate and concentrated. The resulting crude material was purified by silica gel column chromatography (20-70% ethyl acetate in petroleum ether) to give 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.60 g, 12.8 mmol, 98% yield) as a yellow solid. ¹H NMR (400 MHz, DMSO-d₆) δ 8.12 (d, J=8.4 Hz, 1H), 7.92 (d, J=1.6 Hz, 1H), 7.61 (dd, J=2.0, 8.4 Hz, 1H), 3.89-3.76 (m, 1H), 3.48-3.42 (m, 4H), 3.24-3.16 (m, 1H), 2.79 (d, J=11.2 Hz, 2H), 2.04 (d, J=10.8 Hz, 2H), 1.70 (d, J=10.8 Hz, 2H), 1.65-1.59 (m, 2H), 1.53 (s, 6H), 1.34-1.25 (m, 2H).

4-(3-(trans-4-(3-Bromopropoxy)cyclohexyl)-4,4-dimethyl-5-oxo-2-thioxoimidazolidin-1-yl)-2-chlorobenzonitrile. To a solution of 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.8 g, 13.3 mmol) in dichloromethane (50 mL) and N,N-dimethylformamide (5 mL) was added thionyl bromide (2.1 mL, 26.6 mmol, 2 equiv.) at 0° C. After 8 h the reaction solution was diluted with saturated aqueous sodium bicarbonate (100 mL) and extracted with ethyl acetate (3×40 mL). The combined organic layers were washed with brine, dried over anhydrous sodium sulfate and concentrated. The crude material was purified by silica gel column chromatography (0-35% ethyl acetate in petroleum ether) to give 4-(3-(trans-4-(3-bromopropoxy)cyclohexyl)-4,4-dimethyl-5-oxo-2-thioxoimidazolidin-1-yl)-2-chlorobenzonitrile (4.8 g, 9.6 mmol, 72% yield) as a yellow solid. ¹H NMR (400 MHz, DMSO-d₆) δ 8.14-8.11 (m, 1H), 7.93 (d, J=1.6 Hz, 1H), 7.61 (dd, J=1.6, 8.0 Hz, 1H), 3.84 (s, 1H), 3.58-3.51 (m, 4H), 3.27-3.21 (m, 1H), 2.81 (d, J=11.6 Hz, 2H), 2.06 (m, 2H), 1.71 (d, J=11.6 Hz, 2H), 1.53 (s, 6H), 1.33 (d, J=13.2 Hz, 2H).

2-((2R,6S)-4-(3-((trans-4-(3-(3-Chloro-4-cyanophenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a mixture of 4-(3-(trans-4-(3-bromopropoxy)cyclohexyl)-4,4-dimethyl-5-oxo-2-thioxoimidazolidin-1-yl)-2-chlorobenzonitrile (0.100 g, 0.200 mmol, 1 equiv.) in N,N-dimethylformamide (1 mL, 0.2 M) was added 2-((2R,6S)-2,6-dimethylpiperazin-1-yl)-N-(3-(2,4-dioxotetrahydropyrimidin-1(2H)-yl)-1-methyl-1H-indazol-7-yl)acetamide (0.149 g, 0.300 mmol, 1.5 equiv.) and N,N-diisopropylethylamine (0.17 mL, 1 mmol, 5 equiv.), the mixture was stirred at 50° C. After 16 h the reaction solution was filtered and purified by standard methods to give 2-((2R,6S)-4-(3-((trans-4-(3-(3-chloro-4-cyanophenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (0.139 g, 0.166 mmol, 82% yield) as a white solid. MS (ESI) m/z 831.3 [M+H]⁺; ¹H NMR (400 MHz, DMSO-d₆) δ 10.83 (s, 1H), 8.14 (d, J=8.4 Hz, 1H), 7.93 (d, J=2.0 Hz, 1H), 7.63-7.56 (m, 3H), 7.20 (d, J=8.4 Hz, 2H), 3.83 (dd, J=5.2, 11.6 Hz, 4H), 3.65-3.57 (m, 4H), 3.51 (t, J=5.6 Hz, 2H), 3.35-3.19 (m, 2H), 3.10 (s, 2H), 2.87-2.77 (m, 2H), 2.73-2.62 (m, 2H), 2.25-2.16 (m, 1H), 2.15-1.87 (m, 6H), 1.72 (d, J=12.0 Hz, 2H), 1.54 (s, 6H), 1.33 (m, 2H), 1.24 (s, 6H).

Example 10: 2-((2R,6S)-4-(3-(trans-4-(3-(6-Cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

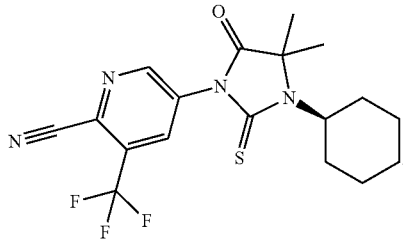

5-(3-(trans-4-(3-Hydroxypropyl)cyclohexyl)-4,4-dimethyl-5-oxo-2-thioxoimidazolidin-1-yl)-3-(trifluoromethyl)picolinonitrile. To a solution of methyl 2-((trans-4-(3-hydroxypropyl)cyclohexyl)amino)-2-methylpropanoate (1.47 g, 5.71 mmol, 1 equiv.) and 5-isothiocyanato-3-(trifluoromethyl)picolinonitrile (1.44 g, 6.28 mmol, 1.1 equiv.) in ethyl acetate (15 mL, 0.38 M) was added N,N-diisopropylethylamine (2.21 g, 17.13 mmol, 3 equiv.) and the reaction solution was stirred 80° C. After 16 h the reaction solution was concentrated under reduced pressure and the crude material was purified by standard methods to afford 5-(3-(trans-4-(3-hydroxypropyl)cyclohexyl)-4,4-dimethyl-5-oxo-2-thioxoimidazolidin-1-yl)-3-(trifluoromethyl)picolinonitrile (1.80 g, 3.96 mmol, 69% yield) as brown solid. MS (ESI) m/z 455.0 [M+1]$^+$; $^1$H NMR (400 MHz, CDCl$_3$) δ 8.99 (d, J=2.0 Hz, 1H), 8.25 (d, J=2.0 Hz, 1H), 3.80-3.72 (m, 1H), 3.65 (t, J=6.4 Hz, 2H), 2.72-2.70 (m, 2H), 1.97-1.94 (m, 2H), 1.85-1.82 (m, 2H), 1.63 (s, 6H), 1.58-1.54 (m, 1H), 1.42-1.29 (m, 4H), 1.12-1.02 (m, 2H).

5-(3-(trans-4-(3-Bromopropyl)cyclohexyl)-4,4-dimethyl-5-oxo-2-thioxoimidazolidin-1-yl)-3-(trifluoromethyl)picolinonitrile. To a solution of 5-(3-(trans-4-(3-hydroxypropyl)cyclohexyl)-4,4-dimethyl-5-oxo-2-thioxoimidazolidin-1-yl)-3-(trifluoromethyl)picolinonitrile (1.80 g, 3.96 mmol, 1 equiv.) in dichloromethane (18 mL, 0.22 M) and N,N-dimethylformamide (1.8 mL) was added thionyl bromide (1.650 g, 7.92 mmol, 2 equiv.) slowly at 0° C. The reaction solution was stirred at 0° C. After 12 h the reaction solution was diluted with water (30 mL) and extracted with dichloromethane (2×25 mL). The combined organic layers were dried over anhydrous sodium sulfate and concentrated. The crude residue was purified by silica gel column chromatography (5-80% ethyl acetate in hexanes) to give 5-(3-(trans-4-(3-bromopropyl)cyclohexyl)-4,4-dimethyl-5-oxo-2-thioxoimidazolidin-1-yl)-3-(trifluoromethyl)picolinonitrile (1.75 g, 3.38 mmol, 85% yield) as brown solid. MS (ESI) m/z 516.9 [M+1]$^+$; $^1$H NMR (400 MHz, CDCl$_3$) δ 8.99 (d, J=2.0 Hz, 1H), 8.25 (d, J=2.0 Hz, 1H), 3.80-3.71 (m, 1H), 3.42 (t, J=6.8 Hz, 2H), 2.74-2.72 (m, 2H), 1.96-1.79 (m, 6H), 1.63 (s, 6H), 1.40-1.33 (m, 3H), 1.13-1.04 (m, 2H).

2-((2R,6S)-4-(3-(trans-4-(3-(6-Cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To the solution of 5-(3-(trans-4-(3-bromopropyl)cyclohexyl)-4,4-dimethyl-5-oxo-2-thioxoimidazolidin-1-yl)-3-(trifluoromethyl)picolinonitrile (0.150 g, 0.28 mmol, 1 equiv.) and 2-((2R,6S)-2,6-dimethylpiperazin-1-yl)-N-(3-(2,4-dioxotetrahydropyrimidin-1(2H)-yl)-1-methyl-1H-indazol-7-yl)acetamide hydrobromide (0.214 g, 0.43 mmol, 1.5 equiv.) in N,N-dimethylformamide (1 mL, 0.28 M) was added N,N-diisopropylethylamine (0.5 mL, 2.90 mmol, 10 equiv.). The reaction solution was heated to 50° C. with stirring. After 12 h the reaction solution was filtered and concentrated. The crude material was purified by standard methods to provide 2-((2R,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (74.98 mg, 0.08 mmol, 30% yield) as a yellow solid. MS (ESI) m/z 850.3 [M+1]$^+$; $^1$H NMR (400 MHz, DMSO-d$_6$) δ 10.58 (s, 1H), 10.31-10.12 (m, 1H), 9.14 (s, 1H), 8.74 (s, 1H), 7.55 (d, J=8.4 Hz, 1H), 7.20 (d, J=6.8 Hz, 1H), 7.13-7.09 (m, 1H), 4.08 (s, 3H), 3.90 (t, J=6.4 Hz, 3H), 3.86-3.82 (m, 1H), 3.02-2.95 (m, 3H), 2.95-2.86 (m, 1H), 2.77 (t, J=6.4 Hz, 5H), 1.86-1.71 (m, 7H), 1.57 (s, 6H), 1.25-1.08 (m, 12H).

Example 11: 2-((2S,6R)-4-(3-(trans-4-(3-(3-Chloro-4-cyanophenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

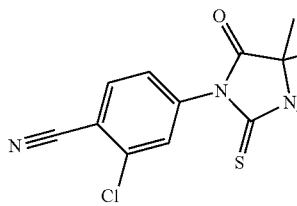 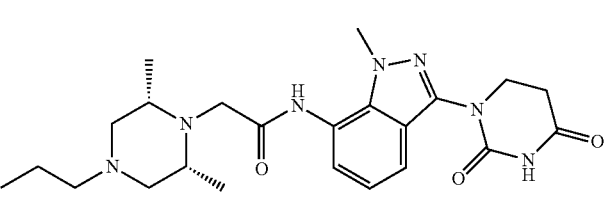

2-Chloro-4-(3-(trans-4-(3-hydroxypropyl)cyclohexyl)-4,4-dimethyl-5-oxo-2-thioxoimidazolidin-1-yl)benzonitrile To a solution of methyl 2-((trans-4-(3-hydroxypropyl)cyclohexyl)amino)-2-methylpropanoate (1.31 g, 5.1 mmol, 1 equiv.) and 2-chloro-4-isothiocyanatobenzonitrile (1.08 g, 5.57 mmol, 1.1 equiv.) in ethyl acetate (25 mL) was added N,N-diisopropylethylamine (2.51 mL, 15.18 mmol, 3 equiv.) and the reaction mixture was stirred at 80° C. After 18 h the reaction solution was concentrated and purified by column chromatography (15-50% ethyl acetate in petroleum ether) to afford 2-chloro-4-(3-(trans-4-(3-hydroxypropyl)cyclohexyl)-4,4-dimethyl-5-oxo-2-thioxoimidazolidin-1-yl)benzonitrile (1.26 g, 3.01 mmol, 59% yield) as a brown oil. MS (ESI) m/z 420.1 [M+1]$^+$.

Example 12: 2-((2R,6S)-4-(3-(trans-4-(3-(5-Chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride

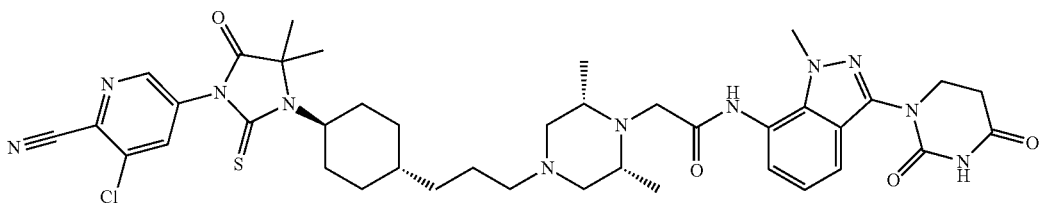 [SMILES: C[C@@H]1CN(CCC[C@H]2CC[C@H](N3C(=S)N(c4cnc(C#N)c(Cl)c4)C(=O)C3(C)C)CC2)C[C@H](C)N1CC(=O)Nc1cccc2c(N3CCC(=O)NC3=O)nn(C)c12]

4-(3-(trans-4-(3-Bromopropyl)cyclohexyl)-4,4-dimethyl-5-oxo-2-thioxoimidazolidin-1-yl)-2-chlorobenzonitrile. To a solution of 2-chloro-4-(3-(trans-4-(3-hydroxypropyl)cyclohexyl)-4,4-dimethyl-5-oxo-2-thioxoimidazolidin-1-yl)benzonitrile (1.26 g, 3.01 mmol) in N,N-dimethylformamide (0.30 mL) and dichloromethane (3 mL) was added thionyl bromide (1.88 g, 9.03 mmol, 3 equiv.) slowly at 0° C. After 12 h the reaction solution was concentrated under reduced pressure and purified by silica gel column chromatography (15-30% ethyl acetate in petroleum ether) to give 4-(3-(trans-4-(3-bromopropyl)cyclohexyl)-4,4-dimethyl-5-oxo-2-thioxoimidazolidin-1-yl)-2-chlorobenzonitrile (1.21 g, 2.50 mmol, 83% yield) as yellow solid. $^1$H NMR (400 MHz, CDCl$_3$) δ 7.79 (d, J=8.4 Hz, 1H), 7.58 (d, J=2.0 Hz, 1H), 7.42 (dd, J=8.4, 2.0 Hz, 1H), 3.87 (m, 1H), 3.43 (t, J=6.8 Hz, 2H), 2.70 (s, 2H), 1.94-1.82 (m, 6H), 1.59 (s, 6H), 1.39-1.36 (m, 3H), 1.12-1.03 (m, 2H).

2-((2S,6R)-4-(3-(trans-4-(3-(3-Chloro-4-cyanophenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a solution of 4-(3-(trans-4-(3-bromopropyl)cyclohexyl)-4,4-dimethyl-5-oxo-2-thioxoimidazolidin-1-yl)-2-chlorobenzonitrile (0.100 g, 0.210 mmol) and 2-((2S,6R)-2,6-dimethylpiperazin-1-yl)-N-(3-(2,4-dioxotetrahydropyrimidin-1(2H)-yl)-1-methyl-1H-indazol-7-yl)acetamide hydrobromide (0.143 g, 0.290 mmol, 1.4 equiv.) in N,N-dimethylformamide (2 mL, 0.1 M) was added N,N-diisopropylethylamine (0.134 g, 1.040 mmol, 5 equiv.) and the reaction mixture was stirred for 12 hours at 50° C. The reaction solution was concentrated under reduced pressure and purified by standard methods to afford 2-((2S,6R)-4-(3-(trans-4-(3-(3-chloro-4-cyanophenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (0.083 g, 0.097 mmol, 47% yield) as a yellow solid. MS (ESI) m/z 815.4 [M+1]$^+$. $^1$H NMR (400 MHz, DMSO-d$_6$) δ 11.36 (s, 1H), 10.58 (s, 1H), 8.14-8.12 (d, J=8.4 Hz, 1H), 7.93-7.92 (d, J=2.0 Hz, 1H), 7.62-7.56 (m, 2H), 7.24-7.22 (d, J=7.2 Hz, 1H), 7.14-7.10 (m, 1H), 4.10 (s, 3H), 3.92-3.89 (m, 4H), 3.84-3.80 (m, 2H), 3.62-3.58 (m, 2H), 3.02 (s, 4H), 2.79-2.67 (m, 5H), 1.85-1.71 (m, 6H), 1.53 (s, 6H), 1.32-1.22 (m, 9H), 1.13-1.04 (m, 2H).

3-Chloro-5-(3-(trans-4-(3-hydroxypropyl)cyclohexyl)-4,4-dimethyl-5-oxo-2-thioxoimidazolidin-1-yl)picolinonitrile. A mixture of methyl 3-chloro-5-isothiocyanato-pyridine-2-carbonitrile (1.600 g, 8.18 mmol, 1 equiv.) and methyl 2-((trans-4-(3-hydroxypropyl)cyclohexyl)amino)-2-methylpropanoate (2.320 g, 9 mmol, 1.1 equiv.) in ethyl acetate (100 mL) was added triethylamine (2.28 mL, 16.36 mmol, 2 equiv.). The reaction was stirred at 90° C. After 6 h the reaction solution was concentrated and purified by silica gel column chromatography (10-100% ethyl acetate in petroleum ether) to give 3-chloro-5-(3-(trans-4-(3-hydroxypropyl)cyclohexyl)-4,4-dimethyl-5-oxo-2-thioxoimidazolidin-1-yl)picolinonitrile (2.000 g, 4.75 mmol, 58% yield) as a yellow solid. MS (ESI) m/z 421.2 [M+1]$^+$; $^1$H NMR (400 MHz, CDCl$_3$) δ 8.67-8.50 (m, 1H), 7.98-7.83 (m, 1H), 3.80-3.48 (m, 4H), 2.75-2.52 (m, 2H), 1.93-1.60 (m, 6H), 1.51-1.28 (m, 3H), 1.27-1.15 (m, 5H), 1.06-0.89 (m, 3H).

5-(3-(trans-4-(3-Bromopropyl)cyclohexyl)-4,4-dimethyl-5-oxo-2-thioxoimidazolidin-1-yl)-3-chloropicolinonitrile. To a solution of 3-chloro-5-(3-(trans-4-(3-hydroxypropyl)cyclohexyl)-4,4-dimethyl-5-oxo-2-thioxoimidazolidin-1-yl)picolinonitrile (2.000 g, 4.75 mmol, 1 equiv.) in dichloromethane (5 mL, 0.1 M) and N,N-dimethylformamide (0.50 mL) was added thionyl bromide (0.61 mL, 9.5 mmol, 2 equiv.) at 0° C. The reaction solution was stirred at 25° C. After 16 h the pH of the reaction solution was adjusted to 8 by addition of saturated sodium carbonate. The aqueous phase was extracted with ethyl acetate (2×100 mL). The combined organic layers were washed with brine (25 mL), dried over anhydrous sodium sulfate, filtered and concentrated. The crude material was purified by silica gel column chromatography (50-100% ethyl acetate in petroleum ether) to give 5-(3-(trans-4-(3-bromopropyl)cyclohexyl)-4,4-dimethyl-5-oxo-2-thioxoimidazolidin-1-yl)-3-chloropicolinonitrile (1.600 g, 3.31 mmol, 70% yield) as a red solid. MS (ESI) m/z 483.1 [M+1]$^+$; $^1$H NMR (400 MHz, CDCl$_3$) δ 8.73-8.50 (m, 1H), 7.98-7.82 (m, 1H), 3.78-3.65 (m, 1H), 3.37-3.29 (m, 2H), 2.77-2.49 (m, 2H), 1.93-1.80 (m, 4H), 1.57-1.52 (m, 6H), 1.30 (br t, J=5.6 Hz, 3H), 1.08-0.97 (m, 2H).

2-((2R,6S)-4-(3-(trans-4-(3-(5-Chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a mixture of 5-(3-(trans-4-(3-bromopropyl)cyclohexyl)-4,4-dimethyl-5-oxo-2-thioxoimidazolidin-1-yl)-3-chloropicolinonitrile (120 mg, 0.25 mmol, 1 equiv.), 2-((2R,6S)-2,6-dimethylpiperazin-1-yl)-N-(3-(2,4-dioxotetrahydropyrimidin-1(2H)-yl)-1-methyl-1H-indazol-7-yl)acetamide hydrobromide (184 mg, 0.37 mmol, 1.5 equiv.) and in N,N-dimethylformamide (4 mL, 0.06 M) was added N,N-diisopropylethylamine (96 mg, 0.74 mmol, 3 equiv.). The mixture was stirred at 60° C. After 16 h the reaction solution was filtered and purified by standard methods to provide 2-((2R,6S)-4-(3-(trans-4-(3-(5-chloro-6-cyanopyridin-3-yl)-5,5-dimethyl-4-oxo-2-thioxo-imidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide hydrochloride (56 mg, 0.09 mmol, 27% yield) as a yellow solid. MS (ESI) m/z 816.3 [M+H]$^+$; $^1$H NMR (400 MHz, DMSO-d$_6$) δ 10.68-10.49 (m, 1H), 8.98-8.72 (m, 1H), 8.59-8.35 (m, 1H), 7.69-7.50 (m, 1H), 7.35-6.97 (m, 2H), 4.15-4.07 (m, 3H), 3.94-3.87 (m, 3H), 3.86-3.78 (m, 3H), 3.65-3.53 (m, 3H), 3.08-2.98 (m, 2H), 2.86-2.67 (m, 5H), 1.91-1.67 (m, 7H), 1.61-1.52 (m, 6H), 1.41-1.05 (m, 12H).

Example 13: 2-((2R,4s,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride equiv.) in THF (100 mL) dropwise at 0° C. The mixture was stirred at 0° C. for 30 min. (2S,6R)-1-benzyl-2,6-dimethylpiperidin-4-one (30.00 g, 138.1 mmol, 1 equiv.) in THF (200 mL) was added to above solution dropwise and the reaction solution was warmed to room temperature. After 12 h the reaction solution was neutralized by addition of ammonium chloride saturated solution and poured into ice-water (200 mL). The aqueous phase was extracted with ethyl acetate (3×500 mL). The combined organic layers were washed with brine (300 mL), dried with anhydrous sodium sulfate, filtered and concentrated. The crude material was purified by flash silica gel chromatography (2.0% ethyl acetate in petroleum ether) (petroleum ether:ethyl acetate=3:1, Rf: 0.65) and then re-purified by semi-preparative reverse phase HPLC (55-85% acetonitrile+0.05% ammonium hydroxide in water, over 20 min). The collected fraction was concentrated, and the aqueous phase was extracted with ethyl acetate (3×500 mL). The combined organic layers were washed with brine (300 mL), dried with anhydrous sodium sulfate, filtered and concentrated to give ethyl 2-((2R,6S)-1-benzyl-2,6-dimethylpiperidin-4-ylidene)acetate (11.7 g, 40.7 mmol, 30% yield) as a yellow oil. MS (ESI) m/z 288.2 [M+1]$^+$; $^1$H NMR (400 MHz, CDCl$_3$) δ 7.45-7.35 (m, 2H), 7.30 (t, J=7.6 Hz, 2H), 7.26-7.16 (m, 1H), 5.63 (s, 1H), 4.15 (q, J=7.2 Hz, 2H), 3.82 (s, 2H), 3.57 (dd, J=2.8, 14.0 Hz, 1H), 2.84-2.62 (m, 2H), 2.29-2.08 (m, 3H), 1.33-1.23 (m, 3H), 1.14 (dd, J=6.4, 16.4 Hz, 6H).

tert-Butyl (2S,6R)-4-(2-ethoxy-2-oxoethyl)-2,6-dimethylpiperidine-1-carboxylate. To a solution of ethyl 2-((2R,6S)-1-benzyl-2,6-dimethylpiperidin-4-ylidene)acetate (5.300 g, 18.44 mmol, 1 equiv.) and di-tert-butyl dicarbonate

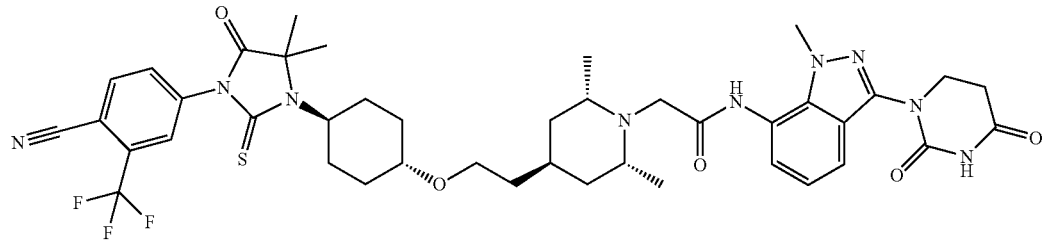 [SMILES: C[C@@H]1C[C@@H](CCO[C@H]2CC[C@H](N3C(=S)N(c4ccc(C#N)c(C(F)(F)F)c4)C(=O)C3(C)C)CC2)C[C@H](C)N1CC(=O)Nc1cccc2c(N3CCC(=O)NC3=O)nn(C)c12]

(6.037 g, 27.66 mmol, 1.5 equiv.) in THF (80 mL, 0.23 M) was added 10% Palladium on carbon (1.500 g, 1.84 mmol, 10 mol %) under nitrogen. The reaction mixture was stirred at room temperature for 12 hours under hydrogen (50 psi). The reaction mixture was filtered and concentrated to give a residue which was purified by flash silica gel chromatography (1% ethyl acetate in petroleum ether, petroleum ether:ethyl acetate=5:1) to give tert-butyl (2S,6R)-4-(2-ethoxy-2-oxoethyl)-2,6-dimethylpiperidine-1-carboxylate (2.630 g, 8.784 mmol, 48% yield) as a yellow oil. $^1$H NMR (400 MHz, CDCl$_3$) δ 4.26 (s, 1H), 4.21 (m, 1H), 4.17-4.10 (m, 2H), 2.26-2.18 (m, 2H), 2.13-2.05 (m, 1H), 1.99-1.84 (m, 1H), 1.66-1.55 (m, 1H), 1.47 (s, 9H), 1.36-1.29 (m, 1H), 1.29-1.25 (m, 3H), 1.24-1.19 (m, 6H), 1.15-1.02 (m, 2H).

tert-Butyl (2S,6R)-4-(2-hydroxyethyl)-2,6-dimethylpiperidine-1-carboxylate. To a solution of lithium aluminumhydride (0.500 g, 13.18 mmol, 1.5 equiv.) in THF (10 mL) was added a solution of tert-butyl (2S,6R)-4-(2-ethoxy-2-oxoethyl)-2,6-dimethylpiperidine-1-carboxylate (2.630 g, 8.780 mmol, 1 equiv.) in THF (40 mL) at 0° C. The reaction solution was slowly warmed to room temperature over 1 h. The reaction solution was quenched by addition water 0.5

(2S,6R)-1-Benzyl-2,6-dimethylpiperidin-4-one. To a solution of 3-oxopentanedioic acid (100.0 g, 684.5 mmol, 1 equiv.) in water (200 mL) was added acetaldehyde (150.8 g, 1368.9 mmol, 2 equiv.) at 20° C. The reaction was stirred at 20° C. for 20 min and then cooled to 0° C. and phenylmethanamine (74.61 mL, 684.5 mmol, 1 equiv.) was added dropwise. The reaction solution was allowed to warm to room temperature and stirred for 48 h. The reaction solution was extracted with ethyl acetate 3000 mL (1000 mL×3) and the combined organic layers were washed with brine 500 mL. The organic layers were dried with anhydrous sodium sulfate, filtrated and concentrated. The crude material was purified by silica gel column chromatography to give (2S,6R)-1-benzyl-2,6-dimethylpiperidin-4-one (27.70 g, 127.5 mmol, 19% yield) as a yellow oil. $^1$H NMR (400 MHz, CDCl$_3$) δ 7.42 (d, J=7.2 Hz, 2H), 7.37-7.29 (m, 2H), 7.27-7.20 (m, 1H), 3.86 (s, 2H), 3.17-3.09 (qd, J=6.4, 13.2 Hz, 2H), 2.42-2.28 (m, 4H), 1.16 (d, J=6.4 Hz, 6H).

Ethyl 2-((2R,6S)-1-benzyl-2,6-dimethylpiperidin-4-ylidene)acetate. To a solution of sodium hydride (8.283 g, 207.1 mmol, 1.5 equiv.) in THF (50 mL) was added ethyl 2-(diethoxyphosphoryl)acetate (40.23 g, 179.5 mmol, 1.3 mL, 15% sodium hydroxide solution (1 mL) and water 1.5 mL. The slurry was stirred for 0.5 h, filtered and concentrated in vacuo. The crude material was diluted with water 100 mL and extracted with ethyl acetate 100 mL×3. The combined organic layers were washed with brine 100 mL, dried over anhydrous sodium sulfate, filtered and concentrated. The residue was purified by silica gel column chromatography (20% ethyl acetate in petroleum ether) to provide tert-butyl (2S,6R)-4-(2-hydroxyethyl)-2,6-dimethylpiperidine-1-carboxylate (2.180 g, 8.470 mmol, 96% yield) as a yellow solid. $^1$H NMR (400 MHz, CDCl$_3$) δ 4.40-4.25 (m, 1H), 4.24-4.07 (m, 1H), 3.77-3.65 (m, 2H), 2.12-2.03 (m, 1H), 1.68-1.56 (m, 2H), 1.55-1.49 (m, 2H), 1.49-1.42 (m, 9H), 1.33-1.26 (m, 1H), 1.25-1.17 (m, 6H), 1.05 (m, 1H).

tert-Butyl (2S,6R)-4-(2-bromoethyl)-2,6-dimethylpiperidine-1-carboxylate. To a solution of tert-butyl (2S,6R)-4-(2-hydroxyethyl)-2,6-dimethylpiperidine-1-carboxylate (2.180 g, 8.470 mmol, 1 equiv.) and triphenylphosphine (3.332 g, 12.71 mmol, 1.5 equiv.) in dichloromethane (40 mL, 0.21 M). To the reaction solution was added carbon tetrabromide (4.214 g, 12.71 mmol, 1.5 equiv.) at 0° C. The reaction mixture was allowed to slowly warm to room temperature. After 2 h the reaction solution was poured into saturated sodium bicarbonate solution (100 mL) and the aqueous phase was extracted with dichloromethane (3×100 mL). The combined organic layers were washed with brine (100 mL), dried over anhydrous sodium sulfate, filtered and concentrated. The crude material was purified by silica gel chromatography (1% ethyl acetate in petroleum ether) to provide tert-butyl (2S,6R)-4-(2-bromoethyl)-2,6-dimethylpiperidine-1-carboxylate (2.160 g, 6.744 mmol, 80% yield) as a clear, colorless oil. $^1$H NMR (400 MHz, CDCl$_3$) δ 4.45-4.27 (m, 1H), 4.26-4.06 (m, 1H), 3.51-3.29 (m, 2H), 2.18-1.96 (m, 2H), 1.89-1.75 (m, 2H), 1.73-1.53 (m, 2H), 1.48-1.39 (m, 9H), 1.33-1.25 (m, 1H), 1.24-1.19 (m, 6H), 1.13-0.97 (m, 1H).

tert-Butyl (2R,6S)-4-(2-((trans-4-(dibenzylamino)cyclohexyl)oxy)ethyl)-2,6-dimethylpiperidine-1-carboxylate. To a solution of trans-4-(dibenzylamino)cyclohexanol (12.18 g, 41.22 mmol, 2 equiv.) and tert-butyl (2S,6R)-4-(2-bromoethyl)-2,6-dimethylpiperidine-1-carboxylate (6.600 g, 20.61 mmol, 1 equiv.) in xylene (120 mL, 0.17 M) was added potassium hydroxide (5.318 g, 94.80 mmol, 4.6 equiv.) and tetrabutylammonium bromide (1.328 g, 4.120 mmol, 0.2 equiv.). The reaction was stirred at 30° C. After 24 h the reaction solution was diluted with water (200 mL) and extracted with ethyl acetate (3×250 mL). The combined organic layers were washed with brine (150 mL), dried over anhydrous sodium sulfate, filtered and concentrated. The crude material was purified by flash silica gel column chromatography (2.5-3% ethyl acetate in petroleum ether) to provide tert-butyl (2R,6S)-4-(2-((trans-4-(dibenzylamino)cyclohexyl)oxy)ethyl)-2,6-dimethylpiperidine-1-carboxylate (2.800 g, 5.236 mmol, 25% yield) as a yellow oil. $^1$H NMR (400 MHz, CDCl$_3$) δ 7.42-7.33 (m, 4H), 7.33-7.27 (m, 4H), 7.24-7.17 (m, 2H), 4.36-4.23 (m, 2H), 4.22-4.15 (m, 1H), 3.62 (s, 4H), 3.48 (t, J=6.4 Hz, 1H), 3.45-3.37 (m, 1H), 3.19-3.06 (m, 1H), 2.53 (m, 1H), 2.09-2.04 (m, 3H), 2.01-1.86 (m, 3H), 1.63-1.59 (m, 1H), 1.57-1.51 (m, 2H), 1.47-1.46 (m, 9H), 1.43-1.33 (m, 2H), 1.28-1.24 (m, 2H), 1.21 (s, 2H), 1.17 (d, J=7.0 Hz, 6H), 1.14-1.08 (m, 1H), 1.07-0.92 (m, 1H).

tert-Butyl (2R,6S)-4-(2-((trans-4-aminocyclohexyl)oxy)ethyl)-2,6-dimethylpiperidine-1-carboxylate. To a solution of tert-butyl (2R,6S)-4-(2-((trans-4-(dibenzylamino)cyclohexyl)oxy)ethyl)-2,6-dimethylpiperidine-1-carboxylate (2.800 g, 5.240 mmol, 1 equiv.) in methanol (60 mL) was added palladium on carbon (2.000 g) under nitrogen. The reaction was stirred at room temperature for 12 hours under hydrogen (15 psi). The reaction mixture was filtered and concentrated to give tert-butyl (2R,6S)-4-(2-((trans-4-aminocyclohexyl)oxy)ethyl)-2,6-dimethylpiperidine-1-carboxylate (1.837 g, 5.180 mmol, 98% yield) yellow oil which was carried forward without further purification. $^1$H NMR (400 MHz, DMSO-d$_6$) δ 4.23-4.08 (m, 2H), 4.08-3.93 (m, 1H), 3.50-3.40 (m, 2H), 3.40-3.33 (m, 1H), 3.18-3.04 (m, 1H), 2.55-2.51 (m, 2H), 2.49 (br s, 1H), 2.05-1.83 (m, 4H), 1.82-1.68 (m, 2H), 1.67-1.47 (m, 2H), 1.46-1.32 (m, 16H), 1.29-1.15 (m, 2H), 1.15-1.07 (m, 9H), 1.07-0.87 (m, 3H).

tert-Butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate. To a solution of tert-butyl (2R,6S)-4-(2-((trans-4-aminocyclohexyl)oxy)ethyl)-2,6-dimethylpiperidine-1-carboxylate (1.837 g, 5.180 mmol, 1 equiv.) in acetonitrile (10 mL, 0.5 M) was added potassium iodide (0.086 g, 0.520 mmol, 10 mol %), potassium carbonate (2.148 g, 15.54 mmol, 3 equiv.) and methyl 2-bromo-2-methylpropanoate (3.75 mL, 25.91 mmol, 5 equiv.). The reaction was stirred at 110° C. After 48 h the reaction solution was filtered and concentrated to give tert-butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate (2.400 g, 5.279 mmol, crude) as a yellow oil which was carried forward without further purification. MS (ESI) m/z 455.5 [M+1]$^+$.

tert-Butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate and tert-butyl (2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate. To a solution of tert-butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate (2.160 g, 4.750 mmol, 1 equiv.) and 4-isothiocyanato-2-(trifluoromethyl)benzonitrile (1.084 g, 4.750 mmol, 1 equiv.) in ethyl acetate (10 mL, 0.47 M) was added N,N-diisoproplyethylamine (1.660 mL, 9.500 mmol, 2 equiv.). The reaction was stirred at 90° C. After 12 h the reaction solution was diluted with water (50 mL) and extracted with ethyl acetate (3×50 mL). The combined organic layers were washed with brine (50 mL), dried over anhydrous sodium sulfate, filtered and concentrated. The crude material was purified by flash silica gel column chromatography to afford the mixture of diastereomers, which were separated by SFC (DAICEL CHIRAL PAK IG:250 mm*30 mm.10 um, 20% methanol+0.1% NH3.H2O) to give tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (1.060 g, 1.629 mmol, 34% yield) and tert-butyl (2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (0.360 g, 0.553 mmol, 12% yield). tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate: $^1$H NMR (400 MHz, CDCl$_3$) δ 7.95 (d, J=8.0 Hz, 1H), 7.85 (d, J=2.0 Hz, 1H), 7.72 (dd, J=2.0, 8.0 Hz, 1H), 4.38-4.22 (m, 2H), 3.72-3.59 (m, 1H), 3.54 (t, J=6.4 Hz, 2H), 3.37-3.24 (m, 1H), 3.03-2.75 (m, 2H), 2.21 (br d, J=12.4 Hz, 2H), 2.03-1.90 (m, 1H), 1.89-1.77 (m, 2H), 1.61 (s, 6H), 1.58 (m, 2H), 1.54-1.48 (m, 2H), 1.47 (s, 9H), 1.40-1.26 (m, 4H), 1.19 (d, J=7.2 Hz, 6H). tert-Butyl (2R, 4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate: ¹H NMR (400 MHz, CDCl₃) δ 7.95 (d, J=8.4 Hz, 1H), 7.85 (d, J=2.0 Hz, 1H), 7.72 (dd, J=2.0, 8.4 Hz, 1H), 4.28-4.10 (m, 2H), 3.76-3.58 (m, 1H), 3.49 (t, J=6.0 Hz, 2H), 3.30 (m, 1H), 3.03-2.76 (m, 2H), 2.19 (br d, J=12.0 Hz, 2H), 2.12-1.98 (m, 2H), 1.89-1.76 (m, 2H), 1.61 (s, 6H), 1.52 (br t, J=6.4 Hz, 2H), 1.47 (s, 9H), 1.40-1.25 (m, 3H), 1.22 (d, J=6.8 Hz, 6H), 1.03 (m, 2H).

4-(3-(trans-4-(2-((2R,4s,6S)-2,6-Dimethylpiperidin-4-yl)ethoxy)cyclohexyl)-4,4-dimethyl-5-oxo-2-thioxoimidazolidin-1-yl)-2-(trifluoromethyl)benzonitrile. To a solution of tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (1.060 g, 1.630 mmol, 1 equiv.) in dichloromethane (5 mL) was added 4 M hydrochloric acid in 1,4-dioxane (20 mL, 80.00 mmol), and the reaction solution was stirred at room temperature. After 2 h the reaction solution was concentrated. The resulting yellow solid was taken up in saturated aqueous sodium bicarbonate (50 mL) and extracted with ethyl acetate (3×100 mL). The combined organic layers were washed with brine (50 mL), dried over anhydrous sodium sulfate and concentrated to provide 4-(3-(trans-4-(2-((2R,4s,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.920 g, 1.67 mmol, 99% yield) as a yellow solid which was carried forward without further purification. MS (ESI) m/z 551.4 [M+1]⁺; ¹H NMR (400 MHz, CDCl₃) δ 7.95 (d, J=8.0 Hz, 1H), 7.84 (d, J=2.0 Hz, 1H), 7.72 (dd, J=2.0, 8.0 Hz, 1H), 3.74-3.59 (m, 1H), 3.51 (t, J=6.8 Hz, 2H), 3.31 (m, 1H), 2.92 (m, 4H), 2.20 (br d, J=12.0 Hz, 2H), 2.02-1.92 (m, 1H), 1.82 (br d, J=12.0 Hz, 2H), 1.70 (q, J=6.8 Hz, 2H), 1.64-1.56 (s, 6H), 1.51 (br d, J=12.8 Hz, 2H), 1.40-1.27 (m, 4H), 1.09 (br d, J=6.0 Hz, 6H).

Benzyl 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate. To a mixture of 4-(3-(trans-4-(2-((2R,4s,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.080 g, 0.150 mmol, 1 equiv.) and benzyl 2-bromoacetate (0.040 g, 0.170 mmol, 1.2 equiv.) in acetonitrile (0.5 mL, 0.3 M) was added N,N-diisopropylethylamine (0.08 mL, 0.440 mmol, 3 equiv.) and the reaction solution was stirred at room temperature. After 12 h the reaction solution was filtered and concentrated, and the crude material purified by preparatory TLC (dichloromethane:methanol=10:1, Rf=0.7) to afford benzyl 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate (0.092 g, 0.132 mmol, 91% yield) as a yellow solid. MS (ESI) m/z 699.2 [M+1]⁺; ¹H NMR (400 MHz, DMSO-d₆) δ 8.33 (d, J=8.0 Hz, 1H), 8.19 (s, 1H), 7.96 (d, J=8.0 Hz, 1H), 7.36-7.34 (m, 5H), 5.10 (s, 2H), 3.53 (s, 2H), 3.43-3.40 (m, 2H), 3.17-3.16 (m, 4H), 2.92 (s, 2H), 2.85-2.75 (m, 2H), 2.05-2.02 (m, 2H), 1.72-1.69 (m, 3H), 1.56 (s, 6H), 1.45-1.35 (m, 2H), 1.30-1.25 (m, 4H), 0.95 (d, J=6.0 Hz, 6H).

2-((2R,4s,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid. To a mixture of benzyl 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate (0.082 g, 0.1200 mmol, 1 equiv.) in THF (1 mL) was added lithium hydroxide (0.011 g, 0.4700 mmol, 4 equiv.). The reaction solution was stirred at 25° C. for 3 h. Hydrochloric acid (1M) was added to the reaction solution and its pH was adjusted to 5-6. The mixture was concentrated in vacuum and purified by semi-preparative reverse phase HPLC (30%-60% acetonitrile in water+0.225% formic acid, 10 min) to afford 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.042 g, 0.069 mmol, 59% yield) as a yellow liquid. MS (ESI) m/z 609.4 [M+1]⁺.

2-((2R,4s,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride. To a mixture of 1-(7-amino-1-methyl-1H-indazol-3-yl)dihydropyrimidine-2,4(1H,3H)-dione (0.019 g, 0.070 mmol, 1.2 equiv.) and 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.037 g, 0.060 mmol, 1 equiv.) in pyridine (1 mL, 0.06 M) was added EDCI (0.023 g, 0.120 mmol, 2 equiv.). The reaction solution was stirred at 50° C. After 12 h the reaction solution was diluted with DMSO and purified by standard methods to give 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride (0.026 g, 0.003 mmol, 50% yield) as a yellow solid. MS (ESI) m/z 850.3 [M+1]⁺; ¹H NMR (400 MHz, DMSO-d₆) δ 10.73-10.68 (m, 1H), 10.67-10.60 (m, 1H), 9.12-9.10 (m, 1H), 8.34 (d, J=7.6 Hz, 1H), 8.19 (s, 1H), 7.97 (d, J=8.0 Hz, 1H), 7.62-7.59 (m, 1H), 7.24-7.22 (m, 1H), 7.16-7.14 (m, 1H), 4.38 (s, 1H), 4.26-4.18 (m, 1H), 4.12-4.05 (m, 3H), 3.94-3.86 (m, 3H), 3.85-3.64 (m, 3H) 3.53-3.44 (m, 2H), 3.26-3.20 (m, 1H), 2.92-2.74 (m, 4H), 2.48-2.44 (m, 1H), 2.10-1.88 (m, 4H), 1.86-1.70 (m, 7H), 1.56 (s, 6H), 1.37-1.32 (m, 3H), 1.30-1.15 (m, 2H), 1.14-1.08 (m, 3H).

Example 14: 2-((2R,4r,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride

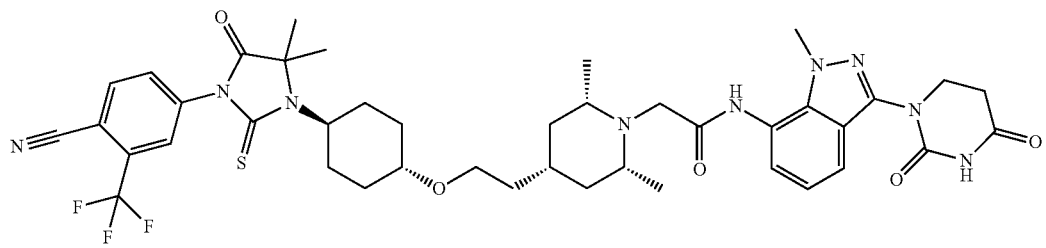 [SMILES: C[C@@H]1C[C@H](CCO[C@H]2CC[C@H](N3C(=S)N(c4ccc(C#N)c(C(F)(F)F)c4)C(=O)C3(C)C)CC2)C[C@H](C)N1CC(=O)Nc1cccc2c(N3CCC(=O)NC3=O)nn(C)c12]

4-(3-(trans-4-(2-((2R,4r,6S)-2,6-Dimethylpiperidin-4-yl)ethoxy)cyclohexyl)-4,4-dimethyl-5-oxo-2-thioxoimidazolidin-1-yl)-2-(trifluoromethyl)benzonitrile. To a solution of tert-butyl (2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (0.360 g, 0.550 mmol, 1 equiv.) in dichloromethane (3 mL, 0.12 M) was added 4M hydrochloric acid in 1,4-dioxane (12 mL, 48 mmol), and the reaction solution was stirred at 15° C. After 14 h the reaction solution was concentrated. The resulting solid was diluted with saturated bicarbonate solution (20 mL) to pH 8-9 and the aqueous was extracted with ethyl acetate (3×50 mL). The combined organic layers were washed with brine (30 mL), dried over anhydrous sodium sulfate and concentrated to give 4-(3-(trans-4-(2-((2R,4r,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.330 g, 0.56 mmol) as a yellow solid which was carried forward without further purification. MS (ESI) m/z 551.4 [M+1]+; 1H NMR (400 MHz, CDCl3) δ 7.95 (d, J=8.4 Hz, 1H), 7.84 (d, J=2.0 Hz, 1H), 7.72 (dd, J=2.0, 8.4 Hz, 1H), 3.73-3.59 (m, 1H), 3.52 (t, J=6.4 Hz, 2H), 3.30 (m, 1H), 3.03-2.80 (m, 2H), 2.74 (m, 2H), 2.20 (br d, J=12.4 Hz, 2H), 1.82 (br d, J=11.6 Hz, 2H), 1.68 (br d, J=13.2 Hz, 2H), 1.61 (s, 6H), 1.54-1.48 (m, 2H), 1.41-1.27 (m, 3H), 1.14 (br d, J=6.4 Hz, 6H), 0.92-0.76 (m, 2H).

Benzyl 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate. To a mixture of 4-(3-(trans-4-(2-((2R,4r,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.060 g, 0.110 mmol, 1 equiv.) and benzyl 2-bromoacetate (0.030 g, 0.130 mmol, 1.2 equiv.) in acetonitrile (0.5 mL, 0.2 M) was added N,N-diisopropylethylamine (0.06 mL, 0.330 mmol, 3 equiv.) and the reaction solution was stirred at room temperature. After 12 h the reaction solution was filtered and concentrated, and the crude material purified by preparatory TLC (dichloromethane:methanol=10:1, Rf=0.7) to afford benzyl 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate (0.063 g, 0.090 mmol, 83% yield) as a yellow solid. MS (ESI) m/z 699.4 [M+1]+.

2-((2R,4r,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid. To a mixture of benzyl 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate (0.063 g, 0.090 mmol, 1 equiv.) in THF (1 mL) was added lithium hydroxide (0.009 g, 0.360 mmol, 4 equiv.). The reaction solution was stirred at 25° C. for 3 h. Hydrochloric acid (1M) was added to the reaction solution and its pH was adjusted to 5-6. The mixture was concentrated in vacuum and purified by semi-preparative reverse phase HPLC (30%-60% acetonitrile in water+0.225% formic acid, 10 min) to afford 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.028 g, 0.046 mmol, 51% yield) as a yellow liquid. MS (ESI) m/z 609.1 [M+1]+.

2-((2R,4r,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride. To a mixture of 1-(7-amino-1-methyl-1H-indazol-3-yl)dihydropyrimidine-2,4(1H,3H)-dione (14.31 mg, 0.0600 mmol, 1.2 equiv.) and 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.028 g, 0.050 mmol, 1 equiv.) in pyridine (1 mL, 0.05 M) was added EDCI (0.018 g, 0.090 mmol, 1.8 equiv.). The reaction solution was stirred at 50° C. After 12 h the reaction solution was diluted with DMSO and purified by standard methods to give 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride (0.012 g, 0.0014 mmol, 31.2% yield) as a yellow solid. MS (ESI) m/z 850.4 [M+1]+; 1H NMR (400 MHz, DMSO-d6) δ 10.85-10.78 (m, H), 10.60-10.60 (m, 1H), 9.14 (s, 1H), 8.34 (d, J=7.6 Hz, 1H), 8.19 (s, 1H), 7.97 (d, J=8.0 Hz, 1H), 7.62-7.59 (m, 1H), 7.24-7.22 (m, 1H), 7.16-7.14 (m, 1H), 4.40 (s, 1H), 4.31-4.20 (m, 1H), 4.12-4.05 (m, 3H), 3.93-3.75 (m, 3H), 3.62-3.56 (m, 1H), 3.55-3.35 (m, 3H), 3.20-3.14 (m, 1H), 2.90-2.70 (m, 4H), 2.12-2.00 (m, 2H), 1.92-1.75 (m, 3H), 1.60-1.50 (m, 6H), 1.51-1.43 (m, 2H), 1.30-1.10 (m, 9H).

Example 15: 4-(3-(trans-4-(2-((3R,5S)-4-(2-((3-(2,4-Dioxotetrahydropyrimidin-1(2H)-yl)-1-methyl-1H-indazol-7-yl)oxy)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride

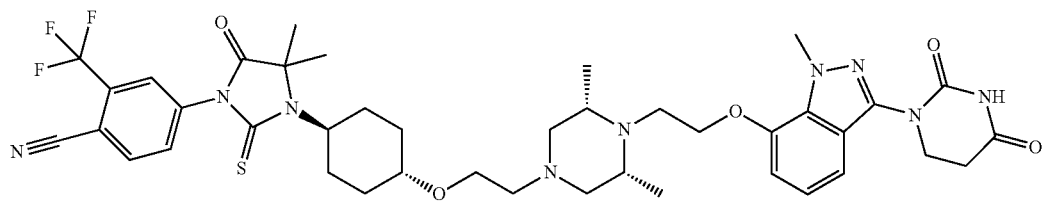 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CCOc1cccc2c(N3CCC(=O)NC3=O)nn(C)c12]

Benzyl (3S,5R)-4-(2-chloroacetyl)-3,5-dimethylpiperazine-1-carboxylate. To a solution of (3S,5R)-benzyl 3,5-dimethylpiperazine-1-carboxylate (5.000 g, 20.14 mmol, 1 equiv.) in dichloromethane (50 mL) was added triethylamine (4.2 mL, 30.20 mmol, 1.5 equiv.) followed by 2-chloroacetyl chloride (1.76 mL, 22.15 mmol, 1.1 equiv.) drop-wise at 0° C. and the reaction mixture was stirred at 0° C. After 2 h the reaction solution was concentrated and purified by silica gel column chromatography (20-50% ethyl acetate in petroleum ether) to afford benzyl (3S,5R)-4-(2-chloroacetyl)-3,5-dimethylpiperazine-1-carboxylate (3.300 g, 10.16 mmol, 51% yield) as a white solid. $^1$H NMR (400 MHz, CDCl$_3$) δ 7.41-7.34 (m, 5H), 5.19 (s, 2H), 4.60 (m, 1H), 4.16-4.07 (m, 5H), 3.07 (br, s, 2H), 1.32 (m, 6H).

Benzyl (3S,5R)-4-(2-((3-amino-1-methyl-1H-indazol-7-yl)oxy)acetyl)-3,5-dimethylpiperazine-1-carboxylate. To a solution of 3-amino-1-methyl-1H-indazol-7-ol (1.600 g, 9.810 mmol, 1 equiv.) and benzyl (3S,5R)-4-(2-chloroacetyl)-3,5-dimethylpiperazine-1-carboxylate (3.180 g, 9.810 mmol, 1 equiv.) in N,N-dimethylformamide (20 mL) was added potassium carbonate (4.070 g, 29.42 mmol, 3 equiv.) and the reaction solution was stirred at 70° C. After 12 h the reaction solution was diluted with water (80 mL) and extracted with ethyl acetate (80 mL×3). The combined organic layers were dried over anhydrous sodium sulfate and concentrated. The resulting crude material was purified by silica gel column chromatography (20% ethyl acetate in petroleum ether) to give benzyl (3S,5R)-4-(2-((3-amino-1-methyl-1H-indazol-7-yl)oxy)acetyl)-3,5-dimethylpiperazine-1-carboxylate (3.800 g, 8.416 mmol, 86% yield) as a brown solid. MS (ESI) m/z 452.1 [M+1]$^+$; $^1$H NMR (400 MHz, CDCl$_3$) δ 7.36-7.31 (m, 5H), 7.14-7.12 (d, J=8.0 Hz, 1H), 6.89-6.85 (t, J=8.0 Hz, 1H), 6.68-6.67 (d, J=7.6 Hz, 1H), 5.19 (s, 2H), 4.81 (s, 2H), 4.68 (br, s, 1H), 4.13 (s, 3H), 4.00 (m, 3H), 3.06-3.05 (m, 2H), 1.31 (m, 6H).

Benzyl (3S,5R)-4-(2-((3-amino-1-methyl-1H-indazol-7-yl)oxy)ethyl)-3,5-dimethylpiperazine-1-carboxylate. To a solution of benzyl (3S,5R)-4-(2-((3-amino-1-methyl-1H-indazol-7-yl)oxy)acetyl)-3,5-dimethylpiperazine-1-carboxylate (7.500 g, 16.61 mmol, 1 equiv.) in THF (80 mL) was added borane-dimethyl sulfide complex (5.81 mL, 58.14 mmol, 3.5 equiv.) and the reaction solution was diluted with 1 M hydrochloric acid (20 mL) and water (120 mL) and stirred for 10 min. The solution was adjusted to pH 6-7 by addition of saturated aqueous sodium bicarbonate and was extracted with ethyl acetate (2×100 mL). The combined organic layers were dried over anhydrous sodium sulfate, concentrated and purified by silica gel column chromatography (20-40% ethyl acetate in petroleum ether) to afford benzyl (3S,5R)-4-(2-((3-amino-1-methyl-1H-indazol-7-yl)oxy)ethyl)-3,5-dimethylpiperazine-1-carboxylate (4.300 g, 9.828 mmol, 59.2% yield) as brown solid. MS (ESI) m/z 438.1 [M+1]$^+$; $^1$H NMR (400 MHz, DMSO-d$_6$) δ 7.52-7.50 (d, J=8.0 Hz, 1H), 7.39-7.22 (m, 5H), 7.10-7.08 (d, J=8.0 Hz, 1H), 7.05-7.01 (t, J=8.0 Hz, 1H), 6.64 (m, 2H), 5.09 (s, 2H), 4.16-4.13 (t, J=6.4 Hz, 2H), 3.87 (s, 3H), 3.82-3.80 (m, 2H), 3.12-3.08 (t, J=6.4 Hz, 2H), 2.61 (m, 4H), 1.07-1.06 (m, 6H).

Benzyl (3S,5R)-4-(2-((3-((3-ethoxy-3-oxopropyl)amino)-1-methyl-1H-indazol-7-yl)oxy)ethyl)-3,5-dimethylpiperazine-1-carboxylate. To a solution of benzyl (3S,5R)-4-(2-((3-amino-1-methyl-1H-indazol-7-yl)oxy)ethyl)-3,5-dimethylpiperazine-1-carboxylate (4.100 g, 9.370 mmol, 1 equiv.) in ethyl acrylate (18.76 g, 187.42 mmol, 20 equiv.) was added aluminum oxide (2.390 g, 23.43 mmol, 2.5 equiv.) and the reaction mixture was stirred at 115° C. after 24 h the reaction solution was diluted with ethyl acetate (150 mL), filtered and concentrated. The resulting material was purified by semi-preparative reverse phase HPLC (20%-60% heptane in ethanol+0.1% ammonium hydroxide, 10 min) to afford benzyl (3S,5R)-4-(2-((3-((3-ethoxy-3-oxopropyl)amino)-1-methyl-1H-indazol-7-yl)oxy)ethyl)-3,5-dimethylpiperazine-1-carboxylate (2.700 g, 5.022 mmol, 54% yield) as a brown oil. MS (ESI) m/z 538.4 [M+1]$^+$.

Benzyl (3S,5R)-4-(2-((3-(1-(3-ethoxy-3-oxopropyl)ureido)-1-methyl-1H-indazol-7-yl)oxy)ethyl)-3,5-dimethylpiperazine-1-carboxylate. To a solution of benzyl (3S,5R)-4-(2-((3-((3-ethoxy-3-oxopropyl)amino)-1-methyl-1H-indazol-7-yl)oxy)ethyl)-3,5-dimethylpiperazine-1-carboxylate (2.700 g, 5.020 mmol, 1 equiv.) in acetic acid (30 mL) was added potassium cyanate (1.220 g, 15.07 mmol, 3 equiv.) and the reaction solution was stirred at room temperature. After 12 h the reaction solution concentrated and purified by silica gel column chromatography (5-10% methanol in dichloromethane) to give benzyl (3S,5R)-4-(2-((3-(1-(3-ethoxy-3-oxopropyl)ureido)-1-methyl-1H-indazol-7-yl)oxy)ethyl)-3,5-dimethylpiperazine-1-carboxylate (1.300 g, 2.239 mmol, 45% yield) as a brown oil. MS (ESI) m/z 581.2 [M+1]$^+$; $^1$H NMR (400 MHz, CDCl$_3$) δ 7.40-7.30 (m, 5H), 7.19-7.17 (d, J=8.0 Hz, 1H), 7.07-7.03 (t, J=8.0 Hz, 1H), 6.74-6.72 (d, J=8.0 Hz, 1H), 5.14 (s, 2H), 4.96 (s, 2H), 4.25 (s, 3H), 4.14-4.11 (m, 4H), 4.06-3.95 (m, 4H), 3.19-3.15 (t, J=6.8 Hz, 2H), 2.72-2.68 (m, 6H), 1.20-1.16 (m, 9H).

1-(7-(2-((2S,6R)-2,6-Dimethylpiperazin-1-yl)ethoxy)-1-methyl-1H-indazol-3-yl)dihydropyrimidine-2,4(1H,3H)-dione. A mixture of benzyl (3S,5R)-4-(2-((3-(1-(3-ethoxy-3-oxopropyl)ureido)-1-methyl-1H-indazol-7-yl)oxy)ethyl)-3,5-dimethylpiperazine-1-carboxylate (1.300 g, 2.240 mmol, 1 equiv.) in concentrated aqueous hydrochloric acid (12 mL) was stirred at 10° C. After 12 h the reaction solution was concentrated. The resulting crude material was purified by semi-preparative reverse phase HPLC (0%-20% acetonitrile in water+0.05% hydrochloric acid, 20 min) to afford 1-(7-(2-((2S,6R)-2,6-dimethylpiperazin-1-yl)ethoxy)-1-methyl-1H-indazol-3-yl)dihydropyrimidine-2,4(1H,3H)-dione (620.65 mg, 1.542 mmol, 69% yield) as an off-white solid. MS (ESI) m/z 401.2 [M+1]$^+$; $^1$H NMR (400 MHz, DMSO-d$_6$) δ 12.49 (s, 1H), 10.55 (s, 1H), 10.14 (s, 2H), 7.24-7.22 (d, J=8.8 Hz, 1H), 7.05-7.02 (m, 2H), 4.55 (s, 2H), 4.20 (s, 3H), 3.99-3.95 (m, 2H), 3.89-3.86 (t, J=6.8 Hz, 4H), 3.58-3.55 (m, 2H), 3.32 (m, 2H), 2.77-2.74 (t, J=6.8 Hz, 2H), 1.48 (s, 6H).

4-(3-(trans-4-(2-((3R,5S)-4-(2-((3-(2,4-Dioxotetrahydropyrimidin-1(2H)-yl)-1-methyl-1H-indazol-7-yl)oxy)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride. To a flask containing 4-(3-(trans-4-(2-bromoethoxy)cyclohexyl)-4,4-dimethyl-5-oxo-2-thioxoimidazolidin-1-yl)-2-(trifluoromethyl)benzonitrile (150 mg, 0.29 mmol, 1 equiv.) was added 1-(7-(2-((2R,6S)-2,6-dimethylpiperazin-1-yl)ethoxy)-1-methyl-1H-indazol-3-yl)dihydropyrimidine-2,4(1H,3H)-dione dihydrochloride (164 mg, 0.35 mmol, 1.2 equiv.), N,N-diisopropylethylamine (0.2 mL, 1.16 mmol, 4 equiv.), sodium iodide (52 mg, 0.35 mmol, 1.2 equiv.), and N,N-dimethylformamide (2.0 mL, 0.15 M). The reaction was stirred at 50° C. After 15 h the reaction solution was diluted with DMSO (1 mL) and purified by standard methods to give 4-(3-(trans-4-(2-((3R,5S)-4-(2-((3-(2,4-dioxotetrahydropyrimidin-1(2H)-yl)-1-methyl-1H-indazol-7-yl)oxy)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride (96 mg, 0.11 mmol, 38% yield) as an off-white solid. MS (ESI) m/z 838.4 [M+1]$^+$; $^1$H NMR (400 MHz, DMSO-d$_6$) δ 10.55 (s, 1H), 8.34 (d, J=8.19 Hz, 1H), 8.19 (d, J=1.59 Hz, 1H), 7.97 (dd, J=1.65, 8.25 Hz, 1H), 7.22 (br d, J=7.70 Hz, 1H), 7.02 (q, J=7.30 Hz, 2H), 4.20 (s, 3H), 3.92-4.03 (m, 4H), 3.74-3.91 (m, 9H), 3.21-3.44 (m, 4H), 2.80-2.91 (m, 2H), 2.73-2.79 (m, 2H), 2.10 (br d, J=11.13 Hz, 2H), 1.72 (br d, J=10.64 Hz, 2H), 1.55 (s, 7H), 1.23-1.51 (m, 8H).

Example 16: 4-(3-(trans-4-(2-((3S,5R)-4-(3-((3-(2,4-dioxotetrahydropyrimidin-1(2H)-yl)-1-methyl-1H-indazol-7-yl)oxy)propyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride

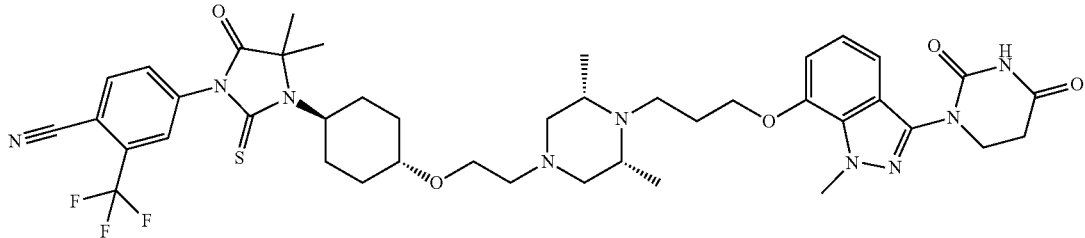 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CCCOc1cccc2c(N3CCC(=O)NC3=O)nn(C)c12]

Benzyl (3R,5S)-4-(3-bromopropyl)-3,5-dimethylpiperazine-1-carboxylate. To a solution of (3R,5S)-benzyl 3,5-dimethylpiperazine-1-carboxylate (5.000 g, 20.140 mmol, 1 equiv.) and 1,3-dibromopropane (40.65 g, 201.35 mmol, 10 equiv.) in acetonitrile (50 mL) was added potassium carbonate (8.350 g, 60.410 mmol, 3 equiv.) and the reaction mixture was stirred at 100° C. After 12 h the reaction solution was diluted with ethyl acetate (100 mL), filtered and concentrated. The resulting crude material was purified y silica gel column chromatography (25-50% ethyl acetate in petroleum ether) to give benzyl (3R,5S)-4-(3-bromopropyl)-3,5-dimethylpiperazine-1-carboxylate (2.000 g, 5.630 mmol, 28% yield) as a colorless oil. MS (ESI) m/z 371.0 [M+1]$^+$; $^1$H NMR (400 MHz, CDCl$_3$) δ 7.39-7.30 (m, 5H), 5.13 (s, 2H), 3.96-3.91 (m, 2H), 3.39-3.36 (t, J=6.4 Hz, 2H), 2.91-2.87 (m, 2H), 2.62-2.54 (m, 4H), 1.97-1.90 (m, 2H), 1.10-1.09 (d, J=5.2 Hz, 6H).

7-Methoxy-1-methyl-1H-indazol-3-amine. To a solution of 2-fluoro-3-methoxybenzonitrile (20.00 g, 132.33 mmol, 1 equiv.) in N,N-dimethylacetamide (200 mL) was added methylhydrazine (76.20 g, 661.64 mmol, 5 equiv.) and N,N-diisopropylethylamine (20.52 g, 158.79 mmol, 1.2 equiv.) and the reaction solution was stirred at 130° C. After 3 h the reaction solution was diluted with ice water (500 mL) and extracted with ethyl acetate (3×300 mL). The combined organic layers were washed with brine (3×100 mL), dried over anhydrous sodium sulfate and concentrated, the crude material was purified by silica gel column chromatography (30-50% ethyl acetate in petroleum ether) to give 7-methoxy-1-methyl-1H-indazol-3-amine (18.20 g, 102.71 mmol, 78% yield) as a brown solid. $^1$H NMR (400 MHz, DMSO-d$_6$) δ 7.25-7.23 (d, J=8.0 Hz, 1H), 6.83-6.79 (m, 1H), 6.73-6.71 (m, 1H), 5.33 (s, 2H), 3.90 (s, 3H), 3.87 (s, 3H).

3-Amino-1-methyl-1H-indazol-7-ol. To a solution of 7-methoxy-1-methyl-1H-indazol-3-amine (18.00 g, 101.58 mmol, 1 equiv.) in dichloromethane (200 mL) was added aluminum trichloride (54.18 g, 406.32 mmol, 4 equiv.) and the reaction mixture was stirred at 45° C. After 12 h the reaction solution was slowly poured into water (500 mL) and extracted with ethyl acetate (3×200 mL). The combined organic layers were concentrated and purified by silica gel column chromatography (50-75% ethyl acetate in petroleum ether) to give 3-amino-1-methyl-1H-indazol-7-ol (6.500 g, 39.833 mmol, 39% yield) as a brown solid. MS (ESI) m/z 164.1 [M+1]$^+$; $^1$H NMR (400 MHz, DMSO-d$_6$) δ 9.81 (s, 1H), 7.10-7.08 (d, J=8.0 Hz, 1H), 6.70-6.66 (m, 1H), 6.60-6.58 (d, J=7.2 Hz, 1H), 5.25 (s, 2H), 3.91 (s, 3H).

Benzyl (3S,5R)-4-(3-((3-amino-1-methyl-1H-indazol-7-yl)oxy)propyl)-3,5-dimethylpiperazine-1-carboxylate. To a solution of 3-amino-1-methyl-1H-indazol-7-ol (1.170 g, 7.150 mmol, 1.1 equiv.) and (3R,5S)-benzyl 4-(3-bromopropyl)-3,5-dimethylpiperazine-1-carboxylate (2.400 g, 6.500 mmol, 1 equiv.) in acetonitrile (20 mL) was added potassium carbonate (2.690 g, 19.50 mmol, 3 equiv.) and the reaction mixture was stirred at 60° C. After 12 h the reaction solution was diluted with water (80 mL) and extracted with ethyl acetate (3×25 mL). The combined organic layers were dried over anhydrous sodium sulfate, concentrated, and purified by silica gel column chromatography (50-75% ethyl acetate in petroleum ether) to give benzyl (3S,5R)-4-(3-((3-amino-1-methyl-1H-indazol-7-yl)oxy)propyl)-3,5-dimethylpiperazine-1-carboxylate (1.300 g, 2.879 mmol, 44% yield) as a brown solid. MS (ESI) m/z 452.4 [M+1]$^+$.

Benzyl (3S,5R)-4-(3-((3-((3-ethoxy-3-oxopropyl)amino)-1-methyl-1H-indazol-7-yl)oxy)propyl)-3,5-dimethylpiperazine-1-carboxylate. To a suspension of (3S,5R)-benzyl 4-(3-((3-amino-1-methyl-1H-indazol-7-yl)oxy)propyl)-3,5-dimethylpiperazine-1-carboxylate (2.500 g, 5.540 mmol, 1 equiv.) and ethyl acrylate (4.430 g, 44.290 mmol, 8 equiv.) was added aluminum oxide (1.410 g, 13.840 mmol, 2.5 equiv.) and the reaction suspension was stirred at 110° C. After 70 h the reaction solution was diluted with ethyl acetate (50 mL) filtered and concentrated. The resulting crude material was purified by semi-preparative reverse phase HPLC (30%-60% acetonitrile in water+0.1% TFA, 20 min). The pH value of the collected fractions was adjusted to 7-8 with saturated sodium bicarbonate. Then it was concentrated to remove organic volatiles and the aqueous solution was extracted with ethyl acetate (3×100 mL). The combined organic layers were dried over anhydrous sodium sulfate, filtered and concentrated under reduced pressure to give benzyl (3S,5R)-4-(3-((3-((3-ethoxy-3-oxopropyl)amino)-1-methyl-1H-indazol-7-yl)oxy)propyl)-3,5-dimethylpiperazine-1-carboxylate (0.800 g, 1.450 mmol, 26% yield) as a brown solid. MS (ESI) m/z 552.2 [M+1]$^+$; 1H NMR (400 MHz, CDCl$_3$) δ 7.40-7.31 (m, 5H), 7.07-7.05 (d, J=8.0 Hz, 1H), 6.87-6.83 (t, J=8.0 Hz, 1H), 6.65-6.64 (d, J=7.6 Hz, 1H), 5.15 (s, 2H), 4.38 (br, s, 1H), 4.19-4.14 (q, J=7.2 Hz, 2H), 4.08-4.06 (m, 5H), 4.01-3.91 (m, 2H), 3.72-3.69 (t, J=6.0 Hz, 2H), 3.04-3.00 (m, 2H), 2.75-2.62 (m, 6H), 2.00-1.93 (m, 2H), 1.29-1.25 (t, J=7.2 Hz, 3H), 1.12 (s, 6H).

Benzyl (3S,5R)-4-(3-((3-(1-(3-ethoxy-3-oxopropyl)ureido)-1-methyl-1H-indazol-7-yl)oxy)propyl)-3,5-dimethylpiperazine-1-carboxylate. To a solution of benzyl (3S,5R)-4-(3-((3-((3-ethoxy-3-oxopropyl)amino)-1-methyl-1H-indazol-7-yl)oxy)propyl)-3,5-dimethylpiperazine-1-carboxylate (1.300 g, 2.360 mmol, 1 equiv.) in acetic acid (12 mL) was added potassium isocyanate (0.478 g, 5.890 mmol, 2 equiv.) and the reaction mixture was stirred at room temperature. After 12 h the reaction solution was concentrated and purified by semi-preparative reverse phase HPLC (15%-45% acetonitrile in water+0.05% hydrochloride, 22 min). The pH of the collected fractions was adjusted to 7-8 with saturated sodium bicarbonate and concentrated to remove organic volatiles and the aqueous solution was extracted with ethyl acetate (30 mL×3). The combined organic layers were dried over anhydrous sodium sulfate, filtered and concentrated under reduced pressure to give benzyl (3S,5R)-4-(3-((3-(1-(3-ethoxy-3-oxopropyl)ureido)-1-methyl-1H-indazol-7-yl)oxy)propyl)-3,5-dimethylpiperazine-1-carboxylate (1.100 g, 1.850 mmol, 79% yield) as a brown solid. MS (ESI) m/z 595.1 [M+1]$^+$; $^1$H NMR (400 MHz, DMSO-d$_6$) δ 7.39-7.31 (m, 5H), 7.07-6.99 (m, 2H), 6.85-6.83 (d, J=7.2 Hz, 1H), 5.88 (s, 2H), 5.08 (s, 2H), 4.17 (s, 3H), 4.15-4.12 (t, J=5.6 Hz, 2H), 3.92-3.79 (m, 6H), 2.92-2.88 (m, 2H), 2.62-2.58 (m, 2H), 2.48-2.47 (m, 4H), 1.91-1.87 (m, 2H), 1.08-1.03 (m, 9H).

1-(7-(3-((2S,6R)-2,6-Dimethylpiperazin-1-yl)propoxy)-1-methyl-1H-indazol-3-yl)dihydropyrimidine-2,4(1H,3H)-dione. A mixture of benzyl (3S,5R)-4-(3-((3-(1-(3-ethoxy-3-oxopropyl)ureido)-1-methyl-1H-indazol-7-yl)oxy)propyl)-3,5-dimethylpiperazine-1-carboxylate (1.700 g, 2.690 mmol, 1 equiv.) in hydrogen chloride (17. mL, 541.70 mmol) was stirred at room temperature. After 12 h the reaction solution was concentrated and purified by semi-preparative reverse phase HPLC (1%-30% acetonitrile in water+0.05% hydrogen chloride, 20 min) to afford 1-(7-(3-((2S,6R)-2,6-dimethylpiperazin-1-yl)propoxy)-1-methyl-1H-indazol-3-yl)dihydropyrimidine-2,4(1H,3H)-dione (0.533 g, 1.287 mmol, 48% yield) as a white solid. MS (ESI) m/z 415.4 [M+1]$^+$; $^1$H NMR (400 MHz, DMSO-d$_6$) δ 12.06 (s, 1H), 10.55 (s, 1H), 9.93 (br, s, 1H), 7.20-7.18 (d, J=8.0 Hz, 1H), 7.04-7.00 (t, J=8.0 Hz, 1H), 6.88-6.86 (d, J=7.6 Hz, 1H), 4.29 (m, 2H), 4.21 (s, 3H), 3.90-3.68 (m, 4H), 3.52-3.44 (m, 6H), 2.78-2.75 (t, J=6.8 Hz, 2H), 2.23 (m, 2H), 1.41 (br, s, 6H).

4-(3-(trans-4-(2-((3S,5R)-4-(3-((3-(2,4-Dioxotetrahydropyrimidin-1(2H)-yl)-1-methyl-1H-indazol-7-yl)oxy)propyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride. To a flask containing 4-(3-(trans-4-(2-bromoethoxy)cyclohexyl)-4,4-dimethyl-5-oxo-2-thioxoimidazolidin-1-yl)-2-(trifluoromethyl)benzonitrile (150 mg, 0.29 mmol, 1 equiv.) was added 1-(7-(3-((2R,6S)-2,6-dimethylpiperazin-1-yl)propoxy)-1-methyl-1H-indazol-3-yl)dihydropyrimidine-2,4(1H,3H)-dione dihydrochloride (169 mg, 0.35 mmol, 1.2 equiv.), N,N-diisopropylethylamine (0.2 mL, 1.16 mmol, 4 equiv.), sodium iodide (52 mg, 0.35 mmol, 1.2 equiv.), and N,N-dimethylformamide (2.0 mL, 0.15 M). The reaction was stirred at 50° C. After 14 h the reaction solution was diluted with DMSO (1 mL) and purified by standard methods to give 4-(3-(trans-4-(2-((3S,5R)-4-(3-((3-(2,4-dioxotetrahydropyrimidin-1(2H)-yl)-1-methyl-1H-indazol-7-yl)oxy)propyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride (61 mg, 0.069 mmol, 24% yield) as an off-white solid. MS (ESI) m/z 852.4 [M+1]$^+$; $^1$H NMR (400 MHz, DMSO-d$_6$) δ 10.54 (s, 1H), 8.34 (d, J=8.31 Hz, 1H), 8.19 (d, J=1.59 Hz, 1H), 7.97 (dd, J=1.71, 8.19 Hz, 1H), 7.18 (d, J=8.19 Hz, 1H), 7.01 (t, J=7.89 Hz, 1H), 6.87 (br d, J=7.58 Hz, 1H), 4.29 (br s, 2H), 4.20 (s, 3H), 3.65-3.91 (m, 14H), 3.45-3.53 (m, 2H), 2.71-2.95 (m, 5H), 2.24 (br s, 1H), 2.12 (br d, J=9.90 Hz, 2H), 1.73 (br d, J=10.88 Hz, 2H), 1.55 (s, 6H), 1.28-1.49 (m, 8H).

Example 17: 2-((2R,6S)-4-(4-(trans-4-(3-(4-Cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(3-(2,4-dioxotetrahydropyrimidin-1(2H)-yl)-1-methyl-1H-indazol-7-yl)acetamide hydrochloride

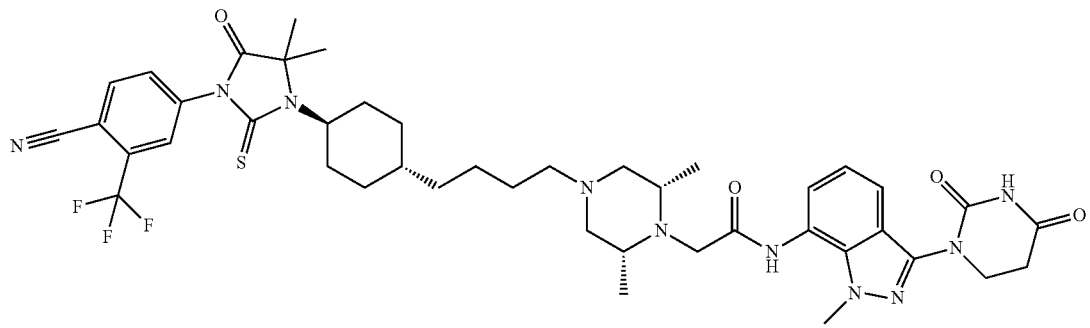 [SMILES: C[C@@H]1CN(CCCC[C@H]2CC[C@H](N3C(=S)N(c4ccc(C#N)c(C(F)(F)F)c4)C(=O)C3(C)C)CC2)C[C@H](C)N1CC(=O)Nc1cccc2c(N3CCC(=O)NC3=O)nn(C)c12]

tert-Butyl (trans-4-(2-(methoxy(methyl)amino)-2-oxoethyl)cyclohexyl)carbamate. To a solution of 2-(trans-4-((tert-butoxycarbonyl)amino)cyclohexyl)acetic acid (2.000 g, 7.770 mmol, 1 equiv.) and N, O-dimethylhydroxylamine hydrochloride (0.830 g, 8.550 mmol, 1.1 equiv.) in N,N-dimethylformamide (20 mL, 0.38 M) was added N,N-diisopropylethylamine (6.94 mL, 38.86 mmol) and HATU (4.430 g, 11.66 mmol, 5 equiv.) and the reaction solution was stirred at room temperature. After 12 h the reaction solution was diluted with water (100 mL) and extracted with ethyl acetate (2×60 mL). The combined organic layers were washed with brine (50 mL), dried over anhydrous sodium sulfate and concentrated. The resulting crude material was purified by silica gel column chromatography (0-30% ethyl acetate in petroleum ether) to give tert-butyl (trans-4-(2-(methoxy(methyl)amino)-2-oxoethyl)cyclohexyl)carbamate (2.200 g, 7.323 mmol, 94% yield) as a white solid. $^1$H NMR (400 MHz, CDCl$_3$) δ 4.41 (s, 1H), 3.66 (s, 3H), 3.37 (s, 1H), 3.17 (s, 3H), 2.31-2.29 (d, J=6.4 Hz, 2H), 2.04-1.97 (m, 2H), 1.85-1.79 (m, 3H), 1.43 (s, 9H), 1.18-1.02 (m, 4H).

tert-Butyl (trans-4-(2-oxoethyl)cyclohexyl)carbamate. To a solution of tert-butyl (trans-4-(2-(methoxy(methyl) amino)-2-oxoethyl)cyclohexyl)carbamate (2.2 g, 7.320 mmol, 1 equiv.) in dichloromethane (10 mL) was added a solution of 70% bis(2-methoxyethoxy)aluminum hydride in toluene (4.08 mL, 14.65 mmol, 2 equiv.) at 0° C. After stirring for 2 h the reaction solution was diluted with water (20 mL) and saturated aqueous ammonium chloride (10 mL). The solution was extracted with dichloromethane (3×30 mL), the combined organic layers were dried over anhydrous sodium sulfate and concentrated. The resulting crude oil was purified by silica gel column chromatography (0-25% ethyl acetate in petroleum ether) to afford tert-butyl (trans-4-(2-oxoethyl)cyclohexyl)carbamate (1.450 g, 6.008 mmol, 82% yield) as a white solid. $^1$H NMR (400 MHz, CDCl$_3$) δ 9.65-9.64 (t, J=2.0 Hz, 1H), 6.69-6.64 (m, 1H), 3.19-3.13 (m, 1H), 2.55-2.52 (m, 1H), 2.29-2.27 (m, 2H), 1.75-1.64 (m, 5H), 1.36 (s, 9H), 1.17-1.08 (m, 2H), 1.06-0.83 (m, 2H).

Ethyl (E)-4-(trans-4-((tert-butoxycarbonyl)amino)cyclohexyl)but-2-enoate. To a solution of tert-butyl (trans-4-(2-oxoethyl)cyclohexyl)carbamate (1.450 g, 6.010 mmol, 1 equiv.) in toluene (10 mL, 0.6 M) was added ethyl 2-(triphenylphosphoranylidene)acetate (2.300 g, 6.610 mmol, 1.1 equiv.) and the reaction mixture was stirred at 80° C. After 12 h the reaction solution was concentrated and the resulting crude material was purified by silica gel column chromatography (0-20% ethyl acetate in hexanes) to give ethyl (E)-4-(trans-4-((tert-butoxycarbonyl)amino)cyclohexyl)but-2-enoate (0.890 g, 2.858 mmol, 48% yield) as a white solid. $^1$H NMR (400 MHz, CDCl$_3$) δ 6.95-6.88 (m, 1H), 5.82-5.78 (m, 1H), 4.36 (s, 1H), 4.24-4.14 (m, 2H), 3.37 (s, 1H), 2.12-2.08 (m, 2H), 2.05-1.99 (m, 2H), 1.79-1.76 (m, 2H), 1.46-1.36 (m, 10H), 1.31-1.27 (t, J=7.2 Hz, 3H), 1.13-0.99 (m, 4H).

tert-Butyl (trans-4-(4-hydroxybutyl)cyclohexyl)carbamate. To a solution of sodium borohydride (0.811 g, 21.43 mmol, 7.5 equiv.) in ethanol (16 mL) and THF (16 mL) was added anhydrous lithium chloride (0.900 g, 21.43 mmol, 7.5 equiv.) at 0° C. and the solution was stirred for 10 min. To the reaction solution was added a solution of ethyl (E)-4-(trans-4-((tert-butoxycarbonyl)amino)cyclohexyl)but-2-enoate (0.890. g, 2.860 mmol, 1 equiv.) in THF (8 mL) and the reaction solution was stirred at 15° C. After 12 h the reaction solution was quenched by slow addition of 1 M aqueous hydrochloric acid (10 mL) and the solution was extracted with ethyl acetate (3×20 mL). The combined organic layers were dried over anhydrous sodium sulfate, concentrated, and purified by silica gel column chromatography (0-25% ethyl acetate in hexanes) to give tert-butyl (trans-4-(4-hydroxybutyl)cyclohexyl)carbamate (0.750 g, 2.763 mmol, 96% yield) as a white solid. $^1$H NMR (400 MHz, CDCl$_3$) δ 4.37 (s, 1H), 3.66-3.62 (t, J=6.8 Hz, 2H), 3.36 (s, 1H), 2.00-1.98 (m, 2H), 1.78-1.75 (m, 2H), 1.58-1.51 (m, 2H), 1.44 (s, 9H), 1.40-1.32 (m, 2H), 1.28-1.14 (m, 4H), 1.08-0.94 (m, 4H).

4-(trans-4-Aminocyclohexyl)butan-1-ol. To a solution of tert-butyl (trans-4-(4-hydroxybutyl)cyclohexyl)carbamate (0.750. g, 2.760 mmol, 1 equiv.) in dichloromethane (2 mL) was added 4 M hydrochloric acid in 1,4-dioxane (4 mL, 16 mmol, 5.8 equiv.) and the reaction solution was stirred at room temperature. After 12 h the reaction solution was concentrated to remove organic solvents and then diluted with saturated sodium bicarbonate (30 mL) and extracted with ethyl acetate (2×30 mL). The combined organic layers were washed with brine (30 mL), dried over anhydrous sodium sulfated and concentrated to give 4-(trans-4-aminocyclohexyl)butan-1-ol (0.410 g, 2.394 mmol, 87% yield) as a white solid which was carried forward without further purification. $^1$H NMR (400 MHz, CDCl$_3$) δ 3.62-3.59 (t, J=6.4 Hz, 2H), 2.61-2.54 (m, 1H), 1.85-1.81 (m, 2H), 1.75-1.72 (m, 2H), 1.56-1.49 (m, 4H), 1.39-1.31 (m, 2H), 1.25-1.12 (m, 3H), 1.10-1.00 (m, 2H), 0.97-0.87 (m, 2H).

Methyl 2-((trans-4-(4-hydroxybutyl)cyclohexyl)amino)-2-methylpropanoate.

To a solution of methyl 2-bromo-2-methylpropanoate (1.733 g, 9.570 mmol, 4 equiv.) and 4-(trans-4-aminocyclohexyl)butan-1-ol (0.410. g, 2.390 mmol, 1 equiv.) in acetonitrile (3 mL) was added potassium carbonate (0.993 g, 7.180 mmol, 3 equiv.) and sodium iodide (0.072 g, 0.480 mmol, 0.2 equiv.) and the reaction solution was stirred at 80° C. After 12 h the reaction solution was diluted with ethyl acetate, filtered and concentrated to provide crude methyl 2-((trans-4-(4-hydroxybutyl)cyclohexyl)amino)-2-methylpropanoate (1.000 g, crude) as a brown oil. MS (ESI) m/z 272.3 [M+1]$^+$.

4-(3-(trans-4-(4-Hydroxybutyl)cyclohexyl)-4,4-dimethyl-5-oxo-2-thioxoimidazolidin-1-yl)-2-(trifluoromethyl)benzonitrile. To a solution of methyl 2-((trans-4-(4-hydroxybutyl)cyclohexyl)amino)-2-methylpropanoate (1.000. g, 2.320 mmol, 1 equiv.) and 4-isothiocyanato-2-(trifluoromethyl)benzonitrile (0.556 g, 2.440 mmol, 1.1 equiv.) in ethyl acetate (12 mL) was added N,N-diisopropylethylamine (1.15 mL, 6.960 mmol, 3 equiv.) and the reaction mixture was stirred for at 80° C. After 3 h the reaction solution was diluted with ethyl acetate (20 mL) and concentrated. The resulting crude oil was purified by silica gel column chromatography (0-35% ethyl acetate in petroleum ether) to give 4-(3-(trans-4-(4-hydroxybutyl)cyclohexyl)-4,4-dimethyl-5-oxo-2-thioxoimidazolidin-1-yl)-2-(trifluoromethyl)benzonitrile (0.360 g, 0.736 mmol, 32% yield) as a brown solid. MS (ESI) m/z 468.1 [M+1]$^+$.

4-(3-(trans-4-(4-Bromobutyl)cyclohexyl)-4,4-dimethyl-5-oxo-2-thioxoimidazolidin-1-yl)-2-(trifluoromethyl)benzonitrile. To a solution of 4-(3-(trans-4-(4-hydroxybutyl)cyclohexyl)-4,4-dimethyl-5-oxo-2-thioxoimidazolidin-1-yl)-2-(trifluoromethyl)benzonitrile (0.360. g, 0.770 mmol, 1 equiv.) in dichloromethane (3 mL) was added N,N-dimethylformamide (0.30 mL) and thionyl bromide (0.400 g, 1.920 mmol, 2.5 equiv.) and the reaction solution was stirred at 15° C. After 12 h the reaction solution was concentrated and purified by silica gel column chromatography (0-20% ethyl acetate in petroleum ether) to give 4-(3-(trans-4-(4-bromobutyl)cyclohexyl)-4,4-dimethyl-5-oxo-2-thioxoimidazolidin-1-yl)-2-(trifluoromethyl)benzonitrile (0.280 g, 0.517 mmol, 67% yield) as a brown solid. MS (ESI) m/z 530.0 [M+1]$^+$; $^1$H NMR (400 MHz, CDCl$_3$) δ 7.96-7.94 (d, J=8.4 Hz, 1H), 7.86-7.85 (d, J=1.6 Hz, 1H), 7.75-7.72 (d, J=8.4, 1.6 Hz, 1H), 3.85 (s, 1H), 3.45-3.41 (t, J=6.8 Hz, 2H), 2.69 (s, 2H), 1.95-1.92 (m, 2H), 1.88-1.83 (m, 4H), 1.61 (s, 6H), 1.50-1.44 (m, 2H), 1.36-1.34 (m, 1H), 1.27-1.25 (m, 2H), 1.11-1.01 (m, 2H).

2-((2R,6S)-4-(4-(trans-4-(3-(4-Cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a mixture of 2-((2R,6S)-2,6-dimethylpiperazin-1-yl)-N-(3-(2,4-dioxotetrahydropyrimidin-1(2H)-yl)-1-methyl-1H-indazol-7-yl)acetamide hydrobromide (0.081 g, 0.200 mmol, 1.3 equiv.) and 44-(3-(trans-4-(4-bromobutyl)cyclohexyl)-4,4-dimethyl-5-oxo-2-thioxoimidazolidin-1-yl)-2-(trifluoromethyl)benzonitrile (0.079 g, 0.150 mmol, 1 equiv.) in N,N-dimethylformamide (1 mL) was added N,N- diisopropylethylamine (0.065 g, 0.500 mmol, 3.3 equiv.) and the reaction solution was stirred at 50° C. After 12 h the reaction solution was diluted with water (50 mL) and extracted with dichloromethane (2×50 mL). The combined organic layers were washed with brine (40 mL), dried over anhydrous sodium sulfate and concentrated. The resulting crude material was purified by standard methods to give 2-((2R,6S)-4-(4-(trans-4-(3-(4-cyano-3-(trifluoromethyl) phenyl)-5,5-dimethyl-4-oxo-2-thioxoimidazolidin-1-yl)cyclohexyl)butyl)-2,6-dimethylpiperazin-1-yl)-N-(3-(2,4-dioxotetrahydropyrimidin-1(2H)-yl)-1-methyl-1H-indazol-7-yl)acetamide hydrochloride (0.050 g, 0.056 mmol, 38% yield). MS (ESI) m/z 863.3 [M+1]+.

Example 18: 4-(3-(trans-4-(2-((3R,5S)-4-(2-((3-(2,4-Dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride

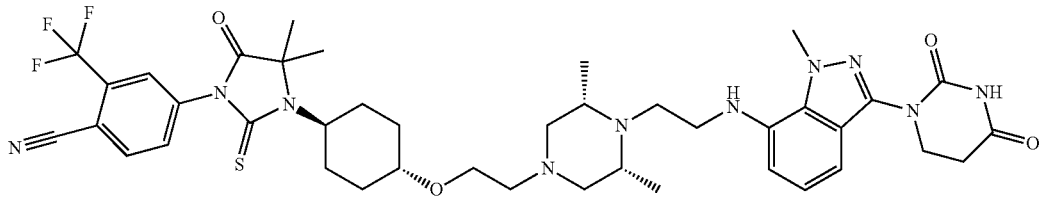 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CCNc1cccc2c(N3CCC(=O)NC3=O)nn(C)c12]

1-Methyl-7-nitro-1H-indazol-3-amine. To a solution of 2-fluoro-3-nitrobenzonitrile (20.000 g, 120.400 mmol, 1 equiv.) in N,N-dimethylacetamide (200 mL) was added methylhydrazine (48 mL, 361.210 mmol, 3 equiv.) and N,N-diisopropylethylamine (23 mL, 132.050 mmol, 1.1 equiv.) and the reaction solution was stirred at room temperature. After 30 min the reaction solution was diluted with water (500 mL) and extracted with ethyl acetate (2×500 mL). The combined organic layers were washed with brine (500 mL), dried over anhydrous sodium sulfate and concentrated to give 1-methyl-7-nitro-1H-indazol-3-amine (13.20 g, 68.689 mmol, 57% yield) as a brown solid. $^1$H NMR (400 MHz, DMSO-$d_6$) δ 8.16 (dd, J=7.6, 1.2 Hz, 1H), 8.08 (dd, J=7.6, 1.2 Hz, 1H), 7.09 (t, J=7.6 Hz, 1H), 5.91 (s, 2H), 3.81 (s, 3H).

3-((1-Methyl-7-nitro-1H-indazol-3-yl)amino)propanoic acid. To a mixture of 1-methyl-7-nitro-1H-indazol-3-amine (12.70 g, 66.090 mmol, 1 equiv.) in 1,4-dioxane (50 mL) was added aluminum oxide (20.214 g, 198.260 mmol, 3 equiv.), tris(trifluoromethylsulfonyloxy)ytterbium (2.050 g, 3.304 mmol, 5 mol %) and acrylic acid (14.29 g, 198.260 mmol, 3 equiv.). and the reaction solution was stirred at 110° C. after 24 h the reaction solution was filtered and concentrated. The resulting crude material was purified by semi-preparative reverse phase HPLC (20%-50% acetonitrile in water+0.225% formic acid, 26 min) to give 3-((1-methyl-7-nitro-1H-indazol-3-yl)amino)propanoic acid (12.000 g, 45.413 mmol, 69% yield) as a black solid. MS (ESI) m/z 265.1 [M+1]+.

Methyl 3-((1-methyl-7-nitro-1H-indazol-3-yl)amino)propanoate. To a mixture of 3-((1-methyl-7-nitro-1H-indazol-3-yl)amino)propanoic acid (12.00 g, 45.410 mmol, 1 equiv.) in toluene (80 mL) and methanol (80 mL) was added diazomethyl(trimethyl)silane (72 mL, 45.410 mmol, 1 equiv.) dropwise at 0° C. under nitrogen atmosphere. The mixture was warmed to 25° C. and stirred for 12 hours. The reaction solution was diluted with water (200 mL) and extracted with ethyl acetate (3×100 mL). the combined organic layers were washed with brine (100 mL), dried over anhydrous sodium sulfate and concentrated. The resulting crude material was purified by semi-preparative reverse phase HPLC (35%-65% acetonitrile in water+0.225% formic acid, 25 min) to give methyl 3-((1-methyl-7-nitro-1H-indazol-3-yl)amino)propanoate (8.600 g, 30.906 mmol, 68% yield) as a black solid. MS (ESI) m/z 279.1 [M+1]+; $^1$H NMR (400 MHz, CDCl$_3$) δ 8.09 (dd, J=7.6, 0.8 Hz, 1H), 7.78 (dd, J=7.6, 0.8 Hz, 1H), 7.03 (t, J=8.0 Hz, 1H), 4.66 (s, 1H), 3.71-3.75 (m, 5H), 2.78 (t, J=6.00 Hz, 2H).

Methyl 3-(1-(1-methyl-7-nitro-1H-indazol-3-yl)ureido) propanoate. To a mixture of methyl 3-((1-methyl-7-nitro-1H-indazol-3-yl)amino)propanoate (8.600 g, 30.910 mmol, 1 equiv.) in acetic acid (80 mL) was added potassium isocyanate (7.521 g, 92.720 mmol, 3 equiv.) and the reaction solution was stirred at room temperature. After 12 h the reaction solution was diluted with water (50 mL) and extracted with ethyl acetate (3×20 mL). The combined organic layers were washed with brine (50 mL), dried over anhydrous sodium sulfate and concentrated. The resulting crus material was purified by semi-preparative reverse phase HPLC (16%-46% acetonitrile in water+0.225% formic acid, 23 min) to give methyl 3-(1-(1-methyl-7-nitro-1H-indazol-3-yl)ureido)propanoate (6.400 g, 19.920 mmol, 64% yield) as a light orange solid. MS (ESI) m/z 322.1 [M+1]+; $^1$H NMR (400 MHz, CDCl$_3$) δ 8.17 (dd, J=7.6, 1.2 Hz, 1H), 7.99 (dd, J=8.0, 0.8 Hz, 1H), 7.27-7.31 (m, 1H), 4.92 (s, 2H), 4.20 (s, 3H), 4.17 (t, J=6.8 Hz, 2H), 3.61 (s, 3H), 2.75 (t, J=6.8 Hz, 2H).

Methyl 3-(1-(7-amino-1-methyl-1H-indazol-3-yl)ureido) propanoate. To a solution of methyl 3-(1-(1-methyl-7-nitro-1H-indazol-3-yl)ureido)propanoate (7.100 g, 22.100 mmol, 1 equiv.) in THF (100 mL) and methanol (100 mL) was added palladium hydroxide (1.000 g, 28.530 mmol) under nitrogen atmosphere. The suspension was degassed under vacuum, purged with hydrogen gas three times, and stirred under hydrogen atmosphere (15 psi) at room temperature. After 5 h the reaction solution was filtered and concentrated to give methyl 3-(1-(7-amino-1-methyl-1H-indazol-3-yl) ureido)propanoate (6.100 g, 20.940 mmol, 95% yield) as a light yellow oil. MS (ESI) m/z 292.1 [M+1]+; $^1$H NMR (400 MHz, CDCl$_3$) δ 7.08 (dd, J=8.0, 0.8 Hz, 1H), 6.93-7.01 (m, 1H), 6.65 (d, J=7.2 Hz, 1H), 4.77 (s, 2H), 4.34 (s, 3H), 4.07-4.17 (m, 2H), 3.91 (s, 2H), 3.59 (s, 3H), 2.65-2.78 (m, 2H).

Benzyl (3S,5R)-4-(2-((3-(1-(3-methoxy-3-oxopropyl) ureido)-1-methyl-1H-indazol-7-yl)amino)ethyl)-3,5-dimethylpiperazine-1-carboxylate. To a solution of benzyl (3S, 5R)-4-(2-hydroxyethyl)-3,5-dimethylpiperazine-1-carboxylate (0.200 g, 0.680 mmol, 1 equiv.) and N,N- diisopropylethylamine (0.36 mL, 2.050 mmol, 3 equiv.) in acetonitrile (4 mL) was added a solution of trifluoromethanesulfonic anhydride (0.14 mL, 0.820 mmol, 1.2 equiv.) in acetonitrile (1 mL) at 0° C. After stirring at 0° C. for 2 h, methyl 3-(1-(7-amino-1-methyl-1H-indazol-3-yl)ureido) propanoate (0.199 g, 0.680 mmol, 1 equiv.) in acetonitrile (10 mL) was added, and the reaction solution was slowly warmed to room temperature. After 12 h the reaction solution was concentrated, re-suspended in water (50 mL) and extracted with ethyl acetate (3×50 mL). The combined organic layers were washed with brine (50 mL, dried over anhydrous sodium sulfate and concentrated. The resulting crude material was purified by silica gel column chromatography (1.5% methanol in dichloromethane) to give benzyl (3S,5R)-4-(2-((3-(1-(3-methoxy-3-oxopropyl)ureido)-1-methyl-1H-indazol-7-yl)amino)ethyl)-3,5-dimethylpiperazine-1-carboxylate (1.500 g, 2.652 mmol, 39% yield) as a yellow solid. MS (ESI) m/z 566.3 [M+1]+; 1H NMR (400 MHz, CDCl3-d) δ 7.46-7.29 (m, 5H), 7.12-6.90 (m, 2H), 6.50 (d, J=7.2 Hz, 1H), 5.15 (br s, 2H), 4.90-4.69 (m, 2H), 4.69-4.50 (m, 1H), 4.35 (s, 3H), 4.13-4.07 (m, 2H), 3.99-3.77 (m, 2H), 3.59 (s, 3H), 3.29-3.13 (m, 2H), 3.06-2.95 (m, 2H), 2.87-2.56 (m, 6H), 1.15 (br d, J=5.6 Hz, 6H).

Benzyl (3S,5R)-4-(2-((3-(2,4-dioxotetrahydropyrimidin-1(2H)-yl)-1-methyl-1H-indazol-7-yl)amino)ethyl)-3,5-dimethylpiperazine-1-carboxylate. To a solution of benzyl (3S,5R)-4-(2-((3-(1-(3-methoxy-3-oxopropyl)ureido)-1-methyl-1H-indazol-7-yl)amino)ethyl)-3,5-dimethylpiperazine-1-carboxylate (1.500 g, 2.650 mmol, 1 equiv.) in THF (30 mL) was added potassium tert-butoxide (0.298 g, 2.650 mmol, 1 equiv.) at 0° C. After stirring for 2 h the reaction was acidified with 1 M aqueous hydrochloric acid (10 mL) and the solution was adjusted to pH 8 by addition of saturated aqueous sodium bicarbonate. The aqueous solution was extracted with ethyl acetate (3×50 mL), and the combined organic layers were washed with brine (10 mL), dried over anhydrous sodium sulfate and concentrated. The resulting crude material was purified by silica gel column chromatography ((1% methanol in dichloromethane) to give benzyl (3S,5R)-4-(2-((3-(2,4-dioxotetrahydropyrimidin-1(2H)-yl)-1-methyl-1H-indazol-7-yl)amino)ethyl)-3,5-dimethylpiperazine-1-carboxylate (1.290 g, 2.364 mmol, 89% yield) as a yellow solid. MS (ESI) m/z 534.3 [M+1]+; 1H NMR (400 MHz, DMSO-d6) δ 10.49 (s, 1H), 7.39-7.30 (m, 5H), 6.92-6.86 (m, 2H), 6.48 (dd, J=1.2, 6.4 Hz, 1H), 5.35 (t, J=5.4 Hz, 1H), 5.08 (s, 2H), 4.23 (s, 3H), 3.90-3.66 (m, 4H), 3.13 (q, J=6.4 Hz, 2H), 3.01-2.85 (m, 2H), 2.74 (t, J=6.4 Hz, 2H), 2.70-2.53 (m, 4H), 1.09 (br d, J=3.6 Hz, 6H).

1-(7-((2-((2S,6R)-2,6-Dimethylpiperazin-1-yl)ethyl) amino)-1-methyl-1H-indazol-3-yl)dihydropyrimidine-2,4 (1H,3H)-dione. To a solution of benzyl (3S,5R)-4-(2-((3-(2,4-dioxotetrahydropyrimidin-1(2H)-yl)-1-methyl-1H-indazol-7-yl)amino)ethyl)-3,5-dimethylpiperazine-1-carboxylate (1.290 g, 2.380 mmol, 1 equiv.) in THF (10 mL) and methanol (10 mL) was added 10% pallidum on carbon (500. mg, 0.4700 mmol). The reaction vessel was degassed, purged with hydrogen and stirred under a hydrogen atmosphere (15 psi) at room temperature. After 12 h the reaction solution was filtered and concentrated to provide 1-(7-((2-((2S,6R)-2,6-dimethylpiperazin-1-yl)ethyl)amino)-1-methyl-1H-indazol-3-yl)dihydropyrimidine-2,4(1H,3H)-dione (0.935 g, 2.289 mmol, 96% yield) as a yellow solid. MS (ESI) m/z 400.2 [M+1]+; 1H NMR (400 MHz, DMSO-d6) δ 10.89-10.00 (m, 1H), 6.98-6.78 (m, 2H), 6.46 (d, J=6.4 Hz, 1H), 5.36 (t, J=5.6 Hz, 1H), 4.24 (s, 3H), 3.83 (t, J=6.4 Hz, 2H), 3.16-3.11 (m, 2H), 2.93-2.84 (m, 2H), 2.79-2.68 (m, 4H), 2.49-2.42 (m, 2H), 2.25 (m, 2H), 1.01 (d, J=6.0 Hz, 6H).

4-(3-(trans-4-(2-((3R,5S)-4-(2-((3-(2,4-dioxotetrahydropyrimidin-1(2H)-yl)-1-methyl-1H-indazol-7-yl)amino) ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride. To a flask containing 4-(3-(trans-4-(2-bromoethoxy)cyclohexyl)-4,4-dimethyl-5-oxo-2-thioxoimidazolidin-1-yl)-2-(trifluoromethyl)benzonitrile (150 mg, 0.29 mmol, 1 equiv.) was added 1-(7-((2-((2R,6S)-2,6-dimethylpiperazin-1-yl)ethyl)amino)-1-methyl-1H-indazol-3-yl)dihydropyrimidine-2,4(1H,3H)-dione (138 mg, 0.35 mmol, 1.2 equiv.), N,N-diisopropylethylamine (0.2 mL, 1.16 mmol, 4 equiv.), sodium iodide (52 mg, 0.35 mmol, 1.2 equiv.), and N,N-dimethylformamide (2.0 mL 0.15 M). The reaction was stirred at 50° C. After 18 h the reaction solution was diluted with DMSO (1 mL) and purified by standard methods to give 4-(3-(trans-4-(2-((3R,5S)-4-(2-((3-(2,4-dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl) benzonitrile hydrochloride (159 mg, 0.182 mmol, 63% yield) as an off-white solid. MS (ESI) m/z 837.4 [M+1]; 1H NMR (400 MHz, DMSO-d6) δ 10.51 (s, 1H), 8.34 (d, J=8.31 Hz, 1H), 8.19 (d, J=1.59 Hz, 1H), 7.97 (dd, J=1.65, 8.25 Hz, 1H), 6.91-7.01 (m, 2H), 6.57 (br s, 1H), 4.30 (s, 3H), 3.90-4.06 (m, 4H), 3.77-3.88 (m, 7H), 3.54-3.67 (m, 4H), 3.19-3.42 (m, 4H), 2.79-2.93 (m, 2H), 2.75 (t, J=6.66 Hz, 2H), 2.05-2.16 (m, 2H), 1.66-1.78 (m, 2H), 1.55 (s, 6H), 1.24-1.49 (m, 8H).

Example 19: 4-(3-(trans-4-(2-((3R,5S)-4-(2-((3-(2,4-Dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl) benzonitrile hydrochloride

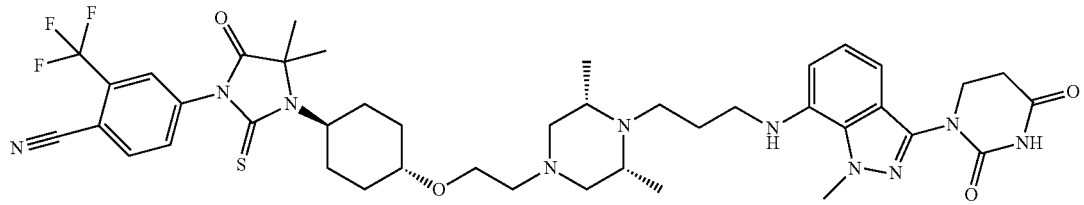 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CCCNc1cccc2c(N3CCC(=O)NC3=O)nn(C)c12]

Benzyl (3S,5R)-4-(3-hydroxypropyl)-3,5-dimethylpiperazine-1-carboxylate. To a mixture of benzyl (3R,5S)-3,5-dimethylpiperazine-1-carboxylate (4.000 g, 16.110 mmol, 1 equiv.) and 3-bromopropan-1-ol (3.360 g, 24.160 mmol, 2.18 mL, 1.5 equiv.) in N,N-dimethylformamide (50 mL) was added sodium iodide (2.410 g, 16.110 mmol, 1 equiv.) and N,N-diisopropylethylamine (6.250 g, 48.320 mmol, 8.42 mL, 3 equiv.) in one portion at 25° C. The mixture was heated to 70° C. and stirred for 12 hours. The aqueous phase was extracted with ethyl acetate (3×30 mL). The combined organic layers were washed with brine (3×30 mL), dried over anhydrous sodium sulfate and concentrated. The resulting crude material was purified by semi-preparative reverse phase HPLC (25%-45% acetonitrile in water+0.05% ammonia hydroxide, 15 min) to give benzyl (3S,5R)-4-(3-hydroxypropyl)-3,5-dimethylpiperazine-1-carboxylate (3.400 g, 11.100 mmol, 69% yield) was obtained as a light yellow oil. MS (ESI) m/z 307.2 [M+1]$^+$; $^1$H NMR (400 MHz, CDCl$_3$) δ 7.29-7.41 (m, 5H), 5.13 (s, 2H), 3.81-4.03 (m, 2H), 3.76 (t, J=5.4 Hz, 2H), 3.60-3.74 (m, 1H), 2.85 (t, J=6.8 Hz, 2H), 2.60-2.78 (m, 2H), 2.40-2.55 (m, 2H), 1.70 (quin, J=6.0 Hz, 2H), 1.17 (d, J=6.0 Hz, 6H).

Benzyl (3S,5R)-3,5-dimethyl-4-(3-((methylsulfonyl)oxy)propyl)piperazine-1-carboxylate. To a mixture of benzyl (3R,5S)-4-(3-hydroxypropyl)-3,5-dimethylpiperazine-1-carboxylate (3.400 g, 11.10 mmol, 1 equiv.) in dichloromethane (50 mL) was added triethylamine (2.250 g, 22.190 mmol, 3.09 mL, 2 equiv.) in one portion at 0° C. To the reaction solution was slowly added methanesulfonyl chloride (1.910 g, 16.640 mmol, 1.29 mL, 1.5 equiv.), and the reaction solution was stirred at 0° C. After 2 h the reaction solution was diluted with water (50 mL) and extracted with ethyl acetate (3×50 mL). The combined organic layers were washed with brine (100 mL), dried over anhydrous sodium sulfate and concentrated. The resulting crude material was purified by silica gel column chromatography (0-2% methanol in dichloromethane) to give benzyl (3S,5R)-3,5-dimethyl-4-(3-((methylsulfonyl)oxy)propyl)piperazine-1-carboxylate (3.250 g, 8.450 mmol, 76% yield) as a light yellow oil. $^1$H NMR (400 MHz, CDCl$_3$) δ 7.29-7.42 (m, 5H), 5.14 (s, 2H), 4.24 (t, J=6.4 Hz, 2H), 3.80-4.07 (m, 2H), 3.02 (s, 3H), 2.80-2.92 (m, 2H), 2.45-2.69 (m, 4H), 1.77-1.91 (m, 2H), 1.09 (d, J=5.2 Hz, 6H).

Benzyl (3S,5R)-4-(3-((3-(1-(3-methoxy-3-oxopropyl)ureido)-1-methyl-1H-indazol-7-yl)amino)propyl)-3,5-dimethylpiperazine-1-carboxylate. To a mixture of methyl 3-(1-(7-amino-1-methyl-1H-indazol-3-yl)ureido)propanoate (2.500 g, 8.580 mmol, 1 equiv.) in acetonitrile (50 mL) was added N,N-diisopropylethylamine (2.218 g, 17.160 mmol, 2 equiv.), benzyl (3S,5R)-3,5-dimethyl-4-(3-((methylsulfonyl)oxy)propyl)piperazine-1-carboxylate (4.289 g, 11.160 mmol, 1.3 equiv.) and sodium iodide (1.286 g, 8.580 mmol, 1 equiv.) and the reaction solution was stirred at 90° C. After 12 h the reaction solution was diluted with water (50 mL) and extracted with ethyl acetate (3×50 mL). the combined organic layers were washed with brine (100 mL), dried over anhydrous sodium sulfate and concentrated. The resulting crude material was purified by semi-preparative reverse phase HPLC (30%-60% acetonitrile in water+0.05% ammonium hydroxide, 20 min) to give benzyl (3S,5R)-4-(3-((3-(1-(3-methoxy-3-oxopropyl)ureido)-1-methyl-1H-indazol-7-yl)amino)propyl)-3,5-dimethylpiperazine-1-carboxylate (1.300 g, 4.463 mmol, 52% yield) as a light pink solid. MS (ESI) m/z 580.3 [M+1]$^+$; $^1$H NMR (400 MHz, CDCl$_3$) δ 7.30-7.41 (m, 5H), 6.99-7.07 (m, 2H), 6.52 (dd, J=7.0, 1.2 Hz, 1H), 5.14 (s, 2H), 4.74 (s, 2H), 4.33 (s, 3H), 4.09-4.15 (m, 2H), 3.85-4.00 (m, 2H), 3.59 (s, 3H), 3.14-3.23 (m, 2H), 2.87-2.94 (m, 2H), 2.69-2.76 (m, 2H), 2.52-2.69 (m, 4H), 1.82-1.90 (m, 2H), 1.12 (s, 6H).

1-(7-((3-((2S,6R)-2,6-Dimethylpiperazin-1-yl)propyl)amino)-1-methyl-1H-indazol-3-yl)dihydropyrimidine-2,4(1H,3H)-dione. To benzyl (3S,5R)-4-(3-((3-(1-(3-methoxy-3-oxopropyl)ureido)-1-methyl-1H-indazol-7-yl)amino)propyl)-3,5-dimethylpiperazine-1-carboxylate (1.620 g, 2.790 mmol, 1 equiv.) was added 12 M aqueous hydrochloric acid (15 mL), and the reaction solution was stirred at room temperature. After 12 h the reaction solution was concentrated and purified by semi-preparative reverse phase HPLC (15%-45% acetonitrile in water+10 mM ammonium carbonate) to give 1-(7-((3-((2S,6R)-2,6-dimethylpiperazin-1-yl)propyl)amino)-1-methyl-1H-indazol-3-yl)dihydropyrimidine-2,4(1H,3H)-dione (0.310 g, 0.750 mmol, 27% yield) as a yellow solid. MS (ESI) m/z 414.1 [M+1]$^+$; $^1$H NMR (400 MHz, DMSO-d$_6$) δ 10.49 (s, 1H), 6.82-6.94 (m, 2H), 6.45 (dd, J=5.6, 1.6 Hz, 1H), 5.43 (s, 1H), 4.24 (s, 3H), 3.83 (t, J=6.8 Hz, 2H), 3.05 (q, J=6.28 Hz, 2H), 2.72-2.85 (m, 4H), 2.62-2.72 (m, 2H), 2.35-2.45 (m, 2H), 2.16-2.32 (m, 2H), 1.67-1.82 (m, 2H), 0.87-1.08 (m, 6H).

4-(3-((trans-4-(2-((3R,5S)-4-(2-((3-(2,4-Dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride. To a flask containing 4-(3-((trans-4-(2-bromoethoxy)cyclohexyl)-4,4-dimethyl-5-oxo-2-thioxoimidazolidin-1-yl)-2-(trifluoromethyl)benzonitrile (150 mg, 0.29 mmol, 1 equiv.) was added 1-(7-((2-((2R,6S)-2,6-dimethylpiperazin-1-yl)ethyl)amino)-1-methyl-1H-indazol-3-yl)dihydropyrimidine-2,4(1H,3H)-dione (138 mg, 0.35 mmol, 1.2 equiv.), N,N-diisopropylethylamine (0.2 mL, 1.16 mmol, 4 equiv.), sodium iodide (52 mg, 0.35 mmol, 1.2 equiv.), and N,N-dimethylformamide (2.0 mL, 0.15 M). The reaction was stirred at 50° C. After 18 h the reaction solution was diluted with DMSO (1 mL) and purified by standard methods to give 4-(3-(trans-4-(2-((3R,5S)-4-(2-((3-(2,4-dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile hydrochloride (159 mg, 0.182 mmol, 63% yield) as an off-white solid. MS (ESI) m/z 837.4 [M+1]$^+$; $^1$H NMR (400 MHz, DMSO-d$_6$) δ 10.51 (s, 1H), 8.34 (d, J=8.31 Hz, 1H), 8.19 (d, J=1.59 Hz, 1H), 7.97 (dd, J=1.65, 8.25 Hz, 1H), 6.91-7.01 (m, 2H), 6.57 (br s, 1H), 4.30 (s, 3H), 3.90-4.06 (m, 4H), 3.77-3.88 (m, 7H), 3.54-3.67 (m, 4H), 3.19-3.42 (m, 4H), 2.79-2.93 (m, 2H), 2.75 (t, J=6.66 Hz, 2H), 2.05-2.16 (m, 2H), 1.66-1.78 (m, 2H), 1.55 (s, 6H), 1.24-1.49 (m, 8H).

Example 20: 2-((R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride

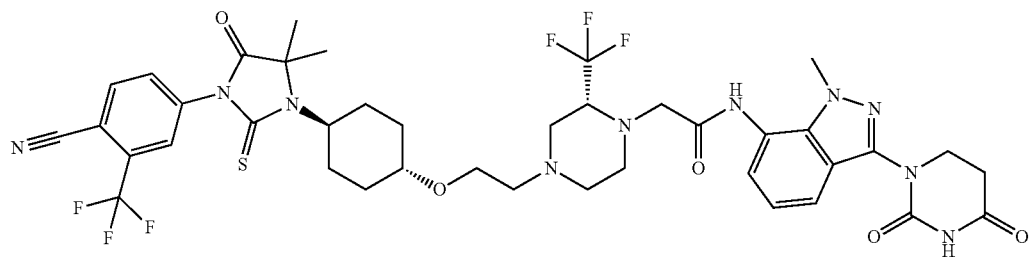 [SMILES: Cn1nc(N2CCC(=O)NC2=O)c2cccc(NC(=O)CN3CCN(CCO[C@H]4CC[C@H](N5C(=S)N(c6ccc(C#N)c(C(F)(F)F)c6)C(=O)C5(C)C)CC4)C[C@@H]3C(F)(F)F)c21]

tert-Butyl (R)-4-(2-methoxy-2-oxoethyl)-3-(trifluoromethyl)piperazine-1-carboxylate. To a 40 ml vial was added tert-butyl (R)-3-(trifluoromethyl)piperazine-1-carboxylate (0.5 g, 1.97 mmol), N,N-diisopropylethylamine (0.69 mL, 3.93 mmol, 2 equiv.), methyl bromoacetate (1.09 mL, 11.8 mmol, 6 equiv.) and THE (20 mL, 0.1 M). The reaction solution was stirred at room temperature. After 18 the solution was diluted with 100 ml ethyl acetate and 100 ml water. The organic layer was removed, and the aqueous layer was extracted with 2×50 ml ethyl acetate. Then combined organic layers were dried over magnesium sulfate and concentrated. The crude material was purified by silica gel column chromatography (1-50% ethyl acetate in hexanes) to provide tert-butyl (R)-4-(2-methoxy-2-oxoethyl)-3-(trifluoromethyl)piperazine-1-carboxylate (0.557 g, 1.71 mmol, 88% yield) as a yellow oil. MS (ESI) m/z 227 [M−99]+.

Methyl (R)-2-(2-(trifluoromethyl)piperazin-1-yl)acetate. tert-Butyl (R)-3-(trifluoromethyl)piperazine-1-carboxylate (250 mg, 0.7 mmol), and trifluoroacetic acid (0.58 mL, 7.6 mmol, 10 equiv.) were combined in dichloromethane (7.6 mL, 1 M) and stirred at room temperature in a screw capped scintillation vial. After 1 h, the solution was concentrated methyl (R)-2-(2-(trifluoromethyl)piperazin-1-yl)acetate (255 mg, 0.75 mmol, 98% yield) as a yellow oil that was carried forward without further purification. MS (ESI) m/z 227 [M+1]+.

Methyl 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)acetate. To a 1-dram vial containing 4-(3-(trans-4-(2-bromoethoxy)cyclohexyl)-4,4-dimethyl-5-oxo-2-thioxoimidazolidin-1-yl)-2-(trifluoromethyl)benzonitrile (0.5 g, 0.96 mmol, 1 equiv.), methyl (R)-2-(2-(trifluoromethyl)piperazin-1-yl)acetate (0.33 g, 0.96 mmol, 1 equiv.) and sodium iodide (2.7 mg, 0.02 mmol, 0.1 equiv.) was added acetonitrile (5 mL) followed by N,N-diisopropylethylamine (0.8 mL, 4.82 mmol, 5 equiv.). The reaction vial was heated with stirring to 60° C. After 16 h the reaction solution was diluted with ethyl acetate (100 mL), washed with saturated aqueous sodium chloride (100 mL), dried over anhydrous sodium sulfate and concentrated. The crude material was purified by silica gel column chromatography (0-100% ethyl acetate in hexane) to afford methyl 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)acetate (0.6 g, 0.89 mmol, 91% yield). MS (ESI) m/z 664.2 [M+1]+.

2-((R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)acetic acid. To a chilled solution of methyl 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)acetate (0.6 g, 0.9 mmol, 1 equiv.) in a mixture of tetrahydrofuran/methanol/water (3:1:1, 5 mL), lithium hydroxide monohydrate (0.58 g, 1.3 mmol, 1.5 equiv.) was added in one portion at 0° C. The resulting solution was stirred at room temperature. After 3 h the reaction solution was diluted with water (20 nL) and extracted with 10% methanol in dichloromethane (4×50 mL). The organic layer was dried over anhydrous magnesium sulfate, filtered and concentrated to give the 2 (trifluoromethyl)phenyl)-5,5-dimethyl-4-oxo-2-thioxoimidazolidin-1-yl)cyclohexyl)oxy)ethyl)-2-(trifluoromethyl)piperazin-1~ yl)acetic acid (0.33 g, 0.46 mmol, 51% yield), which was carried forward without further purification. MS (ESI) m/z 650.2 [M+1]+.

2-((R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride. To a 2 dram vial containing 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl) acetic acid (0.12 g, 0.19 mmol, 1 equiv.) and 1-(7-amino-1-methyl-1H-indazol-3-yl)dihydropyrimidine-2,4(1H,3H)-dione (0.06 g, 0.22 mmol, 1.2 equiv.), added acetonitrile (1.5 mL) and dimethylformamide (1.5 mL), and the solution was stirred until all solids were dissolved. 1-Methylimidazole (0.07 mL, 0.84 mmol, 5 equiv.) was added followed by N-(chloro(dimethylamino)methylene)-N-methylmethanaminium hexafluorophosphate (0.12 g, 0.41 mmol, 2.2 equiv.) and the reaction solution was stirred at room temperature. After 1 h the reaction solution was diluted with dimethylsulfoxide to a total volume of 3 ml, filtered, and purified by standard methods to give 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride (0.09 g, 0.09 mmol, 50.4% yield). MS (ESI) m/z 891.2 [M+1]+. 1H NMR (DMSO-d6, 400 MHz) δ 10.4-10.6 (m, 1H), 9.9-10.1 (m, 1H), 8.2-8.3 (m, 1H), 8.1-8.2 (m, 1H), 7.8-8.0 (m, 1H), 7.4-7.6 (m, 1H), 7.1-7.2 (m, 1H), 7.0-7.1 (m, 1H), 4.2-4.4 (m, 1H), 4.00 (s, 3H), 3.8-3.9 (m, 6H), 3.6-3.7 (m, 4H), 3.4-3.5 (m, 2H), 3.1-3.2 (m, 3H), 2.6-2.9 (m, 4H), 2.0-2.1 (m, 2H), 1.6-1.7 (m, 2H), 1.4-1.5 (m, 6H), 1.2-1.3 (m, 2H).

Example 21: 2-((2R,6S)-4-(2-((trans-4-(3-(4-Cyano-3-(pentafluoro-λ6-sulfaneyl)phenyl)-5,5-dimethyl-4-oxo-2-thioxoimidazolidin-1-yl)cyclohexyl)oxy)ethyl)-2,6-dimethylpiperazin-1-yl)-N-(3-((2,6-dioxopiperidin-3-yl)amino)phenyl)acetamide hydrochloride

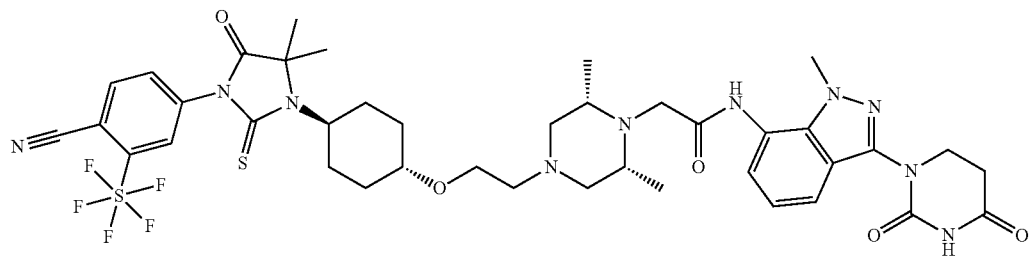 [SMILES: C[C@@H]1CN(CCO[C@H]2CC[C@H](N3C(=S)N(c4ccc(C#N)c(S(F)(F)(F)(F)F)c4)C(=O)C3(C)C)CC2)C[C@H](C)N1CC(=O)Nc1cccc2c(N3CCC(=O)NC3=O)nn(C)c12]

4-Bromo-3-(pentafluoro-%$^6$-sulfanyl)aniline. To a solution of 3-(pentafluoro-λ$^6$-sulfanyl)aniline (2.0 g, 9.12 mmol, 1 equiv.) in dimethylformamide (15 mL) under a nitrogen atmosphere, N-bromosuccinimide (1.9 g, 10.95 mmol, 1.2 equiv.) was added in one portion at 0° C. The resulting mixture was stirred at room temperature for 4 h. The reaction solution was diluted with water (100 mL) and extracted with ethyl acetate (2×100 mL). The combined organic layers were washed with brine (100 mL), dried over magnesium sulfate, filtered and concentrated. The crude material was purified by silica gel chromatography (0-20% ethyl acetate in hexanes) to give the 4-bromo-3-(pentafluoro-λ$^6$-sulfanyl) aniline (1.7 g, 5.7 mmol, 59% yield). $^1$H NMR (CDCl$_3$, 400 MHz) δ 7.4-7.5 (m, 1H), 7.1-7.2 (m, 1H), 6.6-6.7 (m, 1H), 3.8-4.0 (m, 2H).

4-Amino-2-(pentafluoro-λ$^6$-sulfanyl)benzonitrile. A 100 mL round-bottomed flask containing 4-bromo-3-(pentafluoro-λ$^6$-sulfanyl)aniline (1.7 g, 5.7 mmol, 1 equiv.) and copper(I) cyanide (0.61 g, 6.84 mmol, 1.2 equiv.) in N-methyl pyrrolidinone (30 mL) was heated to 180° C. with stirring. After 4 h the reaction solution was diluted with water (100 nL) and extracted with ethyl acetate (2×100 mL). The combined organic layers were washed with brine. dried over magnesium sulfate and concentrated. The residue was purified by silica gel chromatography (0-20% ethyl acetate in hexanes on a 50 g column) to give 4-amino-2-(pentafluoro-λ6-sulfanyl)benzonitrile (1.0 g, 4.09 mmol, 72% yield) as a white solid. MS (ESI) m/z 244.8 [M+1]+.

4-Isothiocyanato-2-(pentafluoro-λ$^6$-sulfaneyl)benzonitrile. To a 100 mL round-bottomed flask containing thiophosgene (0.94 mL, 12.29 mmol, 1.2 equiv.) in water (10 mL) to give an orange solution. 4-amino-2-(pentafluoro-λ$^6$-sulfanyl)benzonitrile (2.5 g, 10.24 mmol, 1 equiv.) in dichloromethane (10 mL) was added. The resulting mixture was stirred at room temperature for 16 h. The reaction was diluted with water (100 mL) and extracted with ethyl acetate (2×100 mL). The combined organic layers were washed with brine, dried over magnesium sulfate and concentrated to afford 4-isothiocyanato-2-(pentafluoro-λ$^6$-sulfaneyl)benzonitrile (1.3 g, 4.54 mmol, 44% yield) as a white solid which was carried forward without further purification. MS (ESI) m/z 286.9 [M+1]+.

4-(3-(trans-4-(2-Hydroxyethoxy)cyclohexyl)-4,4-dimethyl-5-oxo-2-thioxoimidazolidin-1-yl)-2-(pentafluoro-λ$^6$-sulfaneyl)benzonitrile. To a solution of methyl 2-methyl-2-((trans-4-(2-((tetrahydro-2H-pyran-2-yl)oxy)ethoxy) cyclohexyl)amino)propanoate (1.0 g, 2.91 mmol, 1 equiv.) in ethyl acetate (10 mL) was added 4-isothiocyanato-2-(pentafluoro-λ$^6$-sulfanyl)benzonitrile (1.67 g, 5.82 mmol, 1.2 equiv.) and N,N-diisopropylethylamine (1.02 mL, 5.82 mmol, 3 equiv.). The reaction solution was stirred at 80° C. After 18 h the reaction solution was concentrated and purified by column chromatography (0-50% ethyl acetate/ hexane) to give 4-(4,4-dimethyl-5-oxo-3-(trans-4-(2-((tetrahydro-2H-pyran-2-yl)oxy)ethoxy)cyclohexyl)-2-thioxoimidazolidin-1-yl)-2-(pentafluoro-λ$^6$-sulfaneyl)benzonitrile a white solid. The intermediate solid was suspended in dichloromethane (1.5 mL), followed by the addition of 4 M hydrochloric acid in dioxane (4 mL, 16 mmol, 3 equiv.), and allowed to stir at 25° C. for 12 h. The reaction solution was concentrated, the solid was dissolved in dichloromethane and purified by silica gel column chromatography (0-40% ethyl acetate in hexane) to afford 4-(3-(trans-4-(2-hydroxyethoxy)cyclohexyl)-4,4-dimethyl-5-oxo-2-thioxoimidazolidin-1-yl)-2-(pentafluoro-λ$^6$-sulfaneyl)benzonitrile as off white solid (0.80 g, 1.33 mmol, 46% yield). MS (ESI) m/z 513.8 [M+1]+.

4-(3-(trans-4-(2-Bromoethoxy)cyclohexyl)-4,4-dimethyl-5-oxo-2-thioxoimidazolidin-1-yl)-2-(pentafluoro-λ$^6$-sulfaneyl)benzonitrile. To a solution of 4-(3-(trans-4-(2-hydroxyethoxy)cyclohexyl)-4,4-dimethyl-5-oxo-2-thioxoimidazolidin-1-yl)-2-(pentafluoro-λ$^6$-sulfaneyl) benzonitrile (1.0 g, 1.95 mmol, 1 equiv.) in dichloromethane (30 mL) was added dimethylformamide (5 mL) and thionyl bromide (1.0 g, 4.87 mmol, 2.5 equiv.) sequentially. The reaction solution was stirred at room temperature overnight. After 16 h the reaction solution was diluted with brine (100 mL) and extracted with ethyl acetate (100 mL). The organic layer was washed with brine, dried over anhydrous magnesium sulfate and concentrated. The crude material was purified by silica gel column chromatography (0-100% ethyl acetate in hexane) to afford 4-(3-(trans-4-(2-bromoethoxy) cyclohexyl)-4,4-dimethyl-5-oxo-2-thioxoimidazolidin-1-yl)-2-(pentafluoro-λ$^6$-sulfaneyl)benzonitrile (0.59 g, 1.02 mmol, 53% yield) as a light brown solid. MS (ESI) m/z 578.8 [M+1]+.

2-((2S,6R)-4-(2-((trans-4-(3-(4-Cyano-3-(pentafluoro-λ$^6$-sulfaneyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride. To a 1-dram vial containing 4-(3-(trans-4-(2-bromoethoxy)cyclohexyl)-4,4-dimethyl-5-oxo-2-thioxoimidazolidin-1-yl)-2-(pentafluoro-λ$^6$-sulfaneyl)benzonitrile (0.11 g, 0.2 mmol, 1 equiv.), 2-((2S,6R)-2,6-dimethylpiperazin-1-yl)-N-(3-(2,4-dioxotetrahydropyrimidin-1(2H)-yl)-1-methyl-1H-indazol-7-yl)acetamide (0.11 g, 0.26 mmol, 1.3 equiv.) and sodium iodide (2.7 mg, 0.02 mmol, 0.1 equiv.) added acetonitrile (2 mL) followed by N,N-diisopropylethylamine (0.2 mL, 1.2 mmol, 6 equiv.). The reaction vial was heated with stirring to 60° C. After 16 h the reaction solution was diluted to a total volume of 3 ml with dimethylsulfoxide and purified by standard methods to give 2-((2S,6R)-4-(2-((trans-4-(3-(4-cyano-3-(pentafluoro-λ$^6$-sulfaneyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide hydrochloride (0.07 g, 0.07 mmol, 34% yield) as a yellow solid solid. MS (ESI) m/z 910.3 [M+1]$^+$; $^1$H NMR (DMSO-d$_6$, 400 MHz) δ 10.5-10.5 (m, 1H), 9.8-9.9 (m, 1H), 9.5-9.7 (m, 1H), 8.3-8.4 (m, 1H), 8.2-8.3 (m, 1H), 7.8-7.9 (m, 1H), 7.4-7.5 (m, 1H), 7.1-7.2 (m, 1H), 7.0-7.1 (m, 1H), 4.0-4.0 (m, 3H), 3.8-3.9 (m, 2H), 3.7-3.7 (m, 2H), 3.4-3.5 (m, 2H), 3.2-3.4 (m, 3H), 3.1-3.2 (m, 4H), 2.7-2.9 (m, 5H), 2.0-2.1 (m, 2H), 1.6-1.7 (m, 2H), 1.4-1.5 (m, 6H), 1.2-1.4 (m, 3H), 1.1-1.1 (m, 6H).

Example 22: 2-((R)-4-(3-(trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride

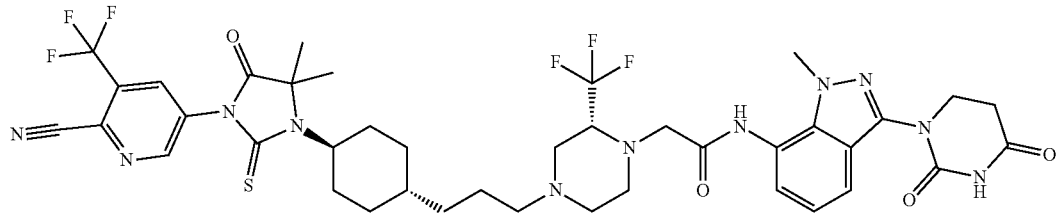 [SMILES: Cn1nc(N2CCC(=O)NC2=O)c2cccc(NC(=O)CN3CCN(CCC[C@H]4CC[C@H](N5C(=S)N(c6cnc(C#N)c(C(F)(F)F)c6)C(=O)C5(C)C)CC4)C[C@@H]3C(F)(F)F)c21]

(R)-tert-Butyl 4-(2-((3-(2,4-dioxotetrahydropyrimidin-1(2H)-yl)-1-methyl-1H-indazol-7-yl)amino)-2-oxoethyl)-3-(trifluoromethyl)piperazine-1-carboxylate. To a solution of (R)-2-(4-(tert-butoxycarbonyl)-2-(trifluoromethyl)piperazin-1-yl)acetic acid (0.460 g, 1.470 mmol) in pyridine (4 mL) was added EDCI (0.565 g, 2.950 mmol), followed by 1-(7-amino-1-methyl-1H-indazol-3-yl)dihydropyrimidine-2,4(1H,3H)-dione (0.401 g, 1.550 mmol) was added and the reaction mixture was stirred at 60° C. After 12 h the reaction solution was concentrated and purified by standard methods to provide (R)-tert-butyl 4-(2-((3-(2,4-dioxotetrahydropyrimidin-1(2H)-yl)-1-methyl-1H-indazol-7-yl)amino)-2-oxoethyl)-3-(trifluoromethyl)piperazine-1-carboxylate (0.500 g, 0.903 mmol, 61% yield) as a brown solid MS (ESI) m/z 498.1 [M−55]+.

(R)—N-(3-(2,4-Dioxotetrahydropyrimidin-1(2H)-yl)-1-methyl-1H-indazol-7-yl)-2-(2-(trifluoromethyl)piperazin-1-yl)acetamide hydrobromide. To a solution of (R)-tert-butyl 4-(2-((3-(2,4-dioxotetrahydropyrimidin-1(2H)-yl)-1-methyl-1H-indazol-7-yl)amino)-2-oxoethyl)-3-(trifluoromethyl)piperazine-1-carboxylate (0.500 g, 0.900 mmol) in dichloromethane (6 mL) was added 30% hydrogen bromide in acetic acid (2.0 mL) and the reaction mixture was stirred at 15° C. After 12 h the reaction solution was concentrated to provide crude (R)—N-(3-(2,4-Dioxotetrahydropyrimidin-1(2H)-yl)-1-methyl-1H-indazol-7-yl)-2-(2-(trifluoromethyl)piperazin-1-yl)acetamide hydrobromide (0.550 g, 1.029 mmol) as a brown solid that was carried forward without further purification MS (ESI) m/z 454.2 [M+1]+.

2-((R)-4-(3-(trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride. To a solution of 5-(3-(((trans)-4-(3-bromopropyl)cyclohexyl)-4,4-dimethyl-5-oxo-2-thioxoimidazolidin-1-yl)-3-(trifluoromethyl)picolinonitrile (0.080 g, 0.150 mmol) in DMF (1 mL) was added R)—N-(3-(2,4-Dioxotetrahydropyrimidin-1(2H)-yl)-1-methyl-1H-indazol-7-yl)-2-(2-(trifluoromethyl)piperazin-1-yl)acetamide hydrobromide (0.107 g, 0.200 mmol) and N-ethyl-N-isopropylpropan-2-amine (0.060 g, 0.460 mmol) and the reaction solution was stirred at 50° C. After 12 h the reaction solution was concentrated, taken up in DMSO and purified by standard methods to provide 2-((R)-4-(3-(trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride (0.050 g, 0.054 mmol, 35% yield) as a white solid. MS (ESI) m/z 890.1 [M+1]+.

$^1$H NMR (400 MHz, DMSO-d$_6$) δ 10.83 (s, 1H), 10.57 (s, 1H), 10.06-9.97 (m, 1H), 9.15-9.14 (d, J=2.0 Hz, 1H), 8.75-8.74 (d, J=2.0 Hz, 1H), 7.55-7.53 (d, J=8.0 Hz, 1H), 7.19-7.15 (m, 1H), 7.12-7.08 (m, 1H), 4.34 (m, 1H), 4.05 (s, 3H), 3.91-3.78 (m, 4H), 3.72-3.65 (m, 2H), 3.55-3.43 (m, 2H), 3.23-3.10 (m, 5H), 2.79-2.75 (m, 4H), 1.85-1.71 (m, 6H), 1.57 (s, 6H), 1.26-1.05 (m, 5H).

Example 23: 2-((R)-4-(3-(trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide

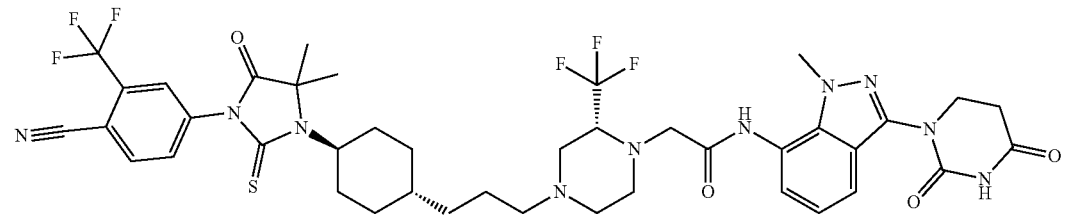 [SMILES: Cn1nc(N2CCC(=O)NC2=O)c2cccc(NC(=O)CN3CCN(CCC[C@H]4CC[C@H](N5C(=S)N(c6ccc(C#N)c(C(F)(F)F)c6)C(=O)C5(C)C)CC4)C[C@@H]3C(F)(F)F)c21]

2-((R)-4-(3-(trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride. To a mixture of 4-(3-((trans)-4-(3-bromopropyl)cyclohexyl)-4,4-dimethyl-5-oxo-2-thioxoimidazolidin-1-yl)-2-(trifluoromethyl)benzonitrile (0.069 g, 0.130 mmol) and (R)—N-(3-(2,4-dioxotetrahydropyrimidin-1(2H)-yl)-1-methyl-1H-indazol-7-yl)-

2-(2-(trifluoromethyl)piperazin-1-yl)acetamide (0.086 g, 0.160 mmol) in DMF (1 mL) was added N,N-diisopropylethylamine (0.04 mL, 0.220 mmol) and the reaction solution was stirred at 50° C. After 8 h the reaction solution was diluted with DMSO, filtered, and purified by standard methods to provide 2-((R)-4-(3-(trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride (0.073 g, 0.082 mmol, 61% yield) as a yellow solid. MS (ESI) m/z 889.5 [M+1]$^+$; $^1$H NMR (400 MHz, DMSO-d$_6$) δ 10.58 (s, 1H), 10.54-10.38 (m, 1H), 10.08-9.89 (m, 1H), 8.34 (d, J=8.4 Hz, 1H), 8.20 (s, 1H), 8.01 (d, J=10.0 Hz, 1H), 7.54 (m, 1H), 7.21-7.08 (m, 2H), 4.38-4.26 (m, 1H), 4.06 (s, 3H), 3.90 (t, J=6.8 Hz, 2H), 3.87-3.63 (m, 4H), 3.59-3.44 (m, 2H), 3.20-3.03 (m, 4H), 2.81-2.71 (m, 4H), 1.88-1.81 (m, 2H), 1.79-1.66 (m, 4H), 1.55 (s, 6H), 1.34-0.99 (m, 6H).

Example 24: 2-((R)-4-(3-(((trans)-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide mmol) in one portion under nitrogen and the reaction solution was stirred at 50° C. After 12 h the reaction solution was diluted with water (100 mL) and extracted with ethyl acetate (4×40 mL). the combined organic layers were washed with brine (80 mL), dried over anhydrous sodium sulfate and concentrated. The resulting crude material was purified by standard methods to provide 2-((R)-4-(3-(((trans)-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride (1.024 g, 1.127 mmol, 71% yield) as a yellow solid. MS (ESI) m/z 906.2 [M+1]$^+$; $^1$H NMR (400 MHz, DMSO-d$_6$) δ11.13 (br s, 1H), 10.57 (s, 1H), 10.09 (s, 1H), 9.14 (d, J=2.0 Hz, 1H), 8.74 (d, J=2.0 Hz, 1H), 7.54 (br d, J=8.0 Hz, 1H), 7.20-7.14 (m, 1H), 7.12-7.07 (m, 1H), 4.06 (s, 3H), 3.90 (br t, J=6.8 Hz, 3H), 3.79 (br d, J=18.4 Hz, 1H), 3.69 (br d, J=18.0 Hz, 2H), 3.57-3.43 (m, 4H), 3.30-3.10 (m, 1H), 3.31-3.07 (m, 6H), 2.87-2.74 (m,

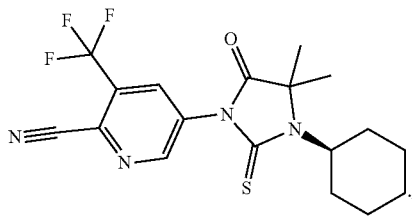

2-((R)-4-(3-(((trans)-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride. To a solution of 5-(3-(((trans)-4-(3-bromopropoxy)cyclohexyl)-4,4-dimethyl-5-oxo-2-thioxoimidazolidin-1-yl)-3-(trifluoromethyl)picolinonitrile (0.850 g, 1.594 mmol) and (R)—N-(3-(2,4-dioxotetrahydropyrimidin-1(2H)-yl)-1-methyl-1H-indazol-7-yl)-2-(2-(trifluoromethyl)piperazin-1-yl)acetamide hydrobromide (1.235 g, 2.310 mmol) in DMF (15 mL) was added N,N-dimethylformamide (1.39 mL, 7.970

4H), 2.07 (br d, J=10.4 Hz, 2H), 1.98 (br s, 2H), 1.71 (br d, J=10.4 Hz, 2H), 1.56 (s, 6H), 1.37-1.28 (m, 2H).

Example 25: 2-((2R,4s,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide

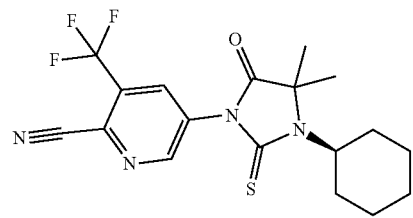

Benzyl 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetate. To a solution of 5-(3-(((trans)-4-(2-((2R,4s,6S)-2,6-dimethylpiperidin-4-yl)ethoxy)cyclohexyl)-4,4-dimethyl-5-oxo-2-thioxoimidazolidin-1-yl)-3-(trifluoromethyl)picolinonitrile (0.300 g, 0.540 mmol) and benzyl 2-bromoacetate (0.187 g, 0.820 mmol) in acetonitrile (8 mL) was added N-ethyl-N-isopropylpropan-2-amine (0.28 mL, 1.63 mmol). The reaction mixture was stirred at 25° C. After 12 h the reaction solution was concentrated and purified by flash silica gel column chromatography (0-3% methanol in dichloromethane) to give benzyl 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetate (350 mg, 0.5001 mmol, 92% yield) as a clear, colorless oil. MS (ESI) m/z: 700.5 [M+1]$^+$.

2-((2R,4s,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid. To a solution of benzyl 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetate (0.365 g, 0.520 mmol) in methanol (10 mL) and was added 10% palladium on activated carbon (0.100 g, 0.940 mmol). The mixture was stirred at 25° C. under an atmosphere of hydrogen gas. After 6 h the reaction slurry was filtered and concentrated to provide 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid (0.290 g, 0.477 mmol, 91% yield) as a yellow oil. MS (ESI) m/z: 610.5 [M+1]$^+$.

2-((2R,4s,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride. To a mixture of 1-(7-amino-1-methyl-1H-indazol-3-yl)dihydropyrimidine-2,4(1H,3H)-dione (0.083 g, 0.320 mmol) and 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid (0.130 g, 0.210 mmol) in pyridine (2 mL) was added 1-(3-dimethylaminopropyl)-3-ethylcarbodiimide hydrochloride (81.75 mg, 0.4300 mmol) and the reaction solution was stirred at 50° C. After 12 h the reaction solution was diluted with water (50 mL) and extracted with ethyl acetate (2×50 mL). the combined organic layers were washed with brine, dried over anhydrous sodium sulfate and concentrated. The resulting crude material was purified by standard methods to provide 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide hydrochloride (0.090 g, 0.102 mmol, 48.0% yield) as a yellow solid. MS (ESI) m/z: 851.6 [M+1]$^+$; $^1$H NMR (400 MHz, DMSO-d$_6$) δ 11.32-10.96 (m, 1H), 10.60 (d, J=2.0 Hz, 1H), 9.15-9.13 (m, 1H), 8.74 (t, J=2.1 Hz, 1H), 7.59 (dd, J=2.9, 7.8 Hz, 1H), 7.25 (t, J=7.8 Hz, 1H), 7.13 (dt, J=3.3, 7.8 Hz, 1H), 4.43-4.32 (m, 2H), 4.12 (s, 3H), 3.90 (dt, J=1.7, 6.6 Hz, 2H), 3.84 (br s, 2H), 3.48-3.45 (m, 1H), 3.27-3.18 (m, 1H), 2.87-2.72 (m, 4H), 2.10-1.94 (m, 4H), 1.86-1.58 (m, 8H), 1.56 (d, J=4.8 Hz, 6H), 1.46-1.19 (m, 9H).

Example 26: 2-((R)-4-(3-(((trans)-4-(3-(4-Cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide

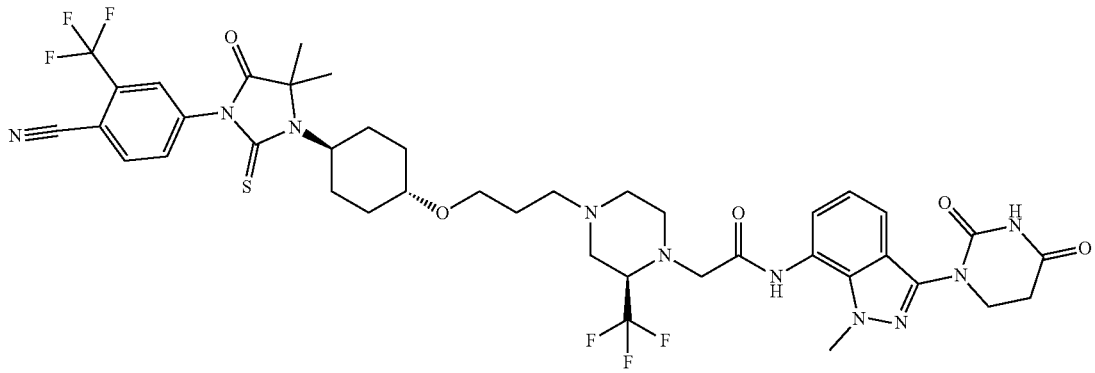 [SMILES: Cn1nc(N2CCC(=O)NC2=O)c2cccc(NC(=O)CN3CCN(CCCO[C@H]4CC[C@H](N5C(=S)N(c6ccc(C#N)c(C(F)(F)F)c6)C(=O)C5(C)C)CC4)C[C@@H]3C(F)(F)F)c21]

2-((R)-4-(3-(((trans)-4-(3-(4-Cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide. To a solution of (R)—N-(3-(2,4-dioxotetrahydropyrimidin-1(2H)-yl)-1-methyl-1H-indazol-7-yl)-2-(2-(trifluoromethyl)piperazin-1-yl)acetamide (0.080 g, 0.150 mmol) and 4-(3-((trans)-4-(3-bromopropoxy)cyclohexyl)-4,4-dimethyl-5-oxo-2-thioxoimidazolidin-1-yl)-2-(trifluoromethyl)benzonitrile (0.082 g, 0.150 mmol) in DMF (2 mL) was added N-ethyl-N-isopropylpropan-2-amine (0.072 g, 0.150 mmol) and the reaction solution was stirred at 50° C. After 12 h the reaction solution was diluted with DMSO and purified by standard methods to give 2-((R)-4-(3-(((trans)-4-(3-(4-cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide (0.054 g, 0.053 mmol, 35% yield) as a yellow solid. MS (ESI) m/z: 905.1 [M+1]$^+$; $^1$HNMR (400 MHz, DMSO-d$_6$) δ10.58 (s, 1H), 10.15-9.87 (m, 1H), 8.34 (d, J=8.4 Hz, 1H), 8.19 (d, J=1.2 Hz, 1H), 7.97 (dd, J=8.19, 1.6 Hz, 1H), 7.60-7.51 (m, 1H), 7.25-7.04 (m, 2H), 4.40-4.23 (m, 1H), 4.09-4.03 (m, 3H), 3.90 (t, J=6.4 Hz, 2H), 3.86-3.63 (m, 4H), 3.62-3.50 (m, 3H), 3.31-3.05 (m, 6H), 2.92-2.71 (m, 4H), 2.20-2.02 (m, 2H), 2.01-1.84 (m, 2H), 1.81-1.63 (m, 2H), 1.55 (s, 6H), 1.42-1.20 (m, 2H).

Example 27: 2-((R)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide

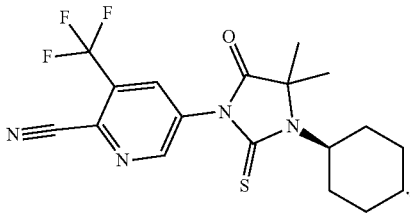

2-((R)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride. To the solution of 5-(3-(((trans)-4-(2-bromoethoxy)cyclohexyl)-4,4-dimethyl-5-oxo-2-thioxoimidazolidin-1-yl)-3-(trifluoromethyl)picolinonitrile (0.097 g, 0.19 mmol) and (R)—N-(3-(2,4-dioxotetrahydropyrimidin-1(2H)-yl)-1-methyl-1H-indazol-7-yl)-2-(2-(trifluoromethyl)piperazin-1-yl)acetamide (0.100 g, 0.19 mmol) in DMF (1 mL) was added N-ethyl-N-isopropylpropan-2-amine (0.22 mL, 1.29 mmol), and the reaction solution was stirred at 50° C. After 12 h the reaction solution was diluted with DMSO and purified by standard methods to provide 2-((R)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide hydrochloride (66.4 mg, 0.0745 mmol, 40% yield) as an off-white solid. MS (ESI) m/z 892.0 [M+1]$^+$; $^1$H NMR (400 MHz, DMSO-d$_6$) δ 10.95-10.91 (m, 1H), 10.57 (s, 1H), 10.16-9.95 (m, 1H), 9.14 (d, J=1.6 Hz, 1H), 8.74 (d, J=2.0 Hz, 1H), 7.54 (d, J=8.0 Hz, 1H), 7.17 (d, J=6.8 Hz, 1H), 7.13-7.07 (m, 1H), 4.48-4.26 (m, 1H), 4.06 (s, 3H), 3.96-3.80 (m, 6H), 3.79-3.69 (m, 2H), 3.59-3.43 (m, 3H), 3.28-3.14 (m, 3H), 2.93-2.82 (m, 2H), 2.77 (t, J=6.8 Hz, 2H), 2.58-2.53 (m, 2H), 2.15-2.06 (m, 2H), 1.78-1.68 (m, 2H), 1.57 (s, 6H), 1.45-1.28 (m, 2H).

Example 28: 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide

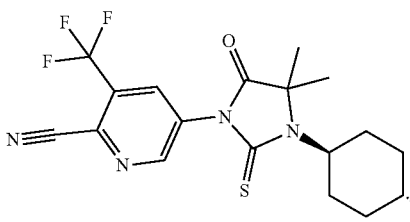

Benzyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetate. To a solution of 5-(3-(((trans)-4-(2-((2R,4r,6S)-2,6-dimethylpiperidin-4-yl)ethoxy)cyclohexyl)-4,4-dimethyl-5-oxo-2-thioxoimidazolidin-1-yl)-3-

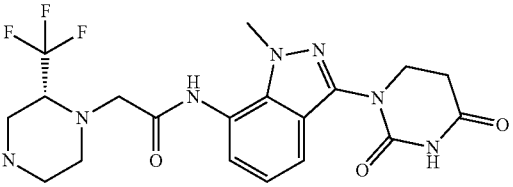

(trifluoromethyl)picolinonitrile (0.300 g, 0.540 mmol) and benzyl 2-bromoacetate (0.187 g, 0.820 mmol) in acetonitrile (10 mL) was added diisopropylethylamine (0.28 mL, 1.63 mmol) and the reaction solution was stirred at room temperature. After 12 h the reaction solution was concentrated and purified by standard methods to provide benzyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetate (370 mg, 0.5287 mmol, 97% yield) as a yellow oil. MS (ESI) m/z 722.4 [M+23]$^+$.

2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid. To a solution of benzyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetate (0.370 g, 0.530 mmol) in methanol (10 mL), and was added 10% palladium on activated carbon (0.112 g, 1.05 mmol) and the reaction solution was stirred at room temperature under an atmosphere of hydrogen gas. After 6 h the reaction slurry was filtered and concentrated to provide crude 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid (290 mg, 0.4756 mmol, 90% yield) as a brown oil. MS (ESI) m/z 610.4 [M+1]$^+$.

2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide. To a mixture of 1-(7-amino-1-methyl-1H-indazol-3-yl)dihydropyrimidine-2,4(1H,3H)-dione (0.128 g, 0.490 mmol) and 22-((2R,4r,6S)-4-(2-(((trans)-4-(3-(6-cyano-5-(trifluoromethyl)pyridin-3-

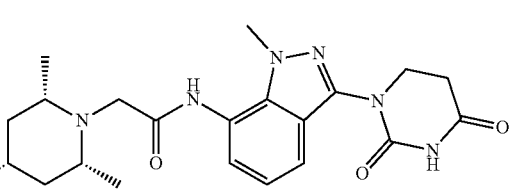

yl)-5,5-dimethyl-4-oxo-2-thioxoimidazolidin-1-yl)cyclohexyl)oxy)ethyl)-2,6-dimethylpiperidin-1-yl)acetic acid (0.200 g, 0.330 mmol) in pyridine (3 mL) was added 1-(3-dimethylaminopropyl)-3-ethylcarbodiimide hydrochloride (0.126 g, 0.660 mmol) and the reaction solution was stirred at 50° C. after 12 h the reaction solution was diluted with water (50 mL) and extracted with ethyl acetate (2×50 mL). the combined organic layers were washed with brine (30 mL), dried over anhydrous sodium sulfate and concentrated. The resulting crude material was purified by standard methods to provide 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide (0.078 g, 0.091 mmol, 28% yield) as a yellow solid. MS (ESI) m/z 851.5 [M+1]$^+$; $^1$H NMR (400 MHz, DMSO-d$_6$) δ 10.60 (d, J=1.6 Hz, 1H), 9.14 (s, 1H), 8.74 (s, 1H), 7.59 (dd, J=3.4, 8.0 Hz, 1H), 7.27-7.21 (m, 1H), 7.13 (dt, J=3.7, 7.7 Hz, 1H), 4.40 (s, 1H), 4.33-4.26 (m, 1H), 4.11 (s, 3H), 3.90 (t, J=6.6 Hz, 2H), 3.67 (d, J=8.4 Hz, 2H), 3.42-3.18 (m, 2H), 2.89-2.75 (m, 4H), 2.12-2.03 (m, 2H), 2.00-1.59 (m, 6H), 1.56 (d, J=4.5 Hz, 6H), 1.53-1.19 (m, 13H).

Example 29: 2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide

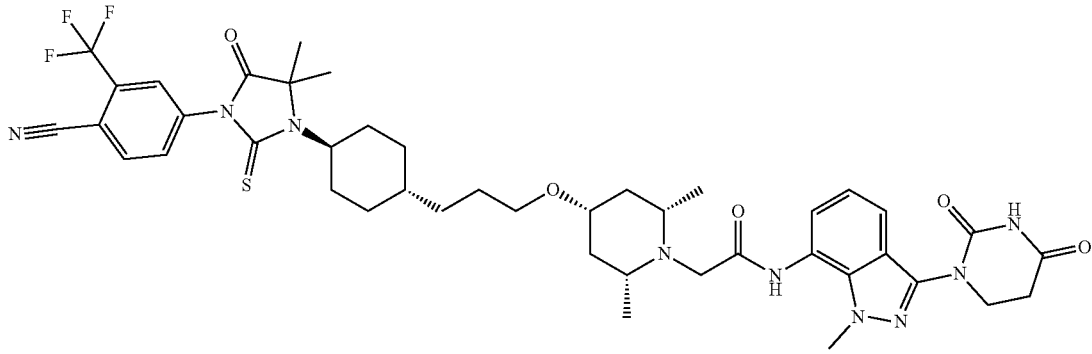 [SMILES: C[C@@H]1C[C@H](OCCC[C@H]2CC[C@H](N3C(=S)N(c4ccc(C#N)c(C(F)(F)F)c4)C(=O)C3(C)C)CC2)C[C@H](C)N1CC(=O)Nc1cccc2c(N3CCC(=O)NC3=O)nn(C)c12]

(2R,4r,6S)-tert-Butyl 4-(3-((trans)-4-(dibenzylamino)cyclohexyl)propoxy)-2,6-dimethylpiperidine-1-carboxylate. To a solution of (2S,4r,6R)-tert-butyl 4-hydroxy-2,6-dimethylpiperidine-1-carboxylate (3.000 g, 13.08 mmol) and (trans)-N,N-dibenzyl-4-(3-bromopropyl)cyclohexanamine (6.290 g, 15.70 mmol) in xylenes (45 mL) was added tetrabutylammonium bromide (0.840 g, 2.620 mmol) and potassium hydroxide (3.5 mL, 65.41 mmol), and the reaction solution was stirred at 30° C. After 12 h the reaction solution was diluted withy water (100 mL) and extracted with ethyl acetate (3×100 mL). The combined organic layers were washed with brine, dried over sodium sulfate and concentrated. The resulting crude material was purified by standard methods to provide (2R,4r,6S)-tert-butyl 4-(3-((trans)-4-(dibenzylamino)cyclohexyl)propoxy)-2,6-dimethylpiperidine-1-carboxylate (5.300 g, 9.657 mmol, 74% yield) as a white solid. $^1$H NMR (400 MHz, DMSO-d$_6$) δ7.34-7.26 (m, 8H), 7.21-7.16 (m, 2H), 4.15-4.02 (m, 2H), 3.57-3.52 (m, 5H), 2.39-2.31 (m, 1H), 1.81 (d, J=11.6 Hz, 2H), 1.76-1.68 (m, 6H), 1.53-1.26 (m, 15H), 1.23 (d, J=7.2 Hz, 6H), 1.16-1.11 (m, 3H), 0.77-0.66 (m, 2H).

(2R,4r,6S)-tert-Butyl 4-(3-((trans)-4-aminocyclohexyl)propoxy)-2,6-dimethylpiperidine-1-carboxylate. To a solution of (2R,4r,6S)-tert-butyl 4-(3-((trans)-4-(dibenzylamino)cyclohexyl)propoxy)-2,6-dimethylpiperidine-1-carboxylate (5.300 g, 9.657 mmol) in methanol (100 mL) and ammonium hydroxide (2 mL) was added 10% palladium on activated carbon (3.000 g, 28.19 mmol) under nitrogen atmosphere. The suspension was degassed under vacuum and purged with hydrogen for three times. The mixture was stirred at 25° C. for 12 h under hydrogen (15 Psi). The reaction mixture was filtered through a pad of celite and the filtrate was concentrated in vacuo to give crude (2R,4r,6S)-tert-butyl 4-(3-((trans)-4-aminocyclohexyl)propoxy)-2,6-dimethylpiperidine-1-carboxylate (3.000 g, 8.140 mmol, 84% yield) which was carried forward without further purification. $^1$H NMR (400 MHz, DMSO-d$_6$) δ 4.17-4.03 (m, 2H), 3.56 (q, J=4.0 Hz, 1H), 3.35 (s, 2H), 2.47-2.39 (m, 1H), 1.77-1.60 (m, 8H), 1.52-1.44 (m, 2H), 1.39 (s, 9H), 1.27-1.12 (m, 9H), 1.01-0.79 (m, 4H).

(2R,4r,6S)-tert-Butyl 4-(3-((trans)-4-((1-methoxy-2-methyl-1-oxopropan-2-yl)amino)cyclohexyl)propoxy)-2,6-dimethylpiperidine-1-carboxylate. To a solution of (2R,4r,6S)-tert-butyl 4-(3-((trans)-4-aminocyclohexyl)propoxy)-2,6-dimethylpiperidine-1-carboxylate (1.500 g, 4.070 mmol) and methyl 2-bromo-2-methylpropanoate (3.680 g, 20.35 mmol) in acetonitrile (5 mL) was added sodium iodide (0.060 g, 0.410 mmol) and potassium carbonate (1.690 g, 12.21 mmol). The mixture was stirred at 110° C. After 12 h the reaction solution was filtered and concentrated to provide crude 2R,4r,6S)-tert-butyl 4-(3-((1r,4R)-4-((1-methoxy-2-methyl-1-oxopropan-2-yl)amino)cyclohexyl)propoxy)-2,6-dimethylpiperidine-1-carboxylate (1.900 g, 4.054 mmol, 99.6% yield) which was carried forward without further purification. MS (ESI) m/z 469.4 [M+1]$^+$.

(2R,4r,6S)-tert-Butyl 4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidine-1-carboxylate. To a solution of (2R,4r,6S)-tert-butyl 4-(3-((trans)-4-((1-methoxy-2-methyl-1-oxopropan-2-yl)amino)cyclohexyl)propoxy)-2,6-dimethylpiperidine-1-carboxylate (1.900 g, 4.050 mmol) and 4-isothiocyanato-2-(trifluoromethyl)benzonitrile (0.930 g, 4.050 mmol) in ethyl acetate (10 mL) was added N,N-diisopropylethylamine (2.11 mL, 12.16 mmol) and the reaction solution was stirred at 90° C. after 12 h the reaction solution was filtered and concentrated and purified by standard methods to provide (2R,4r,6S)-tert-butyl 4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidine-1-carboxylate (2.400 g, 3.610 mmol, 89% yield) as a yellow oil. $^1$H NMR (400 MHz, DMSO-d$_6$) δ 8.33 (d, J=8.0 Hz, 1H), 8.19 (d, J=1.6 Hz, 1H), 7.97 (dd, J=1.6, 8.4 Hz, 1H), 4.14-4.06 (m, 2H), 3.90-3.74 (m, 1H), 3.59-3.54 (m, 1H), 3.40-3.37 (m, 2H), 2.80-2.63 (m, 2H), 1.80 (d, J=12.0 Hz, 2H), 1.75-1.70 (m, 6H), 1.56-1.47 (m, 8H), 1.39 (s, 9H), 1.27-1.23 (m, 9H), 1.18-1.16 (m, 2H).

4-(3-((trans)-4-(3-(((2R,4r,6S)-2,6-Dimethylpiperidin-4-yl)oxy)propyl)cyclohexyl)-4,4-dimethyl-5-oxo-2-thioxoimidazolidin-1-yl)-2-(trifluoromethyl)benzonitrile hydrobromide. To a solution of (2R,4r,6S)-tert-butyl 4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidine-1-carboxylate (2.400 g, 3.610 mmol) in dichloromethane (20 mL) was added 33% hydrogen bromide in acetic acid (20 mL, 3.610 mmol), and the reaction solution was stirred at room temperature. After 12 h the reaction solution was concentrated to provide crude 4-(3-((trans)-4-(3-(((2R,4r,6S)-2,6-dimethylpiperidin-4-yl)oxy)propyl)cyclohexyl)-4,4-dimethyl-5-oxo-2-thioxoimidazolidin-1-yl)-2-(trifluoromethyl)benzonitrile hydrobromide (2.000 g, 3.542 mmol, 98% yield), which was carried forward without further purification. MS (ESI) m/z 565.3 [M+1]$^+$.

Benzyl 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetate. To a solution of 4-(3-((trans)-4-(3-(((2R,4r,6S)-2,6-dimethylpiperidin-4-yl)oxy)propyl)cyclohexyl)-4,4-dimethyl-5-oxo-2-thioxoimidazolidin-1-yl)-2-(trifluoromethyl)benzonitrile and benzyl 2-bromoacetate (1.220 g, 5.310 mmol) in acetonitrile (20 mL) was added N,N-diisopropylethylamine (3.080 mL, 17.71 mmol) and the reaction solution was stirred at room temperature. After 12 h the reaction solution was concentrated and purified by standard methods to provide benzyl 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetate (0.800 g, 1.122 mmol, 32% yield) as a yellow oil. $^1$H NMR (400 MHz, DMSO-d$_6$) δ 8.33 (d, J=8.4 Hz, 1H), 8.20 (d, J=2.0 Hz, 1H), 7.97 (dd, J=1.6, 8.4 Hz, 1H), 7.38-7.32 (m, 5H), 5.09 (s, 2H), 3.83 (s, 1H), 3.53 (s, 2H), 3.23-3.15 (m, 1H), 2.79-2.66 (m, 4H), 1.88-1.77 (m, 4H), 1.71 (d, J=10.4 Hz, 2H), 1.54 (s, 6H), 1.50-1.42 (m, 3H), 1.23-1.15 (m, 4H), 1.06-0.95 (m, 10H).

2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetic acid. To a solution of benzyl 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetate (0.800 g, 1.120 mmol) in THF (3 mL), methanol (3 mL), water (3 mL) was added lithium hydroxide (0.135 g, 5.610 mmol) and the mixture was stirred at room temperature. After 12 h the reaction solution was adjusted to pH=7 by addition of aqueous HCl and concentrated to provide crude 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetic acid (1.000 g, 1.606 mmol) as a yellow oil, which was carried forward without further purification. $^1$H NMR (400 MHz, DMSO-d$_6$) δ 8.34 (d, J=8.4 Hz, 1H), 8.19 (d, J=1.6 Hz, 1H), 7.97 (dd, J=1.6, 8.4 Hz, 1H), 3.83 (s, 1H), 3.36 (s, 3H), 3.18 (s, 4H), 2.67 (d, J=2.0 Hz, 2H), 1.88 (d, J=12.4 Hz, 2H), 1.81-1.78 (m, 2H), 1.70 (d, J=11.6 Hz, 2H), 1.54 (s, 6H), 1.48 (d, J=7.2 Hz, 2H), 1.18 (s, 3H), 1.09 (d, J=6.4 Hz, 10H).

2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide hydrochloride. To a solution of 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetic acid (0.150 g, 0.241 mmol) and 1-(7-amino-1-methyl-1H-indazol-3-yl)dihydropyrimidine-2,4(1H,3H)-dione (0.075 g, 0.290 mmol) in pyridine (2 mL) was added 1-(3-dimethylaminopropyl)-3-ethylcarbodiimidehydrochloride (0.092 g, 0.480 mmol) and the mixture was stirred at 50° C. After 12 h the reaction solution was diluted with water (20 mL) and extracted with ethyl acetate (3×20 mL). the combined organic layers were washed with brine (20 mL), dried over anhydrous sodium sulfate and concentrated. The resulting crude material was purified by standard methods to provide 2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide hydrochloride (51.8 mg, 0.059 mmol, 25% yield) as a white solid. MS (ESI) m/z 864.3 [M+1]$^+$; $^1$H NMR (400 MHz, DMSO-d$_6$) δ 10.95-10.76 (m, 1H), 10.59 (d, J=2.0 Hz, 1H), 9.97-9.12 (m, 1H), 8.34 (d, J=8.4 Hz, 1H), 8.19 (d, J=1.6 Hz, 1H), 7.97 (dd, J=1.6, 8.4 Hz, 1H), 7.63-7.56 (m, 1H), 7.27-7.21 (m, 1H), 7.17-7.10 (m, 1H), 4.44-4.27 (m, 2H), 4.10 (s, 3H), 3.93-3.77 (m, 3H), 3.72-3.50 (m, 3H), 3.46-3.39 (m, 2H), 2.82-2.68 (m, 4H), 2.21-2.08 (m, 2H), 1.82 (d, J=11.2 Hz, 2H), 1.76-1.63 (m, 3H), 1.55 (d, J=2.0 Hz, 7H), 1.46-1.32 (m, 4H), 1.27 (d, J=6.4 Hz, 4H), 1.22 (s, 3H), 1.08 (s, 2H).

Example 30: 2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide

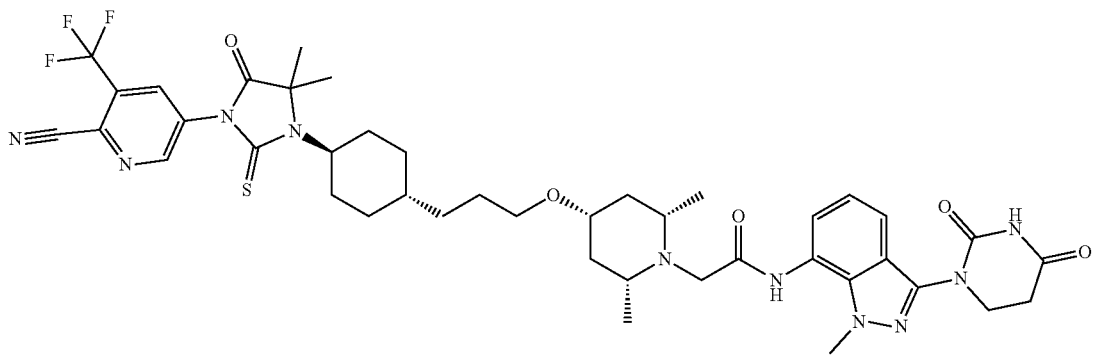 [SMILES: C[C@@H]1C[C@H](OCCC[C@H]2CC[C@H](N3C(=S)N(c4cnc(C#N)c(C(F)(F)F)c4)C(=O)C3(C)C)CC2)C[C@H](C)N1CC(=O)Nc1cccc2c(N3CCC(=O)NC3=O)nn(C)c12]

2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide. To a solution of 2-((2R,4r,6S)-4-(3-((trans)-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)acetic acid (0.120 g, 0.192 mmol) and 1-(7-amino-1-methyl-1H-indazol-3-yl)dihydropyrimidine-2,4(1H,3H)-dione (0.050 g, 0.192 mmol) in pyridine (2 mL) was added 1-(3-dimethylaminopropyl)-3-ethylcarbodiimidehydrochloride (0.074 g, 0.385 mmol) and the reaction solution was stirred at 50° C. After 12 h the reaction solution was diluted with water (20 mL) and washed with ethyl acetate (3×10 mL). the combined organic layers were washed with brine, dried over sodium sulfate and concentrated. The resulting crude material was purified by standard methods to provide 2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide (63.07 mg, 0.070 mmol, 36% yield) as a yellow solid. MS (ESI) m/z 865.3 [M+1]$^+$; $^1$H NMR (400 MHz, DMSO-d$_6$) δ 11.26-10.80 (m, 1H), 10.59 (s, 1H), 10.48-8.99 (m, 2H), 8.75 (s, 1H), 7.59 (dd, J=4.0, 8.0 Hz, 1H), 7.28-7.20 (m, 1H), 7.18-7.09 (m, 1H), 4.38 (s, 2H), 4.12 (d, J=2.0 Hz, 3H), 3.94-3.78 (m, 3H), 3.74-3.51 (m, 3H), 3.45-3.40 (m, 2H), 2.81-2.68 (m, 4H), 2.21-2.07 (m, 2H), 1.82 (d, J=9.6 Hz, 2H), 1.72 (s, 3H), 1.58-1.50 (m, 7H), 1.46-1.34 (m, 4H), 1.32-1.16 (m, 7H), 1.10 (s, 2H).

Example 31: 2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide J=8.0 Hz, 1H), 7.87 (d, J=1.6 Hz, 1H), 7.76-7.73 (dd, J=8.0, 1.6 Hz, 1H), 4.29-4.25 (m, 2H), 3.87 (s, 1H), 3.61-3.56 (m, 1H), 3.49-3.46 (t, J=6.0 Hz, 2H), 2.69 (s, 2H), 1.98-1.91 (m, 4H), 1.88-1.85 (m, 2H), 1.75-1.69 (m, 2H), 1.63 (s, 6H), 1.54-1.51 (m, 3H), 1.49 (s. 9H), 1.35-1.34 (d, J=6.8 Hz, 6H), 1.18-1.07 (m, 2H).

4-(3-((trans)-4-(2-(((2R,4r,6S)-2,6-Dimethylpiperidin-4-yl)oxy)ethyl)cyclohexyl)-4,4-dimethyl-5-oxo-2-thioxoimidazolidin-1-yl)-2-(trifluoromethyl)benzonitrile. To a solution of (2R,4r,6S)-tert-butyl 4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidine-1-carboxylate (1.150 g, 1.770 mmol) in dichloromethane (15 mL) was added 2,2,2-trifluoroacetic acid (5. mL, 65.34 mmol) and the reaction mixture was stirred at room temperature. After 2 h the reaction solution was concentrated, and the resulting material was taken up in saturated aqueous sodium bicarbonate solution and extracted with ethyl acetate (4×50 mL). the combined organic layers were washed with brine (50 mL), dried over anhydrous sodium sulfate and concentrated to provide 4-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-2-(trifluoromethyl)benzonitrile (0.870 g, 1.580 mmol, 90% yield) as a white solid. $^1$H NMR (400 MHz, CDCl$_3$) δ 7.96-7.95 (d, J=8.0 Hz, 1H), 7.86 (d, J=1.6 Hz, 1H), 7.75-7.72 (dd, J=8.0, 1.6 Hz, 1H), 3.86 (s, 1H), 3.52-3.49 (m, 2H), 3.35-3.27 (m, 1H), 2.75-2.59 (m, 4H), 2.02-1.92 (m, 4H), 1.86-1.83 (m, 2H), 1.61 (s, 6H), 1.52-1.49 (m, 3H), 1.16-1.14 (d, J=6.4 Hz, 6H), 1.10-0.96 (m, 4H).

Benzyl 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetate. To a solution of 4-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-2-

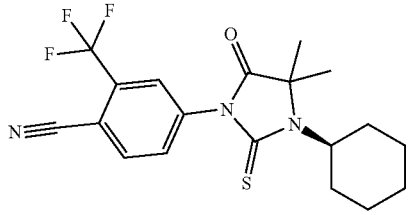
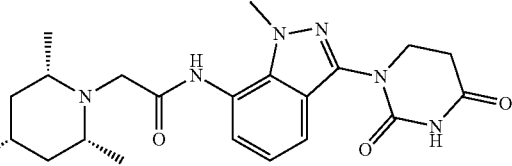

(2R,4r,6S)-tert-Butyl 4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidine-1-carboxylate. To a solution of (2R,4r,6S)-tert-butyl 4-(2-((trans)-4-((1-methoxy-2-methyl-1-oxopropan-2-yl)amino)cyclohexyl)ethoxy)-2,6-dimethylpiperidine-1-carboxylate (2.400 g, 2.640 mmol) and 4-isothiocyanato-2-(trifluoromethyl)benzonitrile (1.200 g, 5.280 mmol) in ethyl acetate (1 mL) was added N-ethyl-N-isopropylpropan-2-amine (1.38 mL, 7.920 mmol) and the reaction mixture was stirred at 80° C. After 12 h the reaction solution was concentrated and purified by standard methods to provide (2R,4r,6S)-tert-butyl 4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidine-1-carboxylate (1.150 g, 1.767 mmol, 67% yield) as a brown oil. MS (ESI) m/z 551.2 [M+1]$^+$; $^1$H NMR (400 MHz, CDCl$_3$) δ 7.97-7.95 (d, (trifluoromethyl)benzonitrile (0.870. g, 1.580 mmol) in acetonitrile (9 mL) was added benzyl 2-bromoacetate (0.723 g, 3.160 mmol) and N-ethyl-N-isopropylpropan-2-amine (0.83 mL, 4.740 mmol) and the reaction solution was stirred at room temperature. After 12 h the reaction solution was concentrated and purified by standard methods to provide benzyl 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetate (1.100 g, 1.574 mmol) as a brown solid. MS (ESI) m/z 699.3 [M+1]$^+$.

2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetic acid. To a solution of benzyl 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetate (1.100 g, 1.570 mmol) in THF (12 mL) and water (1.5 mL) was added lithium hydroxide (0.189 g, 7.870 mmol) and the reaction solution was stirred at 50° C. After 12 h the reaction solution was concentrated and extracted with 10:1 DCM/methanol (3×30 mL). the combined organic layers were dried over sodium sulfate and concentrated to provide 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetic acid (0.900 g, 1.478 mmol, 93% yield) as a brown solid that was carried forward without further purification. MS (ESI) m/z 609.3 [M+1]$^+$; $^1$H NMR (400 MHz, DMSO-d$_6$) δ 8.34-8.32 (d, J=8.0 Hz, 1H), 8.19 (d, J=1.6 Hz, 1H), 7.98-7.96 (dd, J=8.0, 1.6 Hz, 1H), 3.79 (s, 2H), 3.16 (s, 2H), 2.72-2.67 (m, 2H), 2.03-2.00 (m, 2H), 1.81-1.70 (m, 4H), 1.54 (s, 6H), 1.45-1.38 (m, 5H), 1.27-1.19 (m, 7H), 1.15-1.01 (m, 3H), 0.87-0.80 (m, 2H).

2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide. To a solution of 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetic acid (0.100. g, 0.160 mmol) in pyridine (1 mL) was added 1-(7-amino-1-methyl-1H-indazol-3-yl)dihydropyrimidine-2,4(1H,3H)-dione (0.051 g, 0.170 mmol) and 1-ethyl-3-(3-dimethylaminopropyl)carbodiimide hydrochloride (0.063 g, 0.330 mmol), the reaction mixture was stirred at 50° C. After 12 h the reaction solution was concentrated and the resulting crude material was purified by standard methods to provide 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide (0.079 g, 0.089 mmol, 54% yield) as a white solid. MS (ESI) m/z 850.5 [M+1]$^+$; $^1$H NMR (400 MHz, DMSO-d$_6$) δ 11.11-10.92 (m, 1H), 10.60 (s, 1H), 9.20-9.15 (m, 2H), 8.75 (d, J=1.6 Hz, 1H), 7.61-7.58 (m, 1H), 7.26-7.23 (m, 1H), 7.16-7.11 (m, 1H), 4.40-4.37 (m, 2H), 4.11 (s, 3H), 3.92-3.85 (m, 3H), 3.71 (m, 1H), 3.63-3.47 (m, 4H), 2.79-2.67 (m, 4H), 2.20-2.07 (m, 2H), 1.84-1.82 (m, 2H), 1.75-1.66 (m, 3H), 1.56-1.55 (m, 6H), 1.44-1.39 (m, 6H), 1.29-1.28 (m, 4H), 1.13-1.12 (m, 2H).

Example 32: 2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide (2R,4r,6S)-tert-Butyl 4-(2-((trans)-4-(dibenzylamino)cyclohexyl)ethoxy)-2,6-dimethylpiperidine-1-carboxylate. To a solution of (trans)-N,N-dibenzyl-4-(2-bromoethyl)cyclohexanamine (5.660 g, 14.65 mmol) and (2S,4r,6R)-tert-butyl 4-hydroxy-2,6-dimethylpiperidine-1-carboxylate (2.800 g, 12.21 mmol) in o-Xylene (60 mL) was added potassium hydroxide (3.080 g, 54.95 mmol) and tetra-n-butylammonium bromide (0.790 g, 2.440 mmol) and the reaction mixture was stirred at 15° C. After 12 h the reaction solution was concentrated and purified by standard methods to provide (2R,4r,6S)-tert-butyl 4-(2-((trans)-4-(dibenzylamino)cyclohexyl)ethoxy)-2,6-dimethylpiperidine-1-carboxylate (3.500 g, 6.545 mmol, 53.6% yield) as a white solid. $^1$H NMR (400 MHz, CDCl$_3$) δ 7.43-7.36 (m, 5H), 7.30-7.26 (m, 4H), 7.22-7.18 (m, 1H), 4.28-4.20 (m, 2H), 3.63 (s, 3H), 3.56-3.52 (m, 1H), 3.42-3.39 (m, 2H), 2.50-2.44 (m, 1H), 1.97-1.87 (m, 4H), 1.80-1.77 (m, 2H), 1.72-1.66 (m, 2H), 1.62-1.55 (m, 2H), 1.47 (s, 9H), 1.44-1.38 (m, 4H), 1.32-1.30 (m, 6H), 0.90-0.82 (m, 2H).

(2R,4r,6S)-tert-Butyl 4-(2-((trans)-4-aminocyclohexyl)ethoxy)-2,6-dimethylpiperidine-1-carboxylate. To a solution of (2R,4r,6S)-tert-butyl 4-(2-((trans)-4-(dibenzylamino)cyclohexyl)ethoxy)-2,6-dimethylpiperidine-1-carboxylate (3.500 g, 6.540 mmol) in Methanol (40 mL) was added ammoniumhydroxide (0.23 g, 6.54 mmol) and palladium on activated carbon (0.350 g, 0.330 mmol), the reaction mixture was stirred for 12 hours at 20 C under molecular hydrogen atmosphere (15 Psi). The reaction mixture was poured into methanol (50 mL) and filtered, the filter liquor was concentrated under reduced pressure to afford (2R,4r,6S)-tert-Butyl 4-(2-((trans)-4-aminocyclohexyl)ethoxy)-2,6-dimethylpiperidine-1-carboxylate (2.000 g, 5.640 mmol, 86% yield) as colorless oil. $^1$H NMR (400 MHz, DMSO-d$_6$) δ 4.12-4.08 (m, 2H), 3.57-3.55 (m, 1H), 3.41-3.38 (m, 5H), 2.45-2.39 (m, 1H), 1.73-1.65 (m, 8H), 1.39-1.35 (m, 11H), 1.25 (d, J=6.8 Hz, 6H), 0.98-0.84 (m, 4H).

(2R,4r,6S)-tert-Butyl 4-(2-((trans)-4-((1-methoxy-2-methyl-1-oxopropan-2-yl)amino)cyclohexyl)ethoxy)-2,6-dimethylpiperidine-1-carboxylate. To a solution of (2R,4r,6S)-tert-Butyl 4-(2-((trans)-4-aminocyclohexyl)ethoxy)-2,6-dimethylpiperidine-1-carboxylate (1.900 g, 5.360 mmol) and methyl 2-bromo-2-methylpropanoate (3.880 g, 21.44 mmol) in acetonitrile (6 mL) was added potassium carbonate (2.220 g, 16.08 mmol) and sodium iodide (0.080 g, 0.540 mmol) and the reaction solution was stirred at 110° C. After 15 h the reaction solution was diluted with ethyl acetate (15 mL), filtered and concentrated to provide crude (2R,4r,6S)-tert-butyl 4-(2-((trans)-4-((1-methoxy-2-methyl-1-oxopropan-2-yl)amino)cyclohexyl)ethoxy)-2,6-dimethylpiperidine-1-carboxylate (4.8 g), which was carried forward without further purification.

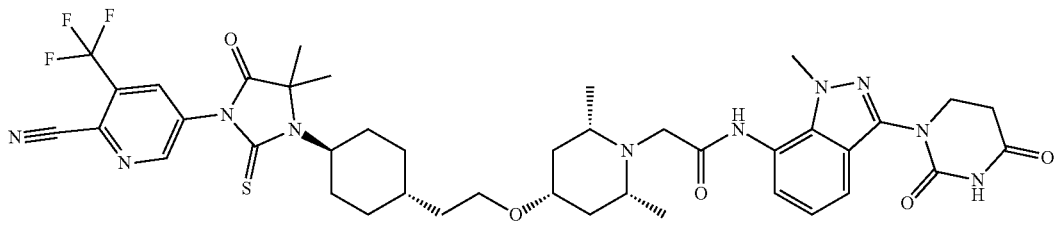 [SMILES: C[C@@H]1C[C@H](OCC[C@H]2CC[C@H](N3C(=S)N(c4cnc(C#N)c(C(F)(F)F)c4)C(=O)C3(C)C)CC2)C[C@H](C)N1CC(=O)Nc1cccc2c(N3CCC(=O)NC3=O)nn(C)c12]

(2R,4r,6S)-tert-Butyl 4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidine-1-carboxylate. To a solution of (2R,4r,6S)-tert-butyl 4-(2-((trans)-4-((1-methoxy-2-methyl-1-oxopropan-2-yl)amino) cyclohexyl)ethoxy)-2,6-dimethylpiperidine-1-carboxylate (2.400 g, 2.64 mmol, 50%) and 5-isothiocyanato-3-(trifluoromethyl)picolinonitrile (0.730 g, 3.170 mmol) in ethyl acetate (15 mL) was added N-ethyl-N-isopropylpropan-2-amine (1.38 mL, 7.920 mmol) and the reaction mixture was stirred for at 80° C. After 3 h the reaction solution was concentrated and purified by standard methods to provide (2R,4r,6S)-tert-butyl 4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidine-1-carboxylate (1.200 g, 1.841 mmol, 70% yield) as a brown oil. MS (ESI) m/z 552.2[M−99]$^+$; $^1$H NMR (400 MHz, DMSO-d$_6$) δ 8.98 (d, J=2.0 Hz, 1H), 8.25 (d, J=2.0 Hz, 1H), 4.29-4.21 (m, 2H), 3.82 (m, 1H), 3.59-3.54 (m, 1H), 3.48-3.45 (t, J=6.4 Hz, 2H), 2.68-2.59 (m, 2H), 1.97-1.89 (m, 4H), 1.85-1.82 (m, 2H), 1.73-1.67 (m, 2H), 1.63 (s, 6H), 1.54-1.49 (m, 3H), 1.47 (s, 9H), 1.34-1.32 (d, J=7.2 Hz, 6H), 1.14-1.05 (m, 2H).

5-(3-((trans)-4-(2-(((2R,4r,6S)-2,6-Dimethylpiperidin-4-yl)oxy)ethyl)cyclohexyl)-4,4-dimethyl-5-oxo-2-thioxoimidazolidin-1-yl)-3-(trifluoromethyl)picolinonitrile. To a solution of (2R,4r,6S)-tert-butyl 4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidine-1-carboxylate (1.200 g, 1.840 mmol) in dichloromethane (15 mL) was added trifluoroacetic acid (5. mL) and the reaction mixture was stirred for 2 hours at 15° C. The reaction mixture was concentrated under reduced pressure to afford a residue. Water (30 mL) was added and the pH adjust to 7-8 by saturated solution of sodium bicarbonate, extracted with ethyl acetate (50 mL×4), organic phase was concentrated under reduce pressure to afford 5-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-3-(trifluoromethyl)picolinonitrile (1.010 g, 1.831 mmol, 99% yield) as brown solid. $^1$H NMR (400 MHz, DMSO-d$_6$) δ 8.98 (d, J=2.0 Hz, 1H), 8.25 (d, J=2.0 Hz, 1H), 3.85 (m, 1H), 3.51-3.49 (m, 2H), 3.36-3.28 (m, 1H), 2.78-2.59 (m, 4H), 2.03-1.92 (m, 5H), 1.86 (m, 2H), 1.63 (s, 6H), 1.54-1.50 (m, 3H), 1.17-1.16 (d, J=6.4 Hz, 6H), 1.10-1.00 (m, 4H).

tert-Butyl 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetate. To a solution of 5-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-3-(trifluoromethyl)picolinonitrile (0.650 g, 1.180 mmol) in acetonitrile (12 mL) was added tert-butyl 2-bromoacetate (0.253 g, 1.300 mmol) and N-ethyl-N-isopropylpropan-2-amine (0.62 mL, 3.530 mmol) and the reaction mixture was stirred at room temperature. After 12 h the reaction solution was concentrated and purified by standard methods to provide tert-butyl 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetate (0.600 g, 0.901 mmol, 77% yield) as a brown oil. MS (ESI) m/z 666.3 [M+1]$^+$.

2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetic acid. To a solution of tert-butyl 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetate (0.600. g, 0.900 mmol) in dichloromethane (6 mL) was added trifluoroacetic acid (2.0 mL) and the reaction mixture was stirred at room temperature. After 12 h the reaction solution was concentrated and purified by standard methods to provide 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetic acid (0.820 mmol) as a brown solid. MS (ESI) m/z 610.3 [M+1]$^+$.

2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide. To a solution of 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetic acid (0.100. g, 0.160 mmol) in pyridine (1 mL) was added 1-(7-amino-1-methyl-1H-indazol-3-yl)dihydropyrimidine-2,4(1H,3H)-dione hydrochloride (0.053 g, 0.180 mmol) and 1-ethyl-3-(3-dimethylaminopropyl)carbodiimidehydrochloride (0.063 g, 0.330 mmol) and the reaction solution was stirred at 50° C. After 12 h the reaction solution was concentrate, taken up in DMSO, and purified by standard methods to provide 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide hydrochloride (0.051 g, 0.058 mmol, 35% yield) as a white solid. MS (ESI) m/z 851.5 [M+1]$^+$; $^1$H NMR (400 MHz, DMSO-d$_6$) δ 11.08-10.91 (m, 1H), 10.62 (s, 1H), 10.13-9.21 (m, 1H), 8.36-8.34 (d, J=8.4 Hz, 1H), 8.21-8.20 (d, J=1.6

Hz, 1H), 7.99-7.97 (m, 1H), 7.62-7.59 (m, 1H), 7.26-7.23 (m, 1H), 7.16-7.11 (m, 1H), 4.41-4.36 (m, 2H), 4.11 (s, 3H), 3.92-3.85 (m, 3H), 3.71 (m, 1H), 3.63-3.47 (m, 4H), 2.79-2.67 (m, 4H), 2.20-2.07 (m, 2H), 1.84-1.82 (m, 2H), 1.72-1.66 (m, 3H), 1.57 (m, 6H), 1.44-1.36 (m, 6H), 1.29-1.24 (m, 4H), 1.14-1.12 (m, 2H).

Example 33: 2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide

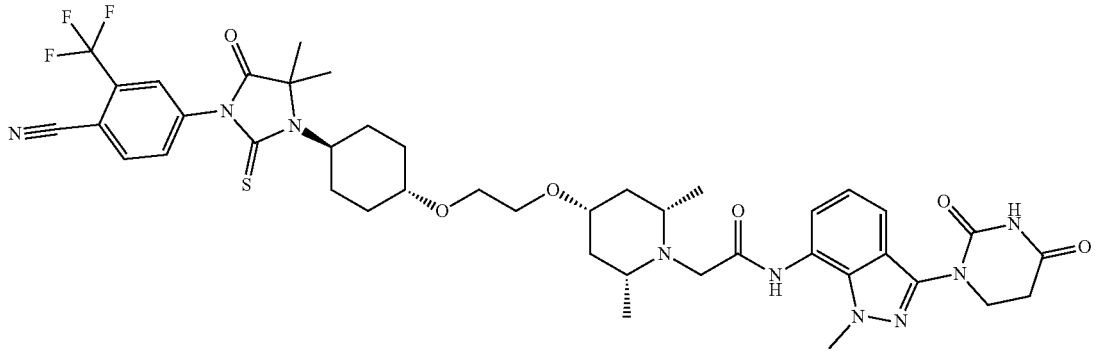 [SMILES: C[C@@H]1C[C@H](OCCO[C@H]2CC[C@H](N3C(=S)N(c4ccc(C#N)c(C(F)(F)F)c4)C(=O)C3(C)C)CC2)C[C@H](C)N1CC(=O)Nc1cccc2c(N3CCC(=O)NC3=O)nn(C)c12]

(2R,4r,6S)-tert-Butyl 4-(2-(((trans)-4-(dibenzylamino)cyclohexyl)oxy)ethoxy)-2,6-dimethylpiperidine-1-carboxylate. To a solution of (2R,4r,6S)-tert-butyl 4-hydroxy-2,6-dimethylpiperidine-1-carboxylate (1.400 g, 6.110 mmol) and (trans)-N,N-dibenzyl-4-(2-bromoethoxy)cyclohexanamine (3.680 g, 9.157 mmol) in xylenes (30 mL) was added tetrabutylammonium bromide (0.394 g, 1.221 mmol) and potassium hydroxide (1.713 g, 30.53 mmol) and the reaction solution was stirred at room temperature. After 12 h the reaction solution was diluted with water (50 mL) and extracted with ethyl acetate (3×50 mL). the combined organic layers were washed with brine (50 mL), dried over anhydrous sodium sulfate and concentrated. The resulting crude material was purified by standard methods to provide (2R,4r,6S)-tert-butyl 4-(2-(((trans)-4-(dibenzylamino)cyclohexyl)oxy)ethoxy)-2,6-dimethylpiperidine-1-carboxylate (2.600 g, 4.721 mmol, 77% yield) as a white solid. $^1$H NMR (400 MHz, DMSO-d$_6$) δ7.41-7.24 (m, 8H), 7.23-7.13 (m, 2H), 4.18-4.01 (m, 2H), 3.63-3.52 (m, 5H), 3.47 (dd, J=2.8, 9.2 Hz, 4H), 3.19 (t, J=10.8 Hz, 1H), 2.39 (t, J=11.6 Hz, 1H), 1.98 (d, J=10.2 Hz, 2H), 1.85-1.66 (m, 6H), 1.39 (s, 11H), 1.24 (d, J=7.2 Hz, 6H), 1.01-0.88 (m, 2H).

(2R,4r,6S)-tert-Butyl 4-(2-(((trans)-4-aminocyclohexyl)oxy)ethoxy)-2,6-dimethylpiperidine-1-carboxylate. To a solution of (2R,4r,6S)-tert-butyl 4-(2-(((trans)-4-(dibenzylamino)cyclohexyl)oxy)ethoxy)-2,6-dimethylpiperidine-1-carboxylate (0.600 g, 1.089 mmol) in methanol (5 mL) and THF (5 mL) was added 10% palladium on activated carbon (0.115 g, 1.089 mmol) under nitrogen atmosphere. The suspension was degassed under vacuum and purged with hydrogen for three times. The mixture was stirred at 25° C. for 12 h under hydrogen (15 Psi). The reaction mixture was filtered through a pad of celite and the filtrate was concentrated in vacuo to give crude (2R,4r,6S)-tert-butyl 4-(2-(((trans)-4-aminocyclohexyl)oxy)ethoxy)-2,6-dimethylpiperidine-1-carboxylate (0.400 g, 1.080 mmol) as a colorless oil, which was carried forward without further purification. MS (ESI) m/z 371.3 [M+1]$^+$.

(2R,4r,6S)-tert-Butyl 4-(2-(((trans)-4-((1-methoxy-2-methyl-1-oxopropan-2-yl)amino)cyclohexyl)oxy)ethoxy)-2,6-dimethylpiperidine-1-carboxylate. To a solution of (2R,4r,6S)-tert-butyl 4-(2-(((trans)-4-aminocyclohexyl)oxy)ethoxy)-2,6-dimethylpiperidine-1-carboxylate (0.400 g, 1.080 mmol) and methyl 2-bromo-2-methylpropanoate (0.977 g, 5.400 mmol) in acetonitrile (1 mL) was added potassium carbonate (0.448 g, 3.239 mmol) and sodium iodide (0.016 g, 0.108 mmol) and the reaction solution was stirred at 110° C. After 12 h the reaction solution was filtered and concentrated to provide crude (2R,4r,6S)-tert-butyl 4-(2-(((trans)-4-((1-methoxy-2-methyl-1-oxopropan-2-yl) amino)cyclohexyl)oxy)ethoxy)-2,6-dimethylpiperidine-1-carboxylate (0.500 g, 1.062 mmol), which was carried forward without further purification. MS (ESI) m/z 471.4 [M+1]$^+$.

(2R,4r,6S)-tert-Butyl 4-(2-(((trans)-4-(dibenzylamino)cyclohexyl)oxy)ethoxy)-2,6-dimethylpiperidine-1-carboxylate. To a solution of (2R,4r,6S)-tert-butyl 4-(2-(((trans)-4-((1-methoxy-2-methyl-1-oxopropan-2-yl)amino) cyclohexyl)oxy)ethoxy)-2,6-dimethylpiperidine-1-carboxylate (0.500 g, 1.062 mmol) and 4-isothiocyanato-2-(trifluoromethyl)benzonitrile (0.242 g, 1.062 mmol) in ethyl acetate (5 mL) was added N,N-diisopropylethylamine (0.55 mL, 3.19 mmol) and the reaction solution was stirred at 90° C. After 12 h the reaction solution was concentrated and purified by silica gel column chromatography to provide (2R,4r,6S)-tert-butyl 4-(2-(((trans)-4-(dibenzylamino)cyclohexyl)oxy)ethoxy)-2,6-dimethylpiperidine-1-carboxylate (0.470 g, 0.705 mmol, 66% yield) as a yellow oil. $^1$H NMR (400 MHz, DMSO-d$_6$) δ 8.33 (d, J=8.0 Hz, 1H), 8.19 (d, J=1.6 Hz, 1H), 7.97 (dd, J=1.6, 8.0 Hz, 1H), 3.82 (s, 1H), 3.62-3.60 (m, 2H), 3.57-3.54 (m, 2H), 3.31-3.25 (m, 1H), 2.81 (d, J=12.8 Hz, 2H), 2.04 (d, J=10.8 Hz, 2H), 1.89 (d, J=11.2 Hz, 2H), 1.75-1.72 (m, 5H), 1.54 (s, 6H), 1.39 (s, 9H), 1.26 (s, 6H), 1.20-1.15 (m, 4H).

4-(3-((trans)-4-(2-(((2R,4r,6S)-2,6-Dimethylpiperidin-4-yl)oxy)ethoxy)cyclohexyl)-4,4-dimethyl-5-oxo-2-thioxoimidazolidin-1-yl)-2-(trifluoromethyl)benzonitrile. To a solution of (2R,4r,6S)-tert-butyl 4-(2-(((trans)-4-(dibenzylamino)cyclohexyl)oxy)ethoxy)-2,6-dimethylpiperidine-1-carboxylate (0.470 g, 0.705 mmol) in dichloromethane (5 mL) was added trifluoroacetic acid (2.0 mL, 25.78 mmol). The mixture was stirred at 25° C. for 2 h. The reaction mixture was concentrated in vacuo to give crude 4-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-2-(trifluoromethyl)benzonitrile (0.400 g, 0.706 mmol), which was carried forward without further purification.

tert-Butyl 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetate. To a solution of 4-(3-(((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-2-(trifluoromethyl)benzonitrile (0.400 g, 0.706 mmol) and tert-butyl 2-bromoacetate (0.206 g, 1.059 mmol) in acetonitrile (5 mL) was added N,N-dimethylformamide (0.61 mL, 3.530 mmol) and the reaction solution was stirred at room temperature. After 12 h the reaction solution was concentrated and purified by standard methods to provide tert-butyl 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetate (0.150 g, 0.220 mmol, 31% yield) as a yellow oil. $^1$H NMR (400 MHz, DMSO-$d_6$) δ8.33 (d, J=8.4 Hz, 1H), 8.19 (d, J=1.6 Hz, 1H), 7.97 (dd, J=1.6, 8.4 Hz, 1H), 3.83 (s, 1H), 3.49 (s, 4H), 3.29-3.22 (m, 2H), 2.83-2.71 (m, 4H), 2.04 (d, J=10.8 Hz, 2H), 1.88 (dd, J=4.0, 11.6 Hz, 2H), 1.70 (d, J=10.4 Hz, 2H), 1.54 (s, 6H), 1.40 (s, 9H), 1.36-1.25 (m, 2H), 1.06-0.92 (m, 10H).

2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetic acid. To a solution of tert-butyl 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetate (0.150 g, 0.220 mmol) in dichloromethane (5 mL) was added trifluoroacetic acid (1.0 mL, 12.89 mmol) and the reaction solution was stirred at room temperature. After 12 h the reaction solution was concentrated to provide crude 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetic acid (0.150 g, 0.240 mmol), which was carried forward without further purification.

2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide. To a solution of 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetic acid (0.100 mg, 0.160 mmol) and 1-(7-amino-1-methyl-1H-indazol-3-yl)dihydropyrimidine-2,4(1H,3H)-dione (0.062 g, 0.240 mmol) in pyridine (3 mL) was added 1-(3-dimethylaminopropyl)-3-ethylcarbodiimide hydrochloride (0.123 g, 0.640 mmol) and the reaction solution was stirred at 50° C. After 12 h the reaction solution was diluted with water (50 mL) and extracted with ethyl acetate (2×50 mL). the combined organic layers were washed with brine, dried over anhydrous sodium sulfate and concentrated. The resulting crude material was purified by standard methods to provide 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide (0.048 g, 0.055 mmol, 34% yield) as a off-white solid. MS (ESI) m/z: 866.5 [M+1]$^+$; $^1$H NMR (400 MHz, DMSO-$d_6$) δ=10.57 (s, 1H), 9.89 (s, 1H), 8.33 (d, J=8.2 Hz, 1H), 8.19 (d, J=1.2 Hz, 1H), 7.97 (dd, J=1.5, 8.2 Hz, 1H), 7.50 (d, J=8.1 Hz, 1H), 7.31 (d, J=7.2 Hz, 1H), 7.08 (t, J=7.8 Hz, 1H), 4.09 (s, 3H), 3.89 (t, J=6.7 Hz, 2H), 3.87-3.77 (m, 1H), 3.52 (s, 4H), 3.32-3.23 (m, 4H), 2.89-2.74 (m, 4H), 2.69-2.59 (m, 2H), 2.07-2.01 (m, 2H), 1.95-1.85 (m, 2H), 1.75-1.67 (m, 2H), 1.54 (s, 6H), 1.39-1.19 (m, 4H), 1.17 (d, J=6.2 Hz, 6H).

Example 34: 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide

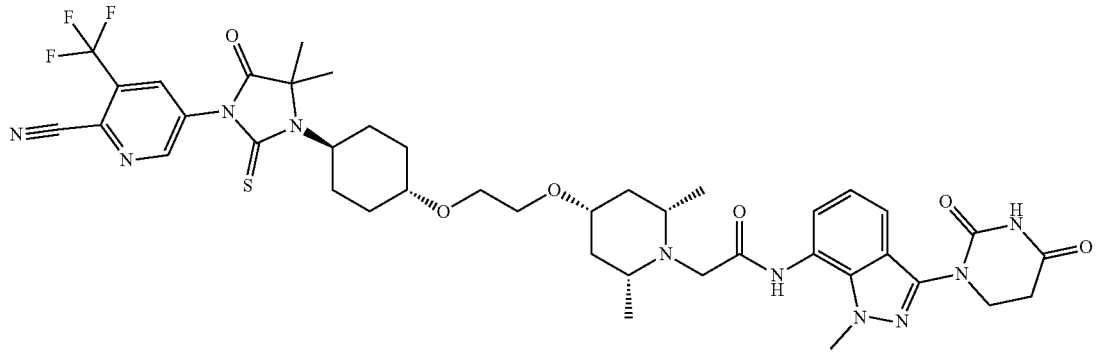 [SMILES: C[C@@H]1C[C@H](OCCO[C@H]2CC[C@H](N3C(=S)N(c4cnc(C#N)c(C(F)(F)F)c4)C(=O)C3(C)C)CC2)C[C@H](C)N1CC(=O)Nc1cccc2c(N3CCC(=O)NC3=O)nn(C)c12]

(2R,4r,6S)-tert-Butyl 4-(2-(((trans)-4-(dibenzylamino)cyclohexyl)oxy)ethoxy)-2,6-dimethylpiperidine-1-carboxylate. To a solution of (2R,4r,6S)-tert-butyl 4-hydroxy-2,6-dimethylpiperidine-1-carboxylate (1.400 g, 6.110 mmol) and (trans)-N,N-dibenzyl-4-(2-bromoethoxy)cyclohexanamine (3.680 g, 9.157 mmol) in xylenes (30 mL) was added tetrabutylammonium bromide (0.394 g, 1.221 mmol) and potassium hydroxide (1.713 g, 30.53 mmol) and the reaction solution was stirred at room temperature. After 12 h the reaction solution was diluted with water (50 mL) and extracted with ethyl acetate (3×50 mL). the combined organic layers were washed with brine (50 mL), dried over anhydrous sodium sulfate and concentrated. The resulting crude material was purified by standard methods to provide (2R,4r,6S)-tert-butyl 4-(2-(((trans)-4-(dibenzylamino)cyclohexyl)oxy)ethoxy)-2,6-dimethylpiperidine-1-carboxylate (2.600 g, 4.721 mmol, 77% yield) as a white solid. $^1$H NMR (400 MHz, DMSO-$d_6$) δ7.41-7.24 (m, 8H), 7.23-7.13 (m, 2H), 4.18-4.01 (m, 2H), 3.63-3.52 (m, 5H), 3.47 (dd, J=2.8, 9.2 Hz, 4H), 3.19 (t, J=10.8 Hz, 1H), 2.39 (t, J=11.6 Hz, 1H), 1.98 (d, J=10.2 Hz, 2H), 1.85-1.66 (m, 6H), 1.39 (s, 11H), 1.24 (d, J=7.2 Hz, 2H), 1.01-0.88 (m, 2H).

(2R,4r,6S)-tert-Butyl 4-(2-(((trans)-4-aminocyclohexyl)oxy)ethoxy)-2,6-dimethylpiperidine-1-carboxylate. To a solution of (2R,4r,6S)-tert-butyl 4-(2-(((trans)-4-(dibenzylamino)cyclohexyl)oxy)ethoxy)-2,6-dimethylpiperidine-1-carboxylate (0.600 g, 1.089 mmol) in methanol (5 mL) and THF (5 mL) was added 10% palladium on activated carbon (0.115 g, 1.089 mmol) under nitrogen atmosphere. The suspension was degassed under vacuum and purged with hydrogen for three times. The mixture was stirred at 25° C. for 12 h under hydrogen (15 Psi). The reaction mixture was filtered through a pad of celite and the filtrate was concentrated in vacuo to give crude (2R,4r,6S)-tert-butyl 4-(2-(((trans)-4-aminocyclohexyl)oxy)ethoxy)-2,6-dimethylpiperidine-1-carboxylate (0.400 g, 1.080 mmol) as a colorless oil, which was carried forward without further purification. MS (ESI) m/z 371.3 [M+1]$^+$.

(2R,4r,6S)-tert-Butyl 4-(2-(((trans)-4-((1-methoxy-2-methyl-1-oxopropan-2-yl)amino)cyclohexyl)oxy)ethoxy)-2,6-dimethylpiperidine-1-carboxylate. To a solution of (2R,4r,6S)-tert-butyl 4-(2-(((trans)-4-aminocyclohexyl)oxy)ethoxy)-2,6-dimethylpiperidine-1-carboxylate (0.400 g, 1.080 mmol) and methyl 2-bromo-2-methylpropanoate (0.977 g, 5.400 mmol) in acetonitrile (1 mL) was added potassium carbonate (0.448 g, 3.239 mmol) and sodium iodide (0.016 g, 0.108 mmol) and the reaction solution was stirred at 110° C. After 12 h the reaction solution was filtered and concentrated to provide crude (2R,4r,6S)-tert-butyl 4-(2-(((trans)-4-((1-methoxy-2-methyl-1-oxopropan-2-yl)amino)cyclohexyl)oxy)ethoxy)-2,6-dimethylpiperidine-1-carboxylate (0.500 g, 1.062 mmol), which was carried forward without further purification. MS (ESI) m/z 471.4 [M+1]$^+$.

(2R,4r,6S)-tert-Butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidine-1-carboxylate. To a solution of (2R,4r,6S)-tert-butyl 4-(2-(((trans)-4-((1-methoxy-2-methyl-1-oxopropan-2-yl)amino)cyclohexyl)oxy)ethoxy)-2,6-dimethylpiperidine-1-carboxylate (0.300 g, 0.637 mmol) and 5-isothiocyanato-3-(trifluoromethyl)picolinonitrile (0.146 g, 0.637 mmol) in ethyl acetate (5 mL) was added N,N-diisopropylethylamine (0.33 mL, 1.910 mmol). The mixture was stirred at 90° C. for 12 h. The reaction mixture was concentrated in vacuo to give the crude product. The residue was purified by flash silica gel chromatography (0~27% ethyl acetate in petroleum ether) to provide (2R,4r,6S)-tert-butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidine-1-carboxylate (0.340 g, 0.509 mmol, 80% yield) as a yellow oil. $^1$H NMR (400 MHz, DMSO-d$_6$) δ 9.14 (d, J=2.0 Hz, 1H), 8.74 (d, J=2.0 Hz, 1H), 3.83 (s, 1H), 3.63 (t, J=4.0 Hz, 1H), 3.57-3.53 (m, 3H), 3.32-3.25 (m, 1H), 2.82 (d, J=11.2 Hz, 2H), 2.04 (d, J=10.8 Hz, 2H), 1.76-1.66 (m, 7H), 1.55 (s, 6H), 1.39 (s, 9H), 1.34-1.23 (m, 10H).

5-(3-((trans)-4-(2-(((2R,4r,6S)-2,6-Dimethylpiperidin-4-yl)oxy)ethoxy)cyclohexyl)-4,4-dimethyl-5-oxo-2-thioxoimidazolidin-1-yl)-3-(trifluoromethyl)picolinonitrile. To a solution of (2R,4r,6S)-tert-butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidine-1-carboxylate (0.340 g, 0.509 mmol) in dichloromethane (5 mL) was added trifluoroacetic acid (2.0 mL, 25.78 mmol). The mixture was stirred at 25° C. for 2 h. The reaction mixture was concentrated in vacuo to give crude 5-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-3-(trifluoromethyl)picolinonitrile (0.290 g, 0.511 mmol) which was carried forward without further purification. MS (ESI) m/z 568.3 [M+1]$^+$.

tert-Butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetate. To a solution of 5-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-3-(trifluoromethyl)picolinonitrile (0.290 g, 0.511 mmol) and tert-butyl 2-bromoacetate (0.149 g, 0.766 mmol) in acetonitrile (5 mL) was added N,N-dimethylformamide (0.44 mL, 2.55 mmol) and the reaction solution was stirred at room temperature. After 12 h the reaction solution was concentrated and purified by silica gel column chromatography to provide tert-butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetate (0.270 g, 0.396 mmol, 78% yield) as a yellow oil. $^1$H NMR (400 MHz, DMSO-d$_6$) δ 9.14 (d, J=2.0 Hz, 1H), 8.74 (d, J=2.0 Hz, 1H), 3.84 (s, 1H), 3.49 (s, 4H), 3.34 (s, 2H), 3.29-3.23 (m, 2H), 2.88-2.70 (m, 4H), 2.04 (d, J=10.4 Hz, 2H), 1.88 (d, J=12.0 Hz, 2H), 1.70 (d, J=11.2 Hz, 2H), 1.56 (s, 6H), 1.40 (s, 9H), 1.32 (d, J=12.8 Hz, 2H), 1.08-0.91 (m, 8H).

2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetic acid. To a solution of tert-butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetate (0.270 g, 0.396 mmol) in dichloromethane (5 mL) was added trifluoroacetic acid (1.0 mL, 12.89 mmol) and the reaction solution was stirred at room temperature. After 12 h the reaction solution was concentrated to provide crude 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetic acid (0.250 g, 0.400 mmol), which was carried forward without further purification. MS (ESI) m/z 626.3 [M+1]$^+$.

2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide. To a solution of 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetic acid (0.150 g, 0.240 mmol) and 1-(7-amino-1-methyl-1H-indazol-3-yl)dihydropyrimidine-2,4(1H,3H)-dione (0.124 g, 0.480 mmol) in pyridine (2 mL) was added 1-(3-dimethylaminopropyl)-3-ethylcarbodiimidehydrochloride (0.184 g, 0.959 mmol) and the reaction solution was stirred at 50° C. After 12 h the reaction solution was diluted with water (20 mL) and extracted with ethyl acetate (3×20 mL). the combined organic layers were washed with brine (20 mL), dried over anhydrous sodium sulfate and concentrated. The resulting crude material was purified by standard methods to provide 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin- 1(2H)-yl)-1-methyl-1H-indazol-7-yl)acetamide (28.32 mg, 0.033 mmol, 14% yield) as an off-white solid. MS (ESI) m/z 867.3 [M+1]$^+$; $^1$H NMR (400 MHz, DMSO-d$_6$) δ 10.56 (s, 1H), 9.89 (s, 1H), 9.14 (d, J=2.0 Hz, 1H), 8.73 (d, J=2.0 Hz, 1H), 7.49 (d, J=8.0 Hz, 1H), 7.30 (d, J=7.2 Hz, 1H), 7.12-7.04 (m, 1H), 4.09 (s, 3H), 3.93-3.77 (m, 3H), 3.52 (s, 3H), 3.35-3.32 (m, 1H), 3.27 (s, 2H), 2.88-2.72 (m, 4H), 2.67 (s, 2H), 2.05 (d, J=10.0 Hz, 2H), 1.88 (d, J=9.6 Hz, 2H), 1.71 (d, J=10.4 Hz, 2H), 1.56 (s, 6H), 1.43-1.25 (m, 4H), 1.25-1.11 (m, 8H).

Example 35: 2-(4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide

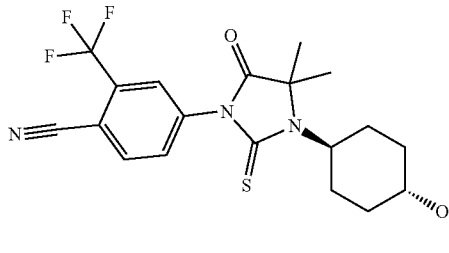
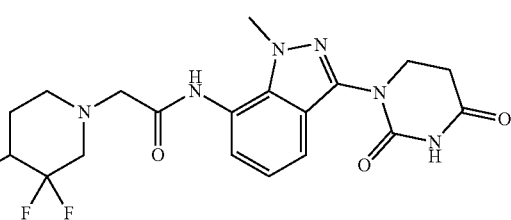

tert-Butyl 4-(2-(((trans)-4-(dibenzylamino)cyclohexyl)oxy)ethyl)-3,3-difluoropiperidine-1-carboxylate. To a solution of tert-butyl 3,3-difluoro-4-(2-((methylsulfonyl)oxy)ethyl)piperidine-1-carboxylate (1.81 g, 5.27 mmol) in xylenes (30 mL) was added (trans4-(dibenzylamino)cyclohexan-1-ol (3.11 g, 10.54 mmol), tetrabutylammonium bromide (0.340 g, 1.054 mmol), and potassium hydroxide (1.479 g, 26.4 mmol). The reaction mixture was heated to 30° C. for 24 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a light yellow solid. The solid was taken up in ethyl acetate and purified on a silica gel column using 0-75% ethyl acetate in hexanes over 2000 mL. Fractions containing desired product were combined and volatile organics were removed under reduced pressure to give tert-butyl 4-(2-(((trans)-4-(dibenzylamino)cyclohexyl)oxy)ethyl)-3,3-difluoropiperidine-1-carboxylate (1.79 g, 3.30 mmol, 63% yield) as a colorless oil. MS (ESI) m/z 543.2 [M+1]$^+$.

tert-Butyl 4-(2-(((trans)-4-aminocyclohexyl)oxy)ethyl)-3,3-difluoropiperidine-1-carboxylate. To a solution of tert-butyl 4-(2-(((trans)-4-(dibenzylamino)cyclohexyl)oxy)ethyl)-3,3-difluoropiperidine-1-carboxylate (2.65 g, 4.88 mmol) in Methanol (50 ml) was added palladium on carbon (500 mg, 4.70 mmol). Air in the flask was evacuated and replaced with hydrogen (3×, 15 psi, balloon). The reaction mixture was stirred at ambient temperature for 18 h. The reaction was filtered through celite. The filter cake was washed with more methanol. The filtrate was taken and volatile organics were removed under reduced pressure to give tert-butyl 4-(2-(((trans)-4-aminocyclohexyl)oxy)ethyl)-3,3-difluoropiperidine-1-carboxylate (1.72 g, 4.75 mmol, 97% yield) as a light yellow oil. MS (ESI) m/z 363.2 [M+1]$^+$.

tert-Butyl 3,3-difluoro-4-(2-(((trans)-4-((1-methoxy-2-methyl-1-oxopropan-2-yl)amino)cyclohexyl)oxy)ethyl)piperidine-1-carboxylate. To a solution of tert-butyl 4-(2-(((trans)-4-aminocyclohexyl)oxy)ethyl)-3,3-difluoropiperidine-1-carboxylate (1.72 g, 4.75 mmol) in acetonitrile (20 ml) was added methyl 2-bromo-2-methylpropanoate (1.718 g, 9.49 mmol), potassium iodide (0.079 g, 0.475 mmol), and potassium carbonate (1.312 g, 9.49 mmol). The reaction mixture was stirred at 110° C. for 20 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and volatile organics were removed under reduced pressure to give tert-butyl 3,3-difluoro-4-(2-(((trans)-4-((1-methoxy-2-methyl-1-oxopropan-2-yl)amino)cyclohexyl)oxy)ethyl)piperidine-1-carboxylate (2.20 g, 4.76 mmol) as a yellow oil, which was carried forward without further purification. MS (ESI) m/z 463.2 [M+1]$^+$.

tert-Butyl-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidine-1-carboxylate. To a solution of tert-butyl 3,3-difluoro-4-(2-(((trans)-4-((1-methoxy-2-methyl-1-oxopropan-2-yl)amino)cyclohexyl)oxy)ethyl)piperidine-1-carboxylate (0.730 g, 1.578 mmol) in ethyl acetate (7 mL) was added 4-isothiocyanato-2-(trifluoromethyl)benzonitrile (0.360 g, 1.578 mmol) and diisopropylethylamine (0.827 mL, 4.73 mmol). The reaction vial was sealed and stirred at 90° C. for 18 h. The reaction mixture was partitioned between water and ethyl acetate. 5 mL of brine were added to reduce emulsion. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a foamy dark orange semi-solid. The solid was taken up in ethyl acetate and purified on a silica gel column using 0-100% ethyl acetate in hexanes over 1000 mL. Fractions containing desired product were combined and volatile organics were removed under reduced pressure to give tert-butyl 4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidine-1-carboxylate (396 mg, 0.601 mmol, 38% yield) as a foamy orange semi-solid. MS (ESI) m/z 559.2 [M−99]$^+$.

4-(3-((trans)-4-(2-(3,3-Difluoropiperidin-4-yl)ethoxy)cyclohexyl)-4,4-dimethyl-5-oxo-2-thioxoimidazolidin-1-yl)-2-(trifluoromethyl)benzonitrile hydrochloride. To a solution of 4-(3-(((trans)-4-(2-(3,3-difluoropiperidin-4-yl)ethoxy)cyclohexyl)-4,4-dimethyl-5-oxo-2-thioxoimidazolidin-1-yl)-2-(trifluoromethyl)benzonitrile, HCl (395 mg, 0.664 mmol, 110% yield) in 1,4-Dioxane (3.0 ml) was added HCl (2.0 ml, 8.00 mmol) (4.0 M in dioxane). The reaction was stirred at ambient temperature for 90 min. Volatile organics were removed under reduced pressure to give 4-(3-(((trans)-4-(2-(3,3-difluoropiperidin-4-yl)ethoxy)cyclohexyl)-4,4-dimethyl-5-oxo-2-thioxoimidazolidin-1-yl)-2-(trifluoromethyl)benzonitrile hydrochloride (395 mg, 0.664 mmol) as a foamy orange semi-solid that was carried forward without further purification. MS (ESI) m/z 559.2 [M+1]$^+$.

2-(4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide hydrochloride. 2-(4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)acetic acid (70 mg, 0.114 mmol) was combined with 1-(7-amino-1-methyl-1H-indazol-3-yl)dihydropyrimidine-2,4(1H,3H)-dione (29.4 mg, 0.114 mmol), 1-methylimidazole (0.036 mL, 0.454 mmol), N-(chloro(dimethylamino)methylene)-N-methylmethanaminium hexafluorophosphate(V) (63.7 mg, 0.227 mmol), DMF (1.000 mL) and acetonitrile (1 mL), and the reaction was stirred at 25° C. After 18 h the reaction solution was diluted with DMSO (1 mL), filtered, and purified by standard methods to provide 2-(4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide hydrochloride (20 mg, 0.022 mmol, 20% yield) as an off-white solid. MS (ESI) m/z 858.2 [M+1]$^+$; $^1$H NMR (DMSO-d$_6$, 400 MHz) δ 10.5-10.6 (m, 1H), 8.2-8.3 (m, 1H), 8.1-8.2 (m, 1H), 7.8-8.0 (m, 1H), 7.4-7.6 (m, 1H), 7.2-7.3 (m, 1H), 7.0-7.1 (m, 1H), 3.9-4.1 (m, 5H), 3.7-3.9 (m, 4H), 3.6-3.7 (m, 2H), 2.9-3.1 (m, 2H), 2.6-2.8 (m, 5H), 1.9-2.2 (m, 4H), 1.8-1.9 (m, 1H), 1.5-1.7 (m, 3H), 1.4-1.5 (m, 6H), 1.3-1.4 (m, 1H), 1.2-1.3 (m, 2H).

Example 36: 2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide mide (0.340 g, 1.054 mmol), and potassium hydroxide (1.479 g, 26.4 mmol). The reaction mixture was heated to 30° C. for 24 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a light yellow solid. The solid was taken up in ethyl acetate and purified on a silica gel column using 0-75% ethyl acetate in hexanes over 2000 mL. Fractions containing desired product were combined and volatile organics were removed under reduced pressure to give tert-butyl 4-(2-(((trans)-4-(dibenzylamino)cyclohexyl)oxy)ethyl)-3,3-difluoropiperidine-1-carboxylate (1.79 g, 3.30 mmol, 63% yield) as a colorless oil. MS (ESI) m/z 543.2 [M+1]$^+$.

tert-Butyl 4-(2-(((trans)-4-aminocyclohexyl)oxy)ethyl)-3,3-difluoropiperidine-1-carboxylate. To a solution of tert-butyl 4-(2-(((trans)-4-(dibenzylamino)cyclohexyl)oxy)ethyl)-3,3-difluoropiperidine-1-carboxylate (2.65 g, 4.88 mmol) in Methanol (50 ml) was added palladium on carbon (500 mg, 4.70 mmol). Air in the flask was evacuated and replaced with hydrogen (3×, 15 psi, balloon). The reaction mixture was stirred at ambient temperature for 18 h. The reaction was filtered through celite. The filter cake was washed with more methanol. The filtrate was taken and volatile organics were removed under reduced pressure to give tert-butyl 4-(2-(((trans)-4-aminocyclohexyl)oxy)ethyl)-3,3-difluoropiperidine-1-carboxylate (1.72 g, 4.75 mmol, 97% yield) as a light yellow oil. MS (ESI) m/z 363.2 [M+1]$^+$.

tert-Butyl 3,3-difluoro-4-(2-(((trans)-4-((1-methoxy-2-methyl-1-oxopropan-2-yl)amino)cyclohexyl)oxy)ethyl)piperidine-1-carboxylate. To a solution of tert-butyl 4-(2-(((trans)-4-aminocyclohexyl)oxy)ethyl)-3,3-difluoropiperidine-1-carboxylate (1.72 g, 4.75 mmol) in acetonitrile (20 ml) was added methyl 2-bromo-2-methyl-propanoate (1.718 g, 9.49 mmol), potassium iodide (0.079 g, 0.475 mmol), and potassium carbonate (1.312 g, 9.49 mmol). The reaction mixture was stirred at 110° C. for 20 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and

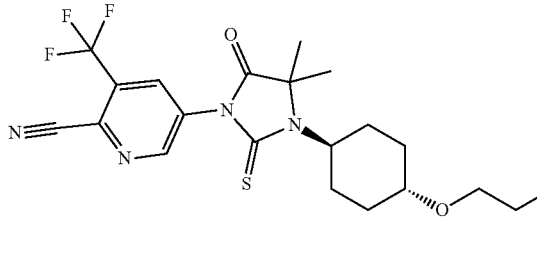
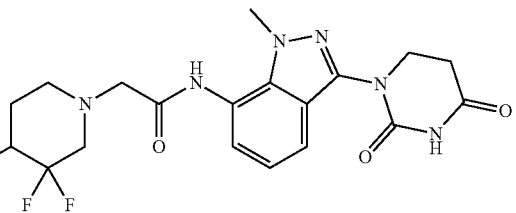

60 tert-Butyl 4-(2-(((trans)-4-(dibenzylamino)cyclohexyl)oxy)ethyl)-3,3-difluoropiperidine-1-carboxylate. To a solution of tert-butyl 3,3-difluoro-4-(2-((methylsulfonyl)oxy)ethyl)piperidine-1-carboxylate (1.81 g, 5.27 mmol) in xylenes (30 mL) was added (1r,4r)-4-(dibenzylamino)cyclohexan-1-ol (3.11 g, 10.54 mmol), tetrabutylammonium brovolatile organics were removed under reduced pressure to give tert-butyl 3,3-difluoro-4-(2-(((trans)-4-((1-methoxy-2-methyl-1-oxopropan-2-yl)amino)cyclohexyl)oxy)ethyl)piperidine-1-carboxylate (2.20 g, 4.76 mmol) as a yellow oil, which was carried forward without further purification. MS (ESI) m/z 463.2 [M+1]$^+$.

tert-Butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidine-1-carboxylate. To a solution of tert-butyl 3,3-difluoro-4-(2-(((trans)-4-((1-methoxy-2-methyl-1-oxopropan-2-yl)amino)cyclohexyl)oxy)ethyl)piperidine-1-carboxylate (1.47 g, 3.18 mmol) in ethyl acetate (14 mL) was added 5-isothiocyanato-3-(trifluoromethyl)picolinonitrile (0.728 g, 3.18 mmol) and diisopropylethylamine (1.665 mL, 9.53 mmol). The reaction vial was sealed and stirred at 90° C. for 18 h. The reaction mixture was partitioned between water and ethyl acetate. A few mL of brine were added to reduce emulsion. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a foamy dark orange semi-solid. The solid was taken up in ethyl acetate and purified on a silica gel column using 0-100% ethyl acetate in hexanes over 1800 mL. Fractions containing desired product were combined and volatile organics were removed under reduced pressure to give tert-butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidine-1-carboxylate (1.10 g, 1.667 mmol, 52% yield) as a foamy light orange semi-solid. MS (ESI) m/z 560.2 [M−99]$^+$.

5-(3-((trans)-4-(2-(3,3-Difluoropiperidin-4-yl)ethoxy)cyclohexyl)-4,4-dimethyl-5-oxo-2-thioxoimidazolidin-1-yl)-3-(trifluoromethyl)picolinonitrile hydrochloride. To a solution of tert-butyl 4-(2-(((1r,4r)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidine-1-carboxylate (1.10 g, 1.667 mmol) in 1,4-dioxane (5.0 ml) was added HCl (5.0 ml, 20.00 mmol) (4.0 M in dioxane). The reaction was stirred at ambient temperature for 90 min. Volatile organics were removed under reduced pressure to give 5-(3-((trans)-4-(2-(3,3-difluoropiperidin-4-yl)ethoxy)cyclohexyl)-4,4-dimethyl-5-oxo-2-thioxoimidazolidin-1-yl)-3-(trifluoromethyl)picolinonitrile hydrochloride (1.08 g, 1.812 mmol) as a foamy orange semi-solid that was carried forward without further purification. MS (ESI) m/z 560.2 [M+1]$^+$.

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate. To a solution of 5-(3-((trans)-4-(2-(3,3-difluoropiperidin-4-yl)ethoxy)cyclohexyl)-4,4-dimethyl-5-oxo-2-thioxoimidazolidin-1-yl)-3-(trifluoromethyl)picolinonitrile, HCl (1.08 g, 1.812 mmol) in acetonitrile (15 mL) was added triethylamine (0.758 mL, 5.44 mmol) and tert-butyl 2-bromoacetate (1.338 mL, 9.06 mmol). The reaction vessel was sealed and stirred at 70° C. for 18 h. Volatile organics were removed under reduced pressure to give an orange solid. Solid was taken up in dichloromethane and purified on a silica gel column using 0-100% ethyl acetate in hexanes over 2200 mL. Fractions containing desired product were combined and volatile organics were removed under reduced pressure to give tert-butyl 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate (0.997 g, 1.480 mmol, 82% yield) as a foamy orange semi-solid. MS (ESI) m/z 674.2 [M+1]$^+$.

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid hydrochloride. To a flask containing tert-butyl 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate (1.0 g, 1.484 mmol) was added HCl (10.0 ml, 40.0 mmol) (4.0 M in dioxane). The reaction mixture was stirred at ambient temperature for 3 h. Volatile organics were removed under reduced pressure to give 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid hydrochloride (1.14 g, 1.743 mmol) as a light brown solid which was carried forward without further purification. MS (ESI) m/z 618.2 [M+1]$^+$.

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(3-((2,6-dioxopiperidin-3-yl)amino)phenyl)acetamide hydrochloride. To a solution of 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid, HCl (100 mg, 0.153 mmol) in Acetonitrile (1.0 mL) was added 3-((3-aminophenyl)amino)piperidine-2,6-dione (40.2 mg, 0.183 mmol), 1-methyl-1H-imidazole (0.049 mL, 0.612 mmol), N-(chloro(dimethylamino)methylene)-N-methylmethanaminium hexafluorophosphate (86 mg, 0.306 mmol) and 1 mL DMF and the reaction solution was stirred at room temperature. After 18 h the reaction solution was diluted with DMSO and purified by standard methods to provide 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(3-((2,6-dioxopiperidin-3-yl)amino)phenyl)acetamide hydrochloride (50 mg, 0.058 mmol, 38% yield) as a white solid. MS (ESI) m/z 819.2 [M+1]$^+$; $^1$H NMR (DMSO-d6, 400 MHz) δ 10.79 (s, 1H), 9.14 (d, 1H, J=2.0 Hz), 8.74 (d, 1H, J=2.0 Hz), 7.0-7.1 (m, 1H), 6.95 (s, 1H), 6.8-6.8 (m, 1H), 6.45 (dd, 1H, J=1.5, 8.1 Hz), 4.26 (dd, 1H, J=4.6, 11.2 Hz), 4.0-4.2 (m, 1H), 3.8-3.9 (m, 1H), 3.7-3.8 (m, 1H), 3.4-3.6 (m, 3H), 3.3-3.4 (m, 1H), 3.2-3.3 (m, 1H), 3.0-3.2 (m, 1H), 2.7-2.9 (m, 3H), 2.6-2.6 (m, 1H), 2.0-2.1 (m, 4H), 1.8-2.0 (m, 2H), 1.6-1.8 (m, 3H), 1.57 (s, 6H), 1.4-1.5 (m, 1H), 1.3-1.4 (m, 2H).

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide. To a solution of 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid hydrochloride (100 mg, 0.153 mmol) in acetonitrile (1.0 mL) was added 1-(7-amino-1-methyl-1H-indazol-3-yl)dihydropyrimidine-2,4(1H,3H)-dione (47.6 mg, 0.183 mmol), 1-methyl-1H-imidazole (0.049 mL, 0.612 mmol), and N-(chloro(dimethylamino)methylene)-N-methylmethanaminium hexafluorophosphate (86 mg, 0.306 mmol) followed by DMF (1 mL) and the reaction was stirred at room temperature. After 18 h the reaction solution was diluted with DMSO (1 mL), filtered, and purified by standard methods to provide 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide (35 mg, 0.041 mmol, 27% yield) as a white solid. MS (ESI) m/z 859.2 [M+1]$^+$; $^1$H NMR (DMSO-d6, 400 MHz) δ 10.58 (s, 1H), 9.14 (d, 1H, J=2.0 Hz), 8.74 (d, 1H, J=2.0 Hz), 7.55 (d, 1H, J=8.2 Hz), 7.29 (d, 1H, J=7.2 Hz), 7.11 (t, 1H, J=7.8 Hz), 4.08 (s, 4H), 3.90 (t, 3H, J=6.7

Hz), 3.5-3.6 (m, 3H), 3.2-3.3 (m, 2H), 2.7-2.9 (m, 5H), 2.0-2.1 (m, 3H), 1.9-2.0 (m, 2H), 1.7-1.8 (m, 2H), 1.57 (s, 7H), 1.3-1.5 (m, 3H).

CELL BASED ASSAYS

VCAP AR Degradation Assay. Test compounds were pre-dispensed into a Corning CellBind 96-well clear bottom plate (Cat #3300) using an acoustic dispenser to make a 10-point concentration series at 1:3 dilution for each compound. The final top concentration of each compound was 5 µM. DMSO at a final concentration of 0.1% was used as a control. VCaP cells cultured in DMEM with 8% fetal bovine serum (FBS) were seeded at 50K cells per well in a 200 µL volume into the compound plate and incubated at 37° C. in a $CO_2$ incubator for 24 h. The medium was carefully removed from the cells and the plate was placed on ice. One hundred of ice-cold 1× cell lysis buffer from Cell Signaling Technologies (Cat #9803) was added to each well of the cells and the plate was incubated at 4° C. on a shaker for 1 h. Fifteen µL of cell lysate was used for AR ELISA detection using a PathScan Total Sandwich AR ELISA kit (Cell Signaling Technology, Cat #12580). AR levels in compound-treated wells were normalized to that of DMSO control and expressed as percent of control (PoC) (y). A Four Parameter Logistic Model (Sigmoidal Dose-Response Model) was used to determine the compound's $DC_{50}$, and $EC_{50}$, using the following equation:

$$y=(A+((B-A)/(1+((C/x)^D))))$$

$A=Y_{Min}$ (lowest AR level normalized to DMSO control in response to compound treatment, as determined by curve fit)
$B=Y_{Max}$ (maximum AR level as determined by curve fit)
$C=EC_{50}$
D=Hill Slope
x=compound concentration
$EC_{50}$=the concentration of compound when $y=(Y_{Max}-Y_{Min})/2$
$DC_{50}$=the concentration of the compound when y=50% of DMSO control (50% AR degradation)
y=AR protein level normalized to DMSO control The lowest measured AR level normalized to DMSO control in response to compound treatment, termed Y value, was used to characterize the compound-mediated AR degradation efficiency.

Each of the compounds in Table 1, was tested in the VCAP AR degradation assay, and was found to have activity therein. All of the compounds in Table 1 were shown to have an $DC_{50}$<1 µM and Y<50% of DMSO control.

Prostate Cancer Cell Proliferation Assay. VCAP or ENZR cells were plated at 10K cells per well in 96-well CellBind (Costar) plates using DMEM+8% FBS media. Cells were incubated overnight at 37° C. and test compound was serially diluted and added to the well.

Following seven-day incubation, the assay media was removed by inversion and the plate was frozen overnight at −80° C. Plates were thawed at room temperature and 100 µL deionized water ($ddH_2O$) was added to each well. Plates were incubated at 37° C. in non-$CO_2$ incubator for 1 h and then frozen at −80° C. overnight. Plates were thawed to room temperature and 100-4, THE buffer (NaCl, Tris, EDTA)+Hoescht dye (1.0 mg/ml, 1:400) was added to each well. Fluorescent signal was measured at 460 nm. All data were normalized as a percentage of the DMSO control. A Four Parameter Logistic Model (Sigmoidal Dose-Response Model) was used to determine the compound's $GI_{50}$ value, using the following equation:

$$y=(A+((B-A)/(1+((C/x)^D))))$$

$A=Y_{Min}$ (lowest cell viability in luminescence unit normalized to DMSO control in response to compound treatment determined by curve fit)
$B=Y_{Max}$ (maximum cell viability measured as luminescence unit normalized to DMSO control as determined by curve fit)
$C=EC_{50}$
D=Hill Slope
$GI_{50}$=the concentration of the compound when $Y=(Y_{Max}+Y_{t_0})/2$
$EC_{50}$=the concentration of compound when $y=(Y_{Max}-Y_{Min})/2$
$IC_{50}$=the concentration of the compound when Y=50% of DMSO control
y=cell viability measured as luminescence unit and normalized as percentage of the DMSO control
$t_0$=time when compound was added
$Y_{t_0}$=value of y at to The compounds provided herein have been, or will be tested in the prostate cancer cell proliferation assay, and have shown, or will be shown, to have activity therein.

IN VIVO ASSAYS

AR Degradation Assay. In vivo AR degradation assays were performed in NSG mice bearing VCaP prostate cancer xenograft tumors. Male NSG mice were inoculated with VCaP cells in the flank region above the right leg. Following inoculation of the animals, the tumors were allowed to grow to approximately 500 $mm^3$ prior to randomization. The randomized animals were administered with test compounds formulated in 20% Labrasol, 80% 25 mM citrate buffer pH 3. The compounds were administered orally once daily for 3 days. After the last dose of compound administration, the plasma and tumors were collected and processed for AR degradation assays. Intratumoral AR levels were measured using western blot analysis. Statistical analysis was performed using a one-way analysis of variance (ANOVA).

The compounds provided herein have been, or will be tested in the in vivo AR degradation assay, and have shown, or will be shown, to have activity therein.

VCaP Prostate Cancer Xenograft model. The xenograft study was conducted with male NSG mice bearing VCaP prostate cancer xenograft tumors. Male NSG mice were inoculated subcutaneously with VCaP cells in the flank region above the right hind leg. Following inoculation of the animals, the tumors were allowed to grow to approximately 200 $mm^3$ prior to randomization. During randomization, the mice bearing VCaP tumors ranging between 75 and 250 $mm^3$ were pooled together and randomized into various treatment groups. Test compounds formulated in 20% Labrasol, 80% 25 mM citrate buffer pH 3 were administered in a dose volume of 5 mL/kg. The compounds were administered orally once daily for the duration of the study. Tumors were measured twice a week using calipers and tumor volumes were calculated using the formula $W^2 \times L/2$. Statistical analysis was performed using a one-way or two-way analysis of variance (ANOVA).

The compounds provided herein have been, or will be tested in the VCAP prostate cancer xenograft model and have shown, or will be shown, to be effective as treatments of prostate cancer in the models.

ACTIVITY TABLE

Each of the compounds in Table 1, was tested in one or more of the AR degradation assays shown above, for example, the VCAP AR Degradation Assay, and was found to have activity therein.

All of the compounds in Table 1 were shown to have a $DC_{50}<10$ μM and Y<60% of DMSO control, with some compounds having a $DC_{50}$ value D: $DC_{50} \leq 0.002$ some a $DC_{50}$ value C: $0.002$ μM$<DC_{50} \leq 0.010$ and some a $DC_{50}$ value B: $0.010$ μM$<DC_{50} \leq 0.1$ μM and some a $DC_{50}$ value A: $0.1$ μM$<DC_{50} \leq 10$ μM.

Additionally the compounds were shown to have an AR degradation efficiency Y value<60% of DMSO control, with some compounds having $0<Y \leq 20\%$ (shown as \*), some compounds having $20\%<Y \leq \%$ (shown as \*\*), and others having $30\%<Y<60\%$ (shown as \*\*\*),

TABLE 1

| Cmpd No. | Cmpd Structure | Cmpd Name | MH+ Obs. | DC50 | Y |
|---|---|---|---|---|---|
| 1 | | 2-((2S,6R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethyl-piperazin-1-yl)-N-(3-(2,4-dioxotetrahydro-pyrimidin-1(2H)-yl)-1-methyl-1H-indazol-7-yl)acetamide | 851.0 | B | \*\*\* |
| 2 | | 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydro-pyrimidin-1(2H)-yl)-1-methyl-1H-indazol-7-yl)acetamide | 849.4 | C | \*\* |
| 3 | | 2-((2R,6S)-4-(2-((trans-4-(3-(3-chloro-4-cyano-phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydro-pyrimidin-1(2H)-yl)-1-methyl-1H-indazol-7-yl)acetamide | 817.0 | C | \*\*\* |

TABLE 1-continued

| Cmpd No. | Cmpd Structure | Cmpd Name | MH+ Obs. | DC50 | Y |
|---|---|---|---|---|---|
| 4 | | 2-((2R,6S)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide | 853.0 | C | ** |
| 5 | | 3-((2R,6S)-4-2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethyl-piperazin-1-yl)-N-(3-(2,4-dioxotetrahydropyrimidin-1(2H)-yl)-1-methyl-1H-indazol-7-yl)propanamide | 865.0 | C | *** |
| 6 | | 2-((2R,6S)-4-(2-((trans-4-(3-(5-chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide | 818.3 | D | * |
| 7 | | 2-((2R,6S)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide | 866.3 | D | ** |

TABLE 1-continued

| Cmpd No. | Cmpd Structure | Cmpd Name | MH+ Obs. | DC50 | Y |
|---|---|---|---|---|---|
| 8 | | 2-((2R,6S)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide | 865.2 | D | * |
| 9 | | 2-((2R,6S)-4-(3-((trans-4-(3-(3-chloro-4-cyanophenyl)-5,5-dimethyl-4-oxo-2-thioxo-imidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide | 831.3 | D | * |
| 10 | | 2-((2R,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide | 850.3 | C | * |
| 11 | | 2-((2S,6R)-4-(3-(trans-4-(3-(3-chloro-4-cyanophenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide | 815.4 | B | *** |

TABLE 1-continued

| Cmpd No. | Cmpd Structure | Cmpd Name | MH+ Obs. | DC50 | Y |
|---|---|---|---|---|---|
| 12 | | 2-((2R,6S)-4-(3-(trans-4-(3-(5-chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide | 816.3 | C | ** |
| 13 | | 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide | 850.3 | C | * |
| 14 | | 2-((2R,4r,6S)-4-2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide | 850.4 | C | * |
| 15 | | give 4-(3-(trans-4-(2-((3R,5S)-4-(2-((3-(2,4-dioxotetrahydropyrimidin-1(2H)-yl)-1-methyl-1H-indazol-7-yl)oxy)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile | 838.4 | A | ** |

TABLE 1-continued

| Cmpd No. | Cmpd Structure | Cmpd Name | MH+ Obs. | DC50 | Y |
|---|---|---|---|---|---|
| 16 | | 4-(3-(trans-4-(2-((3S,5R)-4-(3-((3-(2,4-dioxotetrahydropyrimidin-1(2H)-yl)-1-methyl-1H-indazol-7-yl)oxy)propyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile | 852.4 | A | *** |
| 17 | | 2-((2R,6S)-4-(4-(trans-4-(3-(4-cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(3-(2,4-dioxotetrahydropyrimidin-1(2H)-yl)-1-methyl-1H-indazol-7-yl)acetamide | 863.3 | C | ** |
| 18 | | 4-(3-(trans-4-(2-((3R,5S)-4-(2-((3-(2,4-dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile | 837.4 | B | *** |
| 19 | | 4-(3-(trans-4-(2-((3R,5S)-4-(2-((3-(2,4-dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile | 837.4 | A | *** |

TABLE 1-continued

| Cmpd No. | Cmpd Structure | Cmpd Name | MH+ Obs. | DC50 | Y |
|---|---|---|---|---|---|
| 20 | | 2-((S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydro-pyrimidin-1(2H)-yl)-1-methyl-1H-indazol-7-yl)acetamide | 891.2 | D | ** |
| 21 | | 2-((2S,6R)-4-(2-((trans-4-(3-(4-cyano-3-(pentafluoro-$\lambda^6$-sulfaneyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydro-pyrimidin-1(2H)-yl)-1-methyl-1H-indazol-7-yl)acetamide | 910.3 | A | *** |
| 22 | | 2-((R)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydro-pyrimidin-1(2H)-yl)-1-methyl-1H-indazol-7-yl)acetamide | 890.1 | C | * |
| 23 | | 2-((R)-4-(3-(trans-4-(3-(4-cyano-3-(trifluoromethyl)phenyl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydro-pyrimidin-1(2H)-yl)-1-methyl-1H-indazol-7-yl)acetamide | 889.5 | C | ** |

TABLE 1-continued

| Cmpd No. | Cmpd Structure | Cmpd Name | MH+ Obs. | DC50 | Y |
|---|---|---|---|---|---|
| 24 | | 2-((R)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide | 906.2 | D | * |
| 25 | | 2-((2R,4s,6S)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide | 851.6 | D | * |
| 26 | | 2-((R)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide | 905.1 | C | * |
| 27 | | 2-((R)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide | 892.0 | D | ** |

TABLE 1-continued

| Cmpd No. | Cmpd Structure | Cmpd Name | MH+ Obs. | DC50 | Y |
|---|---|---|---|---|---|
| 28 | | 2-((2R,4r,6S)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide | 851.5 | D | * |
| 29 | | 2-((2R,4r,6S)-4-(3-(trans-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide | 864.3 | B | * |
| 30 | | 2-((2R,4r,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide | 865.3 | C | * |
| 31 | | 2-((2R,4r,6S)-4-(2-(trans-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide | 850.5 | C | ** |

TABLE 1-continued

| Cmpd No. | Cmpd Structure | Cmpd Name | MH+ Obs. | DC50 | Y |
|---|---|---|---|---|---|
| 32 | | 2-((2R,4r,6S)-4-(2-(trans-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide | 851.5 | C | * |
| 33 | | 2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide | 866.5 | C | ** |
| 34 | | 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide | 867.3 | D | ** |
| 35 | | 2-(4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide | 858.2 | D | * |

TABLE 1-continued

| Cmpd No. | Cmpd Structure | Cmpd Name | MH+ Obs. | DC50 | Y |
|---|---|---|---|---|---|
| 36 | 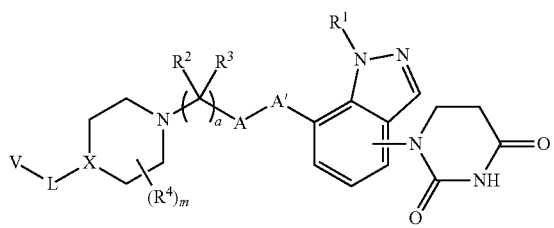 | 2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide | 859.2 | D | * |

What is claimed is:

1. A compound of formula I

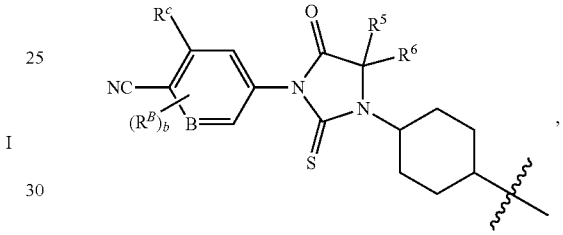

or a pharmaceutically acceptable salt, tautomer, isotopolog, or stereoisomer thereof, wherein $R^1$ is $C_{1-3}$ alkyl;

A is $CH_2$ or C=O;

A' is NH or O;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

L is substituted or unsubstituted —O($C_{1-6}$ alkyl)-, —($C_{1-6}$ alkyl)O—, —O($C_{1-6}$ alkyl)O— or —($C_{1-9}$ alkyl)-;

X is N or $CR^X$;

$R^X$ is hydrogen, halogen, —O($C_{1-6}$ alkyl) or —($C_{1-9}$ alkyl);

V is wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

2. The compound of claim 1, wherein $R^1$ is methyl.

3. The compound of claim 1, wherein a is 1, and $R^2$ and $R^3$ are both H.

4. The compound of claim 1, wherein each $R^4$ is substituted or unsubstituted methyl.

5. The compound of claim 1, wherein m is 0, 1, 2, 3 or 4.

6. The compound of claim 1, wherein L is substituted or unsubstituted —O($CH_2$)$_p$—, O($CH_2$)$_p$O— or —($CH_2$)$_p$—, and p is 1-4.

7. The compound of claim 1, wherein L is —O($CH_2$)($CH_2$)—, —O($CH_2$)($CH_2$)O— or —($CH_2$)($CH_2$)($CH_2$)—.

8. The compound of claim 1, wherein $R^C$ is $CF_3$, Cl or $SF_5$.

9. The compound of claim 1, wherein $R^5$ and $R^6$ are methyl.

10. The compound of claim 1, having formula II

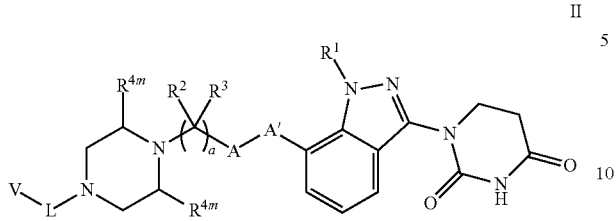

or a pharmaceutically acceptable salt, tautomer, isotopolog, or stereoisomer thereof.

11. The compound of claim 1, wherein the compound is selected from the group consisting of 2-((2S,6R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(2-((trans-4-(3-(3-chloro-4-cyanophenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide, 3-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)propenamide, 2-((2R,6S)-4-(2-((trans-4-(3-(5-chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(3-((trans-4-(3-(3-chloro-4-cyanophenyl)-5,5-dimethyl-4-oxo-2-thioxoimidazolidin-1-yl)cyclohexyl)oxy)propyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide, 2-((2S, 6R)-4-(3-(trans-4-(3-(3-chloro-4-cyanophenyl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide, 2-((2R,6S)-4-(3-(trans-4-(3-(5-chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(3-(2,4-dioxotetrahydropyrimidin-1(2H)-yl)-1-methyl-1H-indazol-7-yl)acetamide, 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide, 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(3-(2,4-dioxotetrahydropyrimidin-1(2H)-yl)-1-methyl-1H-indazol-7-yl)acetamide, 4-(3-(trans-4-(2-((3R, 5S)-4-(2-((3-(2,4-dioxotetrahydropyrimidin-1(2H)-yl)-1-methyl-1H-indazol-7-yl)oxy)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile, 4-(3-(trans-4-(2-((3S,5R)-4-(3-((3-(2,4-dioxotetrahydropyrimidin-1(2H)-yl)-1-methyl-1H-indazol-7-yl)oxy)propyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile, 2-((2R,6S)-4-(4-(trans-4-(3-(4-cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(3-(2,4-dioxotetrahydropyrimidin-1(2H)-yl)-1-methyl-1H-indazol-7-yl)acetamide, 4-(3-(trans-4-(2-((3R, 5S)-4-(2-((3-(2,4-dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile, 4-(3-(trans-4-(2-((3R, 5S)-4-(2-((3-(2,4-dioxotetrahydropyrimidin-1(2H)-yl)-1-methyl-1H-indazol-7-yl)amino)ethyl)-3,5-dimethylpiperazin-1-yl)ethoxy)cyclohexyl)-4,4-dimethyl-5-oxo-2-thioxoimidazolidin-1-yl)-2-(trifluoromethyl)benzonitrile, 2-((S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(3-(2,4-dioxotetrahydropyrimidin-1(2H)-yl)-1-methyl-1H-indazol-7-yl)acetamide, 2-((2S, 6R)-4-(2-((trans-4-(3-(4-cyano-3-(pentafluoro-k⁶-sulfaneyl)phenyl)-5,5-dimethyl-4-oxo-2-thioxoimidazolidin-1-yl)cyclohexyl)oxy)ethyl)-2,6-dimethylpiperazin-1-yl)-N-(3-(2,4-dioxotetrahydropyrimidin-1(2H)-yl)-1-methyl-1H-indazol-7-yl)acetamide, 2-((R)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide, 2-((R)-4-(3-(trans-4-(3-(4-cyano-3-(trifluoromethyl)phenyl)-5,5-dimethyl-4-oxo-2-thioxoimidazolidin-1-yl)cyclohexyl)propyl)-2-(trifluoromethyl)piperazin-1-yl)-N-(3-(2,4-dioxotetrahydropyrimidin-1(2H)-yl)-1-methyl-1H-indazol-7-yl)acetamide, 2-((R)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl) piperazin-1-yl)-N-(3-(2,4-dioxotetrahydropyrimidin-1 (2H)-yl)-1-methyl-1H-indazol-7-yl)acetamide, 2-((2R,4s,6S)-4-(2-(((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2, 6-dimethylpiperidin-1-yl)-N-(3-(2,4-dioxotetrahydropyrimidin-1 (2H)-yl)-1-methyl-1H-indazol-7-yl)acetamide, 2-((R)-4-(3-((trans-4-(3-(4-cyano-3-(trifluoromethyl) phenyl)-5,5-dimethyl-4-oxo-2-thioxoimidazolidin-1-yl)cyclohexyl)oxy)propyl)-2-(trifluoromethyl)piperazin-1-yl)-N-(3-(2,4-dioxotetrahydropyrimidin-1(2H)-yl)-1-methyl-1H-indazol-7-yl)acetamide, 2-((R)-4-(2-((trans-4-(3-(6-cyano-5-(trifluoromethyl) pyridin-3 -yl)-5,5-dimethyl-4-oxo-2-thioxoimidazolidin-1-yl)cyclohexyl)oxy)ethyl)-2-(trifluoromethyl)piperazin-1-yl)-N-(3 -(2,4-dioxotetrahydropyrimidin-1(2H)-yl)-1-methyl-1H-indazol-7-yl)acetamide, 2-((2R,4r,6S)-4-(2-(((trans-4-(3-(6-cyano-5-(trifluoromethyl)pyridin-3-yl)-5,5-dimethyl-4-oxo-2-thioxoimidazolidin-1 -yl)cyclohexyl)oxy)ethyl)-2, 6-dimethylpiperidin-1-yl)-N-(3-(2,4-dioxotetrahydropyrimidin-1 (2H)-yl)-1-methyl-1H-indazol-7-yl)acetamide, 2-((2R,4r,6S)-4-(3-(trans-4-(3-(4-cyano-3-(trifluoromethyl)phenyl)-5,5 -dimethyl-4-oxo-2-thioxoimidazolidin-1 -yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide, 2-((2R,4r,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(3-(2,4-dioxotetrahydropyrimidin-1(2H)-yl)-1-methyl-1H-indazol-7-yl)acetamide, 2-((2R,4r,6S)-4-(2-(trans-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin-1(2H)-yl)-1-methyl-1H-indazol-7-yl)acetamide, 2-((2R,4r,6S)-4-(2-(trans-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(3-(2,4-dioxotetrahydropyrimidin- 1(2H)-yl)-1-methyl-1H-indazol-7-yl)acetamide, 2-((2R,4r,6S)-4-(2-(((trans)-4-(3-(4-Cyano-3 -(trifluoromethyl)phenyl)-5,5 -dimethyl-4-oxo-2-thioxoimidazolidin-1-yl)cyclohexyl)oxy)ethoxy)-2,6-dimethylpiperidin-1-yl)-N-(3 -(2,4-dioxotetrahydropyrimidin-1 (2H)-yl)-1-methyl-1H-indazol-7-yl)acetamide, 2-((2R,4r,6 S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(3-(2,4-dioxotetrahydropyrimidin-1(2H)-yl)-1-methyl-1H-indazol-7-yl)acetamide, 2-(4-(2-(((trans)-4-(3-(4-Cyano-3-(trifluoromethyl)phenyl)-5,5 -dimethyl-4-oxo-2-thioxoimidazolidin-1-yl)cyclohexyl)oxy)ethyl)-3,3-difluoropiperidin-1-yl)-N-(3-(2,4-dioxotetrahydropyrimidin-1(2H)-yl)-1-methyl-1H-indazol-7-yl)acetamide, and 2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3 -difluoropiperidin-1-yl)-N-(3-(2,4-dioxotetrahydropyrimidin-1(2H)-yl)-1-methyl-1H-indazol-7-yl)acetamide, or a pharmaceutically acceptable salt, tautomer, isotopolog, or stereoisomer thereof.

12. A pharmaceutical composition comprising an effective amount of the compound of claim 1 or a pharmaceutically acceptable salt, tautomer, isotopologue, or stereoisomer thereof, and a pharmaceutically acceptable carrier, excipient or vehicle.

13. A method for the treatment of an androgen receptor mediated disease, the method comprising administering to a subject in need thereof an effective amount of the compound of claim 1.

14. The method of claim 13, wherein the androgen mediated disease is prostate cancer.

15. The method of claim 14, wherein the prostate cancer is castration resistant prostate cancer (CRPC).

16. A method for the treatment of an androgen receptor mediated disease, the method comprising administering to a subject in need thereof an effective amount of the pharmaceutical composition of claim 12.

17. The method of claim 16, wherein the androgen mediated disease is prostate cancer.

18. The method of claim 17, wherein the prostate cancer is castration resistant prostate cancer (CRPC).

* * * * *